US008158391B2

(12) United States Patent
Gross et al.

(10) Patent No.: US 8,158,391 B2
(45) Date of Patent: Apr. 17, 2012

(54) **PRODUCTION OF AN α-CARBOXYL-ω-HYDROXY FATTY ACID USING A GENETICALLY MODIFIED *CANDIDA* STRAIN**

(75) Inventors: Richard A. Gross, New York, NY (US); Wenhua Lu, Brooklyn, NY (US); Jon Ness, Redwood City, CA (US); Jeremy Minshull, Los Altos, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 228 days.

(21) Appl. No.: 12/436,729

(22) Filed: May 6, 2009

(65) Prior Publication Data

US 2010/0285545 A1 Nov. 11, 2010

(51) Int. Cl.
*C12P 7/64* (2006.01)
*C12N 9/00* (2006.01)
*C12N 1/00* (2006.01)
*C12N 15/00* (2006.01)
*C12N 15/74* (2006.01)

(52) U.S. Cl. ............ 435/134; 435/183; 435/254.22; 435/320.1; 435/471; 536/23.2

(58) Field of Classification Search ................ None
See application file for complete search history.

(56) References Cited

U.S. PATENT DOCUMENTS

| 4,661,450 | A | 4/1987 | Kempe et al. |
|---|---|---|---|
| 5,254,466 | A | 10/1993 | Picataggio et al. |
| 5,849,524 | A | 12/1998 | Kondo et al. |
| 5,908,926 | A | 6/1999 | Pirrung et al. |
| 6,472,522 | B1 | 10/2002 | Horn et al. |
| 2003/0233675 | A1 | 12/2003 | Cao et al. |
| 2004/0014198 | A1 | 1/2004 | Craft et al. |
| 2004/0146999 | A1 | 7/2004 | Fallon et al. |
| 2008/0293928 | A1 | 11/2008 | Farinas et al. |
| 2009/0098626 | A1 | 4/2009 | Chang et al. |

FOREIGN PATENT DOCUMENTS

| JP | 07059576 A | 8/1993 |
|---|---|---|
| WO | WO 02/081490 A2 | 10/2002 |

OTHER PUBLICATIONS

Craft et al. Appl Environ Microbiol. Oct. 2003;69(10):5983-91.*
Eirich et al. Appl Environ Microbiol. Aug. 2004;70(8):4872-9.*
Meesapyodsuk et al. Biochemistry. Oct. 3, 2000;39(39):11948-54.*
Eschenfeldt et al., 2003, "Transformation of Fatty Acids Catalyzed by Cytochrome P450 Monooxygenase Enzymes of *Candida tropicalis*," Applied and Environmental Microbiology 69, 5992-5999.
Kusunose et al., 1964, Enzymatic w-Oxidation of Fatty Acids, The Journal of Biological Chemistry 239, 2135-2139.
Okazaki et al., 1986, "Two acyl-coenzyme A oxidases in peroxisomes of the yeast *Candida tropicalis*: Primary structures deduced from genomic DNA sequence," Proc. Natl. Acad. Sci. USA 83, 1232-1236.
Waché et al., 2001, "role of β-Oxidation Enzymes in γ-Declactone Production by the Yeast *Yarrowia lipolytica*," Applied and Environmental Microbiology 67, 5700-5704.
ISA/US, PCT Invitation to Pay Additional Fees and, Where Applicable, Protest Fee dated Feb. 11, 2011 for PCT/US10/01361.
Mukherjee et al., "Alcohol Dehydrogenase Restricts the Ability of the Pathogen *Candida albicans* To Form a Biofilm on Catheter Surfaces through an Ethanol-Based Mechanism," Infection and Immunity, Jul. 2006;74(7):3804-3816.
NCBI, "adhA4 NADP-dependent alcohol dehydrogenase [*Streptomyces avermitilis* MA-4680]," retrieved from the internet Feb. 8, 2011 from <http://www.ncbi.nim.nih.gov/sites/entrez>.
Umemura et al., "A novel promoter, derived from the isocitrate lyase gene of *Candida tropicalis*, inducible with acetate in *Saccharomyces cerevisae*," Appl Microbiol Biotechnol., Jul. 1995;43(3):489-92.
ISA/US, PCT Invitation to Pay Additional Fees and, Where Applicable, Protest Fee dated Mar. 1, 2011 for application No. PCT/US2010/01362.
ISA/US, International Search Report and Written Opinion dated Jun. 5, 2008 for application No. PCT/US2005/015593.
EPO, Communication and Supplementary European Search Report dated Mar. 17, 2011 for application No. 05780055.9.
ISA/US, PCT International Search Report and Written Opinion dated Apr. 29, 2011 for application No. PCT/US2010/001362.
Okazaki et al., "Two acyl-coenzyme A oxidases in peroxisomes of the yeast *Candida tropicalis*: Primary structures deduced from genomic DNA sequence," Proc. Natl. Acad. Sci. USA, 1986, vol. 83, pp. 1232-1236.
Murray et al., "The primary structure of a peroxisomal fatty acyl-CoA oxidase from the yeast *Candida tropicalis* pK233," Gene, 1987, vol. 51, pp. 119-128.
Pubwest, Electronic Search History dated Apr. 26, 2011 in connection with International Search Report and Written Opinion dated Apr. 29, 2011 for application No. PCT/US2010/001362.

* cited by examiner

*Primary Examiner* — Christian Fronda
(74) *Attorney, Agent, or Firm* — Morgan Lewis & Bockius LLP

(57) ABSTRACT

A substantially pure *Candida* host cell for the production of a α-carboxyl-ω-hydroxy fatty acid having a carbon chain length in the range from C6 to C22, a α,ω-dicarboxylic fatty acid having a carbon chain length in the range from C6 to C22, or mixtures thereof, is provided. The *Candida* host cell is characterized by a first genetic modification class and a second genetic modification class. The first genetic modification class comprises one or more genetic modifications that disrupt the peroxisomal β-oxidation pathway. The second genetic modification class comprises one or more genetic modifications that collectively or individually disrupt at least one gene selected from the group consisting of a CYP52A type cytochrome P450, a fatty alcohol oxidase, and an alcohol dehydrogenase.

12 Claims, 26 Drawing Sheets

PRODUCTION OF AN α-CARBOXYL-ω-HYDROXY FATTY ACID USING A GENETICALLY MODIFIED *CANDIDA* STRAIN

STATEMENT REGARDING FEDERALLY SPONSORED RESEARCH OR DEVELOPMENT

This invention was made with government support under grant number DAAD19-03-1-0091, W911QY-04-C-0082 and NBCH1070004 awarded by the Defense Advanced Research Projects Agency (DARPA) to Richard A. Gross. The United States Government has certain rights in this invention.

SEQUENCE LISTING

This application includes a Sequence Listing submitted as filename Sequence_Listing_888651_999018.TXT, of size 292,000 bytes, created May 6, 2009. The Sequence Listing is incorporated by reference herein in its entirety.

1. FIELD

Methods for biological production of α,ω-hydroxyacids and diacids using genetically modified strains of the yeast *Candida* are provided. Also provided are methods for the genetic modification of the yeast *Candida*. Also provided are biological methods for the conversion of α,ω-hydroxyacids and diacids to oligomers and polymers.

2. BACKGROUND

The primary source of hydroxyfatty acids is castor oil that contains ~90% ricinoleic acid (12-hydroxy-cis-9-octadecenoic acid, 18:1 (OH)). Its hydroxyl functional group is highly valued since it provides a site for facile chemical derivatization. Unfortunately, castor plant surfaces harbor allergenic compounds that harm workers harvesting these plants. An additional concern is residual ricin, a toxic byproduct from castor oil production. Ricinoleic acid is used in high-volume products that include coatings, surfactants, polymers and cosmetics. Competitive chemical routes to ricinoleic analogs require multiple steps, use harsh chemical reagents, and generally lack selectivity. Furthermore, there is a need for a broadened spectrum of agro-based hydroxyl fatty acids that are more reactive primary substituents.

Unlike rinoleic acid, the ω-hydroxyfatty acids produced by the novel method described herein can be derived from a wide range of oil sources while also providing hydroxyl functional groups. Furthermore, ω-hydroxyfatty acids have primary instead of secondary hydroxyl groups which increase their reactivity for esterification and urethane synthesis. As such, they can replace ricinoleic acid and hydrostearic acid in certain applications requiring higher performance.

Owing to their unique attributes of new functional ω-hydroxy fatty acids and α,ω-dicarboxylic acids, they can be used in a wide variety of applications including as monomers to prepare next generation polyethylene-like polyhydroxyalkanoates, surfactants, emulsifiers, cosmetic ingredients and lubricants. They also can serve as precursors for vinyl monomers used in a wide-variety of carbon back bone polymers. Direct polymerization of ω-hydroxy fatty acids via condensation polymerization gives next generation polyethylene-like polyhydroxyalkanoates that can be used for a variety of commodity plastic applications. Alternatively, the polymers can be designed for use as novel bioresorbable medical materials. Functional groups along polymers provide sites to bind or chemically link bioactive moieties to regulate the biological properties of these materials. Another use of functional polyesters is in industrial coating formulations, components in drug delivery vehicles and scaffolds that support cell growth during tissue engineering and other regenerative medicine strategies.

2.1 Polymer Properties

Aliphatic polyesters are a group of biodegradable polymers that may be synthesized from readily renewable building blocks such as lactic acid and fatty acid-derived materials. Such polyesters can be synthesized via polycondensation reactions between aliphatic dicarboxylic acids with diols, transesterification of diesters with diols, polymerization of hydroxy acids, and ring-opening polymerization of lactones. Resulting products can be used in industrial and biomedical applications such as for controlled release drug carriers, implants and surgical sutures. Moreover, polyesters with functional groups along chains or in pendant groups are attracting increased interest since these groups can be used to regulate polymeric material properties. Furthermore, functional polymers can be post-modified to attach biologically active groups that allow the preparation of biomaterials for use in drug delivery system and as scaffold materials for tissue engineering. Polymers from ricinoleic acid have proved highly valuable for controlled drug delivery system. However, high purity ricinoleic acid is extremely expensive due to difficulties in its purification from the natural mixture.

2.2 Polymerization Reactions

Both chemical and enzymatic approaches have been explored to synthesize polyesters from diol/diacid and hydroxyacid monomers. Chemical synthetic methods often require harsh reaction conditions and metal catalysts that are difficult to remove subsequent to polymerization. Introduction of functional groups along chains or in pendant groups is difficult to accomplish by chemical methods due to the lack of selectivity of chemical catalysts and associated harsh reaction conditions. Typically, to incorporate functional groups in chains or pendant groups using a chemical catalyst, protection-deprotection steps are required. In other words, prior to polymerization, functional groups are protected and after polymerization a deprotection step is performed to liberate functional groups. Such methods required by chemical polymerization catalysts are tedious, costly, and produce undesirable by-products.

Compared to chemical synthesis, enzyme-catalyzed polymerizations can be performed under mild reaction conditions, using proteins that are metal-free and that have high enantio- and regioselectivities. Regioselectivity of enzyme-catalysts circumvents the need for protection of functional groups and allows the preparation of polymers from multifunctional monomers with control of branching.

In recent years it has been shown that lipase-catalyzed condensation polymerizations may be performed using non-activated diacids and diols. Resulting products were obtained in high yield and with useful molecular weights. Mahapatro et al., 2004, Macromolecules 37, 35-40, describes catalysis of condensation polymerizations between adipic acid and 1,8-octanediol using immobilized Lipase B from *Candida antarctica* (CALB) as the catalyst. Furthermore, effects of substrates and solvents on lipase-catalyzed condensation polymerizations of diacids and diols have been documented. See Olsson, et al., 2003, Biomacromolecules 4: 544-551. These publications demonstrate the feasibility of lipase-catalyzed polymerizations between diacids and diols.

Lipase-catalyzed polymerization of monomers containing functional groups including alkenes and epoxy groups to prepare polyesters has also been disclosed. Warwel et al. report the polymerization through transesterification reactions of long-chain unsaturated or epoxidized α,ω-dicarboxylic acid diesters (C18, C20 and C26 α,ω-dicarboxylic acid methyl esters) with diols using Novozym 435 as catalyst. See Warwel, 1995, et al. J. Mol. Catal. B: Enzymatic. 1, 29-35, which is hereby incorporated by reference herein. The α,ω-dicarboxylic acid methyl esters were synthesized by metathetical dimerization of 9-decenoic, 10-undecenioc and 13-tetradecenioc acid methyl esters, and polycondensation with 1,4-butanediol in diphenyl ether yielded the polyesters with molecular weight ($M_w$) of 7800-9900 g mol$^{-1}$. Uyama et al. report polymerization of epoxidized fatty acids (in sidechain) with divinyl sebacate and glycerol to prepare epoxide-containing polyesters in good yields. See Uyama, et al., 2003, Biomacromolecules 4, 211-215, which is hereby incorporated by reference herein. Cis-9,10-epoxy-18-hydroxyoctadecanoic acid, isolated from suberin in the outer bark of birch, was used as a monomer to synthesize an epoxy-functionalized polyester by Novozym 435 catalysis (Biomacromolecules 8, 757-760 (2007)). Thus, prior work describes the preparation of functional polyesters using Novozym 435 catalysis. However, in each instance, monomer synthesis was performed either by (i) a chemical method that lacks selectivity, gives undesirable by-products and/or uses a toxic catalyst or (ii) an inefficient extraction of the monomer from a plant source.

2.3 Production of Monomers Prior to Polymerization

Currently, α,ω-dicarboxylic acids are almost exclusively produced by chemical conversion processes. However, the chemical processes for production of α,ω-dicarboxylic acids from non-renewable petrochemical feedstocks usually produces numerous unwanted byproducts, requires extensive purification and gives low yields (Picataggio et al., 1992, Bio/Technology 10, 894-898). Moreover, α,ω-dicarboxylic acids with carbon chain lengths greater than 13 are not readily available by chemical synthesis. While several chemical routes to synthesize long-chain α,ω-dicarboxylic acids are available, their synthesis is difficult, costly and requires toxic reagents. Furthermore, most methods result in mixtures containing shorter chain lengths. Furthermore, other than four-carbon α,ω-unsaturated diacids (e.g. maleic acid and fumaric acid), longer chain unsaturated α,ω-dicarboxylic acids or those with other functional groups are currently unavailable since chemical oxidation cleaves unsaturated bonds or modifies them resulting in cis-trans isomerization and other by-products.

Many microorganisms have the ability to produce α,ω-dicarboxylic acids when cultured in n-alkanes and fatty acids, including *Candida tropicalis, Candida cloacae, Cryptococcus neoforman* and *Corynebacterium* sp. (Shiio et al., 1971, Agr. Biol. Chem. 35, 2033-2042; Hill et al., 1986, Appl. Microbiol. Biotech. 24: 168-174; and Broadway et al., 1993, J. Gen. Microbiol. 139, 1337-1344). *Candida tropicalis* and similar yeasts are known to produce α,ω-dicarboxylic acids with carbon lengths from C12 to C22 via an ω-oxidation pathway. The terminal methyl group of n-alkanes or fatty acids is first hydroxylated by a membrane-bound enzyme complex consisting of cytochrome P450 monooxygenase and associated NADPH cytochrome reductase that is the rate-limiting step in the ω-oxidation pathway. Two additional enzymes, the fatty alcohol oxidase and fatty aldehyde dehydrogenase, further oxidize the alcohol to create ω-aldehyde acid and then the corresponding α,ω-dicarboxylic acid (Eschenfeldt et al., 2003, Appl. Environ. Microbiol. 69, 5992-5999). However, there is also a β-oxidation pathway for fatty acid oxidation that exists within *Candida tropicalis*. Both fatty acids and α,ω-dicarboxylic acids in wild type *Candida tropicalis* are efficiently degraded after activation to the corresponding acyl-CoA ester through the β-oxidation pathway, leading to carbon-chain length shortening, which results in the low yields of α,ω-dicarboxylic acids and numerous by-products.

Mutants of *C. tropicalis* in which the β-oxidation of fatty acids is impaired may be used to improve the production of α,ω-dicarboxylic acids (Uemura et al., 1988, J. Am. Oil. Chem. Soc. 64, 1254-1257; and Yi et al., 1989, Appl. Microbiol. Biotech. 30, 327-331). Recently, genetically modified strains of the yeast *Candida tropicalis* have been developed to increase the production of α,ω-dicarboxylic acids. An engineered *Candida tropicalis* (Strain H5343, ATCC No. 20962) with the POX4 and POX5 genes that code for enzymes in the first step of fatty acid β-oxidation disrupted was generated so that it can prevent the strain from metabolizing fatty acids, which directs the metabolic flux toward ω-oxidation and results in the accumulation of α,ω-dicarboxylic acids (FIG. 3). See U.S. Pat. No. 5,254,466 and Picataggio et al., 1992, Bio/Technology 10: 894-898, each of which is hereby incorporated by reference herein. Furthermore, by introduction of multiple copies of cytochrome P450 and reductase genes into *C. tropicalis* in which the β-oxidation pathway is blocked, the *C. tropicalis* strain AR40 was generated with increased ω-hydroxylase activity and higher specific productivity of diacids from long-chain fatty acids. See, Picataggio et al., 1992, Bio/Technology 10: 894-898 (1992); and U.S. Pat. No. 5,620,878, each of which is hereby incorporated by reference herein. Although the mutants or genetically modified *C. tropicalis* strains have been used for the biotransformation of saturated fatty acids (C12-C18) and unsaturated fatty acids with one or two double bonds to their corresponding diacids, the range of substrates needs to be expanded to produce more valuable diacids that are currently unavailable commercially, especially for those with internal functional groups that can be used for the potential application in biomaterials. The production of dicarboxylic acids by fermentation of saturated or unsaturated n-alkanes, n-alkenes, fatty acids or their esters with carbon number of 12 to 18 using a strain of the species *C. tropicalis* or other special microorganisms has been disclosed in U.S. Pat. Nos. 3,975,234; 4,339,536; 4,474,882; 5,254,466; and 5,620,878. However, all of the known processes for the preparation of dicarboxylic acids by means of yeast only give straight-chain saturated or unsaturated (containing one double bond) dicarboxylic acids with carbon number of 12 to 18. Furthermore, the resulting dicarboxylic acids are not readily purified and used for polymer synthesis. Thus, no process is known for the preparation of ricinoleic acid analogs containing internal functionality that may consist of double bonds, triple bonds, epoxide, secondary hydroxyl, Si—O—Si and other moieties, in which the functional groups are transferred into the resulting dicarboxylic acids without change, especially in large scale, and also no processes are known for the preparation of an ω-hydroxy fatty acids with double bond and secondary hydroxyl group.

In some instances it may be advantageous to polymerize long-chain ω-hydroxy fatty acids. These cannot be prepared using any described strain of *Candida* because the ω-hydroxy fatty acid is oxidized to form an α,ω-dicarboxylic acid. Furthermore, neither the general classes nor the specific sequences of the *Candida* enzymes responsible for the oxidation from ω-hydroxy fatty acids to α,ω-dicarboxylic acids have been identified. There is therefore a need in the art for methods to produce ω-hydroxy fatty acids from fatty acids by fermentation.

3. SUMMARY

Biological methods for the production of aliphatic polyesters are disclosed.

One aspect of the disclosed subject matter are methods for the preparation of a new family of ricinoleic acid analogs (e.g., functional long-chain ω-hydroxy fatty acids, α,ω-dicarboxylic acids or mixtures of these two products) in high yield. The methods involve a biocatalytic step in which fatty acids are transformed to their ω-hydroxy, ω-carboxy, or a mixture of both ω-hydroxy and ω-carboxy ricinoleic analogs. Similar to ricinoleic acid, the analogs prepared herein have two functionalities that can be converted via reactions with carboxylic acids or hydroxyl bearing molecules to ester moieties. Furthermore, the ricinoleic analogs prepared herein have an internal functionality that may consist of a double bond, triple bond, epoxide, Si—O—Si and other moieties. In other words, the preparation of a family of ricinoleic analogs that are defined as having one or more internal functional groups (double bond, triple bond, epoxide, Si—O—Si, conjugated diene, conjugated triene) and two other functionalities that can be used to synthesize oligoesters, polyol-polyesters, surfactants or polyesters are provided. Whereas ricinoleic acid has 12-hydroxyl and α-carboxyl groups, ricinoleic analogs described herein have either α-/ω-carboxyl groups, α-carboxyl/ω-hydroxyl groups, or consist of a mixture of these products.

Synthesis of the ricinoleic acid analogs is accomplished using a whole-cell biocatalyst (e.g., *Candida* species including *Candida tropicalis*) for conversions of readily renewable fatty acid substrates. These functional building blocks comprise ω-hydroxy fatty acids and α,ω-dicarboxylic acids with carbon chain lengths from C14 to C22 that contain one or more additional functional groups along fatty acid chains that can be selected from the following: alkenes, alkynes, conjugated alkenes, conjugated alkynes, ether, silicone, epoxy, quaternary ammonium salt, secondary amine, imine, and other moieties including —S— and —P(X)—. These products may be used without further processing, as monomers for oligomer, prepolymer and polymer synthesis, and building blocks for surfactants and emulsifiers. Polymerizations of these monomers may be carried out by chemical or enzymatic methods. Preferably ricinoleic acid building blocks are further modified or converted to oligomers or polymers via enzymatic polymerizations using a lipase catalyst. The lipase catalyst catalyzes ester bond hydrolysis thereby catalyzing homo- and copolymerizations of these monomers under reverse equilibrium conditions. This results in a new family of oligomers and polymers with functional groups for post-modification. Furthermore, high molecular weight polymers can be formed that are biodegradable in the environment or used as bioresorbable materials for medical applications. Also disclosed are methods for polymerizing these monomers.

One embodiment provides a substantially pure *Candida* host cell for the production of a α-carboxyl-ω-hydroxy fatty acid having a carbon chain length in the range from C6 to C22, an α,ω-dicarboxylic fatty acid having a carbon chain length in the range from C6 to C22, or mixtures thereof. The *Candida* host cell is characterized by a first genetic modification class and a second genetic modification class. The first genetic modification class comprises one or more genetic modifications that disrupt the β-oxidation pathway in the substantially pure *Candida* host cell. The second genetic modification class comprises one or more genetic modifications that collectively or individually disrupt at least one gene in the substantially pure *Candida* host cell selected from the group consisting of a CYP52A type cytochrome P450, a fatty alcohol oxidase, and an alcohol dehydrogenase.

Another embodiment provides a method for producing an α-carboxyl-ω-hydroxy fatty acid having a carbon chain length in the range from C6 to C22, a α,ω-dicarboxylic fatty acid having a carbon chain length in the range from C6 to C22, or mixtures thereof in a *Candida* host cell. The method comprises (A) making one or more first genetic modifications in a first genetic modification class to the *Candida* host cell. The method further comprises (B) making one or more second genetic modifications in a second genetic modification class to the *Candida* host cell, where steps (A) and (B) collectively form a genetically modified *Candida* host cell. The method further comprises (C) producing a α-carboxyl-ω-hydroxy fatty acid having a carbon chain length in the range from C6 to C22, a α,ω-dicarboxylic fatty acid having a carbon chain length in the range from C6 to C22, or mixtures thereof, by fermenting the genetically modified *Candida* host cell in a culture medium comprising a nitrogen source, an organic substrate having a carbon chain length in the range from C6 to C22, and a cosubstrate. Here, the first genetic modification class comprises one or more genetic modifications that disrupt the β-oxidation pathway of the *Candida* host cell. Also, the second genetic modification class comprises one or more genetic modifications that collectively or individually disrupt at least one gene selected from the group consisting of a CYP52A type cytochrome P450, a fatty alcohol oxidase, and an alcohol dehydrogenase in the *Candida* host cell.

Another embodiment provides a substantially pure *Candida* host cell for the production of a α-carboxyl-ω-hydroxy fatty acid having a carbon chain length in the range from C6 to C22, an α,ω-dicarboxylic fatty acid having a carbon chain length in the range from C6 to C22, or mixtures thereof, where the *Candida* host cell is characterized by a first genetic modification class and a second genetic modification class. The first genetic modification class comprises one or more genetic modifications that disrupt the β-oxidation pathway. The second genetic modification class comprises one or more genetic modifications that collectively or individually add to the host cell genome at least one gene selected from the group consisting of a desaturase, a lipase, a fatty alcohol oxidase, an alcohol dehydrogenase, a glycosyl transferase or a cytochrome P450 that is not identical to a naturally occurring counterpart gene in the *Candida* host cell; or a desaturase, a lipase, a fatty alcohol oxidase, an alcohol dehydrogenase, a glycosyl transferase or a cytochrome P450 that is expressed under control of a promoter other than the promoter that controls expression of the naturally occurring counterpart gene in the *Candida* host cell.

In some embodiments, first genetic modification class comprises disruption of a gene that has at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to *Candida tropicalis* PXP-4 (SEQ ID NO: 134) or at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity *Candida tropicalis* PXP-5 (SEQ ID NO: 135) in the *Candida* host cell.

In some embodiments the second genetic modification class comprises disruption of at least one CYP52A type cytochrome P450 selected from the group consisting of CYP52A13, CYP52A14, CYP52A17, CYP52A18, CYP52A12, and CYP52A12B.

In some embodiments the second genetic modification class comprises disruption of CYP52A13, CYP52A14, CYP52A17, CYP52A18, CYP52A12, and CYP52A12B.

In one embodiment, processes are disclosed for the preparation of ricinoleic acid analogs with high productivity by fermentation utilizing a strain of *Candida*, subsequent purification of ricinoleic acid analogs, and conversion to oligomers and polymers for a variety of applications.

3.1 Production of Monomers

Disclosed are biosynthetic routes that convert (oxidize) fatty acids to their corresponding α,ω-dicarboxylic acids, α-carboxyl-ω-hydroxyl fatty acids, or a mixture of these products. This is accomplished by culturing fatty acid substrates with a yeast, preferably a strain of *Candida* and more preferably a strain of *Candida tropicalis*. The yeast converts fatty acids to long-chain ω-hydroxy fatty acids and α,ω-dicarboxylic acids, and mixtures thereof. Methods by which yeast strains may be engineered by the addition or removal of genes to modify the oxidation products formed are disclosed. Fermentations are conducted in liquid media containing fatty acids as substrates. Biological conversion methods for these compounds use readily renewable resources such as fatty acids as starting materials rather than non-renewable petrochemicals, and give the target ricinoleic acid analogs with relatively higher selectivity and fewer by-products. For example, ω-hydroxy fatty acids and α,ω-dicarboxylic acids can be produced from inexpensive long-chain fatty acids, which are readily available from renewable agricultural and forest products such as soybean oil, corn oil and tallow. Moreover, a wide range of α,ω-dicarboxylic acids and α-carboxyl-ω-hydroxyl fatty acids with different carbon length can be prepared because the biocatalyst accepts a wide range of fatty acid substrates. Products described herein produced by the biocatalytic methods described herein are new and not commercially available since chemical methods are impractical to prepare the compounds and biocatalytic methods to these products were previously unknown. Furthermore, biosynthesis to new ricinoleic acid analogs is conducted under mild reaction conditions and functional groups presented by fatty acid substrates remain intact during the biotransformation.

3.2 Polymerization of Monomers

One aspect describes the conversion of α,ω-dicarboxylic acids and α-carboxyl-ω-hydroxyl fatty acids into a new family of aliphatic functional polyesters. These polyesters are biodegradable, which means they can be converted through biological processes into carbon dioxide, methane, water, lignocellulosic substances and other natural products. They also can function as bioresorbable materials for medical applications. Polymerizations of these monomers is performed by lipase-catalysis. The resulting copolyesters can have variable contents of alkyne, alkene, epoxides and hydroxyl functionalities. The new ricinoleic acid analogs may be copolymerized with a wide array of other monomers such as lactones such as dioxanone and ε-caprolactone, those with silicone segments, polyols such as glycerol and sorbitol, polyethylene glycol, cyclic monomers or linear segments bearing anhydride or carbonate linkages and much more.

One aspect disclosed herein provides the combination of a method in which (i) ricinoleic analogs are synthesized by an oxidative biotransformation catalyzed by a yeast belonging to the genus *Candida* followed by (ii) enzyme-catalyzed homo- or copolymerization of ricinoleic acids using an enzyme that in nature functions for ester hydrolysis but is used under reverse equilibrium conditions to prepare polyesters. Enzyme-catalyzed homo- and copolymerizations allow control of branching when using monomers with 3 or more reactive groups. Furthermore, enzyme-catalysis allows the synthesis of carbonate, ester, amide and anhydride linkages between monomers. Moreover, mild conditions during enzyme-catalysis allows functional groups along monomers such as alkynes, alkenes, conjugated alkynes, conjugated alkenes, epoxides, hydroxyl, silicone and more to remain intact during polymer synthesis.

A schematic representation showing the production of hydroxy fatty acid monomers and dicarboxylic acid monomers using whole cell biotransformation by *Candida*, followed by polymerization catalyzed by lipase is shown in FIG. 1.

4. BRIEF DESCRIPTION OF THE FIGURES

Figure 3:
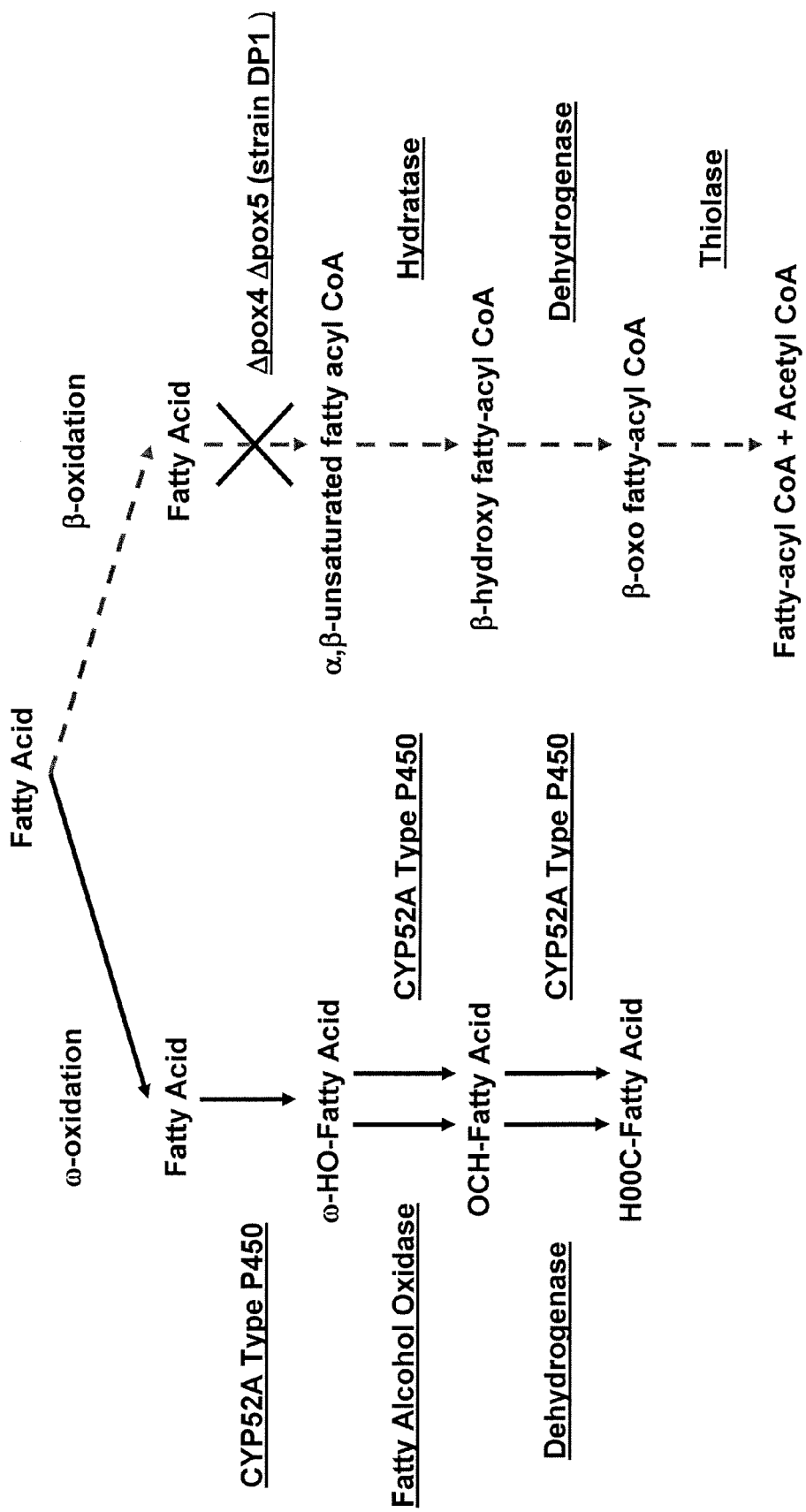

FIG. 3 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows. By inactivating the genes encoding acyl coA oxidase (pox4 and pox5), the β-oxidation pathway is blocked (indicated by broken arrows), so that fatty acids are not used as substrates for growth. This genetic modification allows *Candida* species of yeast including *Candida tropicalis* to be used as a biocatalyst for the production of α,ω-diacids. See, for example, Picataggio et al., 1991, Mol Cell Biol 11, 4333-4339; and Picataggio et al., 1992, Biotechnology 10, 894-898. The β-oxidation pathway may be disrupted by any genetic modification or treatment of the host cells with a chemical for example an inhibitor that substantially reduces or eliminates the activity of one or more enzymes in the β-oxidation pathway, including the hydratase, dehydrogenase or thiolase enzymes, and thereby reduces the flux through that pathway and thus the utilization of fatty acids as growth substrates.

Figure 4:
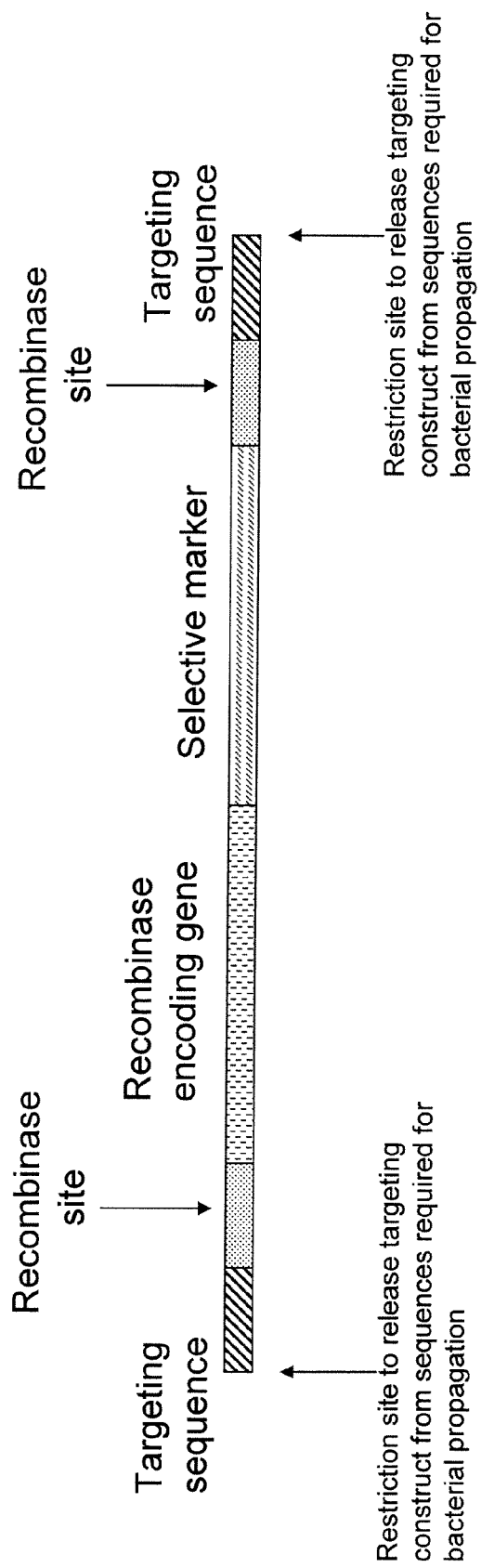

FIG. 4 shows a schematic representation of a DNA "genomic targeting" construct for deleting sequences from the genome of yeasts. The general structure is that the construct has two targeting sequences that are homologous to the sequences of two regions of the target yeast chromosome. Between these targeting sequences are two sites recognized by a site-specific recombinase (indicated as "recombinase site"). Between the two site specific recombinase sites are sequence elements, one of which encodes a selective marker and the other of which (optionally) encodes the site-specific recombinase that recognizes the recombinase sites. In one embodiment the sequences of the DNA construct between the targeting sequences is the "SAT1 flipper", a DNA construct for inserting and deleting sequences into the chromosome of *Candida*. See, for example, Reuss et al., 2004, Gene 341, 119-127. In the "SAT1 flipper", the recombinase is the flp recombinase from *Saccharomyces cerevisiae* (Vetter et al., 1983, Proc Natl Acad Sci USA 80, 7284-7288.) (FLP) and the flanking sequences recognized by the recombinase are recognition sites for the flp recombinase (FRT). The selective marker is the gene encoding resistance to the Nourseothricin resistance marker from transposon Tn1825 (Tietze et al., 1988, J. Basic Microbiol 28, 129-136). The DNA sequence of the SAT1-flipper is given as SEQ ID NO: 1. The genomic targeting sequence can be propagated in bacteria, for example *E coli*, in which case the complete plasmid will also contain sequences required for propagation in bacteria, comprising a bacterial origin of replication and a bacterial selective marker such as a gene conferring antibiotic resistance. The targeting construct can be released from this plasmid in a linear form by digestion with one or more restriction enzymes with recognition sites that flank the targeting sequences.

Figure 5:
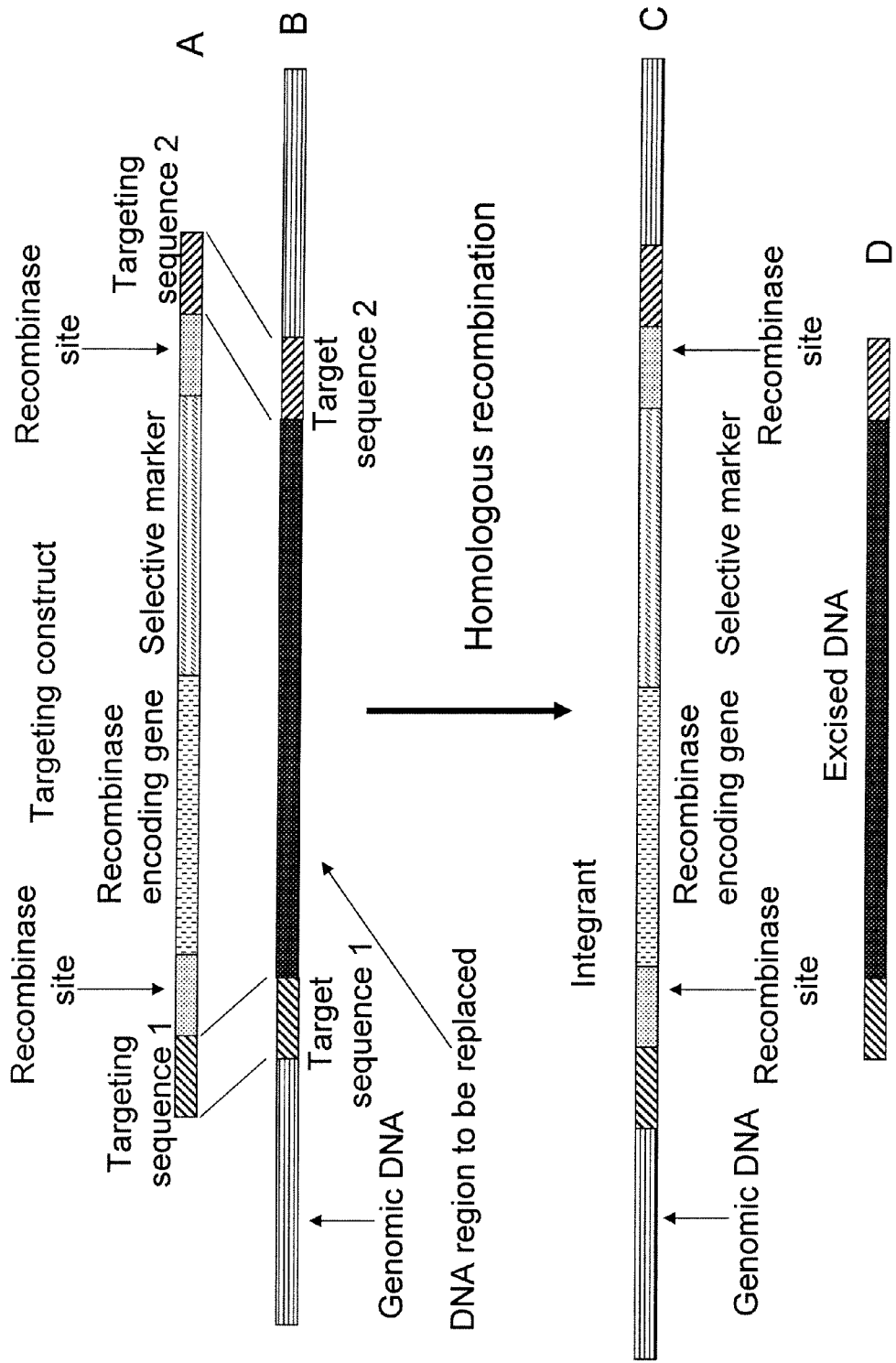

FIG. 5 shows a schematic representation of the homologous recombination between a "genomic targeting" construct of the form shown in FIG. 4, with the DNA contained in a yeast genome (either in the chromosome or in the mitochondrial DNA). The targeting construct (A) contains two regions of sequence homology to the genomic sequence (B); the corresponding sequences in the genomic sequence flank the DNA region to be replaced. Introduction of the targeting construct into the host cell is followed by homologous recombination catalyzed by host cell enzymes. The result is an integrant of the targeting construct into the genomic DNA (C) and the excised DNA (D) which will generally be lost from the cell.

Figure 6:
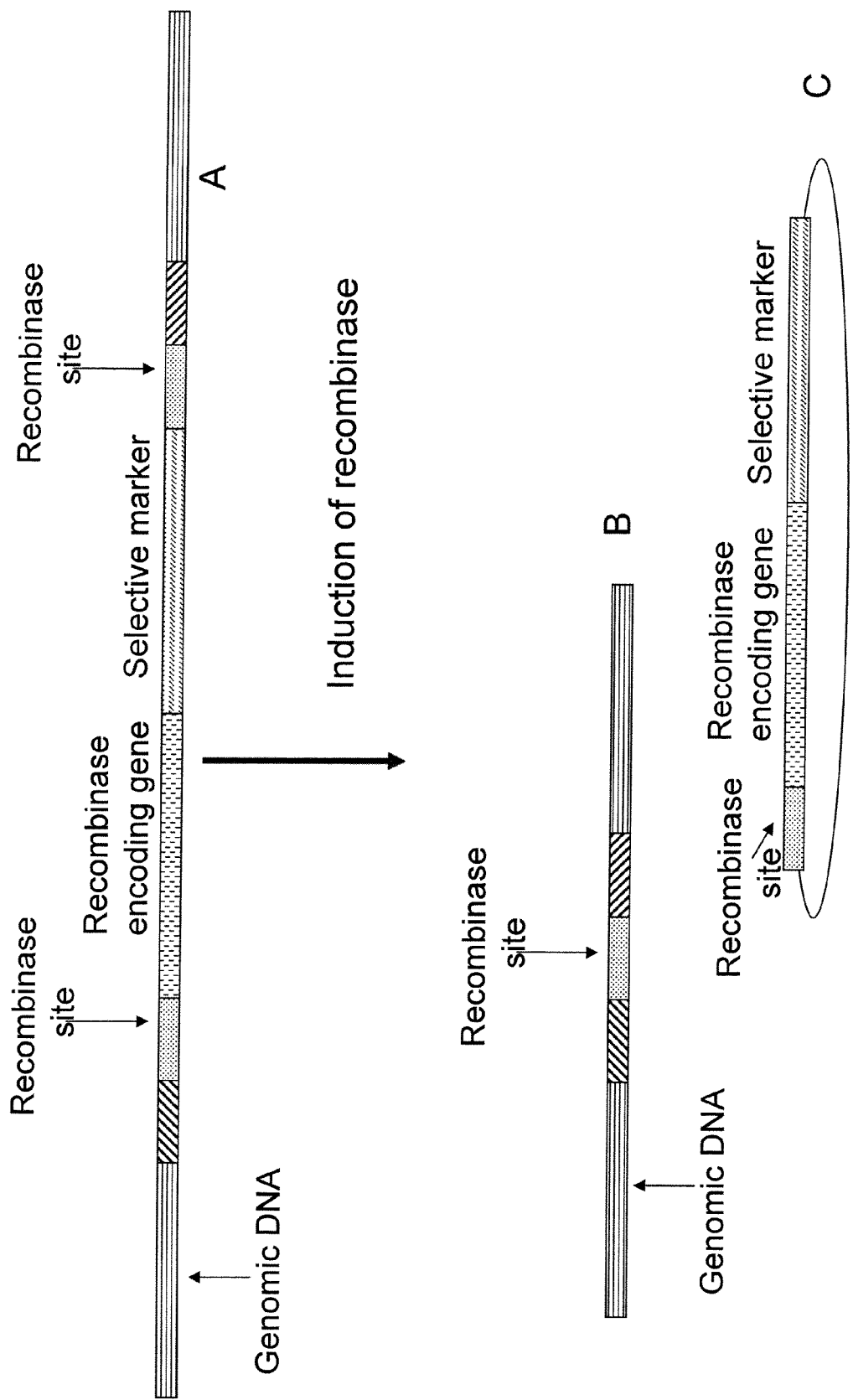

FIG. 6 shows a schematic representation of excision of the targeting construct from the yeast genome that occurs when expression of the recombinase in the targeting construct is induced in the integrant (A) shown in FIG. 5. Induction of the site-specific recombinase causes recombination between the two recombinase recognition sites. The result is the excision of the sequences between the two recombinase sites (C) leaving a single recombinase site in the genomic DNA (B).

Figure 7:
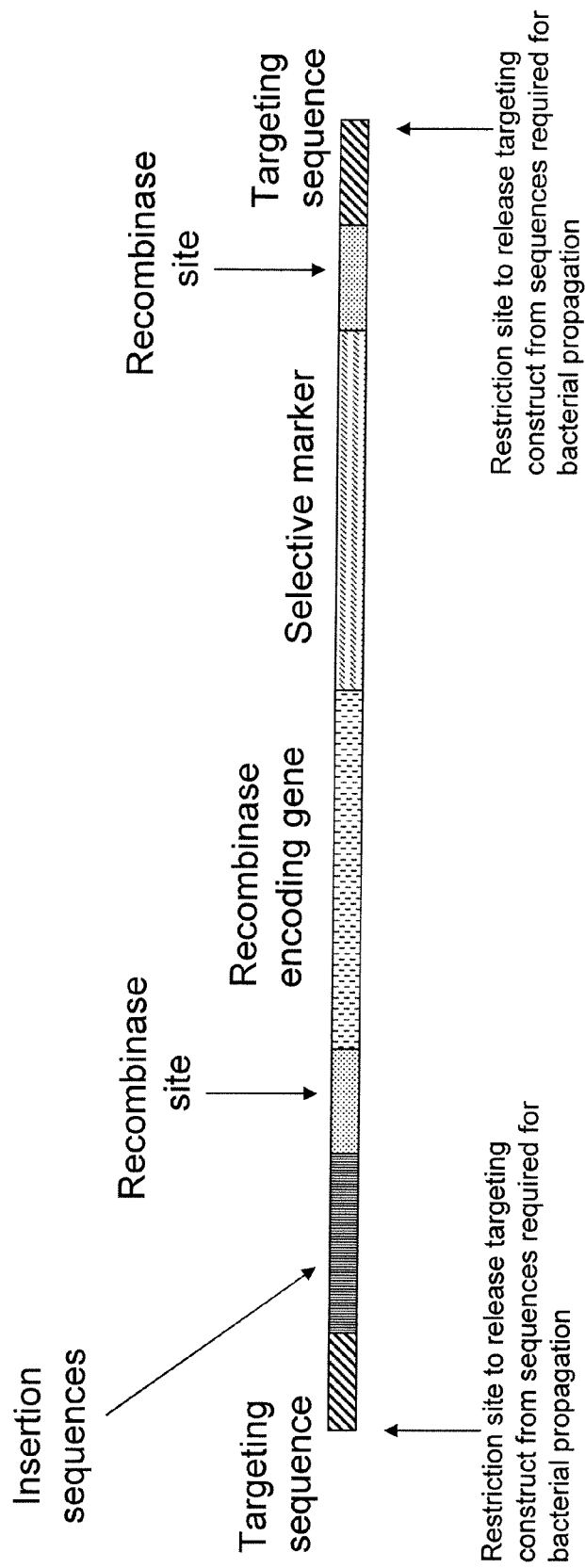

FIG. 7 shows a schematic representation of a DNA "genomic targeting" construct for inserting sequences into the genome of yeasts. The general structure is that the construct has two targeting sequences that are homologous to the sequences of two regions of the target yeast chromosome. Between these targeting sequences are two sites recognized by a site-specific recombinase (indicated as "recombinase site"). Between the two site specific recombinase sites are sequence elements, one of which encodes a selective marker and the other of which (optionally) encodes the site-specific recombinase that recognizes the recombinase sites. Insertion of additional sequences between one of the targeting sequences and its closest recombinase recognition site will result in those sequences being inserted into the chromosome after excision of the targeting construct ("Insertion sequences"). The genomic targeting sequence can be propagated in bacteria, for example *E coli*, in which case the complete plasmid will also contain sequences required for propagation in bacteria, comprising a bacterial origin of replication and a bacterial selective marker such as a gene conferring antibiotic resistance. The targeting construct can be released from this plasmid in a linear form by digestion with one or more restriction enzymes with recognition sites that flank the targeting sequences.

Figure 8:
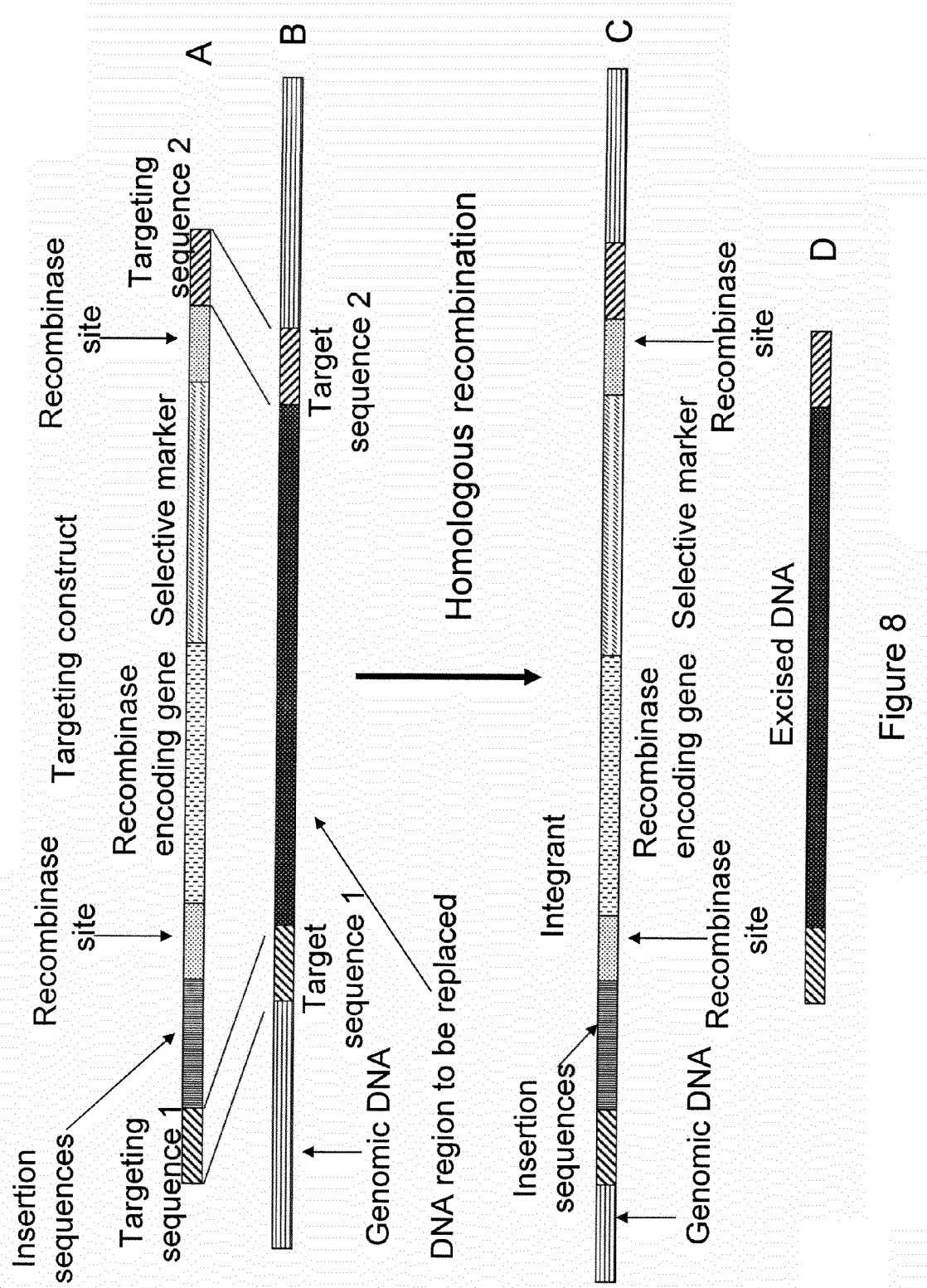

FIG. 8 shows a schematic representation of the homologous recombination between a "genomic targeting" construct of the form shown in FIG. 7, with the DNA contained in a yeast genome (either in the chromosome or in the mitochondrial DNA). The targeting construct (A) contains two regions of sequence homology to the genomic sequence (B); the corresponding sequences in the genomic sequence flank the DNA region to be replaced. Introduction of the targeting construct into the host cell is followed by homologous recombination catalyzed by host cell enzymes. The result is an integrant of the targeting construct into the genomic DNA (C) and the excised DNA (D) which will generally be lost from the cell.

Figure 9:
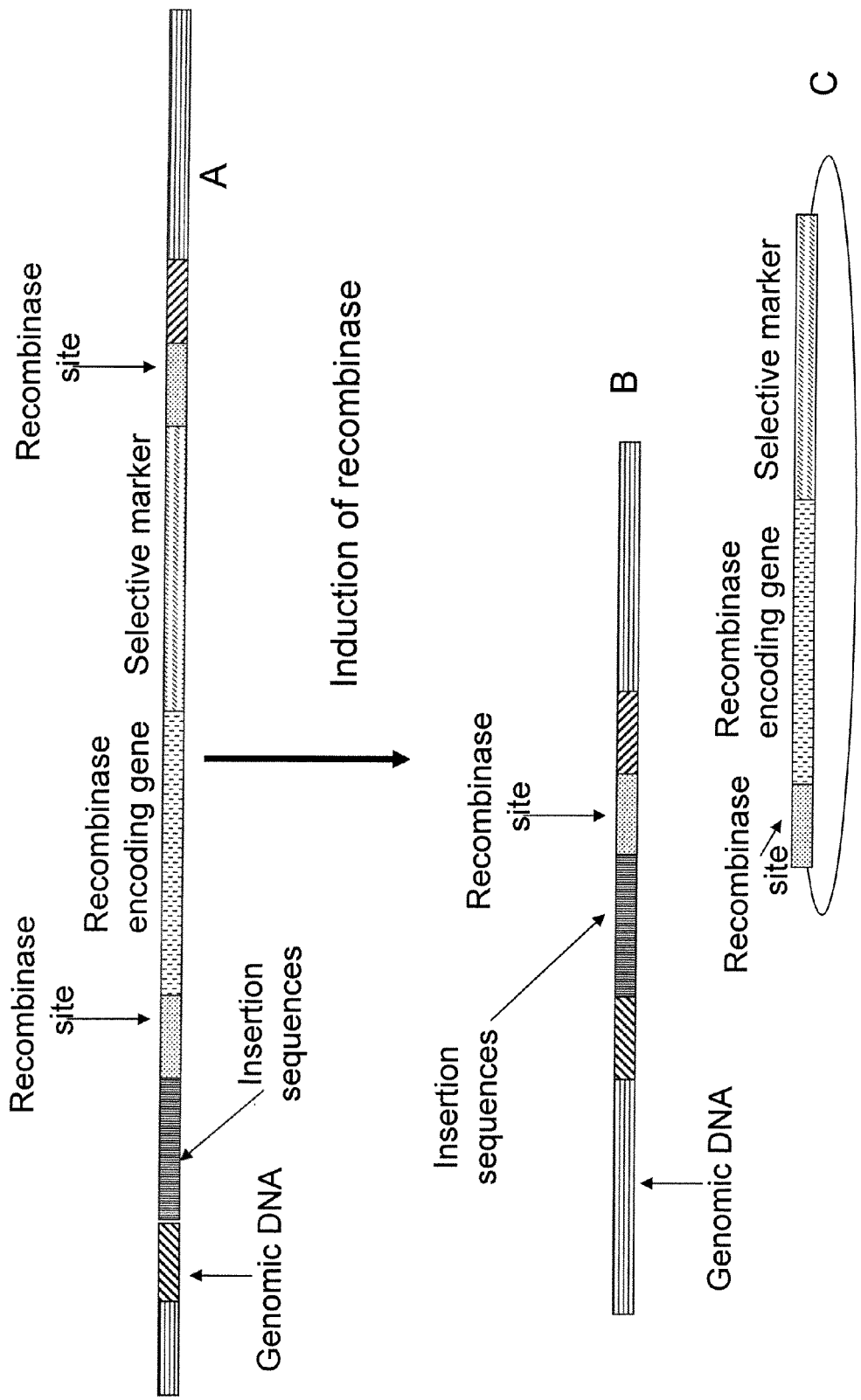

FIG. 9 shows a schematic representation of excision of the targeting construct from the yeast genome that occurs when expression of the recombinase in the targeting construct is induced in the integrant (A) shown in FIG. 8. Induction of the site-specific recombinase causes recombination between the two recombinase recognition sites. The result is the excision of the sequences between the two recombinase sites (C) leaving a single recombinase site together with the additional sequences that were included between the targeting sequences and the recombinase site (see FIG. 7) in the genomic DNA (B).

Figure 10:
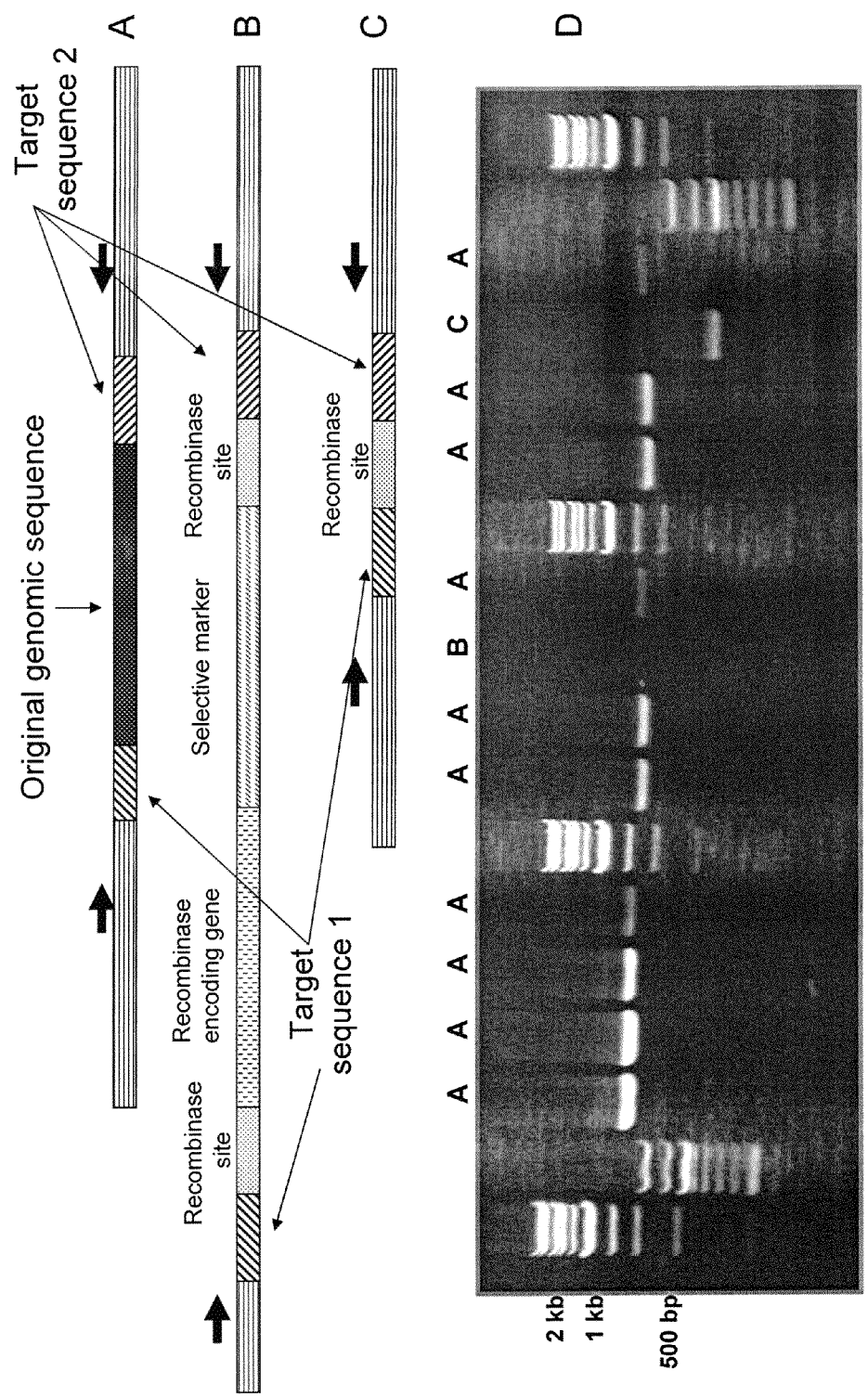

FIG. 10 shows a schematic representation of three stages in generation of a targeted deletion in a yeast genome (either in the chromosome or in the mitochondrial DNA), and the results of a PCR test to distinguish between the three stages. (A) PCR primers (thick arrows) are designed to flank the targeted region. (B) Insertion of a genomic targeting construct into the genome inserts two recombinase sites, a recombinase gene and a selection marker between the two target sequences. This changes the size of the DNA segment between the two PCR primers; in the case shown the size is increased. (C) Induction of the recombinase results in excision of the recombinase encoding gene, the selective marker and one of the recombinase sites. This again changes the size of the DNA segment between the two PCR primers. (D) PCR amplification from yeast genomic DNA unmodified (gel lanes marked A), with integrated genomic targeting vector (gel lanes marked B) or after excision of the genomic targeting vector (gel lanes marked C).

Figure 11:
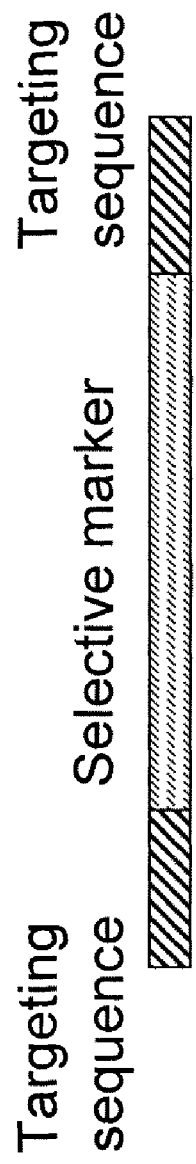

FIG. 11 shows a schematic representation of a DNA "genomic targeting" construct for inserting or deleting sequences in the genome of yeasts. The general structure is that the construct has two targeting sequences that are homologous to the sequences of two regions of the target yeast chromosome. Between these targeting sequences is a sequence that encodes a selective marker.

Figure 12:
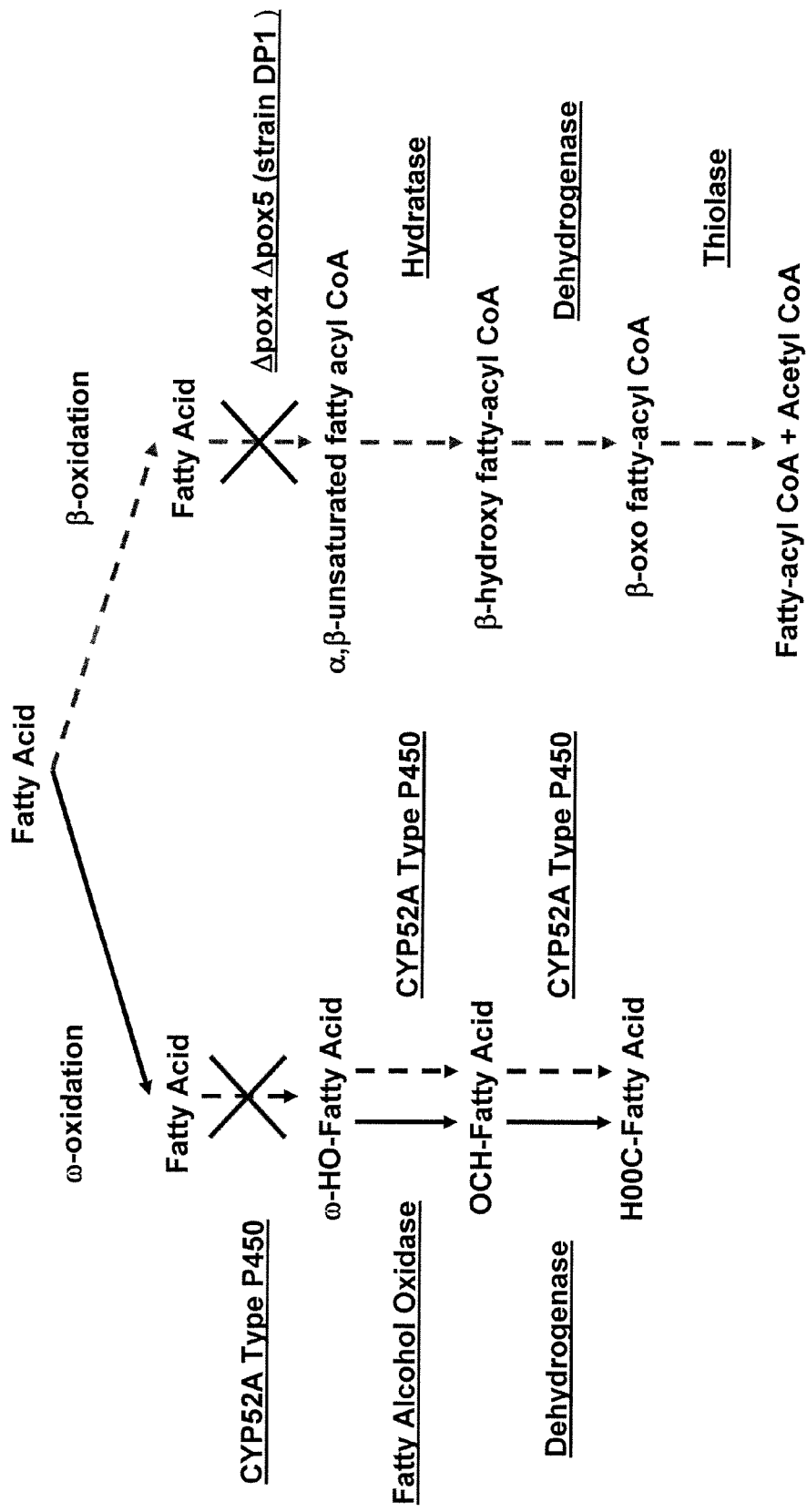

FIG. 12 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows. By inactivating the *Candida tropicalis* genes pox4 and pox5 (or their functional homologs in other *Candida* species), the β-oxidation pathway is blocked (indicated by broken arrows), so that fatty acids are not used as substrates for growth. Furthermore, inactivation of CYP52A type cytochrome P450 enzymes, as illustrated in the Figure, prevents the ω-oxidation of these fatty acids. These enzymes may also be responsible for some or all of the transformations involved in oxidizing ω-hydroxy fatty acids to α,ω-dicarboxylic acids. See Eschenfeldt, et al., 2003, Appli. Environ. Microbiol. 69, 5992-5999, which is hereby incorporated by reference herein.

Figure 13:
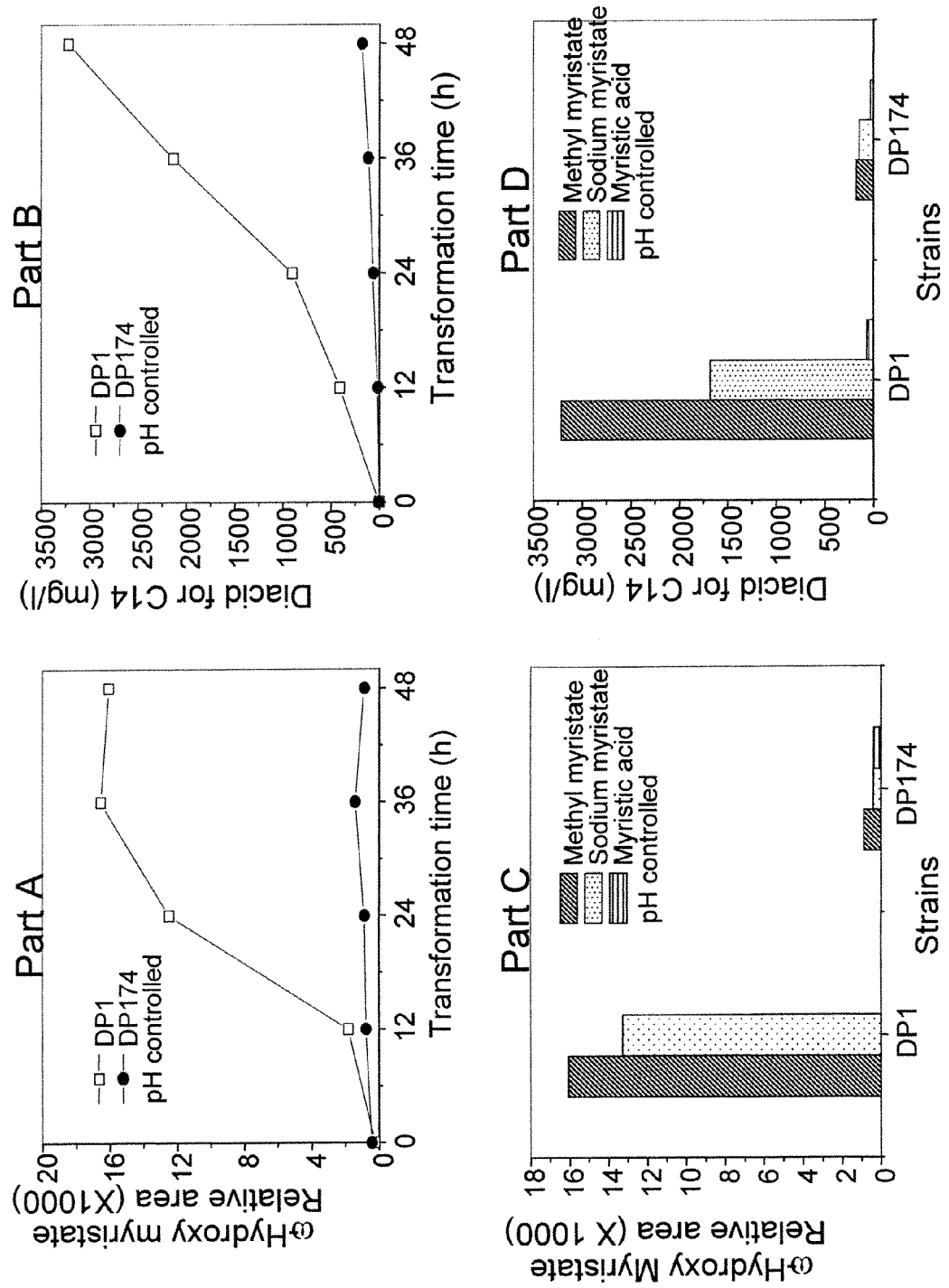

FIG. 13 shows the levels of ω-hydroxy myristate and the over-oxidized C14 diacid produced by *Candida tropicalis* strains DP1 (ura3A/ura3B pox5A::ura3A/pox5B::ura3A pox4A::ura3A/pox4B::URA3A) and DP174 (ura3A/ura3B pox5A::ura3A/pox5B::ura3A pox4A::ura3A/pox4B:: URA3A ΔCYP52A17/ΔCYP52A18 ΔCYP52A13/ ΔCYP52A14). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, K₂HPO₄ 7.2 g/l, KH₂PO₄ 9.3 g/l) plus 30 g/l glucose. After 16 hours 0.5 ml of culture was added to 4.5 ml fresh media F plus 60 g/l glucose in a 125 ml flask, and grown at 30° C. and 250 rpm for 12 hours before addition of substrate. After addition of substrates growth was continued at 30° C. and 250 rpm. Parts A and B: the substrate methyl myristate was then added to a final concentration of 10 g/l and the pH was adjusted to between 7.5 and 8. The culture was pH controlled by adding 2 mol/l NaOH every 12 hours and glucose was fed as a cosubstrate by adding 400 g/l glucose every 8 hours. Samples were taken at the times indicated, cell culture was acidified to pH~1.0 by addition of 6 N HCl, products were extracted from the cell culture by diethyl ether and the concentrations of ω-hydroxy myristate and of the C14 diacid produced by oxidation of the ω-hydroxy myristate were measured by LC-MS (liquid chromatography mass spectroscopy). The diacid was quantified relative to a known standard. No such standard was available for the ω-hydroxy myristate, so it was quantified by measuring the area under the peak in the MS chromatogram. Parts C and D: the substrates methyl myristate, sodium myristate or myristic acid were added to a final concentration of 10 g/l and the pH was adjusted to between 7.5 and 8. The culture was pH controlled by adding 2 mol/l NaOH every 12 hours and glucose was fed as a cosubstrate by adding 400 g/l glucose every 8 hours. Samples were taken after 48 hours, cell culture was acidified to pH~1.0 by addition of 6 N HCl, products were extracted from the cell culture by diethyl ether and the concentrations of ω-hydroxy myristate and of the C14 diacid produced by oxidation of the ω-hydroxy myristate were measured by LC-MS (liquid chromatography mass spectroscopy).

Figure 14:
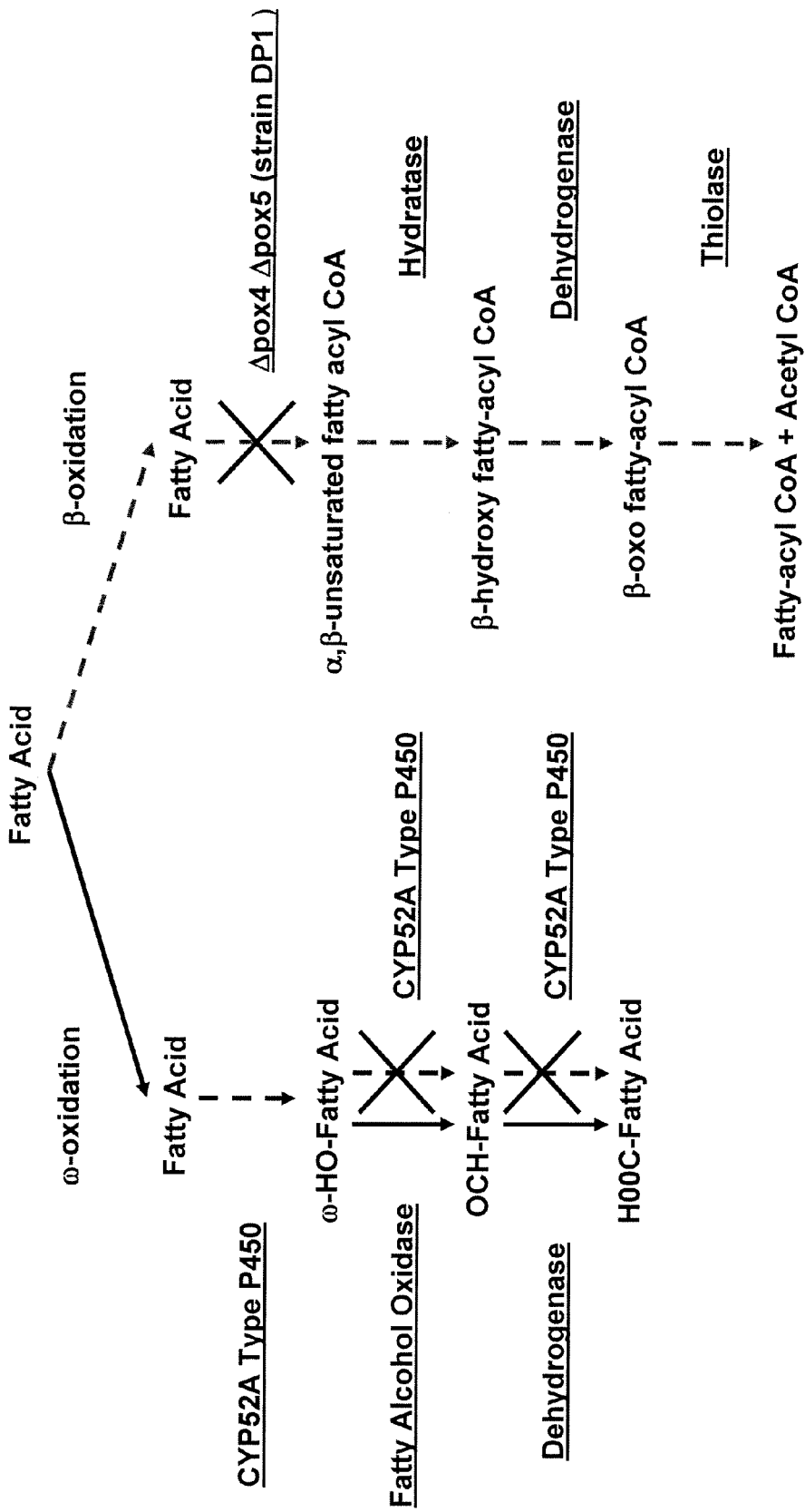

FIG. 14 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows. By inactivating the *Candida tropicalis* genes pox4 and pox5 (or their functional homologs in other *Candida* species), the β-oxidation pathway is blocked (indicated by broken arrows), so that fatty acids are not used as substrates for growth. Furthermore, inactivation of CYP52A type cytochrome P450 enzymes prevents the ω-oxidation of fatty acids. Several enzymes including, but not limited to CYP52A type P450s, are responsible for transformations involved in oxidizing ω-hydroxy fatty acids to α,ω-dicarboxylic acids. If other enzymes involved in oxidation of ω-hydroxy fatty acids are present in the strain, then the strain will convert ω-hydroxy fatty acids fed in the media to α,ω-dicarboxylic acids. If other enzymes involved in oxidation of ω-hydroxy fatty acids have been eliminated from the strain, then the strain will convert ω-hydroxy fatty acids fed in the media to α,ω-dicarboxylic acids.

Figure 15:
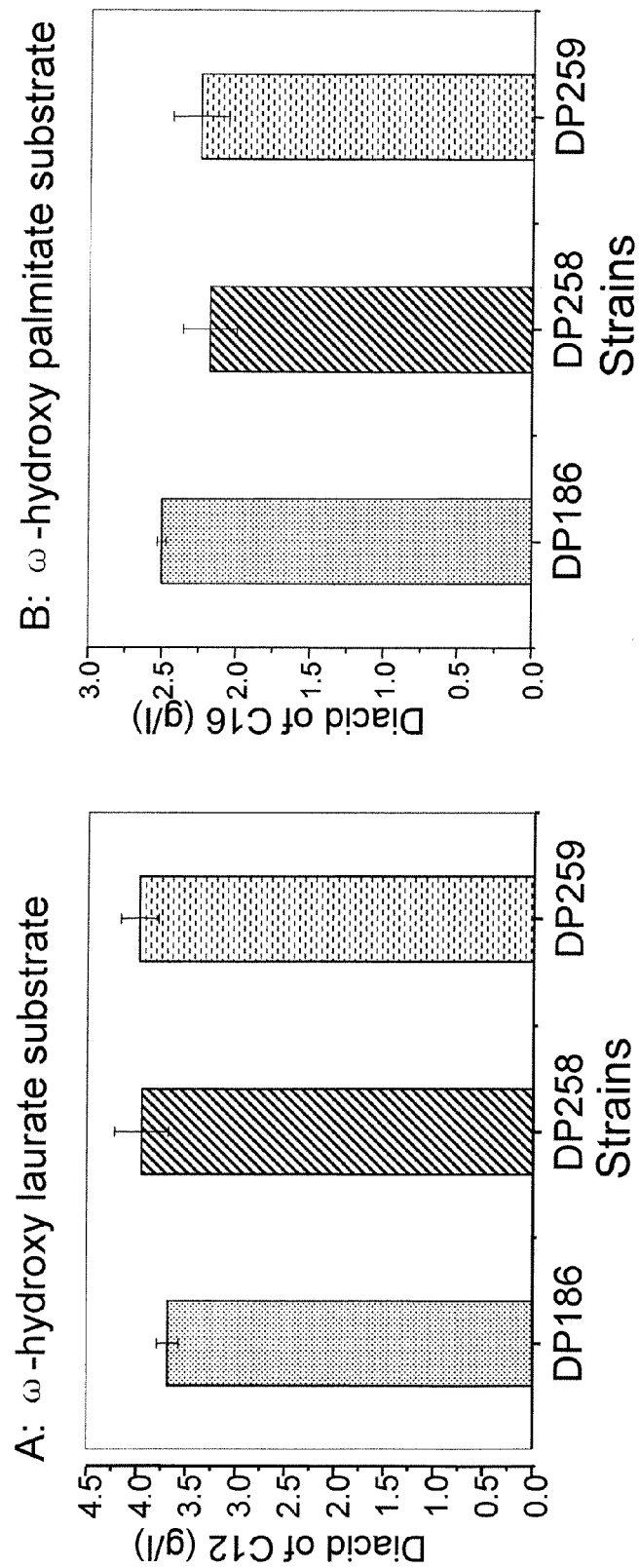

FIG. 15 shows the levels of α,ω-dicarboxylic acids produced by *Candida tropicalis* strains DP186, DP258 and DP259 (see Table 3 for genotypes). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, K₂HPO₄ 7.2 g/l, KH₂PO₄ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours before addition of substrate. After addition of substrates growth was continued at 30° C. and 250 rpm. Part A: the substrate ω-hydroxy laurate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy). Part B: the substrate ω-hydroxy palmitate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 16:
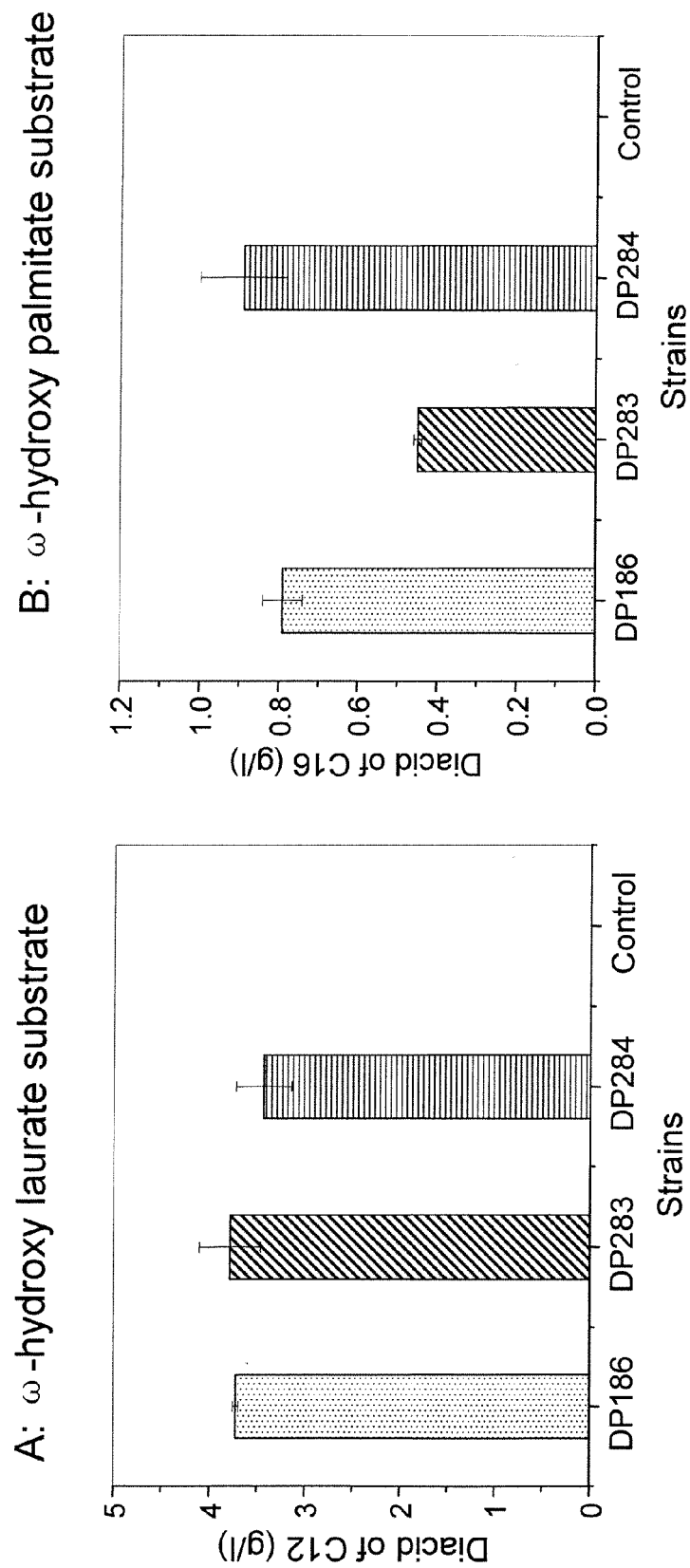

FIG. 16 shows the levels of α,ω-dicarboxylic acids produced by *Candida tropicalis* strains DP186, DP283 and DP284 (see Table 3 for genotypes). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, K₂HPO₄ 7.2 g/l, KH₂PO₄ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours before addition of substrate. After addition of substrates growth was continued at 30° C. and 250 rpm. Part A: the substrate ω-hydroxy laurate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy). Part B: the substrate ω-hydroxy palmitate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 17:
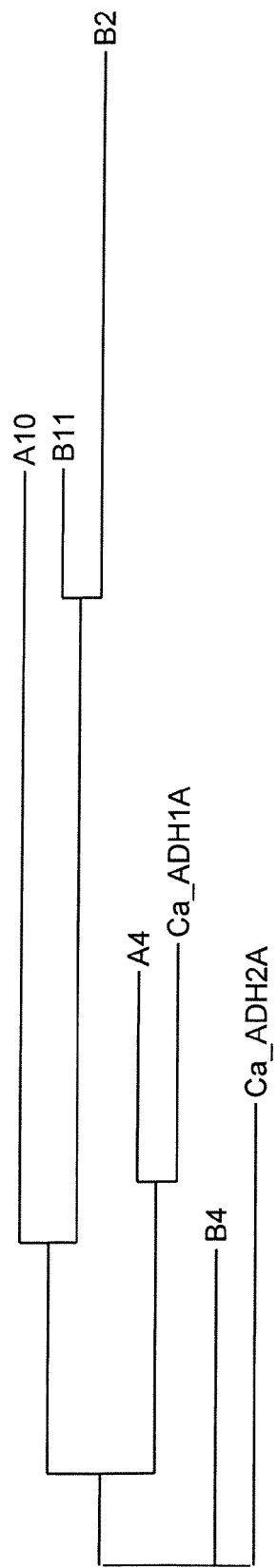

FIG. 17 shows a phylogenetic tree with five *Candida tropicalis* alcohol dehydrogenase sequences (A10, B11, B2, A4 and B4) and two alcohol dehydrogenases from *Candida albicans* (Ca_ADH1A and Ca_ADH2A).

Figure 18:
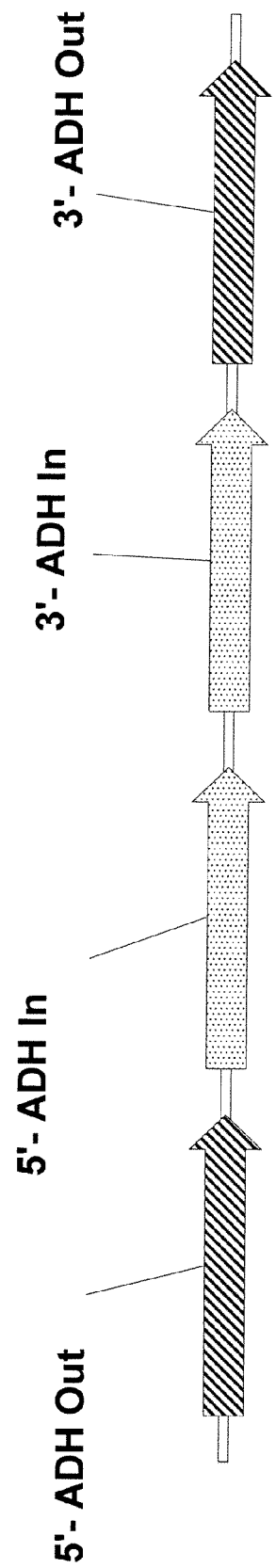

FIG. 18 shows a schematic design for selecting two sets of nested targeting sequences for the deletion of two alleles of a gene whose sequences are very similar, for example the alcohol dehydrogenase genes. The construct for the first allele uses ~200 base pair at the 5' end and ~200 base pair at the 3' end as targeting sequences (5'-ADH Out and 3'-ADH Out). The construct for the second allele uses two sections of ~200 base pair between the first two targeting sequences (5'-ADH In and 3'-ADH In). These sequences are eliminated by the first targeting construct from the first allele of the gene and will thus serve as a targeting sequence for the second allele of the gene.

Figure 19:
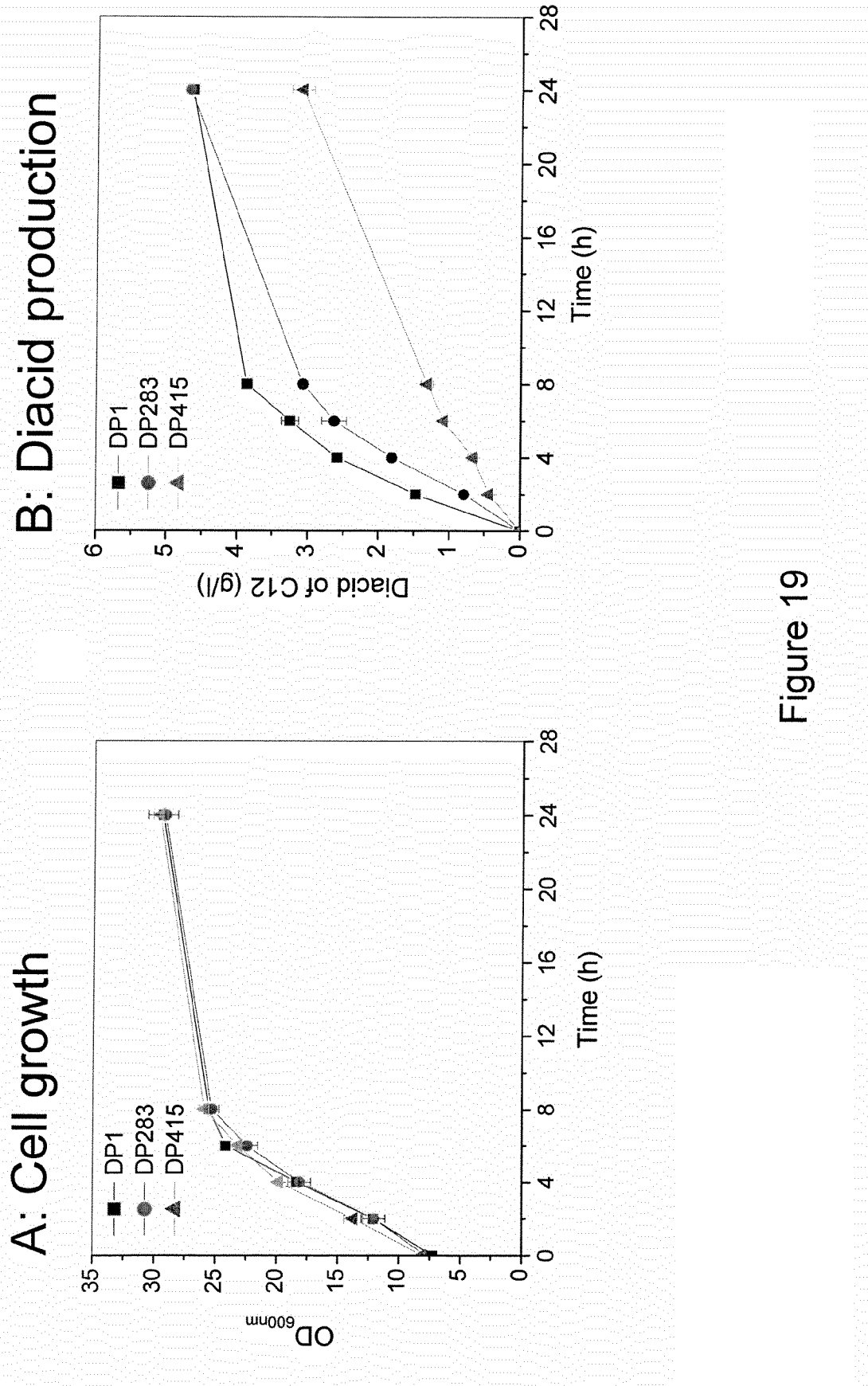

FIG. 19 shows the levels of α,ω-dicarboxylic acids produced by *Candida tropicalis* strains DP1, DP283 and DP415 (see Table 3 for genotypes). Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Part A: cell growth was followed by measuring the $A_{600}$ every 2 hours. Part B: formation of diacid; every 2 hours a sample of the cell culture was taken, acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 20:
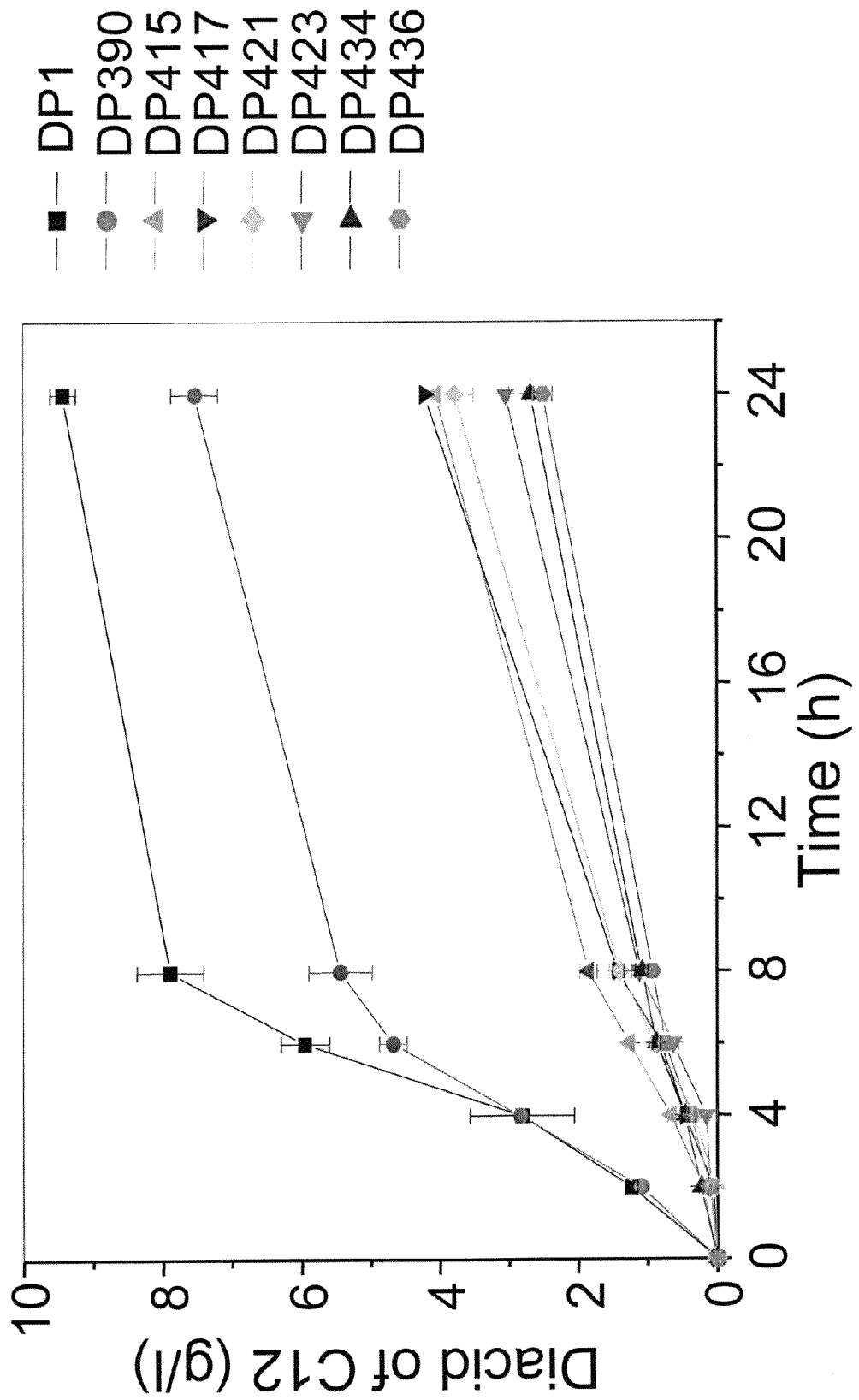

FIG. 20 shows the levels of α,ω-dicarboxylic acids produced by *Candida tropicalis* strains DP1, DP390, DP415, DP417, DP421, DP423, DP434 and DP436 (see Table 3 for genotypes). Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Formation of diacid was measured at the indicated intervals by taking a sample of the cell culture and acidifying to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 21:
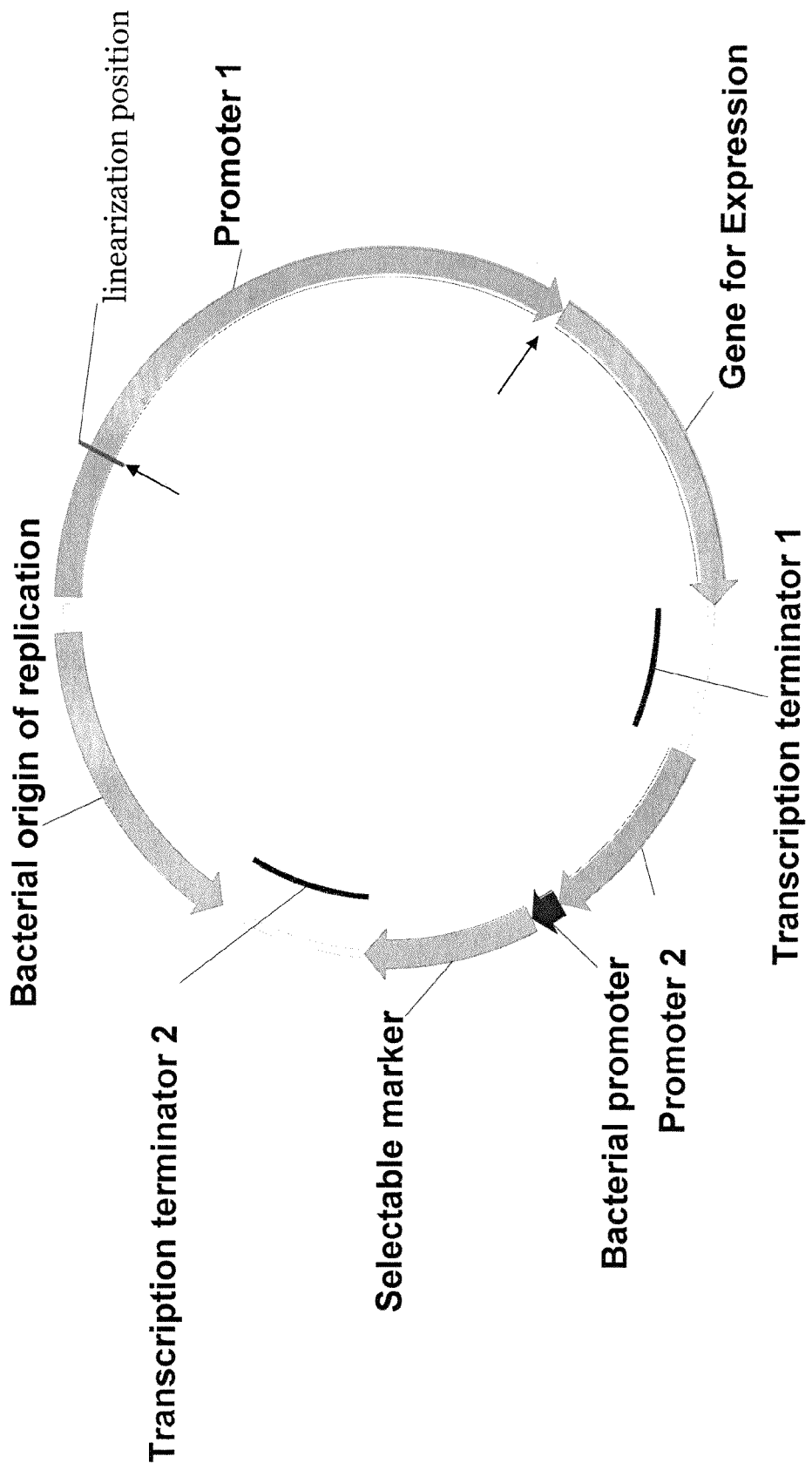

FIG. 21 shows a schematic representation of a DNA "genomic insertion" construct for inserting sequences to be expressed into the genome of yeasts. The general structure is that the construct has a gene for expression which is preceded by a promoter that is active in the yeast (Promoter 1). Promoter 1 comprises a linearization position which may be a site recognized by a restriction enzyme which cleaves the genomic insertion construct once to linearize it, or an annealing site for PCR primers to amplify a linear molecule from the construct. Three positions (A, B and C) are marked in Promoter 1 for reference in FIG. 22 when the construct is linearized. The gene for expression is optionally followed by a transcription terminator (Transcription terminator 1). The genomic insertion construct also comprises a selectable marker. The selectable marker is preferably one that is active in both bacterial and yeast hosts. To achieve this, the selectable marker may be preceded by a yeast promoter (promoter 2) and a bacterial promoter, and optionally it may be followed by a transcription terminator (transcription terminator 2). The genomic insertion construct also comprises a bacterial origin of replication.

Figure 22:
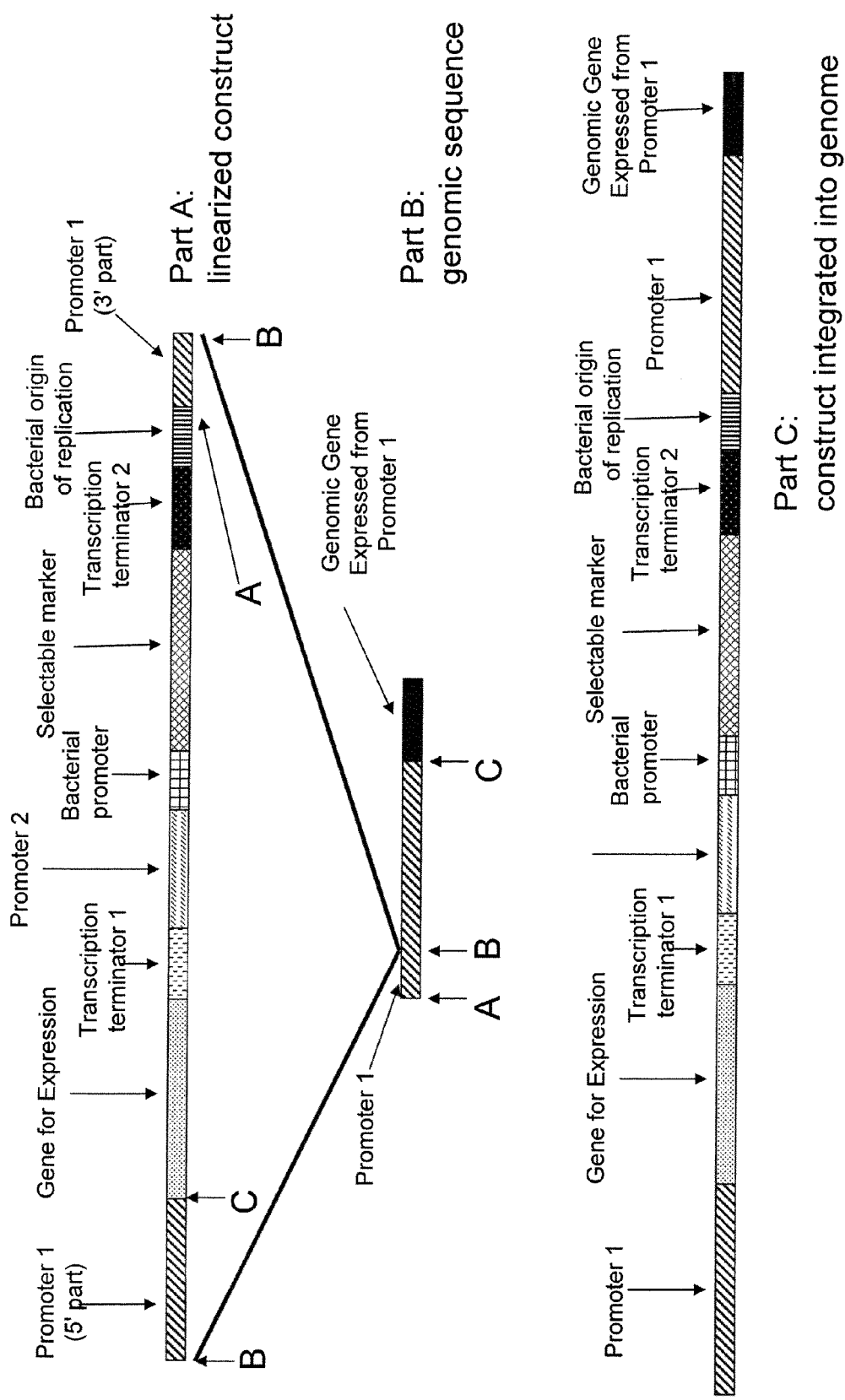

FIG. 22 shows a schematic representation of the integration of a DNA "genomic insertion" construct into the DNA of a yeast genome. Part A shows an integration construct of the structure shown in FIG. 22, with parts marked. The construct is linearized, for example by digesting with an enzyme that recognizes a unique restriction site within promoter 1, or by PCR amplification, or by any other method, so that a portion of promoter 1 is at one end of the linearized construct (5' part), and the remainder at the other end (3' end). Three positions (A, B and C) are marked in Promoter 1, these refer to the positions in FIG. 21. Part B shows the intact Promoter 1 in the yeast genome, followed by the gene that is normally transcribed from Promoter 1 (genomic gene expressed from promoter 1). Three positions (A, B and C) are also marked in the genomic copy of Promoter 1. Part C shows the genome after integration of the construct. The construct integrates at position B in Promoter 1, the site at which the construct was linearized. This results in a duplication of promoter 1 in the genome, with one copy of the promoter driving transcription of the introduced gene for expression and the other copy driving the transcription of the genomic gene expressed from promoter 1.

Figure 23:
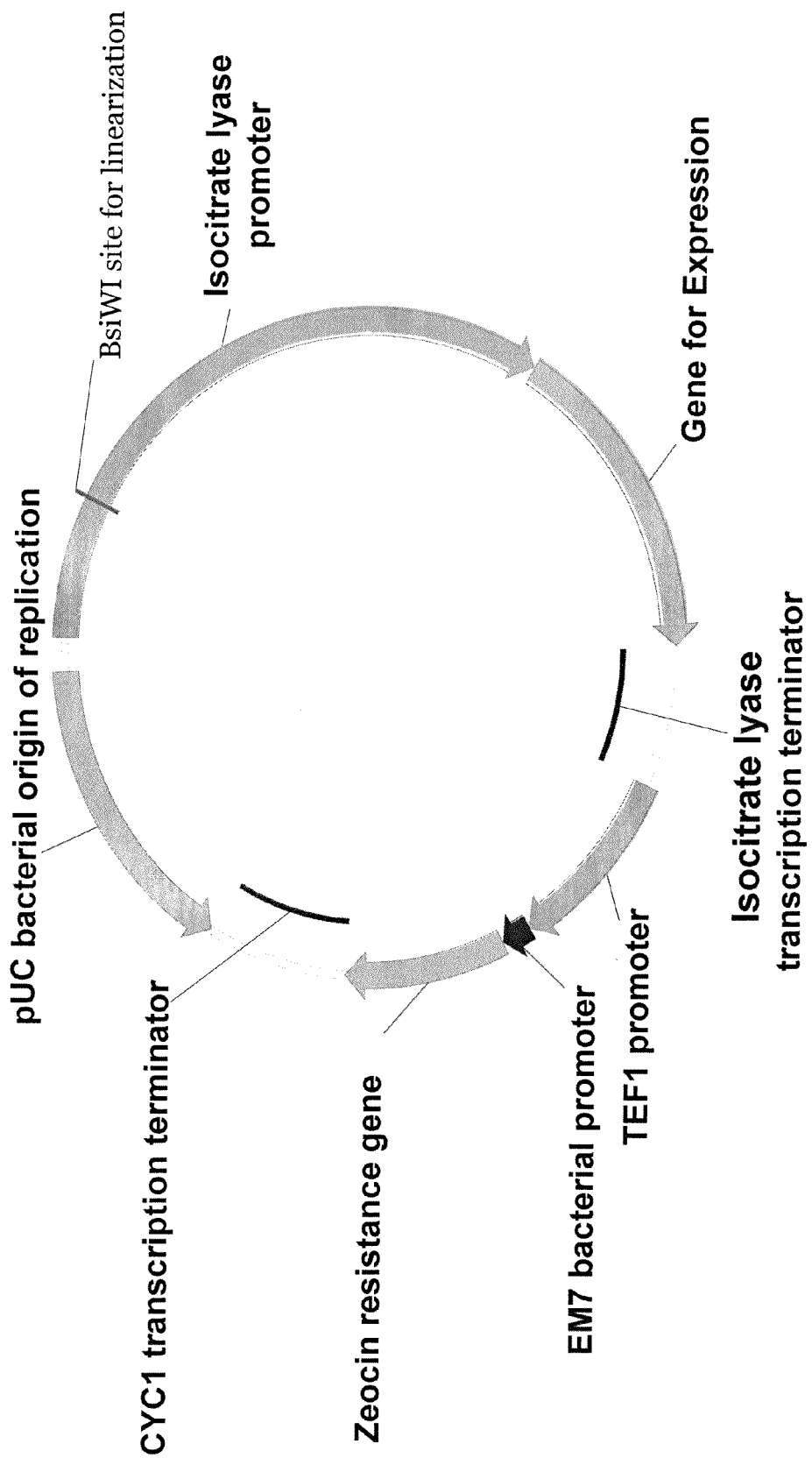

FIG. 23 shows a specific embodiment of the DNA "genomic insertion" construct shown in FIG. 21. The general structure is that the construct has a gene for expression which is preceded by a promoter that is active in the yeast (the *Candida tropicalis* isocitrate lyase promoter). The isocitrate lyase promoter comprises a unique BsiWI site whereby the construct may be cleaved by endocunclease BsiWI once to linearize it. The gene for expression is followed by a transcription terminator (isocitrate lyase transcription terminator). The genomic insertion construct also comprises a selectable marker conferring resistance to the antibiotic zeocin. This selectable marker is active in both bacterial and yeast hosts and preceded by a yeast promoter (the TEF1 promoter) and a Bacterial promoter (the EM7 promoter), and followed by a transcription terminator (the CYC1 transcription terminator 2). The genomic insertion construct also comprises a bacterial origin of replication (the pUC origin of replication.

Figure 24:
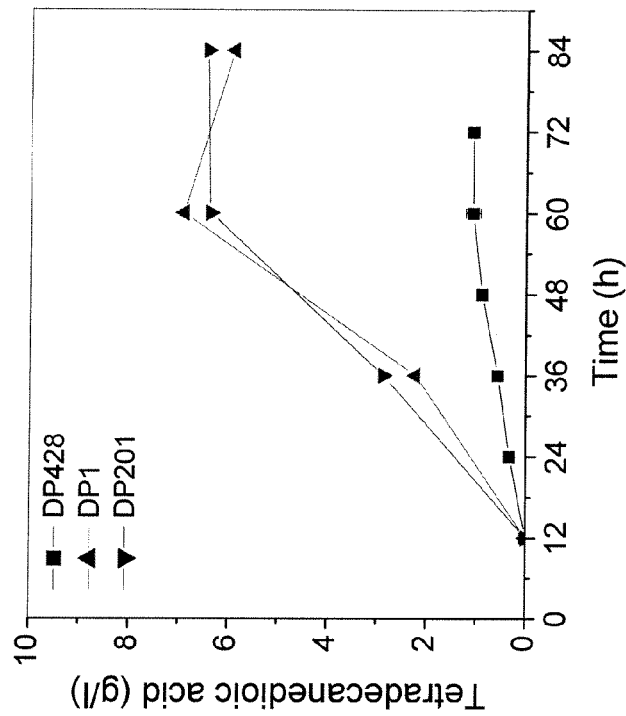
Figure 24:
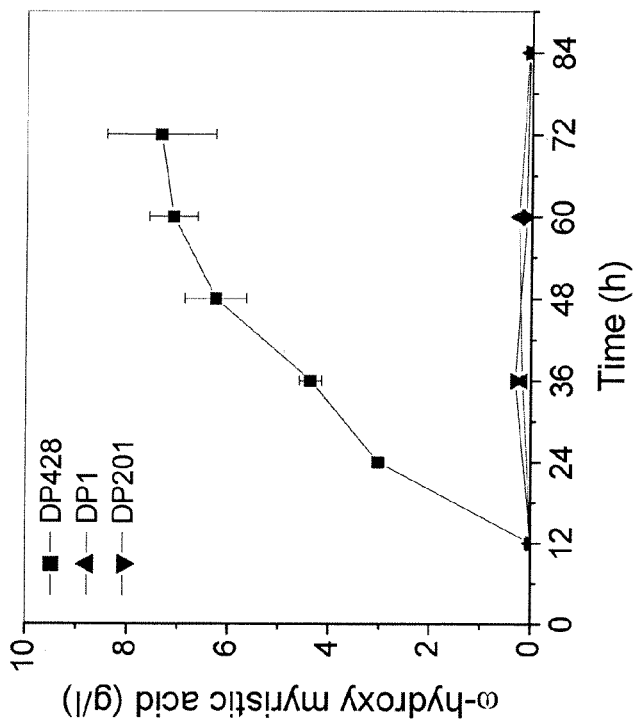

FIG. 24 shows the levels of α,ω-dicarboxylic acids and ω-hydroxy fatty acids produced by *Candida tropicalis* strains DP1, DP201 and DP428 (see Table 3 for genotypes). Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glucose plus 5 g/l ethanol. After 18 hours 3 ml of preculture was added to 27 ml fresh media F plus 20 g/l glucose plus 5 g/l ethanol in a 500 ml flask, and grown at 30° C. and 250 rpm for 20 hours before addition of substrate. Biocatalytic conversion was initiated by adding 40 g/l of methyl myristate, the pH was adjusted to ~7.8 with 2M NaOH. The culture was pH controlled by adding 2 mol/l NaOH every 12 hours, glycerol was fed as cosubstrate by adding 500 g/l glycerol and ethanol was fed as a inducer by adding 50% ethanol every 12 hours. Samples were taken at the times indicated, cell culture was acidified to pH~1.0 by addition of 6 N HCl, products were extracted from the cell culture by diethyl ether and the concentrations of ω-hydroxy myristate and α,ω-dicarboxymyristate were measured by LC-MS (liquid chromatography mass spectroscopy).

Figure 25:
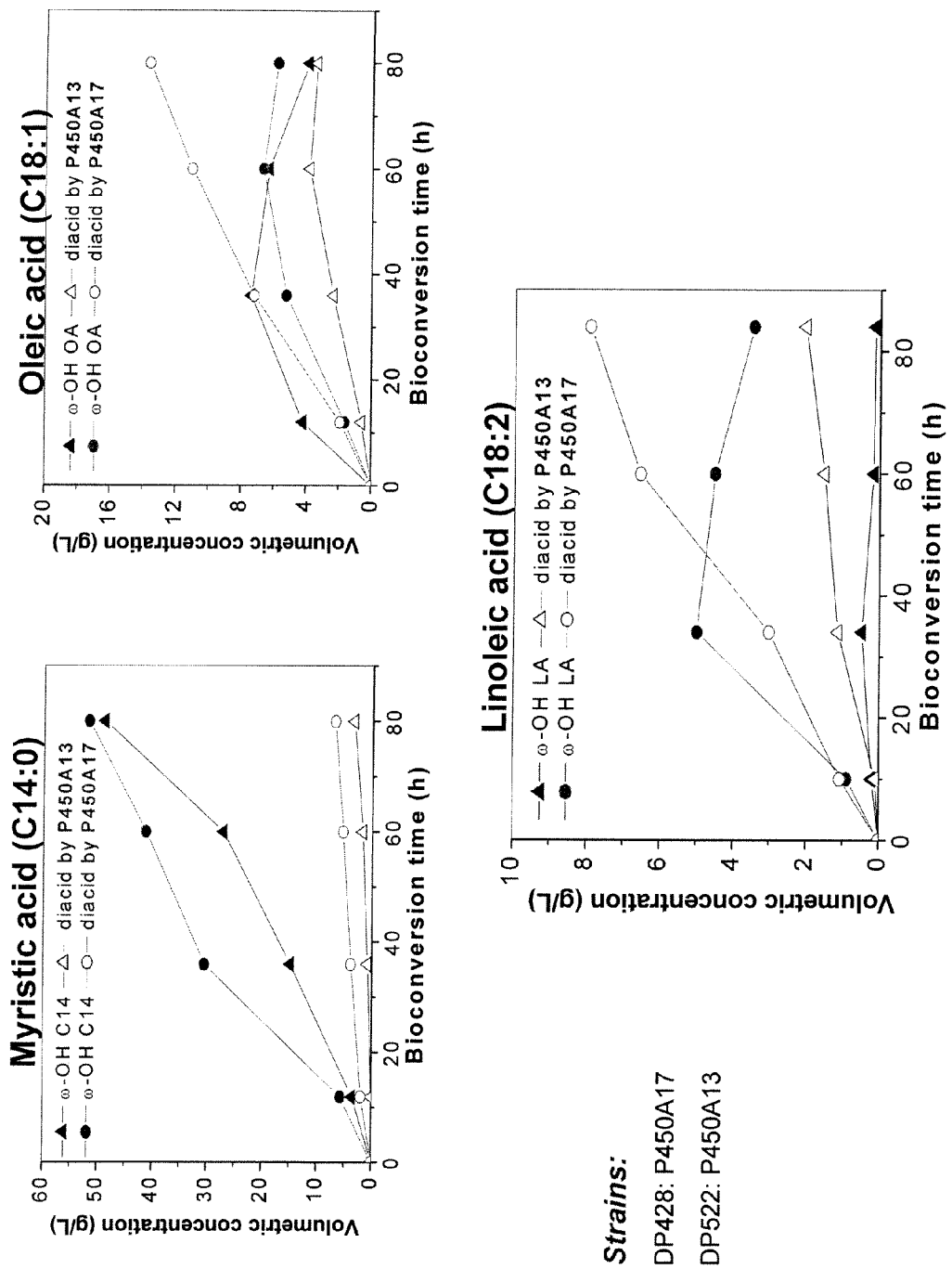

FIG. 25 shows the levels of α,ω-dicarboxylic acids and ω-hydroxy fatty acids produced by *Candida tropicalis* strains DP428 and DP522 (see Table 3 for genotypes). Cultures of the yeast strains were grown at 30° C. in a DASGIP parallel fermentor containing 200 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. The pH was maintained at 6.0 by automatic addition of 6 M NaOH or 2 M $H_2SO_4$ solution. Dissolved oxygen was kept at 70% by agitation and $O_2$-cascade control mode. After 6 hour growth, ethanol was fed into the cell culture to 5 g/l. After 12 h growth, biocatalytic conversion was initiated by adding (A) 20 g/l of methyl myristate, (B) 20 g/l oleic acid or (C) 10 g/l linoleic acid. During the conversion phase, 80% glycerol was fed as co-substrate for conversion of methyl myristate and 500 g/l glucose was fed as co-substrate for conversion of oleic acid and linoleic acid by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l, and fatty acid substrate was added to 20 g/l until the total substrate concentration added was (A) 60 g/l of methyl myristate, (B) 60 g/l oleic acid or (C) 30 g/l linoleic acid. Formation of products was measured at the indicated intervals by taking samples and acidifying to pH~1.0 by addition of 6 N HCl; products were extracted from the cell culture by diethyl ether and the concentrations of ω-hydroxy fatty acids and α,ω-dicarboxylic acids were measured by LC-MS (liquid chromatography mass spectroscopy).

Figure 26:
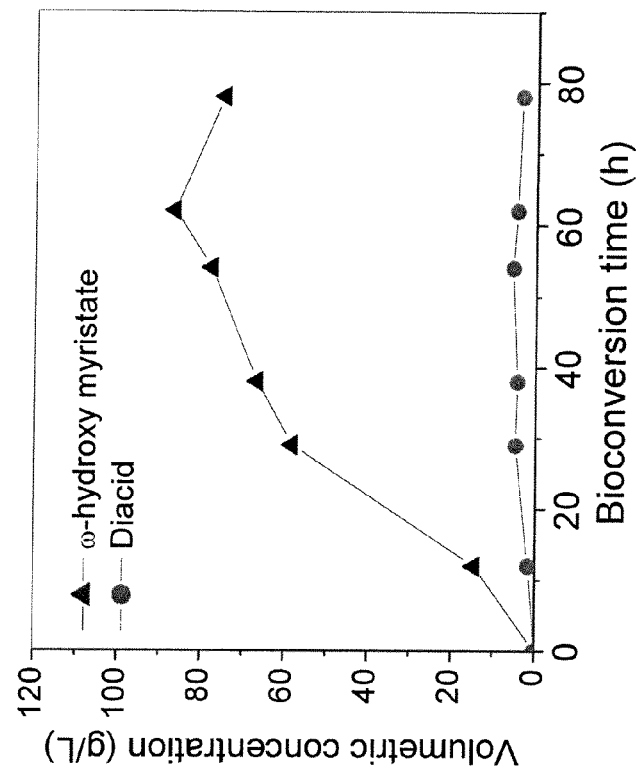
Figure 26:
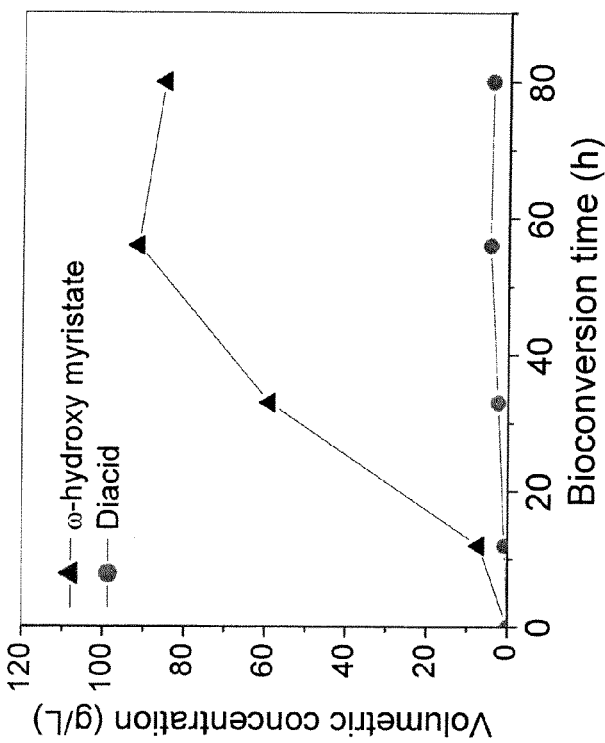

FIG. 26 shows the levels of α,ω-dicarboxylic acids and ω-hydroxy fatty acids produced by *Candida tropicalis* strain DP428 (see Table 3 for genotype) in two separate fermentor runs. *C. tropicalis* DP428 was taken from a glycerol stock or fresh agar plate and inoculated into 500 ml shake flask containing 30 mL of YPD medium (20 g/l glucose, 20 g/l peptone and 10 g/l yeast extract) and shaken at 30° C., 250 rpm for 20 hours. Cells were collected by centrifugation and re-suspended in FM3 medium for inoculation. (FM3 medium is 30 g/l glucose, 7 g/l ammonium sulfate, 5.1 g/l potassium phosphate, monobasic, 0.5 g/l magnesium sulfate, 0.1 g/l calcium chloride, 0.06 g/l citric acid, 0.023 g/l ferric chloride, 0.0002 g/l biotin and 1 ml/l of a trace elements solution. The trace elements solution contains 0.9 g/l boric acid, 0.07 g/l cupric sulfate, 0.18 g/l potassium iodide, 0.36 g/l ferric chloride, 0.72 g/l manganese sulfate, 0.36 g/l sodium molybdate, 0.72 g/l zinc sulfate.) Conversion was performed by inoculating 15 ml of preculture into 135 ml FM3 medium, methyl myristate was added to 20 g/l and the temperature was kept at 30° C. The pH was maintained at 6.0 by automatic addition of 6 M NaOH or 2 M $H_2SO_4$ solution. Dissolved oxygen was kept at 70% by agitation and $O_2$-cascade control mode. After six hour growth, ethanol was fed into the cell culture to 5 g/l. During the conversion phase, 80% glycerol was fed as co-substrate by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l, and methyl myristate was added to 40 g/l until the total methyl myristate added was 140 g/l (e.g. the initial 20 g/l plus 3 subsequent 40 g/l additions). Formation of products was measured at the indicated intervals by taking samples and acidifying to pH~1.0 by addition of 6 N HCl; products were extracted from the cell culture by diethyl ether and the concentrations of ω-hydroxy myristate and α,ω-dicarboxymyristate were measured by LC-MS (liquid chromatography mass spectroscopy).

5. DETAILED DESCRIPTION

It is to be understood that what is disclosed herein is not limited to the particular methodology, devices, solutions or apparatuses described, as such methods, devices, solutions or apparatuses can, of course, vary.

5.1 Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like. Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed in the disclosed embodiments. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also encompassed. Where a combination is disclosed, each subcombination of the elements of that combination is also specifically disclosed and is within the scope of the disclosed embodiments. Conversely, where different elements or groups of elements are individually disclosed, combinations thereof are also disclosed. Where any embodiment is disclosed as having a plurality of alternatives, examples of that embodiment in which each alternative is excluded singly or in any combination with the other alternatives are also hereby disclosed; more than one element of a disclosed embodiment can have such exclusions, and all combinations of elements having such exclusions are hereby disclosed.

Unless defined otherwise herein, all technical and scientific terms used herein have the same meaning as commonly understood by one of ordinary skill in the art. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, N.Y., 1991, provide one of ordinary skill in the art with a general dictionary of many of the terms used herein. Although any methods and materials similar or equivalent to those described herein can be used in the practice or testing of the disclosed embodiments, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

As used, herein, computation of percent identity takes full weight of any insertions in two sequences for which percent identity is computed. To compute percent identity between two sequences, they are aligned and any necessary insertions in either sequence being compared are then made in accordance with sequence alignment algorithms known in the art. Then, the percent identity is computed, where each insertion in either sequence necessary to make the optimal alignment between the two sequences is counted as a mismatch.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like.

Standard A-T and G-C base pairs form under conditions which allow the formation of hydrogen bonds between the N3-H and C4-oxy of thymidine and the NI and C6-$NH_2$, respectively, of adenosine and between the C2-oxy, N3 and C4-$NH_2$, of cytidine and the C2-$NH_2$, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., which is hereby incorporated by reference herein in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other nonnatural base pairs may be synthesized by the method described in Piccirilli et al., 1990, Nature 343:33-37, hereby incorporated by reference in it entirety, for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al., 1992, J. Am. Chem. Soc. 114, 3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs. DNA sequences are written from 5' to 3' unless otherwise indicated.

The term "protein" refers to contiguous "amino acids" or amino acid "residues." Typically, proteins have a function. However, for purposes of this disclosure, proteins also encompass polypeptides and smaller contiguous amino acid sequences that do not have a functional activity. The functional proteins of this disclosure include, but are not limited to, esterases, dehydrogenases, hydrolases, oxidoreductases, transferases, lyases, ligases, receptors, receptor ligands, cytokines, antibodies, immunomodulatory molecules, signaling molecules, fluorescent proteins and proteins with insecticidal or biocidal activities. Useful general classes of enzymes include, but are not limited to, proteases, cellulases, lipases, hemicellulases, laccases, amylases, glucoamylases, esterases, lactases, polygalacturonases, galactosidases, ligninases, oxidases, peroxidases, glucose isomerases, nitrilases, hydroxylases, polymerases and depolymerases. In addition to enzymes, the encoded proteins which can be used in this disclosure include, but are not limited to, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting. All of these proteins are well defined in the literature and are so defined herein. Also included are deletion mutants of such proteins, individual domains of such proteins, fusion proteins made from such proteins, and mixtures of such proteins; particularly useful are those which have increased half-lives and/or increased activity.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "expression system" refers to any in vivo or in vitro biological system that is used to produce one or more protein encoded by a polynucleotide.

The term "translation" refers to the process by which a polypeptide is synthesized by a ribosome 'reading' the sequence of a polynucleotide.

In some embodiments, the term "disrupt" means to reduce or diminish the expression of a gene in a host cell organism.

In some embodiments, the term "disrupt" means to reduce or diminish a function of a protein encoded by a gene in a host cell organism. This function may be, for example, an enzymatic activity of the protein, a specific enzymatic activity of the protein, a protein-protein interaction that the protein undergoes in a host cell organism, or a protein-nucleic acid interaction that the protein undergoes in a host cell organism.

In some embodiments, the term "disrupt" means to eliminate the expression of a gene in a host cell organism.

In some embodiments, the term "disrupt" means to eliminate the function of a protein encoded by a gene in a host cell organism. This function may be, for example, an enzymatic activity of the protein, a specific enzymatic activity of the protein, a protein-protein interaction that the protein undergoes in a host cell organism, or a protein-nucleic acid interaction that the protein undergoes in a host cell organism.

In some embodiments, the term "disrupt" means to cause a protein encoded by a gene in a host cell organism to have a modified activity spectrum (e.g., reduced enzymatic activity) relative to wild-type activity spectrum of the protein.

In some embodiments, disruption is caused by mutating a gene in a host cell organism that encodes a protein. For example, a point mutation, an insertion mutation, a deletion mutation, or any combination of such mutations, can be used to disrupt the gene. In some embodiments, this mutation causes the protein encoded by the gene to express poorly or not at all in the host cell organism. In some embodiments, this mutation causes the gene to no longer be present in the host cell organism. In some embodiments, this mutation causes the gene to no longer encode a functional protein in the host cell organism. The mutation to the gene may be in the portion of the gene that encodes a protein product (exon), it may be in any of the regulatory sequences (e.g., promoter, enhancer, etc.) that regulate the expression of the gene, or it may arise in an intron.

In some embodiments, the disruption (e.g., mutation) of a gene causes the protein encoded by the gene to have a mutation that diminishes a function of the protein relative to the function of the wild type counterpart of the mutated protein.

As used, herein, the wild type counterpart of a mutated protein is the unmutated protein, occurring in wild type host cell organism, which corresponds to the mutated protein. For example, if the mutated protein is a protein encoded by mutated *Candida tropicalis* POX 5, the wild type counterpart of the mutated protein is the gene product from naturally occurring *Candida tropicalis* POX 5 that is not mutated.

As used herein, the wild type counterpart of a mutated gene is the unmutated gene occurring in wild type host cell organism, which corresponds to the mutated gene. For example, if the mutated gene is *Candida tropicalis* POX 5 containing a point mutation, the wild type counterpart is *Candida tropicalis* POX 5 without the point mutation.

In some embodiments, a gene is deemed to be disrupted when the gene is not capable of expressing protein in the host cell organism.

In some embodiments, a gene is deemed to be disrupted when the disrupted gene expresses protein in a first host cell organism that contains the disrupted gene in amounts that are 20% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 30% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 40% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 50% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 60% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 70% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the abundance of mRNA transcripts that encode the disrupted gene in a first host cell organism that has the disrupted gene are 20% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 30% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 40% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 50% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 60% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 70% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a protein is deemed to be disrupted when the protein has an enzymatic activity that is 20% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 30% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 40% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 50% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 60% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 70% or less than the activity of the wild type counterpart of the protein when the disrupted protein and the wild type counterpart of the protein are under the same conditions (e.g., temperature, concentration, pH, concentration of substrate, salt concentration, etc.).

In some embodiments enzymatic activity is defined as moles of substrate converted per unit time=rate×reaction volume. Enzymatic activity is a measure of the quantity of active enzyme present and is thus dependent on conditions, which are to be specified. The SI unit for enzyme activity is the katal, 1 katal=1 mol s-1. In some embodiments enzymatic activity is expressed as an enzyme unit (EU)=1 μmol/min, where 1 U corresponds to 16.67 nanokatals. See Nomenclature Committee of the International Union of Biochemistry (NC-IUB) (1979), "Units of Enzyme Activity," Eur. J. Biochem. 97: 319-320, which is hereby incorporated by reference herein.

In some embodiments, a protein is deemed to be disrupted when a sample of the disrupted protein "disrupted sample" having a purity of 50% weight per weight (w/w) or weight per volume (w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 20% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 30% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 40% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 50% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 60% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 70% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, the enzymatic activity or enzymatic specific activity is measured by an assay that measures the consumption of substrate or the production of product over time such as those disclosed in Schnell et al., 2006, Comptes Rendus Biologies 329, 51-61, which is hereby incorporated by reference herein.

In some embodiments, the enzymatic activity or enzymatic specific activity is measured by an initial rate experiment. In such an assay, the protein (enzyme) is mixed with a large excess of the substrate, the enzyme-substrate intermediate builds up in a fast initial transient. Then the reaction achieves a steady-state kinetics in which enzyme substrate intermediates remains approximately constant over time and the reaction rate changes relatively slowly. Rates are measured for a short period after the attainment of the quasi-steady state, typically by monitoring the accumulation of product with time. Because the measurements are carried out for a very short period and because of the large excess of substrate, the approximation free substrate is approximately equal to the initial substrate can be made. The initial rate experiment is relatively free from complications such as back-reaction and enzyme degradation.

In some embodiments, the enzymatic activity or enzymatic specific activity is measured by progress curve experiments. In such experiments, the kinetic parameters are determined from expressions for the species concentrations as a function of time. The concentration of the substrate or product is recorded in time after the initial fast transient and for a sufficiently long period to allow the reaction to approach equilibrium.

In some embodiments, the enzymatic activity or enzymatic specific activity is measured by transient kinetics experiments. In such experiments, reaction behaviour is tracked during the initial fast transient as the intermediate reaches the steady-state kinetics period.

In some embodiments, the enzymatic activity or enzymatic specific activity is measured by relaxation experiments. In these experiments, an equilibrium mixture of enzyme, substrate and product is perturbed, for instance by a temperature, pressure or pH jump, and the return to equilibrium is monitored. The analysis of these experiments requires consideration of the fully reversible reaction.

In some embodiments, the enzymatic activity or enzymatic specific activity is measured by continuous assays, where the assay gives a continuous reading of activity, or discontinuous assays, where samples are taken, the reaction stopped and then the concentration of substrates/products determined.

In some embodiments, the enzymatic activity or enzymatic specific activity is measured by a fluorometric assay (e.g., Bergmeyer, 1974, "Methods of Enzymatic Analysis", Vol. 4, Academic Press, New York, N.Y., pp. 2066-2072), a calorimetric assay (e.g., Todd and Gomez, 2001, Anal Biochem. 296, 179-187), a chemiluminescent assay, a light scattering assay, a radiometric assay, or a chromatrographic assay (e.g., Churchwella et al., 2005, Journal of Chromatography B 825, 134-143).

In some embodiments, a protein is deemed to be disrupted when the protein has a function whose performance is 20% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 30% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 40% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 50% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 60% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 70% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is disrupted by a genetic modification. In some embodiments, a protein is disrupted by exposure of a host cell to a chemical (e.g., an inhibitor that substantially reduces or eliminates the activity of the enzyme). In some embodiments, this compound satisfies the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a LogP under 5. The "Rule of Five" is so called because three of the four criteria involve the number five. See, Lipinski, 1997, Adv. Drug Del. Rev. 23, 3, which is hereby incorporated herein by reference in its entirety.

As used, herein, computation of percent identity takes full weight of any insertions in two sequences for which percent identity is computed. To compute percent identity between two sequences, they are aligned and any necessary insertions in either sequence being compared are then made in accordance with sequence alignment algorithms known in the art. Then, the percent identity is computed, where each insertion in either sequence necessary to make the optimal alignment between the two sequences is counted as a mismatch. Unless explicitly indicated otherwise, the percent identity of two sequences is the percent identity across the entire length of each of the sequences being compared, with gaps insertions processed as specified in this paragraph.

5.2 Production of Long-Chain ω-Hydroxy Fatty Acids and α,ω-Dicarboxylic Acids

Figure 1:
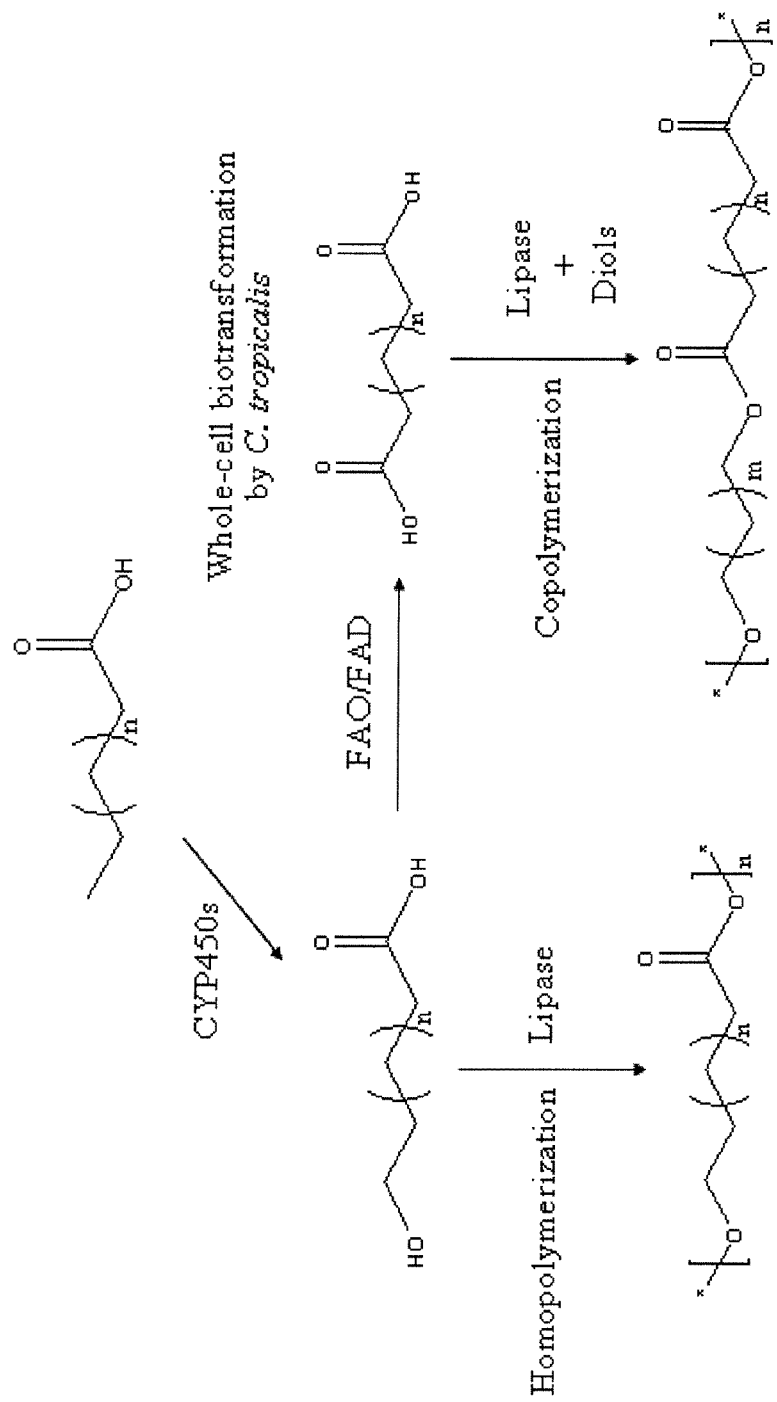
FIG. 1 shows the overall scheme of one embodiment in which aliphatic fatty acids are converted to α-carboxyl-ω-hydroxyl fatty acids or to α,ω-dicarboxylic acids by whole cell biotransformation using cells of *Candida* species. These are then enzymatically polymerized, either to form homopolymers or copolymers with other monomers.
Figure 2:
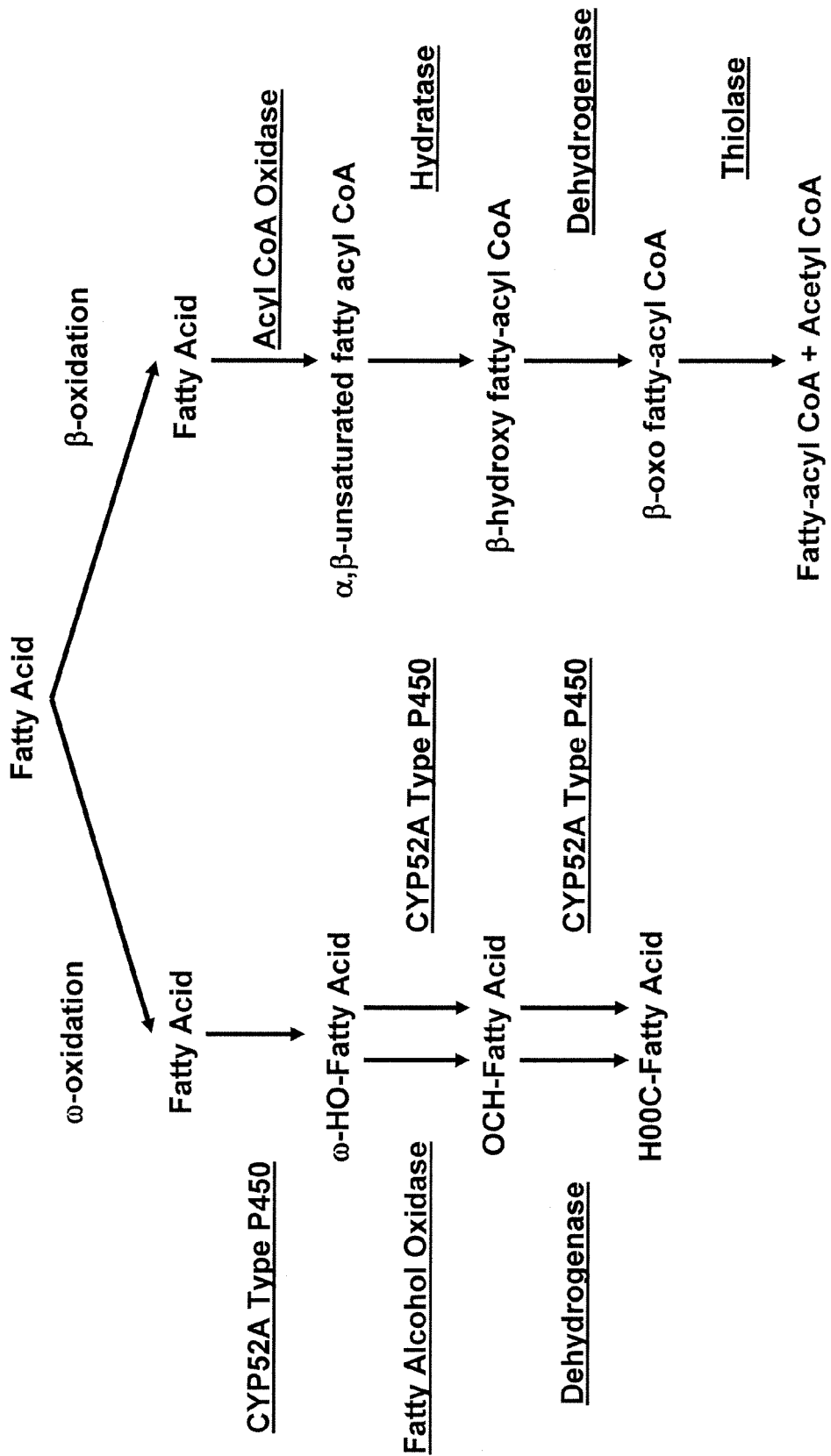
FIG. 2 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows.

Whole-cell biocatalysts currently used to oxidize long chain fatty acids include *Candida tropicalis, Candida cloacae, Cryptococcus neoforman* and *Corynebacterium* sp. One preferred microorganisms is *Candida tropicalis* ATCC20962 in which the β-oxidation pathway is blocked by disrupting POX 4 and POX 5 genes which respectively encode the acyl-coenzyme A oxidases PXP-4 (SEQ ID NO: 134) and PXP-5 (SEQ ID NO: 135). This prevents metabolism of the fatty acid by the yeast (compare FIGS. 2 and 3). The fatty acids or alkynes used have 14 to 22 carbon atoms, can be natural materials obtained from plants or synthesized from natural fatty acids, such as lauric acid (C12:0), myristic acid (C14:0), palmitic acid (C16:0), stearic acid (C18:0), oleic acid (C18:1), linoleic acid (C18:2), α-linolenic acid (ω3, C18:3) ricinoleic acid (12-hydroxy-9-cis-octadecenoic acid, 12-OH-C18:1), erucic acid (C22:1), epoxy stearic acid. Examples of other substrates that can be used in biotransformations to produce α,ω-dicarboxylic acid and ω-hydroxyacid compounds are 7-tetradecyne and 8-hexadecyne. Disclosed herein, naturally derived fatty acids, chemically or enzymatically modified fatty acids, n-alkane, n-alkene, n-alkyne and/or fatty alcohols that have a carbon chain length from 12 to 22 are used as carbon sources for the yeast-catalyzed biotransformation. For example, *Candida tropicalis* ATCC20962 can be used as a catalyst under aerobic conditions in liquid medium to produce ω-hydroxy fatty acids and α,ω-dicarboxylic acids. *Candida tropicalis* ATCC20962 is initially cultivated in liquid medium containing inorganic salts, nitrogen source and carbon source. The carbon source for initial cultivations can be saccharide such as sucrose, glucose, sorbitol, etc., and other carbohydrates such as glycerol, acetate and ethanol. Then, the substrate such as naturally derived fatty acids, chemically or enzymatically modified fatty acids, n-alkane, n-alkene, n-alkyne and fatty alcohol for oxidation of terminal methyl or hydroxyl moieties is added into the culture. The pH is adjusted to 7.5-8.0 and fermentations are conducted under aerobic conditions with agitation in a shaker incubator, fermentor or other suitable bioreactor.

For example, the fermentation process may be divided into two phases: a growth phase and a transformation phase in which ω-oxidation of the substrate is performed. The seeds inoculated from fresh agar plate or glycerol stock are firstly cultivated in a pre-culture medium for 16-20 hours, at 30° C. and pH 6.5 in a shaker. Subsequently, this culture is used to inoculate the conversion medium with co-substrates. The growth phase of the culture is performed for 10-12 hours to generate high cell density cultures at pH 6.5 and 30° C. The transformation phase is begun with addition of the fatty acid or other substrate for the bio-oxidation. The medium pH is adjusted to 7.5-8.0 by addition of a base solution. Co-substrates are fed during the transformation phase to provide energy for cell growth. By use of this method, the terminal methyl group of fatty acids, synthetically derived substrates, n-alkanes, n-alkenes, n-alkynes and/or fatty alcohols that have a carbon chain length from 12 to 22 are converted to a hydroxyl or carboxyl group. Examples of ricinoleic analogs formed via the methods disclosed herein include, but are not limited to, 1,18-cis-9-octadecenedioic acid, 1,22-cis-9-docosenedioic acid, 1,18-cis-9,12-octadecadienedioic acid, 7-hydroxy-1,18-cis-9-octadecenedioic acid, 12,18-dihydroxy-cis-9-octadecenoic acid, cis-9,10-epoxy-1,18-octadecanedioic acid, 7-tetradecynedioic acid and 8-hexadecynedioic acid. In some embodiments, productivity values of these products, using a standard fermentation process, is about 0.1~0.5 g/l/h, and product concentrations are from 10~30 g/l.

The ω-hydroxy fatty acids and α,ω-dicarboxylic acids in fermentation broth can be extracted and purified as follows. The liquid culture medium containing these products is acidified with concentrated hydrochloric acid to pH about 1.0~4.0 and extracted into diethyl ether. Solvent in ether extract is evaporated under vacuum with a rotary evaporator. Resulting product mixtures can be further purified by silica gel column chromatography using silica gel. Chromatographic separations can generally be conducted using an eluent that consists of a two-solvent system. Solvents pairs can be selected so that one is of low polarity (e.g. n-hexane) while the other is of higher polarity (e.g. diethyl ether). Fractions containing impurities and products can be eluted separately by adjusting the ratio of strong-to-weak solvent. Alternatively, resulting products mixture can be purified by liquid chromatography methods with various column types including those that are reverse-phase. Chromatographic separations can be conducted using a mixed solvent that consists of various contents of methanol, water, formic acid and acetonitrile. Fractions containing impurities and products can be eluted separately depending on their polarity. Alternatively, ricinoleic acid analogs that have two carboxylic acids or have sufficient polarity to dissolve in alkaline medium can be extracted and precipitated from fermentation broths by a method such as the following. An alkaline material such as sodium hydroxide or potassium hydroxide is added to the fermentation broth and the pH of the solution is adjusted to 11~13 to dissolve dicarboxylic acids formed. Then, diatomaceous earth in an amount of 2-8% by weight is added to the fermentation broth to selectively absorb lower polarity components of the mixture such as unreacted hydrocarbons and monocarboxylic acids. Subsequently, the fermentation broth is filtered under pressure by using a filter press and the cake formed after this filtration is washed with two to three times with water. The obtained filtrate is then acidified to pH at 4.0 or below by addition of an acid such as sulfuric acid or hydrochloric acid to precipitate dicarboxylic acid products. The precipitated dicarboxylic acids can then be further purified by recrystallization using an organic solvent. Generally such an organic solvent would be of low polarity (e.g. n-hexane). Purified ω-hydroxy fatty acids and α,ω-dicarboxylic acids can be identified as set forth in the following non-limiting example. Sample is esterified with $BF_3$ in methanol (10%, w/w) at 70° C. for 20 minutes followed by silylation of methyl esters with HMDS/TMCS/Pyridine at 70° C. for 10 minutes. Analysis of derivatized products is performed by gas chromatography/mass spectrometry (GC/MS). Structures of products are confirmed by $^1$H- and $^{13}$C-NMR. Quantification of product formation during biotransformations is performed by liquid chromatography/mass spectrometry (LC/MS) using purified products as standards.

5.3 Polymerization of Long-Chain ω-Hydroxy Fatty Acids and α,ω-Dicarboxylic Acids Another aspect provides the subsequent polymerization of ω-oxidized products from the biotransformation. For example, by first synthesizing a family of novel ricinoleic acid analogs by a yeast-catalyzed biotransformation and then using these products as monomers for polymerizations, a novel family of functional polyesters can be prepared.

In one example, polymerizations were performed using an immobilized enzyme catalyst. One example of an immobilized enzyme catalyst that can be used is immobilized *Candida antartica* Lipase B (CALB). Novozym 435 is an example of immobilized *Candida antartica* Lipase B (CALB) where the immobilization support consists of macroporous polymethylmethacrylate beads. Examples of novel functional polyesters prepared include polymers with repeat units containing double bonds, triple bonds, hydroxyl and epoxide moieties. This was accomplished by homopolymerization of 12,18-dihydroxy-cis-9-octadecenoic acid as well as by copolymerization of α,ω-dicarboxylic acids that include 1,18-cis-9-octadecenedioic acid, 1,22-cis-9-docosenedioic acid, 7-hydroxy-1,18-cis-9-octadecenedioic acid, cis-9,10-epoxy-1,18-octadecanedioic acid and 7-tetradecynedioic acid with diols such as 1,8-octanediol, 1,3-propanediol and glycerol.

In the example, polymerizations were performed in a parallel synthesizer in bulk as well as in diphenyl ether, or in round bottom flasks in toluene at 70 to 90° C. Equal molar ratios of diacids and diols were transferred into reactor tubes in a parallel synthesizer or round bottom flasks and 10%-by-wt Novozym 435 was added. For solution polymerizations minimal volumes of diphenyl ether or toluene was added to decrease diffusion constraints that would otherwise limit molecular weights formed and the rate at which polymerizations occur. For homopolymerizations of ω-hydroxy fatty acids, only ω-hydroxy fatty acid is added. Although copolymerizations of ω-hydroxy fatty acid monomers can also be performed with other hydroxyl fatty acids and/or with diacids and diols as long as care is taken to retain equimolar stoichiometry of reactive acid and hydroxyl groups. Vacuum is applied to remove water formed. Reactions were terminated by addition of cooled chloroform and the enzyme-catalyst was removed by filtration. Alternatively, products can be separated from the catalyst by filtration without addition of solvents as long as the product has sufficiently low viscosity. Also, the catalyst can be deactivated by another method such as denaturation by heating the product. Catalyst can also be left within the product after the catalyst is deactivated. If product fractionation is desired to increase molecular weight or to isolate components of the product then precipitation can be performed. Preferably the product is used without fractionation. To precipitate polymeric products the resulting chloroform solution was slowly added with stirring to methanol. The precipitated polymer is washed with methanol three times and then dried using vacuum evaporator at 50° C.

5.4 Novel Polymers

Properties of resulting polyesters were analyzed by the following methods. The molecular weight averages and polydispersity of functional polyesters were determined by gel permeation chromatography (GPC). Structures were analyzed by $^1$H-NMR and $^{13}$C-NMR. The thermal properties were determined by thermogravimetric analysis (TGA) and differential scanning calorimetry (DSC). Exemplary novel functional polyesters were synthesized. In all cases in these examples, functional groups of ricinoleic acid analogs such as alkene, alkyne, and epoxide moieties remained intact during enzyme-catalyzed polymer synthesis due to the mild reaction conditions used. Polymers with $M_w$ values ranging from 20,000 to 80,000 with polydispersities ($M_w/M_n$) of between 2.0 and 3.1 were prepared.

5.5 Genetic Modifications of *Candida*

*Candida* species including *Candida tropicalis* contains two pathways for the metabolism of fatty acids: ω-oxidation and β-oxidation. These pathways are shown schematically in FIG. 2, together with some classes of enzymes capable of catalyzing the chemical conversions in each pathway. In order for *Candida* to be used to transform fatty acids into useful compounds such as diacids and hydroxyl fatty acids, it is advantageous to eliminate metabolic pathways that can divert either the substrates or products of the desired pathway. For example it is desirable to prevent *Candida* from metabolizing fatty acids through the β-oxidation pathway, so that more fatty acids are available for conversion to α,ω-diacids and ω-hydroxy fatty acids by the ω-oxidation pathway. This can be accomplished by deleting the acyl coenzyme A oxidase genes, as shown in FIG. 3 (Picataggio et al., 1991, Mol Cell Biol 11, 4333-4339; Picataggio et al., 1992, Biotechnology 10, 894-898).

*Candida tropicalis* strains lacking both alleles of each of two acyl coenzyme A oxidase isozymes, encoded by the pox4 and pox5 genes, are efficient biocatalysts for the production of α,ω-diacids (Picataggio et al., 1991, Mol Cell Biol: 11, 4333-4339; Picataggio et al., 1992, Biotechnology 10, 894-898). However for the production of ω-hydroxy fatty acids, additional enzymes must be eliminated to prevent the oxidation of the ω-hydroxyl group to a carboxyl group.

To prevent the oxidation of the ω-hydroxyl group to a carboxyl group, in some embodiments it is particularly advantageous to eliminate or inactivate one or more genes encoding a cytochrome P450.

To prevent the oxidation of the ω-hydroxyl group to a carboxyl group, in some embodiments it is particularly advantageous to eliminate or inactivate one or more genes encoding a fatty alcohol dehydrogenase.

To prevent the oxidation of the ω-hydroxyl group to a carboxyl group, in some embodiments it is particularly advantageous to eliminate or inactivate one or more genes encoding an alcohol dehydrogenase.

In one embodiment yeast genes can be inactivated by deleting regions from the yeast genome that encode a part of the yeast gene that encodes the protein product (the open reading frame) so that the full-length protein can no longer be made by the cell. In another embodiment yeast genes can be inactivated by inserting additional DNA sequences into the part of the yeast gene that encodes the protein product so that the protein that is made by the cell contains changes that prevent it from functioning correctly. In another embodiment yeast genes are inactivated by inserting or deleting sequences from control regions of the gene, so that the expression of the gene is no longer correctly controlled; for example additions or deletions to the promoter can be used to prevent transcription of the gene, additions or deletions to the polyadenylation signal can be used to affect the stability of the mRNA, additions or deletions to introns or intron splicing signals can be used to prevent correct splicing or nuclear export of the processed mRNA.

For the production of oxidized compounds in yeast including ω-hydroxy fatty acids and α,ω-hydroxy fatty acids, it may also be advantageous to add certain new genes into the yeast cell. For example to facilitate the production of ω-hydroxy fatty acids from fatty acids with different chain lengths or degrees or positions of unsaturation, the enzymes that are naturally present in the yeast are often inadequate; they may oxidise the fatty acid to the ω-hydroxy fatty acid too slowly, they may only oxidise a subset of the fatty acids in a mixture to their corresponding ω-hydroxy fatty acids, they may oxidise the fatty acid in the wrong position or they may oxidise the ω-hydroxy fatty acid itself to a diacid. Advantageous enzymes could thus be those that oxidise a fatty acid to its corresponding ω-hydroxy fatty acid more rapidly, those that accept as substrates a wider range of fatty acids and those that do not over-oxidise ω-hydroxy fatty acids to diacids.

To achieve novel phenotypes in *Candida* species, including the ability to perform biotransformations such as novel chemical conversions, or increased rates of conversion of one or more substrates to one or more products, or increased specificity of conversion of one or more substrates to one or more products, or increased tolerance of a compound by the yeast, or increased uptake of a compound by the yeast, it may be advantageous to incorporate a gene encoding a polypeptide into the genome of the yeast.

Preferred sites of integration include positions within the genome where the gene would be under control of a promoter that transcribes high levels of an endogenous protein, or under control of a promoter that leads to regulated transcription for example in response to changes in the concentrations of one or more compound in the cellular or extracellular environment. Examples of preferred sites of integration include sites in the genome that are under control of the promoter for an isocitrate lyase gene, sites in the genome that are under control of the promoter for a cytochrome P450 gene, sites in the genome that are under control of the promoter for a fatty alcohol oxidase gene and sites in the genome that are under control of the promoter for an alcohol dehydrogenase gene to obtain high levels of expression of a polypetidepolypeptide or expression of a polypeptide under specific circumstances.

To achieve such novel phenotypes in *Candida* species, it may be advantageous to modify the activity of a polypeptide by altering its sequence, and to test the effect of the polypeptide with altered sequence within the yeast. Polypeptides of particular interest for conferring the ability to synthesize novel hydroxyfatty acids include cytochrome P450s and their reductases, glycosyl transferases and desaturases. A preferred method for testing the effect of sequence changes in a polypeptide within yeast is to introduce a plurality of genes of known sequence, each encoding a unique modified polypeptide, into the same genomic location in a plurality of strains.

Some embodiments described herein make use of a selective marker. A selective marker can be a gene that produces a selective advantage for the cells under certain conditions such as a gene encoding a product that confers resistance to an antibiotic or other compound that normally inhibits the growth of the host cell.

A selective marker can be a reporter, such as, for example, any nucleic acid sequence encoding a detectable gene product. The gene product may be an untranslated RNA product such as mRNA or antisense RNA. Such untranslated RNA may be detected by techniques known in the art, such as PCR, Northern or Southern blots. The selective marker may encode a polypeptide, such as a protein or peptide. A polypeptide may be detected immunologically or by means of its biological activity. The selective marker may be any known in the art. The selective marker need not be a natural gene. Useful selective markers may be the same as certain natural genes, but may differ from them either in terms of non-coding sequences (for example one or more naturally occurring introns may be absent) or in terms of coding sequences. One example of such a detectable gene product is one that causes the yeast to adopt a unique characteristic color associated with the detectable gene product. For example, if the targeting construct contains a selective marker that is a gene that directs the cell to synthesize a fluorescent protein, then all of the colonies that contain the fluorescent protein are carrying the targeting construct and are therefore likely to be integrants. Thus the cells that will be selected for further analysis are those that contain the fluorescent protein.

The selective marker may encode a protein that allows the yeast cell to be selected by, for example, a nutritional requirement. For example, the selective marker may be the ura4 gene that encodes orotidine-5'-phosphate decarboxylase. The ura4 gene encodes an enzyme involved in the biosynthesis of uracil and offers both positive and negative selection. Only cells expressing ura4 are able to grow in the absence of uracil, where the appropriate yeast strain is used. Cells expressing ura4 die in the presence of 5-fluoro-orotic acid (FOA) as the ura4 gene product converts FOA into a toxic product. Cells not expressing ura4 can be maintained by adding uracil to the medium. The sensitivity of the selection process can be adjusted by using medium containing 6-azauracil, a competitive inhibitor of the ura4 gene product. The his3 gene, which encodes imidazoleglycerol-phosphate dehydratase, is also suitable for use as a selective marker that allows nutritional selection. Only cells expressing his3 are able to grow in the absence of histidine, where the appropriate yeast strain is used.

The selective marker may encode for a protein that allows the yeast to be used in a chromogenic assay. For example, the selective marker may be the lacZ gene from *Escherichia coli*. This encodes the β-galactosidase enzyme which catalyses the hydrolysis of β-galactoside sugars such as lactose. The enzymatic activity of the enzyme may be assayed with various specialized substrates, for example X-gal (5-bromo-4-chloro-3-indoyl-β-D-galactoside) or o-nitrophenyl-β-D-galactopyranoside, which allow selective marker enzyme activity to be assayed using a spectrophotometer, fluorometer or a luminometer.

In some embodiments, the selective marker comprises a gene that encodes green fluorescent protein (GFP), which is known in the art.

In some embodiments, the selective marker encodes a protein that is capable of inducing the cell, or an extract of a cell, to produce light. For example, the selective marker encodes luciferase in some embodiments. The use of luciferase is known in the art. They are usually derived from firefly (*Photinous pyralis*) or sea pansy (*Renilla reniformis*). The luciferase enzyme catalyses a reaction using D-luciferin and ATP in the presence of oxygen and $Mg^{2+}$ resulting in light emission. The luciferase reaction is quantitated using a luminometer that measures light output. The assay may also include coenzyme A in the reaction that provides a longer, sustained light reaction with greater sensitivity. An alternative form of enzyme that allows the production of light and which can serve as a selective marker is aequorin, which is known in the art.

In some embodiments the selective marker encodes β-lactamase. This selective marker has certain advantages over, for example, lacZ. There is no background activity in mammalian cells or yeast cells, it is compact (29 kDa), it functions as a monomer (in comparison with lacZ which is a tetramer), and has good enzyme activity. This may use CCF2/AM, a FRET-based membrane permeable, intracellularly trapped fluorescent substrate. CCF2/AM has a 7-hydroxycoumarin linked to a fluorescein by a cephalosporin core. In the intact molecules, excitation of the coumarin results in efficient FRET to the fluorescein, resulting in green fluorescent cleavage of the CCF2 by β-lactamase results in spatial separation of the two dyes, disrupting FRET and causing cells to change from green to blue when viewed using a fluorescent microscope. The retention of the cleaved product allows the blue colour to develop over time, giving a low detection limit of, for example, 50 enzyme molecules per cell. This results in the selective maker being able to be assayed with high sensitivity. It also allows the ability to confirm results by visual inspection of the cells or the samples.

In some embodiments, the selective marker comprises any of the aforementioned genes under the control of a promoter. In some embodiments, the selective marker comprises any of the aforementioned genes under the control of a promoter as well as one or more additional regulatory elements, such as upstream activating sequences (UAS), termination sequences and/or secretory sequences known in the art. The secretory sequences may be used to ensure that the product of the reporter gene is secreted out of the yeast cell.

5.5.1 Methods for Deletion of Sequences from the *Candida* Genome

Many yeasts recombine DNA in regions of sequence homology. A linear DNA molecule that is introduced into a yeast cell can recombine homologously with the chromosomal DNA if its ends share sufficient sequence identity with chromosomal sequences. Since the sequences of the ends of the DNA molecule are the primary determinant of where in the yeast chromosome the homologous recombination event occurs, it is possible to construct a DNA molecule that encodes one or more functional genes, and to target that molecule to integrate at a specific location in the yeast chromosome. In this way, yeast genes in the chromosome or mitochondria may be disrupted, by interrupting the gene sequence with other sequences.

In one embodiment, a DNA construct comprises two sequences with homology to two sequences in the target yeast genome ("targeting sequences"), separated by a selective marker, as shown in FIG. 11. The two target sequences within the yeast genome are preferably located on the same molecule of DNA (e.g. the same nuclear or mitochondrial chromosome), and are preferably less than 1,000,000 base pairs apart, more preferably they are less than 100,000 base pairs apart, and more preferably they are less than 10,000 base pairs apart. Cells containing a genomic integration of the targeting construct can be identified using the selective marker.

A schematic representation of one form of a DNA molecule for yeast genomic integration (a "genomic targeting construct") is shown in FIG. 4. In this embodiment the genomic targeting construct has two targeting sequences that are homologous to the sequences of two regions of the target yeast genome. In some embodiments these sequences are each at least 100 base pairs in length, or between 100 and 300 base pairs in length. The targeting sequences are preferably 100% identical to sequences in the host genome or between 95% and 100% identical to sequences in the host genome. Between these targeting sequences are two sites recognized by a site-specific recombinase such as the natural or modified versions of cre or flp or PhiC31 recombinases or serine recombinases such as those from bacteriophage R4 or bacteriophage TP901-1. Between the two site specific recombinase recognition sites are functional sequence elements which may include sequences that encode a site-specific recombinase that recognizes the recombinase sites and which may also encode a selective marker as illustrated in FIG. 4. In one embodiment this DNA construct incorporates the "SAT1 flipper", a DNA construct for inserting and deleting sequences into the chromosome of Candida (Reuss et al., 2004, Gene 341, 119-27.). In the "SAT1 flipper" the recombinase is the flp recombinase from Saccharomyces cerevisiae (Vetter et al., 1983, Proc Natl Acad Sci USA: 80, 7284-7288) (FLP) and the flanking sequences recognized by the recombinase are recognition sites for the flp recombinase (FRT). The selective marker is the gene encoding resistance to the Nourseothricin resistance marker from transposon Tn1825, J. Basic Microbiol 28, 129-136). The entire construct can then be targeted to the Candida chromosome by adding flanking sequences with homology to a gene in the Candida chromosome. The DNA sequence of the SAT1-flipper is SEQ ID NO: 1.

Yeast preferentially recombines linear DNA. It is therefore advantageous to prepare the targeting construct as a linear molecule prior to transforming it into the yeast target. In some embodiments it is desirable to prepare and propagate the targeting construct as plasmid DNA in a bacterial host such as E. coli. For propagation in a bacterial host it is generally preferred that plasmid DNA be circular. It is thus sometimes necessary to convert the targeting construct from a circular molecule to a linear molecule. Furthermore for propagation of the targeting construct in a bacterial host, additional sequence elements may be necessary, so a targeting construct may, in addition to the elements shown in FIGS. 4 and 7, comprise an origin of replication and a bacterial selectable marker. It may therefore be advantageous to place restriction sites in the targeting construct to cleave between the elements of the targeting construct shown in FIGS. 4 and 7 and the elements not shown but required for propagation in a bacterial host. Cleavage with restriction enzymes that recognize these sites will linearize the DNA and leave the targeting sequences at the ends of the molecule, favoring homologous recombination with the target host genome. One of ordinary skill in the art will recognize that there are alternative ways to obtain linear DNA, for example by amplifying the desired segment of DNA by PCR. It is also possible to prepare the DNA directly and transform it into the target yeast strain without propagating as a plasmid in a bacterial host.

Introduction of the linearized targeting construct into a yeast host cell such as a Candida host cell is followed by homologous recombination catalyzed by host cell enzymes. This event is represented schematically in FIG. 5. Homologous recombination occurs between each of the two targeting sequences in the genomic targeting construct and the homologous sites in the yeast genome. The result is an integration of the targeting construct into the genomic DNA. Cells containing a genomic integration of the targeting construct can be identified using the selective marker.

Cells containing a genomic integration of the targeting construct can optionally be tested to ensure that the integration has occurred at the desired site within the genome. In one embodiment, such testing is performed by amplification of a section of the genomic DNA by the polymerase chain reaction. Integration of the targeting construct into the yeast genome will replace genomic sequences with targeting construct sequences. This replacement may be detected by a difference in size of amplicon using oligonucleotide primers that anneal to sequences outside the targeted sequence. This is illustrated in FIG. 10. One of ordinary skill in the art will readily appreciate that there are many alternative ways to design oligonucleotides to produce diagnostic amplicons using the polymerase chain reaction. For example one oligonucleotide that anneals inside the targeted region and one oligonucleotide that anneals outside but close to the targeted region can be used to produce an amplicon from the natural genomic sequence but will not produce an amplicon if the targeting construct has eliminated the targeted genomic sequence. Conversely one oligonucleotide that anneals inside the targeting construct and one oligonucleotide that anneals outside but close to the targeted region outside will not produce an amplicon from the natural genomic sequence but will produce an amplicon if the targeting construct has integrated at the targeted genomic location. In general oligonucleotide pairs for producing diagnostic amplicons should be oriented with their 3' ends towards each other and the sites in the genome where the two oligonucleotides anneal should be separated by between 100 and 10,000 bases, more preferably by between 150 and 5,000 bases and more preferably by between 200 and 2,000 bases. In some instances it may not be possible to distinguish between two possible genotypes based on the size of the amplicons produced by PCR from genomic DNA. In these cases an additional test is possible, for example digestion of the amplicon with one or more restriction enzymes and analysis of the sizes may enable the two possible genotypes to be distinguished, or sequencing of the amplicon may enable the two possible genotypes to be distinguished.

The same selectable marker may be used for the disruption of more than one genomic target. This can be achieved by removing the selectable marker from the yeast genome after each disruption. In one embodiment, this is achieved when the selectable marker separates two sites that are recognized by a recombinase. When the recombinase is present and active, it effects a recombination reaction between the two sites, excising the sequences between them. In the targeting construct shown in FIG. 6 this is done by induction of the gene encoding the recombinase present in the targeting construct. Expression of the recombinase causes a recombination event between the two recombinase recognition sites of the targeting construct, as shown schematically in FIG. 6. The result is that the sequences between the two recombinase sites are excised from the genome. In other embodiments it is possible to integrate a recombinase into a second site in the host genome instead of having it present in the targeting construct.

Cells from which a genomic integration of the targeting construct has been excised can optionally be tested to ensure that the excision has occurred by testing cells from individual colonies to determine whether they still carry the selective marker. In some embodiments, such testing is performed by amplification of a section of the genomic DNA by the polymerase chain reaction. Excision of part of the targeting construct from the yeast genome may be detected by a difference in size of amplicon using oligonucleotide primers that anneal to sequences outside the targeted sequence. This is illustrated in FIG. 10. One of ordinary skill in the art will readily appreciate that there are many alternative ways to design oligonucleotides to produce diagnostic amplicons using the polymerase chain reaction. For example one oligonucleotide that anneals inside the targeting construct (example.g. within the selective marker) and one oligonucleotide that anneals outside but close to the targeted region can be used to produce an amplicon from the integrated targeting construct but will not produce an amplicon if the targeting construct has been excised. In general oligonucleotide pairs for producing diagnostic amplicons should be oriented with their 3' ends towards each other and the sites in the genome where the two oligonucleotides anneal should be separated by between 100 and 10,000 bases, more preferably by between 150 and 5,000 bases and more preferably by between 200 and 2,000 bases. In some instances it may not be possible to distinguish between two possible genotypes based on the size of the amplicons produced by PCR from genomic DNA. In these cases an additional test is possible, for example digestion of the amplicon with one or more restriction enzymes and analysis of the sizes may enable the two possible genotypes to be distinguished, or sequencing of the amplicon may enable the two possible genotypes to be distinguished.

In some embodiments it may be advantageous to delete sequences whose deletion will result in the inactivation of a cytochrome P450; in some embodiments it may be advantageous to delete sequences whose deletion will result in the inactivation of a fatty alcohol oxidase; in some embodiments it may be advantageous to delete sequences whose deletion will result in the inactivation of an alcohol dehydrogenase.

5.5.2 Methods for Addition of Sequences to the *Candida* Genome

In some embodiments, new DNA sequences can be inserted into the yeast genome at a specific location using variations of the targeting construct. Because many yeasts recombine DNA in regions of sequence homology, a linear DNA molecule that is introduced into a yeast cell can recombine homologously with the chromosomal DNA if its ends share sufficient sequence identity with chromosomal sequences. It is thus possible to insert a DNA sequence into the yeast genome at a specific location by flanking that sequence with sequences homologous to sequences within the yeast genome that surround the desired genomic insertion site. Such replacements are quite rare, generally occurring less than 1 time in 1,000 yeast cells, so it is often advantageous to use a selective marker to indicate when new DNA sequences have been incorporated into the yeast genome. A selective marker can be used in conjunction with a sequence to be integrated into the yeast genome by modifying the strategy described for deleting sequences form the yeast genome.

If a targeting construct comprises additional sequences between one of the targeting sequences and the proximal recombinase site, those sequences will be retained in the genome following integration and excision of the targeting construct. An example of such a construct is shown in FIG. 7, with the additional sequences indicated as "insertion sequences". Integration of the targeting construct for insertion into the yeast genome is shown schematically in FIG. 8. Homologous recombination occurs between each of the two targeting sequences in the genomic targeting construct and the homologous sites in the yeast genome. The result is an integration of the targeting construct into the genomic DNA. Cells containing a genomic integration of the targeting construct can be identified using the selective marker.

Cells containing a genomic integration of the targeting construct can optionally be tested to ensure that the integration has occurred at the desired site within the genome. In one embodiment, such testing may be performed by amplification of a section of the genomic DNA by the polymerase chain reaction, for example as illustrated in FIG. 10. One of ordinary skill in the art will readily appreciate that there are many alternative ways to design oligonucleotides to produce diagnostic amplicons using the polymerase chain reaction.

The selectable marker and other sequences from the targeting construct can be removed from the yeast genome using a recombinase-based strategy: the recombinase effects a recombination reaction between the two recombinase sites, excising the sequences between them. In the targeting construct shown in FIG. 7 this is done by induction of the gene encoding the recombinase present in the targeting construct. Expression of the recombinase causes a recombination event between the two recombinase recognition sites of the targeting construct, as shown schematically in FIG. 9. The result is that the sequences between the two recombinase sites are excised from the genome, leaving the insertion sequences integrated into the yeast genome.

Cells to which a genomic integration has been introduced can optionally be tested to ensure that the addition has occurred correctly by polymerase chain reaction amplification of DNA from the yeast genome. These amplicons may then be tested to measure their size (for example by agarose gel electrophoresis), or their sequence may be determined to ensure that precisely the desired changes have been effected.

In some embodiments, it may be advantageous to insert sequences into a site in the genome that is known to be transcriptionally active. For example inserting a sequence encoding a polypeptide into a genomic site where transcription is regulated by a promoter that expresses high levels of mRNA can produce high levels of mRNA encoding the polypeptide. In some embodiments this can be done by replacing a polypeptide encoding sequence in the genome with a sequence encoding a different polypeptide, for example using the genomic targeting constructs of the form shown in FIG. 7.

In some embodiments, the insertion of a sequence encoding a polypeptide into a genomic site where transcription is regulated by a promoter that expresses high levels of mRNA is accomplished by adding a polypeptide encoding sequence into the genome at a position where a part of the genomic sequence is duplicated so that the gene that was originally present in the genome remains. In some embodiments this can be effected using a DNA construct comprising a promoter sequence found in the yeast genome positioned such that transcription initiated by the promoter produces RNA that can subsequently encode the polypeptide. Such a construct also comprises a selectable marker that will function in the yeast and optionally a selectable marker that will function in a bacterial host. These may optionally be the same selectable marker. An example of such a construct is shown in FIG. 21. Integration of this construct into the yeast genome is shown schematically in FIG. 22.

In some embodiments, a sequence encoding a polypeptide is inserted under control of the promoter for an isocitrate lyase gene or the promoter for a cytochrome P450 gene including the promoter of CYP52A12 or the promoter of CYP52A13 or the promoter of CYP52A14 or the promoter of CYP52A17 or the promoter of CYP52A18 or the promoter for a fatty alcohol oxidase gene including the promoter of FAO1 or the promoter of FAO1B or the promoter of FAO2A or the promoter of FAO2B, or the promoter for an alcohol dehydrogenase gene including the promoter of ADH-A4 or the promoter of ADH-A4B or the promoter of ADH-B4 or the promoter of ADH-B4B or the promoter of ADH-A10 or the promoter of ADH-B11 or the promoter of ADH-A10B or the promoter of ADH-B11B to obtain high levels of expression of a polypeptide.

5.5.3 Other Microorganisms of Interest for the Production of Oxidized Fatty Acids Homology-based recombination occurs in the Saccharomycetacaeae Family (which is in the Saccharomycotina Subphylum); Saccharomycetacaeae include the Genera *Ascobotryozyma, Candida, Citeromyces, Debaryomyces, Dekkera (Brettanomyces), Eremothecium, Issatchenkia, Kazachstania, Kluyveromyces, Kodamaea, Kregervanrija, Kuraishia, Lachancea, Lodderomyces, Nakaseomyces, Pachysolen, Pichia (Hansenula), Saccharomyces, Saturnispora, Tetrapisispora, Torulaspora, Vanderwaltozyma, Williopsis,*

*Zygosaccharomyces*. The deletion and insertion methods described here are therefore expected to work in these Genera.

Within the Subphylum Saccharomycotina is a monophyletic clade containing organisms that translate CTG as serine instead of leucine (Fitzpatrick et al., 2006, *BMC Evolutionary Biology* 6, 99) including the species *Candida lusitaniae*, *Candida guilliermondii* and *Debaryomyces hansenii*, and the second group containing *Candida albicans*, *Candida dubliniensis*, *Candida tropicalis*, *Candida parapsilosis* and *Lodderomyces elongisporus*. Of particular interest are modifications of the activities of cytochrome P450s, fatty alcohol oxidases and alcohol dehydrogenases to modulate the host's production of oxidized molecules by yeasts in this clade.

Yeast species of particular interest and industrial relevance within this clade include, but are not limited to *Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopellicurosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida* vartiovaarae, *Candida versatilis, Candida vini, Candida viswanathii, Candida wickerhamii, Candida wounanorum, Candida wyomingensis, Candida xylopsoci, Candida yuchorum, Candida zemplinina*, and *Candida zeylanoides*.

5.6 Engineering of Additional Enzymes into *Candida* to further Diversify Structures of Products Formed Different fatty acids are hydroxylated at different rates by different cytochrome P450s. To achieve efficient hydroxylation of a desired fatty acid feedstock, one strategy is to express P450 enzymes within *Candida* that are active for ω-hydroxylation of a wide range of highly abundant fatty acid feedstocks. Of particular interest are P450 enzymes that catalyze ω-hydroxylation of lauric acid (C12:0), myristic acid (C14:0), palmitic acid (C16:0), stearic acid (C18:0), oleic acid (C18:1), linoleic acid (C18:2), and α-linolenic acid (ω3, C18:3). Examples of P450 enzymes with known ω-hydroxylation activity on different fatty acids that may be cloned into *Candida* are the following: CYP94A1 from *Vicia sativa* (Tijet et al., 1988, Biochemistry Journal 332, 583-589); CYP 94A5 from *Nicotiana tabacum* (Le Bouquin et al., 2001, Eur J Biochem 268, 3083-3090); CYP78A1 from *Zea mays* (Larkin, 1994, Plant Mol Biol 25, 343-353); CYP 86A1 (Benveniste et al., 1998, Biochem Biophys Res Commun 243, 688-693) and CYP86A8 (Wellesen et al., 2001, Proc Natl Acad Sci USA 98, 9694-9699) from *Arabidopsis thaliana*; CYP 92B1 from *Petunia hybrida* (Petkova-Andonova et al., 2002, Biosci Biotechnol Biochem 66, 1819-1828); CYP102A1 (BM-3) mutant F87 from *Bacillus megaterium* (Oliver et al., 1997, Biochemistry 36, 1567-1572); and CYP 4 family from mammal and insect (Hardwick, 2008, Biochem Pharmacol 75, 2263-2275).

A second strategy to obtain efficient hydroxylation (or further oxidation of the hydroxy group to an aldehyde or dicarboxylic acid) of a modified fatty acid is to perform the hydroxylation first and then to expose the hydroxylated fatty acid or aldehyde or dicarboxylic acid to an additional enzyme.

For example incorporating one or more desaturase enzymes into engineered *Candida* would allow the introduction of double bonds into ω-hydroxyl fatty acids or aldehydes or dicarboxylic acids at desired positions. Examples of desaturases with known specificity that may be cloned into *Candida* are the following: $\Delta^4$ desaturase from rat liver microsomes (Savile et al., 2001, J Am Chem Soc 123, 4382-4385), $\Delta^5$ desaturase from *Bacillus subtilis* (Fauconnot and Buist, 2001, Bioorg Med Chem Lett 11, 2879-2881), $\Delta^6$ desaturase from *Tetrahymena thermophila* (Fauconnot and Buist, 2001, J Org Chem 66, 1210-1215), $\Delta^9$ desaturase from *Saccharomyces cerevisiae* (Buist and Behrouzian, 1996, J Am Chem Soc 118, 6295-6296); $\Delta^{11}$ desaturase from *Spodoptera littoralis* (Pinilla et al., 1999, Biochemistry 38, 15272-15277), $\Delta^{12}$ desaturase from *Arabidopsis thaliana* (Buist and Behrouzian, 1998, J Am Chem Soc 120, 871-876); $\Delta^{15}$ desaturase from *Caenorhabditis elegans* (Meesapyodsuk et al., 2000, Biochemistry 39, 11948-11954). Many other desaturases are known in the literature that can also be expressed in engineered *Candida* strains including *Candida tropicalis* strains to introduce unsaturation at specific sites of fatty acid substrates prior to ω-hydroxylation or to catalyze carbon-carbon double bond formation after ω-hydroxylation of fatty acids.

Expression in engineered *Candida* strains of P450 enzymes that are known in the literature to introduce additional internal hydroxylation at specific sites of fatty acids or ω-hydroxyfatty acids can be used to produce internally oxidized fatty acids or ω-hydroxyfatty acids or aldehydes or dicarboxylic acids. Examples of P450 enzymes with known in-chain hydroxylation activity on different fatty acids that may be cloned into *Candida* are the following: CYP81B1 from *Helianthus tuberosus* with ω-1 to ω-5 hydroxylation (Cabello-Hurtado et al, 1998, J Biol Chem 273, 7260-7267); CYP790C1 from *Helianthus tuberosus* with ω-1 and ω-2 hydroxylation (Kandel et al., 2005, J Biol Chem 280, 35881-35889); CYP726A1 from *Euphorbia lagscae* with epoxidation on fatty acid unsaturation (Cahoon et al., 2002, Plant Physiol 128, 615-624); CYP152B1 from *Sphingomonas paucimobilis* with α-hydroxylation (Matsunaga et al., 2000, Biomed Life Sci 35, 365-371); CYP2E1 and 4A1 from human liver with ω-1 hydroxylation (Adas et al., 1999, J Lip Res 40, 1990-1997); $P450_{BSβ}$ from *Bacillus substilis* with α- and β-hydroxylation (Lee et al., 2003, J Biol Chem 278, 9761-9767); and CYP102A1 (BM-3) from *Bacillus megaterium* with ω-1, ω-2 and ω-3 hydroxylation (Shirane et al., 1993, Biochemistry 32, 13732-13741).

In addition to naturally occurring enzymes, modified enzymes may be added into the host genome. For example enzymes may be altered by incorporating systematically varied sets of amino acid changes, with the resulting changes in phenotypes measured and used to identify sequence changes conferring improved function. See, for example, United States Patent Publications Nos. 20060136184 and 20080050357; Liao et al., 2007, BMC Biotechnol 7, 16; Ehren et al., 2008, Protein Eng Des Sel 21, 699-707 and Heinzelman et al., 2009, Proc Natl Acad Sci USA 106, 5610-5615. Using these methods, modified versions of cytochrome P450s may be obtained with improved ability to oxidise fatty acids of different lengths (for example C6, C7, C8, C9, C10, C11, C12, C13, C14, C15, C16, C17, C18, C19, C20, C21, C22, C23, C24) or different degrees of saturation (for example fatty acids with one carbon-carbon double bond, fatty acids with two carbon-carbon double bonds and fatty acids with three carbon-carbon double bonds) or with unsaturated fatty acids where the unsaturated bond is at different positions relative to the carboxyl group and the ω-position, to hydroxy fatty acids or to dicarboxylic fatty acids. Further, using these methods modified versions of fatty alcohol oxidases or alcohol dehydrogenases may be obtained with improved ability to oxidise hydroxy-fatty acids of different lengths (for example C6, C7, C8, C9, C10, C11, C12, C13, C14, C15, C16, C17, C18, C19, C20, C21, C22, C23, C24) or different degrees of saturation (for example fatty acids with one carbon-carbon double bond, fatty acids with two carbon-carbon double bonds and fatty acids with three carbon-carbon double bonds) or with unsaturated fatty acids where the unsaturated bond is at different positions relative to the carboxyl group and the ω-position. A gene that has been modified by these methods may be made more useful in the genome of the host by amplification, that is by genetic manipulations causing the presence of more than one copy of the gene within the host cell genome and frequently resulting in higher activity of the gene. Expression of one or more additional enzymes may also be used to functionalize the oxidized fatty acid, either the hydroxyl group or more highly oxidized groups such as aldehydes or carboxylic acids Another family of enzymes that can be expressed in the newly engineered *Candida* strains is glycosyltransferases. A prominent example of a glycosyltransferase for this purpose is glycosyltransferase I which is responsible for glycosidically coupling glucose (position C1') to the hydroxyl group of fatty acids in the metabolic pathway towards sophorolipid synthesis. See Van Bogaert et al., 2007, Applied Microbiology and Biotechnology 76, 23-34. Other glycosyl transferases can also be added that further extend the glycosidically bound glucose so that di-, tri- or even longer chain carbohydrate moities are linked to the hydroxyl group of w-hydroxylfatty acids. Resulting products can be used as surfactants. Also, glycosyltransferases with different specificity can be introduced to *Candida* strains including *Candida tropicalis* to allow the glycosidation of w-hydroxylfatty acids to occur with a range of sugar structures. For example, glycosidation can be carried out to transfer galactose or rhamnose specifically to hydroxylfatty acids creating new biobased unsymmetrical bola-amphiphiles.

5.6.1 Chemical Modifications of ω-Hydroxylfatty Acids

Mono- or oligoglycosides can be conjugated to the ω-hydroxyl moiety of ω-hydroxylfatty acids via enzymatic or chemical methods. The result will be biobased unsymmetrical bola-amphiphiles that can be used as surfactants. Typical industrial methods make use of the Fischer synthesis. In such a process the carbohydrate source can be either a polymeric form of glucose such as starch or glucose syrup with low dextrose equivalent (DE), or monomeric glucose. It is well known to those skilled in the art that depending on the type of carbohydrate used, all manufacturing processes for the Fischer synthesis for conjugation of carbohydrates to hydroxyl moieties derived from fatty acids are carried out by either a direct synthesis. See Hill, W. Wuest, J. Wollmann, M. Biermann, H. Rossmaier, R. Eskuchen, A. Bruns, G. Hellmann, K. H. Ott, W. Winkle, K. Wollmann (Henkel KGaA), DE-B 3833780, EP-B 0437460, 1988 (Chem. Abstr. 1990, 113, 99889) of by the transacetalization process (M. Biermann, K. Hill, W. Wuest, R. Eskuchen, J. Wollmann, A. Bruns, G. Hellmann, K. H. Ott, W. Winkle, K. Wollmann (Henkel KGaA), DE-B 3723826, EP-B 301298, 1987 (Chem. Abstr. 1989, 110, 195187)).

Ethoxylation of hydroxyfatty acids resulting from the present invention can be performed to form a family of biobased unsymmetrical bola-amphiphiles. Many methods are known to those skilled in the art to perform ethoxylation reactions. In one example, ethoxylation can be performed by adding to hydroxylfatty acids a desired quantity of ethylene oxide, using $HBF_4$ as catalyst and carrying out reactions in a high-pressure stainless steel Parr reactor at 35 to 45° C. See Ionescu et al., 2007, *J Polym Environ* 15, 237-243.

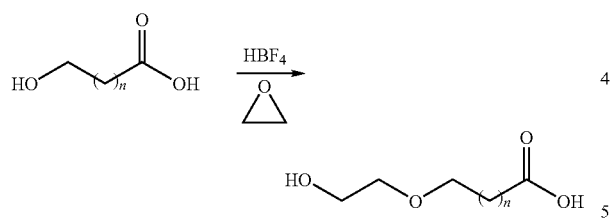

Various esters of hydroxyfatty acids described herein can be prepared by methods that are well known to those skilled in the art. For example, ester formation can be catalyzed by a lipase using an excess of an alcohol such as ethanol, propanol, and butanol.

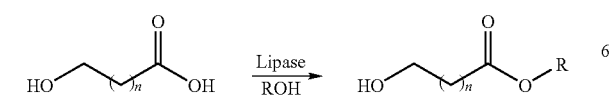

Hydroxyfatty acid amides can be synthesized from hydroxyl fatty acids or their esters by reactions with a wide range of primary and secondary amines, hydroxylamine, and amino acids following methods known to those skilled in the art. Representative examples of fatty acid derivatives include, but are not limited to, stearamide (Hofmann, 1882, Chem. Ber. 15, 977), isobutyl alkanamides (Kim et al., 2007, Org. Lett. 9, 1157), laurohydroxamic acid (Inoue and Hansaburo, 1940, J. Agr. Chem. Soc. Japan 16, 504), and hydroxyethyl tallowate (Feairheller et al., 1994, J. Am. Oil. Chem. Soc. 71, 863).

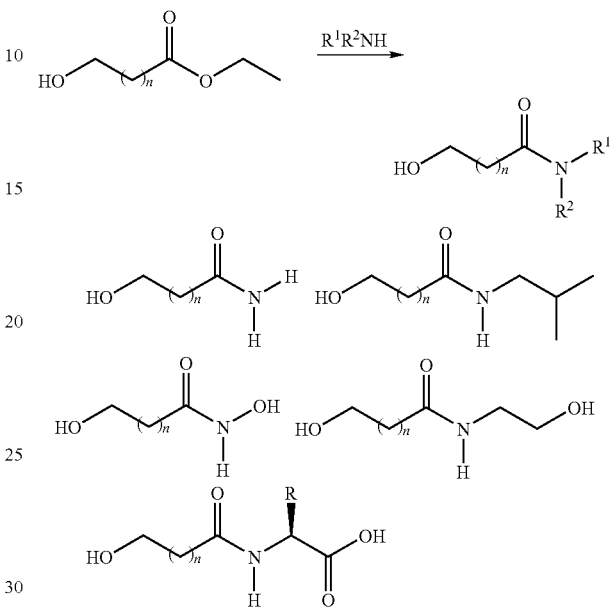

In another example, hydroxyl groups of ω-hydroxylfatty acids described herein can be acrylated or maleinized following methods known to those skilled in the art. A representative method for these chemical transformations is described by Khot et al., 2001, J. Polym. Sci., Part A: Polym. Chem. 82, 703-723. The products of such reactions can be used to prepare composite materials with glass fibers as well as natural flax and hemp fibres. Alternatively, these products can be copolymerized with a variety of vinyl monomers such as styrene and methylmethacrylate.

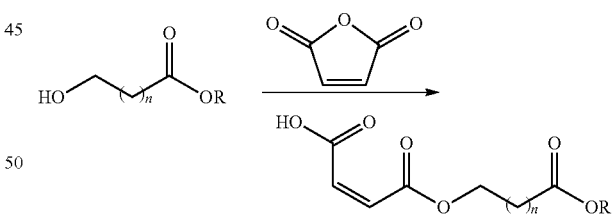

Terminal alkenoic acids can be synthesized from w-hydroxylfatty acids by dehydration. A representative method for this transformation yields linoleic acid from ricinoleic acid is described in Villeneuve et al., 2005, M. J. Am. Oil. Chem. Soc. 82, 261.

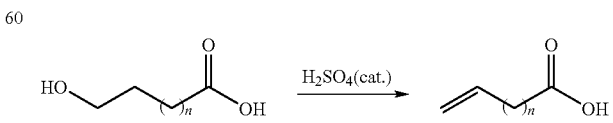

Unsaturated hydroxylfatty acids synthesized by the recombinant *Candida* strains described herein can be further modified as follows. Maleic anhydride in an ene reaction can be used to introduce a maleate residue by following literature methods (Eren et al., 2003, J. Appl. Polym. Sci. 90, 197-202). The resulting maleinized hydroxylfatty acids are $AB_2$ monomers that can be polymerized by condensation methods to obtain soft, flexible solids or viscous oily polymers.

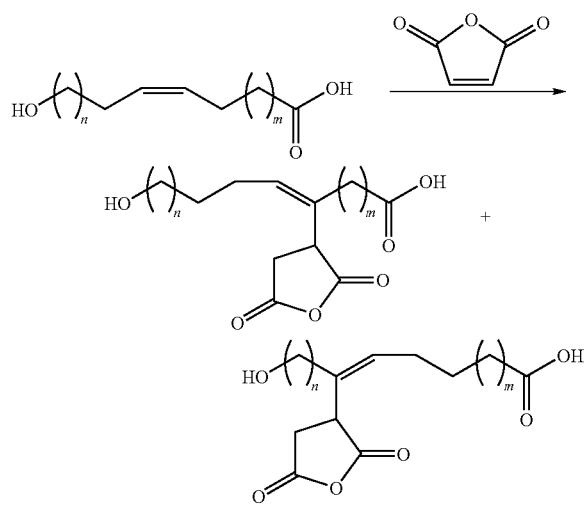

Several methods are well known to those skilled in the art for oxidative conversions of carbon-carbon double bonds. For example, ozonolysis can be used to convert unsaturated hydroxyl fatty acids to a mixture of diacids and ω-hydroxylalkanoic acids where the chain length of these products will be dependent on the position of the double bond

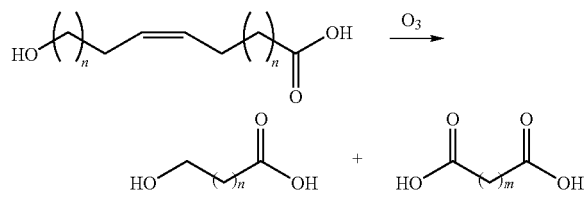

Metathesis is an alternative approach to convert double bonds present in ω-hydroxyl unsaturated fatty acid derivatives to polymerizable monomers (Warwel et al., 200, Ind. Crops Prod. 20, 301-309). For example, metathetical ethenolysis of hydroxylfatty acids will result in a mixture of heterobifunctional compounds containing both terminal double bond and carboxyl moieties or double bond and carboxylic acid groups. For additional possibilities for chemical conversions of unsaturated groups within hydroxylfatty acids, review articles are available. See, for example, Mol, 2004, Top. Catal. 27, 97-104.

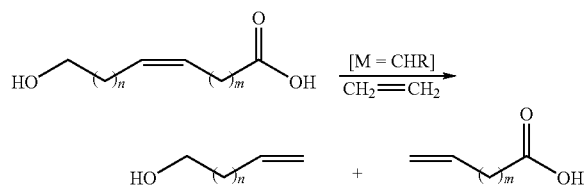

Epoxidation of unsaturated hydroxylfatty acid double bonds can be achieved by reaction with, e.g., molecular oxygen, hydrogen peroxide as well as by chemo-enzymatic reactions. See, for example, Biermann et al., 2000, Angew. Chem., Int. Ed. 39, 2206-2224. Epoxidized hydroxyfatty acids or esters can be converted to carbonated derivatives that contain five membered ring cyclic carbonates by reaction with carbon dioxide in the presence of tetrabutylammonium bromide as catalyst at 110° C. in high yield. Resulting cyclic carbonates can be reacted with di- or tri-primary amines to give corresponding nonisocyanate urethane bonds. See, for example, Tamami et al., 2004, J. Appl. Polym. Sci. 92, 883-891.

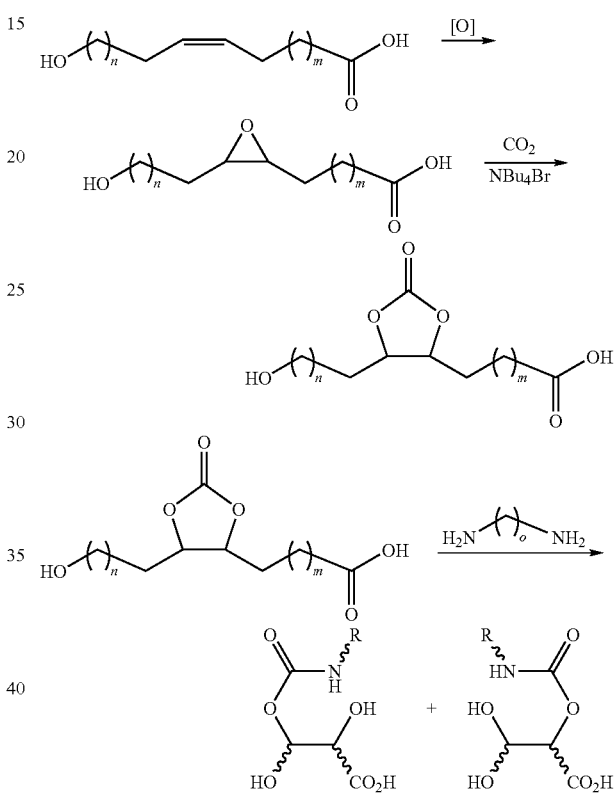

6. BIOTRANSFORMATION EXAMPLES

The following examples are set forth so as to provide those of ordinary skill in the art with a complete description of how to practice, make and use exemplary embodiments of the disclosed methods, and are not intended to limit the scope of what is regarded as the invention.

6.1 General Biotransformation Procedure in Shake-Flask

*C. tropicalis* ATCC20962 from fresh agar plate or glycerol stock was precultured in 30 ml YPD medium consisting of (g $1^{-1}$): yeast extract, 10; peptone, 10; glucose, 20 and shaken at 250 rpm, 30° for 20 hours in 500 ml flask. After 16 hours of cultivation at 250 rpm, 30° C., preculture was inoculated at 10% (v/v) to 30 ml conversion medium consisting of (g $1^{-1}$): peptone, 3; yeast extract, 6; yeast nitrogen base, 6.7; acetic acid, 3; $K_2HPO_4$, 7.2; $KH_2PO_4$ 9.3; glucose/glycerol, 20 in 500 ml flask and shaked at 250 rpm. The initial concentration of substrate was about 10-20 g $1^{-1}$. pH was adjusted to 7.5 by addition of 2 mol 1-1 NaOH solution after 12 hour culture. During biotransformation, concentrated co-substrate (glucose/glycerol/sodium acetate/ethanol) was fed (1-2.5% per day) and pH was maintained at 7.5~8.0 by addition of NaOH solution. Samples were taken on a daily basis to determine levels of product by LC-MS.

6.2 General Biotransformation Procedure in Fermentor

Fermentation was carried out in 3-1 Bioflo3000 fermentor (New Brunswick Scientific Co., USA) in fed-batch culture. The conversion medium mentioned above was used except for addition of 0.05% antifoam 204 (Sigma) and 0.5% substrate. The seed culture from fresh agar plate or glycerol stock was prepared in 50 ml of conversion medium for 20 hours at 30° C., 250 rpm prior to inoculation into the fermentor vessel. Following inoculation, the culture was maintained at pH 6.3 and grown at 30 °, 900 rpm with aeration rate of 1.5 vvm. After 12 hour fermentations (growth phase), biotransformation phase was started with feeding of substrate (2 ml $1^{-1}$). Concentrated glucose (500 g $1^{-1}$) as co-substrate was fed continuously at the rate of 1.2 g 1-1 h-1. During the biotransformation phase, pH was maintained at 7.6 automatically by addition of 4 mol $1^{-1}$ NaOH solution. Antifoam (Antifoam 204) was also added to the fermentor as necessary. Samples were taken on a daily basis to determine levels of product by LC-MS.

6.3 General Extraction and Purification Procedure of Biotransformation Products

The fermentation broth was acidified to pH 1.0 with HCl and extracted twice with diethyl ether. To avoid the epoxy ring-opening during acidification, the fermentation broth with products containing epoxy groups was slowly acidified to pH 3.0 with 5 N HCl. Solvent was evaporated under vacuum with a rotary evaporator. The residual obtained was separated by silica gel column chromatography using silica gel 60. The fractions containing impurities, un-reacted mono fatty acids and products were gradually eluted with a mixture of n-hexane/diethyl ether that their ratio ranges from 90:30 to 10:90. The fractions containing same compound were collected together and the solvents were evaporated under vacuum with a rotary evaporator.

6.4 Synthesis of cis-9,10-Epoxy-1,18-Octadecanoic Acid by Lipase-Mediated Epoxidation of Oleic Acid Cis-9,10-epoxy-1,18-octadecanoic acid was synthesized from oleic acid by the chemo-enzymatic method. The reaction was performed in 50-ml bottom flask containing 0.5 molar oleic acid in 20 milliliters toluene and 300 mg immobilized C. antarctica lipase (Novozym 435). Hydrogen peroxide (30%, w/w) was added stepwise at the rate of 0.5 ml every one hour during the first 4 hours. The reaction mixtures were stirred at 600 rpm and reaction temperature was maintained at 50° C. After an 8 hour reaction, the reaction was terminated and Novozym 435 was removed from solvent by filter. Cis-9,10-epoxy-1, 18-octadecanoic acid was obtained by removing toluene under vacuum with a rotary evaporator.

6.5 General Procedure for Polymer Synthesis Catalyzed by Novozym 435

Reaction was carried out in a parallel synthesizer (Advantage™ 2050, Argonaut) in bulk or in diphenyl ether. Purified functional diacids (1.0 mmol) and 1,8-octanediol or 1,3-propanediol (1.0 mmol) were transferred into reactor tubes in the parallel synthesizer and 10%-by-wt Novozym 435 was added. For homopolymerizaiton, only ω-hydroxy fatty acid (2.0 mmol) was added. Vacuum (2.0 psi) was applied after 2 hours. To follow the progress of polymerizations aliquots were withdrawn at 2, 6, 12, 24, 36 and 48 hours. Reactions were terminated by addition of cooled chloroform and Novozym 435 was removed by filtration. The filtrates were directly analyzed by gel permeation chromatography (GPC) to determine molecular weight averages and polydispersity.

The final product mixtures without precipitation were directly analyzed by $^1$H-NMR.

The reaction was also carried out in toluene in 250 ml round bottom flask. Purified functional diacids (20 mmol) and 1,8-octanediol or 1,3-propanediol (20 mmol) were transferred into flask with 100 ml toluene and 10%-by-wt Novozym 435 was added. Vacuum (2.0 psi) was applied after 2 hours. Reactions were terminated by addition of cooled chloroform and Novozym 435 was removed by filtration. The filtrates were directly analyzed by gel permeation chromatography (GPC) to determine molecular weight averages and polydispersity. The product mixture at the final time point was dissolved in chloroform and then filtered to remove the catalyst. The resulting chloroform solution was slowly added with stirring to methanol to precipitate polymeric product. The precipitated polymer was washed with methanol three times and then dried using vacuum evaporator at 50° C. for the analysis of $^1$H-NMR and thermal properties.

6.6 Production of 1,18-cis-9-Octadecenedioic Acid from Oleic Acid by Biotransformation with C. tropicalis ATCC20962 in Shake-Flask The biotransformation of oleic acid was carried out in 500 ml flask according to the culture condition described in Example 6.1. Glucose was used as co-substrate and initial concentration was 20 g/l. After a 12 hour culture, 20 g/l of oleic acid was added into the culture and pH was adjusted to about 7.5. After a 48 hour biotransformation, oleic acid was largely transformed to the corresponding 1,18-cis-9-octadecenedioic acid which reached 18 g/l. The productivity of the unsaturated diacid was about 0.38 g/l/h. The double bond remained untouched during biotransformation.

6.7 Production of 1,18-cis-9-Octadecenedioic Acid from Oleic Acid by Biotransformation with C. tropicalis ATCC20962 in Fermentor Fermentation was carried out in 3 liter fermentor according to the fermentation conditions described in Example 6.2. The culture was grown at 30° C., and pH 6.3 with aeration at a rate of 2 liters/minute for 12 hours. Conversion was initiated by feeding of oleic acid at the rate of 2 ml/hour. pH was maintained at 7.6 with automatically addition of 4 mol/liter NaOH. Glucose solution was fed at the rate of 1.2 gram/liter/hour. After a 60 hour biotransformation, the concentration of 1,18-cis-9-octadecenedioic acid reached to 31 gram/liter with the productivity of 0.52 gram/liter/hour. The double bond remained untouched during biotransformation.

6.8 Production of 1,22-cis-9-Docosenedioic Acid from Erucic Acid by Biotransformation with C. tropicalis ATCC20962

The biotransformation of erucic acid was carried out in 500 ml flask according to the culture condition described in Example 6.1. Glucose or glycerol was used as co-substrate and initial concentration was 20 gram/liter. After a 12 hour culture, 20 gram/liter of erucic acid was added into the culture and pH was adjusted to about 7.5. After a 72 hour biotransformation, the concentration of 1,22-cis-9-docosenedioic acid reached to 15 gram/liter with the productivity of 0.21 gram/liter/hour. The double bond remained untouched during biotransformation.

6.9 Production of 1,18-cis-9,12-Octadecadienedioic Acid from Linoleic Acid by Biotransformation with C. Tropicalis ATCC20962

The biotransformation of linoleic acid was carried out in 500 ml flask according to the culture condition described in Example 6.1. Glucose was used as co-substrate and initial concentration was 20 gram/liter. After a 12 hour culture, 20 gram/liter of linoleic acid was added into the culture and pH was adjusted to about 7.5. After a 24 hour biotransformation, the concentration of 1,18-cis-9,12-octadecadienedioic acid reached to 7 gram/liter. Thereafter, increase in the fermentation time resulted in decreased diacid concentration. The double bonds remained untouched during biotransformation.

6.10 Production of 12,18-Dihydroxy-cis-9-Octadecenoic Acid and 7-Hydroxy-1,18-cis-9-Octadecenedioic Acid from Ricinoleic Acid by Biotransformation with *C. tropicalis* ATCC20962 in Shaker-Flask Biotransformation of ricinoleic acid was carried out in 500 ml flask according to the culture condition described in Example 6.1. Mixtures of 12,18-dihydroxy-cis-9-octadecenoic acid and 7-hydroxy-1,18-cis-9-octadecenedioic acid were obtained with retention of the secondary hydroxyl group at the 12-position. The ratio of 12,18-dihydroxy-cis-9-octadecenoic acid to 7-hydroxy-1,18-cis-9-octadecenedioic acid was significantly affected by the culture conditions. The conversion rate of ricinoleic acid was greater with increased aeration of cultures that was achieved by using higher shake-flask agitation rates. Cultures performed with relatively higher agitation (250 rpm) rapidly convert 12,18-dihydroxy-cis-9-octadecenoic acid that accumulates in flasks to 7-hydroxy-1,18-cis-9-octadecenedioic acid. After 72 hours, the concentration of 7-hydroxy-1,18-cis-9-octadecenedioic acid reached to 9 g/l. By decreasing the agitation rate in flasks, the ratio of ω-hydroxy to diacid increased. At 150 rpm shaker speed, the molar ratio of these products is 1:1 with a total conversion from ricinoleic acid of 75 mol %. By using glycerol as co-substrate, >90% conversion of ricinoleic acid to 7-hydroxy-1,18-cis-9-octadecenedioic acid was achieved. In contrast, using ethanol as a co-substrate resulted in lower conversion of ricinoleic acid but the major product formed was 12,18-dihydroxy-cis-9-octadecenoic acid that reached to about 5 g/l. The ratio of ω-hydroxy to diacid was also increased by increasing the initial concentration of ricinoleic acid in culture medium.

6.11 Production of 12,18-Dihydroxy-cis-9-Octadecenoic Acid and 7-Hydroxy-1,18-cis-9-Octadecenedioic Acid from Ricinoleic Acid by Biotransformation with *C. tropicalis* ATCC20962 in Fermentor Fermentation was carried out in 3 l fermentor according to the fermentation condition described in Example 6.2. The culture was grown at 30° C., and pH 6.3 for 12 hours. The dissolved oxygen was controlled at 30% and 60%, respectively. At high DO (60%), all ricinoleic acid was converted to 7-hydroxy-1,18-cis-9-octadecenedioic acid and the concentration was about 12 g/l after a 72 hour conversion. A mixture of 12, 18-dihydroxy-cis-9-octadecenoic acid (4.7 g/l) and 7-hydroxy-1, 18-cis-9-octadecenedioic acid (4.9 g/l) was obtained at lower DO (30%). The secondary hydroxyl group remained untouched during biotransformation.

6.12 Production of cis-9,10-Epoxy-1,18-Octadecanedioic Acid from cis-9,10-Epoxy-1,18-Octadecanoic Acid by Biotransformation with *C. tropicalis* ATCC20962 in Shaker-Flask Cis-9,10-epoxy-1,18-octadecanoic acid was synthesized from oleic acid using chemo-enzymatic method according to the procedure described in Example 6.4. Biotransformation of cis-9,10-epoxy-1,18-octadecanoic acid was carried out in 500 ml flask according to the culture condition described in Example 6.1. Glucose was used as co-substrate and initial concentration was 20 gram/liter. After 12 hour culture, 20 gram/liter of cis-9,10-epoxy-1,18-octadecanoic acid was added into the culture and pH was adjusted to about 7.5. After a 72 hour biotransformation, the concentration of cis-9,10-epoxy-1,18-octadecanedioic acid reached to 19.1 gram/liter with the productivity of 0.27 gram/liter/hour. The epoxy group remained untouched during biotransformation.

6.13 Production of 7-Tetradecynedioic Acid from 7-Tetradecyne by Biotransformation with *C. tropicalis* ATCC20962 in Shaker-Flask Experiment Biotransformation of 7-tetradecyne was carried out in 500 ml flasks according to the culture condition described in Example 6.1. Glucose was used as co-substrate and initial concentration was 20 gram/liter. After a 12 hour culture, 20 gram/liter of 7-tetradecyne was added into the culture and pH was adjusted to about 7.5. After a 96 hour biotransformation, the concentration of 7-tetradecynedioic acid reached to 11 gram/liter with the productivity of 0.12 gram/liter/hour. The triple bond remained untouched during biotransformation.

6.14 Production of 8-Hexadecynedioic Acid from 8-Hexadecyne by Biotransformation with *C. tropicalis* ATCC20962 in Shaker-Flask Biotransformation of 8-hexadecyne was carried out in 500 ml flask according to the culture condition described in Example 6.1. Glucose was used as co-substrate and initial concentration was 10 gram/liter. After a 12 hour culture, 20 gram/liter of 8-hexadecyne was added into the culture and pH was adjusted to about 7.5. After a 96 hour biotransformation, the concentration of 8-hexadecynedioic acid reached to 6.5 gram/liter with the productivity of 0.07 gram/liter/hour. The triple bond remained untouched during biotransformation.

6.15 Synthesis of Polyesters Containing Double Bonds from 1, 18-cis-9-Octadecenedioic Acid and 1,8-Octanediol Catalyzed by Novozym 435

Copolymerization of 1,18-cis-9-octadecenedioic acid (ω-carboxyoleic acid, ω-HOOC—OA) with 1,8-octanediol (OD) was carried out in both diphenyl ether and in bulk catalyzed by N435 described in Example 6.5. The reaction temperature was 90° C. The copolymers were successfully synthesized. Molecular weights (Mw) of poly (ω-HOOC—OA-co-OD) were 57,000 (PDI=2.02) at 36 hours and 44,000 (PDI=2.61) at 48 hours in diphenyl ether and in bulk, respectively. $^1$H-NMR results showed double bonds were untouched during polymerization.

Copolymerization of 1,18-cis-9-octadecenedioic acid (ω-carboxyoleic acid, ω-HOOC—OA) with 1,8-octanediol (OD) was also carried out in toluene in round bottom flask catalyzed by N435 described in Example 6.5. The reaction temperature was 90° C. Molecular weight (Mw) and PDI of poly(ω-HOOC—OA-co-OD) were 94,000 and 2.05, respectively.

6.16 Synthesis of Polyesters Containing Double Bonds from 1, 18-cis-9-Octadecenedioic Acid and 1,3-Propanediol Catalyzed by Novozym 435

Copolymerization of 1,18-cis-9-octadecenedioic acid (ω-carboxyoleic acid, ω-HOOC—OA) with 1,3-propanediol (PD) was carried out in both diphenyl ether and in bulk catalyzed by N435 described in Example 6.5. The reaction temperature was 90° C. The copolymers were successfully synthesized. Molecular weights (Mw) of poly(ω-HOOC—OA-co-PD) were 53,000 (PDI=2.32) at 36 hours and 26,000 (PDI=1.75) at 48 hours in diphenyl ether and in bulk, respectively. $^1$H-NMR results showed double bonds were untouched during polymerization.

6.17 Synthesis of Polyesters Containing Double Bonds from 1, 18-cis-9-Octadecenedioic Acid and Glycerol Catalyzed by Novozym 435

Copolymerization of 1,18-cis-9-octadecenedioic acid (ω-carboxyoleic acid, ω-HOOC—OA) with glycerol (GL) was carried out in diphenyl ether described in Example 6.5. After a 36 hour reaction, molecular weight (Mw) of the copolymer, poly(ω-HOOC—OA-co-GL) reached to 29,000 with PDI of 2.17. Double bonds remained untouched during polymerization.

6.18 Synthesis of Polyesters Containing Double Bonds from 1, 22-cis-9-Docosenedioic Acid and 1,8-Octanediol Catalyzed by Novozym 435

Copolymerization of 1,22-cis-9-docosenedioic acid (ω-carboxyerucic acid, ω-HOOC-EA) with 1,8-octanediol (OD) was carried out in both diphenyl ether and in bulk catalyzed by N435 described in Example 6.5. The reaction temperature was 90° C. The copolymers were successfully synthesized. Molecular weights (Mw) of poly(ω-HOOC-EA-co-OD) were 32,000 (PDI=1.95) and 29,000 (PDI=2.14) after 36 hour in diphenyl ether and in bulk, respectively. The double bonds were untouched during polymerization.

6.19 Synthesis of Polyesters Containing Double Bonds and Hydroxyl Groups from 7-Hydroxy-cis-9-Octadecenedioic Acid and 1,8-Octanediol Catalyzed by Novozym 435

Copolymerization of 7-hydroxy-cis-9-octadecenedioic acid (ω-carboxyricinoleic acid, ω-HOOC—RA) and 1,8-octanediol was catalyzed by N435 described in Example 6.5. Copolymer molecular weights for polymerizations in diphenyl ether and in-bulk were 40,000 and 28,000 with PDI (Mw/Mn) of 2.00 and 2.22, respectively. $^{13}$C-NMR analysis of copolymers showed about 7% of polymerization was happed in secondary hydroxyl groups.

6.20 Synthesis of Polyesters Containing Double Bonds and Hydroxyl Groups from 12,18-Dihydroxy-cis-9-Octadecenoic Acid Catalyzed by Novozym 435

Homopolymerization of 12,18-dihydroxy-cis-9-octadecenoic acid (ω-hydroxy ricinoleic acid, ω-HO-RA) was catalyzed by N435 in diphenyl ether described in Example 6.5. The molecular weight increased gradually throughout the 48 hour reaction and reached Mw 67,000 and PDI (Mw/Mn) of 2.30. $^{13}$C-NMR analysis of the polymer showed that the polymerization was both in primary hydroxyl group (864%) and in secondary hydroxyl group (14%).

6.21 Synthesis of Polyesters Containing Epoxy Groups from cis-9,10-Epoxy-1,18-Octadecanedioic Acid and 1,8-Octanediol Catalyzed by Novozym 435

N435-catalyzed copolymerization of cis-9,10-epoxy-1,18-octadecanedioic acid with 1,8-octanediol (OD) to prepare epoxy-functionalized polyesters were conducted both in-bulk and in diphenyl ether described in Example 6.5. The copolymer was successfully synthesized. For N435-catalyzed polymerizations in diphenyl ether, the highest molecular weights (Mw) of poly(ω-HOOC-Epoxy SA-co-OD) were 26,000 with PDI of 2.90. Mw decreased after 36 hour reactions. By performing polymerizations in-bulk, poly(ω-HOOC-Epoxy SA-co-OD) was prepared with Mw and PDI values of 39,000 and 3.10, respectively. $^1$H-NMR results showed epoxy group were untouched during the polymerization.

6.22 Synthesis of Polyesters Containing Epoxy Groups from cis-9,10-Epoxy-1,18-Octadecanedioic Acid and 1,3-Propanediol Catalyzed by Novozym 435

N435-catalyzed copolymerization of cis-9,10-epoxy-1,18-octadecanedioic acid with 1,3-propanediol (PD) to prepare epoxy-functionalized polyesters was conducted in diphenyl ether described in Example 6.5. The highest molecular weights (Mw) of poly(ω-HOOC-Epoxy SA-co-PD) was 73,000 with PDI of 2.99 after a 24 hour reaction.

$^1$H-NMR results showed the epoxy groups were untouched during the polymerization.

6.23 Synthesis of Polyesters Containing Triple Bonds from 7-Tetradecynedioic Acid and 1,8-Octanediol Catalyzed by Novozym 435

Copolymerization of 7-tetradecynedioic acid and 1,8-octanediol was catalyzed by N435 in diphenyl ether described in Example 6.5. The molecular weights (Mw) and PDI values of the resulting polyester were 62,000 and 2.15 after 36 hour reaction, respectively. $^1$H-NMR results showed the triple bond remained untouched during the polymerization.

6.24 Synthesis of Polyesters from 1,18-Octadecanedioic Acid and 1,8-Octanediol Catalyzed by Novozym 435

Copolymerization of 1,18-octadecanedioic acid (ω-carboxystearic acid, ω-HOOC—SA) with 1,8-octanediol (OD) was carried out in toluene in round bottom flask catalyzed by N435 described in Example 6.5. The reaction temperature was 90° C. After 48 hour reaction, the molecular weight and PDI of Poly(ω-HOOC—SA-co-OD) were 76,000 and 2.00, respectively. The resulting saturated polyester was used for the comparison of thermal properties to the polyesters with functional groups.

6.25 Thermal Properties of the Polyesters with Functional Groups

The thermal properties of synthesized polyesters with functional groups were analyzed by thermogravimetric Analysis (TGA) and differential scanning calorimetry (DSC). The details are showed in Table 1.

TABLE 1

Thermal properties of polyesters with functional groups

| Polyester | $M_w$ | $M_w/M_n$ | $T_d$ (° C.)[a] | $T_m$ (° C.)[b] |
|---|---|---|---|---|
| Poly(ω-HOOC-OA-co-OD) | 44,000 | 2.61 | 388 | 23/36 |
| Poly(ω-HOOC-EA-co-OD) | 29,000 | 2.14 | 385 | 35/40 |
| Poly(ω-HOOC-RA-co-OD) | 28,000 | 2.22 | 364 | −0.3/21 |
| Poly(ω-HOOC-Epoxy SA-co-OD) | 39,000 | 3.10 | 381 | 33 |
| Poly(ω-HOOC-SA-co-OD) | 76,000 | 2.00 | 360 | 77/88 |

[a]Data from TGA in nitrogen atmosphere at a heating rate of 10° min$^{-1}$ from 25° to 700°.
[b]Data from DSC based on the second heating run at 10° min$^{-1}$.

7. GENETIC MODIFICATION EXAMPLES

The following examples are set forth so as to provide those of ordinary skill in the art with a description of how to practice, make and use various disclosed exemplary embodiments, and are not intended to limit the scope of what is regarded as the invention.

The strains shown in Table 2 and further described in this section were constructed by the synthesis and cloning of DNA and its subsequent transformation into the appropriate *C. tropicalis* strain. Table 2 summarizes the DNA sequences synthesized and used in these examples. Table 3 summarizes the *C. tropicalis* strains constructed in these examples. Section 7.1 describes the methods used for transformation of *Candida tropicalis*.

TABLE 2

| NAME | SEQ ID NO: | GI No. | SOURCE/ CONSTRUCTION | APPLICATION |
|---|---|---|---|---|
| SAT1 Flipper | 1 | 50059745 | Joachim Morschhauser | Source of the SAT1 Flipper |

TABLE 2-continued

| NAME | SEQ ID NO: | GI No. | SOURCE/ CONSTRUCTION | APPLICATION |
|---|---|---|---|---|
| CYP52A17 | 2 | 29469874 | | Used to design CYP52A17_Δ |
| CYP52A17_Δ | 3 | Not applicable | Gene synthesis | Used to construct CYP52A17::SAT1 |
| CYP52A17::SAT1 | 4 | Not applicable | Subcloning of SAT1 flipper into CYP52A17_Δ | Used to delete CYP52A17 |
| CYP52A13 | 5 | 29469864 | | Used to design CYP52A13_Δ |
| CYP52A13_Δ | 6 | Not applicable | Gene synthesis | Used to construct CYP52A13::SAT1 |
| CYP52A13::SAT1 | 7 | Not applicable | Subcloning of SAT1 flipper into CYP52A13_Δ | Used to delete CYP52A13 |
| CYP52A18 | 8 | 29469876 | | Used to design CYP52A18_Δ |
| CYP52A18_Δ | 9 | Not applicable | Gene synthesis | Used to construct CYP52A18::SAT1 |
| CYP52A18::SAT1 | 11 | Not applicable | Subcloning of SAT1 flipper into CYP52A18_Δ | Used to delete CYP52A18 |
| CYP52A14 | 13 | 29469866 | | Used to design CYP52A14_Δ_Gene#1179 |
| CYP52A14_Δ | 14 | Not applicable | Gene synthesis | Used to construct CYP52A14::SAT1 |
| CYP52A14::SAT1 | 15 | Not applicable | Subcloning of SAT1 flipper into CYP52A14_Δ | Used to delete CYP52A14 |
| FAO1 | 16 | 44194456 | | Used to design FAO1_Δ |
| FAO1_Δ | 17 | Not applicable | Gene synthesis | Used to construct FAO1::SAT1 |
| FAO1::SAT1 | 18 | Not applicable | Subcloning of SAT1 flipper into FAO1_Δ | Used to delete FAO1 |
| FAO1B | 19 | Not applicable | | Used to design FAO1B_Δ |
| FAO1B_Δ | 20 | Not applicable | Assembly PCR. Product not cloned. | Used to construct FAO1B::SAT1 |
| FAO1B::SAT1 | 21 | Not applicable | Ligation of SAT1 flipper to assembly PCR product of FAO1B_Δ | Used to delete FAO1B |
| FAO2A | 22 | 44194479 | | Used to design FAO2A_Δ |
| FAO2A_Δ | 23 | Not applicable | Gene synthesis | Used to construct FAO2A::SAT1 |
| FAO2A::SAT1 | 24 | Not applicable | Subcloning of SAT1 flipper into FAO2A_Δ | Used to delete FAO2A |
| FAO2B | 25 | 44194514 | | Used to design FAO2B_Δ |
| FAO2B_Δ | 26 | Not applicable | Gene synthesis | Used to construct FAO2B::SAT1 |
| FAO2B::SAT1 | 27 | Not applicable | Subcloning of SAT1 flipper into FAO2B_Δ | Used to delete FAO2B |
| CYP52A12 | 28 | 29469862 | | Used to design CYP52A12_Δ |
| CYP52A12_Δ | 29 | Not applicable | Gene synthesis | Used to construct CYP52A12::SAT1 |
| CYP52A12::SAT1 | 30 | Not applicable | Subcloning of SAT1 flipper into CYP52A12_Δ | Used to delete CYP52A12 |
| CYP52A12B | | Not applicable | | Used to design CYP52A12B_Δ |
| CYP52A12B_Δ | 31 | Not applicable | Gene synthesis | Used to construct CYP52A12B::SAT1 |
| CYP52A12B::SAT1 | 32 | Not applicable | Subcloning of SAT1 flipper into CYP52A12B_Δ | Used to delete CYP52A12B |
| ADH-A4 | 39 | Not applicable | | Used to design ADH-A4_Δ |
| ADH-A4_Δ | 44 | Not applicable | Gene synthesis | Used to construct ADH-A4::SAT1 |
| ADH-A4::SAT1 | 45 | Not applicable | Subcloning of SAT1 flipper into ADH-A4_Δ | Used to delete ADH-A4 |
| ADH-A4B | | Not applicable | | Used to design ADH-A4B_Δ |

TABLE 2-continued

| NAME | SEQ ID NO: | GI No. | SOURCE/ CONSTRUCTION | APPLICATION |
|---|---|---|---|---|
| ADH-A4B_Δ | 46 | Not applicable | Gene synthesis | Used to construct ADH-A4B::SAT1 |
| ADH-A4B::SAT1 | 47 | Not applicable | Subcloning of SAT1 flipper into ADH-A4B_Δ | Used to delete ADH-A4B |
| ADH-B4 | 42 | Not applicable | | Used to design ADH-B4_Δ |
| ADH-B4_Δ | 48 | Not applicable | Gene synthesis | Used to construct ADH-B4::SAT1 |
| ADH-B4::SAT1 | 49 | Not applicable | Subcloning of SAT1 flipper into ADH-B4_Δ | Used to delete ADH-B4 |
| ADH-B4B | | Not applicable | | Used to design ADH-B4B_Δ |
| ADH-B4B_Δ | 50 | Not applicable | Gene synthesis | Used to construct ADH-B4B::SAT1 |
| ADH-B4B::SAT1 | 51 | Not applicable | Subcloning of SAT1 flipper into ADH-B4B_Δ | Used to delete ADH-B4B |
| ADH-A10 | 40 | Not applicable | | Used to design ADH-A10_Δ |
| ADH-A10_Δ | 52 | Not applicable | Gene synthesis | Used to construct ADH-A10::SAT1 |
| ADH-A10::SAT1 | 53 | Not applicable | Subcloning of SAT1 flipper into ADH-A10_Δ | Used to delete ADH-A10 |
| ADH-B11 | 43 | Not applicable | | Used to design ADH-B11_Δ |
| ADH-B11_Δ | 54 | Not applicable | Gene synthesis | Used to construct ADH-B11::SAT1 |
| ADH-B11::SAT1 | 55 | Not applicable | Subcloning of SAT1 flipper into ADH-B11_Δ | Used to delete ADH-B11 |
| ADH-A10B | 56 | Not applicable | | Used to design ADH-A10B_Δ |
| ADH-A10B_Δ | 57 | Not applicable | Gene synthesis | Used to construct ADH-A10B::SAT1 |
| ADH-A10B::SAT1 | 58 | Not applicable | Subcloning of SAT1 flipper into ADH-A10B_Δ | Used to delete ADH-A10B |
| ADH-B11B | 59 | Not applicable | | Used to design ADH-B11B_Δ |
| ADH-B11B_Δ | 60 | Not applicable | Gene synthesis | Used to construct ADH-B11B::SAT1 |
| ADH-B11B::SAT1 | 61 | Not applicable | Subcloning of SAT1 flipper into ADH-B11B_Δ | Used to delete ADH-B11B |
| ICL promoter | 62 | Not applicable | Gene synthesis | Used as a component of genomic integration and expression constructs (e.g. SEQ ID NO: 70, SEQ ID NO: 71, SEQ ID NO: 74, etc.) |
| ICL terminator | 63 | Not applicable | Gene synthesis | Used as a component of genomic integration and expression constructs (e.g. SEQ ID NO: 70, SEQ ID NO: 71, SEQ ID NO: 74, etc.) |
| TEF1 promoter | 64 | Not applicable | Gene synthesis | Used as a component of genomic integration and expression constructs (e.g. SEQ ID NO: 70, SEQ ID NO: 71, SEQ ID NO: 74, etc.) |
| EM7 promoter | 65 | Not applicable | Gene synthesis | Used as a component of genomic integration and expression constructs (e.g. SEQ ID NO: 70, SEQ ID NO: 71, SEQ ID NO: 74, etc.) |
| ZeoR | 66 | Not applicable | Gene synthesis of gene optimized for Candida | Used as a component of genomic integration and expression constructs (e.g. SEQ ID NO: 70, SEQ ID NO: 71, SEQ ID NO: 74, etc.) |

TABLE 2-continued

| NAME | SEQ ID NO: | GI No. | SOURCE/ CONSTRUCTION | APPLICATION |
|---|---|---|---|---|
| CYC1 transcription terminator | 67 | Not applicable | Gene synthesis | Used as a component of genomic integration and expression constructs (e.g. SEQ ID NO: 70, SEQ ID NO: 71, SEQ ID NO: 74, etc.) |
| pUC origin of replication | 68 | Not applicable | Gene synthesis | Used as a component of genomic integration and expression constructs (e.g. SEQ ID NO: 70, SEQ ID NO: 71, SEQ ID NO: 74, etc.) |
| CYP52A17 | 69 | Not applicable | Gene synthesis | Cloned into genomic integration and expression constructs to express (e.g. SEQ ID No: 70) |
| pXICL::CYP52A17 | 70 | Not applicable | CYP52A17 cloned into genomic integration vector | Used to express CYP52A17 in *Candida tropicalis* under control of the isocitrate lyase promoter |
| CYP52A13 | 71 | Not applicable | Gene synthesis | Cloned into genomic integration and expression constructs to express(e.g. SEQ ID NO: 71) |
| pXICL::CYP52A13 | 72 | Not applicable | CYP52A13 cloned into genomic integration vector | Used to express CYP52A13 in *Candida tropicalis* under control of the isocitrate lyase promoter |
| CYP52A12 | 73 | Not applicable | Gene synthesis | Cloned into genomic integration and expression constructs to express(e.g. SEQ ID NO: 74) |
| pXICL::CYP52A12 | 74 | Not applicable | CYP52A12 cloned into genomic integration vector | Used to express CYP52A12 in *Candida tropicalis* under control of the isocitrate lyase promoter |
| mCherry | 75 | Not applicable | Gene synthesis | Cloned into genomic integration and expression constructs to express mCherry (e.g. SEQ ID NO: 76) |
| pXICL::mCherry | 76 | Not applicable | mCherry cloned into genomic integration vector | Used to express mCherry in *Candida tropicalis* under control of the isocitrate lyase promoter |

TABLE 3

| STRAIN NAME | GENOTYPE | DESCRIPTION |
|---|---|---|
| DP1 | ura3A/ura3B pox5::ura3A/pox5::ura3A pox4A::ura3A/pox4B::UPA3A | American Type Culture Collection (ATCC 20962) |
| DP65 | DP1 CYP52A17::SAT1 | Electroporation of DP1 with CYP52A17::SAT1 (SEQ ID NO: 4) and selection for nourseothricin resistance followed by PCR screens for targeting construct insertion into CYP52A17 |
| DP78 | DP1 ΔCYP52A17 | Growth of DP65 with maltose followed by agar plate screen for loss of nourseothricin resistance and PCR screen for excision of targeting construct from CYP52A17 |

TABLE 3-continued

| STRAIN NAME | GENOTYPE | DESCRIPTION |
| --- | --- | --- |
| DP107 | DP1 ΔCYP52A17 CYP52A13::SAT1 | Electroporation of DP78 with CYP52A13::SAT1 (SEQ ID NO: 7) and selection for nourseothricin resistance followed by PCR screens for targeting construct insertion into CYP52A13 |
| DP113 | DP1 ΔCYP52A17 ΔCYPS2A13 | Growth of DP107 with maltose followed by agar plate screen for loss of nourseothricin resistance and PCR screen for excision of targeting construct from CYP52A13 |
| DP140 | DP1 ΔCYP52A17/CYP52A18::SAT1 ΔCYP52A13 | Electroporation of DP113 with CYP52A18::SAT1 (SEQ ID NO: 11) and selection for nourseothricin resistance followed by PCR screens for targeting construct insertion into CYP52A18 |
| DP142 | DP1 ΔCYP52A17/ΔCYP52A18 ΔCYP52A13 | Growth of DP140 with maltose followed by agar plate screen for loss of nourseothricin resistance and PCR screen for excision of targeting construct from CYP52A18 |
| DP170 | DP1 ΔCYP52A17/ΔCYP52A18 ΔCYP52A13/CYP52A14::SAT1 | Electroporation of DP142 with CYP52A14::SAT1(SEQ ID NO: 15) and selection for nourseothricin resistance followed by PCR screens for targeting construct insertion into CYP52A14 |
| DP174 | DP1 ΔCYP52A17/ΔCYP52A18 ΔCYP52A13/ΔCYP52A14 | Growth of DP170 with maltose followed by agar plate screen for loss of nourseothricin resistance and PCR screen for excision of targeting construct from CYP52A14 |
| DP182 | DP1 ΔCYP52A17/ΔCYP52A18 ΔCYP52A13/ΔCYP52A14 FAO1::SAT1 | Electroporation of DP174 with FAO1::SAT1(SEQ ID NO: 18) and selection for nourseothricin resistance followed by PCR screens for targeting construct insertion into FAO1 |
| DP186 | DP1 ΔCYP52A17/ΔCYP52A18 ΔCYP52A13/ΔCYP52A14 ΔFCAO1 | Growth of DP182 with maltose followed by agar plate screen for loss of nourseothricin resistance and PCR screen for excision of targeting construct from FAO1 |
| DP201 | DP1 ΔCYP52A17/ΔCYP52A18 ΔCYP52A13/ΔCYP52A14 ΔFAO1 pXICL::CYP52A17 | Electroporation of DP186 with pXICL::CYP52A17 (SEQ ID NO: 70) and selection for zeocin resistance followed by PCR screens for targeting construct insertion into the isocitrate lyase gene |
| DP238 | DP1 ΔCYP52A17/ΔCYP52A18 ΔCYP52A13/ΔCYP52A14 ΔFAO1/FAO1B::SAT1 | Electroporation of DP186 with FAO1B::SAT1(SEQ ID NO: 21) and selection for nourseothricin resistance followed by PCR screens for targeting construct insertion into FAO1B |
| DP240 | DP1 ΔCYP52A17/ΔCYP52A18 ΔCYP52A13/ΔCYP52A14 ΔFAO1/ΔFAO1B | Growth of DP238 with maltose followed by agar plate screen for loss of nourseothricin resistance and PCR screen for excision of targeting construct from FAO1B |
| DP255 | DP1 ΔCYP52A17/ΔCYP52A18 ΔCYP52A13/ΔCYP52A14 ΔFAO1/ΔFAO1B FAO2A::SAT1 | Electroporation of DP240 with FAO2A::SAT1(SEQ ID NO: 21) and selection for nourseothricin resistance followed by PCR screens for targeting construct insertion into FAO2A |

TABLE 3-continued

| STRAIN NAME | GENOTYPE | DESCRIPTION |
|---|---|---|
| DP256 | DP1 ΔCYP52A17/ΔCYP52A18 ΔCYP52A13/ΔCYP52A14 ΔFAO1/ΔFAO1B ΔFAO2A | Growth of DP255 with maltose followed by agar plate screen for loss of nourseothricin resistance and PCR screen for excision of targeting construct from FAO2A |
| DP258 DP259 | DP1 ΔCYP52A17/ΔCYP52A18 ΔCYP52A13/ΔCYP52A14 ΔFAO1/ΔFAO1B ΔFAO2A/FAO2B::SAT1 | Electroporation of DP256 with FAO2B::SAT1(SEQ ID NO: 27) and selection for nourseothricin resistance followed by PCR screens for targeting construct insertion into FAO2B |
| DP261 | DP1 ΔCYP52A17/ΔCYP52A18 ΔCYP52A13/ΔCYP52A14 ΔFAO1/ΔFAO1B ΔFAO2A/ΔFAO2B | Growth of DP259 with maltose followed by agar plate screen for loss of nourseothricin resistance and PCR screen for excision of targeting construct from FAO2B |
| DP268 | DP1 ΔCYP52A17/ΔCYP52A18 ΔCYP52A13/ΔCYP52A14 ΔFAO1/ΔFAO1B ΔFAO2A/ΔFAO2B CYP52A12::SAT1 | Electroporation of DP261 with CYP52A12::SAT1 (SEQ ID NO: 30) and selection for nourseothricin resistance followed by PCR screens for targeting construct insertion into CYP52A12 |
| DP272 | DP1 ΔCYP52A17/ΔCYP52A18 ΔCYP52A13/ΔCYP52A14 ΔFAO1/ΔFAO1B ΔFAO2A/ΔFAO2B ΔCYP52A12 | Growth of DP268 with maltose followed by agar plate screen for loss of nourseothricin resistance and PCR screen for excision of targeting construct from CYP52A12 |
| DP282 | DP1 ΔCYP52A17/ΔCYP52A18 ΔCYP52A13/ΔCYP52A14 ΔFAO1/ΔFAO1B ΔFAO2A/ΔFAO2B ΔCYP52A12/CYP52A12B::SAT1 | Electroporation of DP272 with CYP52A12B::SAT1 (SEQ ID NO: 32) and selection for nourseothricin resistance followed by PCR screens for targeting construct insertion into CYP52A12B |
| DP283 DP284 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B | Growth of DP282 with maltose followed by agar plate screen for loss of nourseothricin resistance and PCR screen for excision of targeting construct from CYP52A12B |
| DP387 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ADH-A4::SAT1 | Electroporation of DP283 with ADH-A4::SAT1(SEQ ID NO: 45) and selection for nourseothricin resistance followed by PCR screens for targeting construct insertion into ADH-A4 |
| DP388 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4 | Growth of DP387 with maltose followed by agar plate screen for loss of nourseothricin resistance and PCR screen for excision of targeting construct from ADH-A4 |
| DP389 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ADH-A4B::SAT1 | Electroporation of DP388 with ADH-A4B::SAT1 (SEQ ID NO: 47) and selection for nourseothricin resistance followed by PCR screens for targeting construct insertion into ADH-A4B |
| DP390 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B | Growth of DP389 with maltose followed by agar plate screen for loss of nourseothricin resistance and PCR screen for excision of targeting construct from ADH-A4B |
| DP397 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ADH-B4::SAT1 | Electroporation of DP390 with ADH-B4::SAT1 (SEQ ID NO: 49) and selection for nourseothricin resistance followed by PCR screens for targeting construct insertion into ADH-B4 |

TABLE 3-continued

| STRAIN NAME | GENOTYPE | DESCRIPTION |
|---|---|---|
| DP398 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4 | Growth of DP397 with maltose followed by agar plate screen for loss of nourseothricin resistance and PCR screen for excision of targeting construct from ADH-B4 |
| DP409 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ADH-B4B::SAT1 | Electroporation of DP398 with ADH-B4B::SAT1 (SEQ ID NO: 49) and selection for nourseothricin resistance followed by PCR screens for targeting construct insertion into ADH-B4B |
| DP411 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B | Growth of DP409 with maltose followed by agar plate screen for loss of nourseothricin resistance and PCR screen for excision of targeting construct from ADH-B4B |
| DP415 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ADH-A10::SAT1 | Electroporation of DP411 with ADH-A10::SAT1 (SEQ ID NO: 53) and selection for nourseothricin resistance followed by PCR screens for targeting construct insertion into ADH-A10 |
| DP416 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 | Growth of DP415 with maltose followed by agar plate screen for loss of nourseothricin resistance and PCR screen for excision of targeting construct from ADH-A10 |
| DP417 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ADH-B11::SAT1 | Electroporation of DP416 with ADH-B11::SAT1 (SEQ ID NO: 55) and selection for nourseothricin resistance followed by PCR screens for targeting construct insertion into ADH-B11 |
| DP421 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 | Growth of DP417 with maltose followed by agar plate screen for loss of nourseothricin resistance and PCR screen for excision of targeting construct from ADH-B11 |
| DP423 DP424 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ADH-A10B::SAT1 ΔADH-B11 | Electroporation of DP421 with ADH-A10B::SAT1 (SEQ ID NO: 58) and selection for nourseothricin resistance followed by PCR screens for targeting construct insertion into ADH-A10B |
| DP427 DP428 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A17 | Electroporation of DP421 with pXICL::CYP52A17 (SEQ ID NO: 70) and selection for zeocin resistance followed by PCR screens for targeting construct insertion into the isocitrate lyase gene |
| DP431 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11 | Growth of DP424 with maltose followed by agar plate screen for loss of nourseothricin resistance and PCR screen for excision of targeting construct from ADH-A10B |

TABLE 3-continued

| STRAIN NAME | GENOTYPE | DESCRIPTION |
|---|---|---|
| DP433 DP434 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11/ADHB11B::SAT1 | Electroporation of DP431 with ADH-B11B::SAT1 (SEQ ID NO: 61) and selection for nourseothricin resistance followed by PCR screens for targeting construct insertion into ADH-B11B |
| DP436 DP437 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11/ΔADHB11B | Growth of DP433 with maltose followed by agar plate screen for loss of nourseothricin resistance and PCR screen for excision of targeting construct from ADH-B11B |
| DP522 DP523 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A13 | Electroporation of DP421 with pXICL::CYP52A13 (SEQ ID NO: 72) and selection for zeocin resistance followed by PCR screens for targeting construct insertion into the isocitrate lyase gene |
| DP526 DP527 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A12 | Electroporation of DP421 with pXICL::CYP52A12 (SEQ ID NO: 74) and selection for zeocin resistance followed by PCR screens for targeting construct insertion into the isocitrate lyase gene |

7.1 General Protocols for Transformation of *Candida*

The protocols described in this section have been performed using *Candida tropicalis*. However it is expected that they will work in the Saccharomycetacaeae Family in general and the *Candida* genus in particular without undue experimentation since the methods rely upon homologous recombination which is found throughout this Family.

7.1.1 Preparation of DNA Targeting Constructs Prior to Integration into *Candida tropicalis*

A linear segment of DNA of the form shown schematically in either FIG. 4 or FIG. 7 was prepared by digesting between 2.5 and 5 μg of the plasmid containing the targeting construct with flanking restriction enzymes, in the examples below the restriction enzyme BsmBI from New England Biolabs was used according to the manufacturer's instructions. The digest was purified using Qiagen's PCR purification kit, eluted in 75 μl of Qiagen's EB buffer (elution buffer) and transformed into *C. tropicalis* by electroporation.

7.1.2 Preparation of Electrocompetent *Candida tropicalis*

The desired *C. tropicalis* strain was densely streaked from a culture stored at −80° C. in growth media (YPD) containing 10% glycerol, onto 2-3 100 mm YPD Agar plates and incubated overnight at 30° C. The next morning 10 ml YPD broth was spread onto the surface of the YPD agar plates and the yeast cells were scraped from the plates with the aid of a sterile glass spreader. Cells (of the same strain) from the 2-3 plates were combined in a 50 ml conical tube, and the $A_{600}$ of a 1:20 dilution determined. Sufficient cells to prepare 50 ml of YPD containing yeast cells at an $A_{600}$ of 0.2 were placed in each of two 50 ml conical tubes and pelleted in a centrifuge for 5 min at 400×g. The cells in each tube were suspended in 10 ml of TE/Li mix (100 mM LiCl, 10 mM Tris-Cl, 1 mM EDTA, pH 7.4). Both tubes were incubated in a shaking incubator for 1 hour at 30° C. and 125 rpm, then 250 μl of 1M DTT was added to each 10 ml cell suspension and incubation continued for a further 30 min at 30° C. and 125 rpm.

The cells were then washed twice in water and once in sorbitol. Sterile, ice-cold purified water (40 ml) was added to each of the cell suspensions which were then centrifuged for 5 min at 400×g at 4° C. and the supernatant decanted off. The cells in each tube were resuspended in 50 ml of sterile, ice-cold purified water, centrifuged for 5 min at 400×g at 4° C., the supernatant decanted off supernatant. The cells in each tube were then resuspended in 25 ml of ice cold 1 M Sorbitol (prepared with purified water) and centrifuged for 5 min at 400×g. The supernatant was decanted from each tube and cells resuspended in the small residual volume of Sorbitol solution (the volume of each suspension was approximately 200 μl). The cell suspensions from both tubes were then pooled, this provided enough cells for 4-8 electroporations. In a 1.5 ml eppendorf tube on ice, 60 μl of cells were mixed with 60 μl (~2.5 μg) of BsmBI digested vector DNA containing the genomic targeting construct. A No DNA Control was prepared for every transformation by mixing cells with Qiagen EB (elution buffer) instead of DNA. The cell-DNA mixtures were mixed with a vortexer and transferred to an ice-cold Bio-Rad 0.2 cm electrode gap Gene Pulser cuvette. The cells were then electroporated at 1.8 kV using a Bio-Rad *E. coli* Pulser, 1 ml of 1M D-Sorbitol was added and the electroporated cells were transferred to a 14 ml culture tube and 1 ml of 2×YPD broth was added. Cells were then rolled on a Roller-drum for 1 hour at 37° C. before spreading 100 ul on 100 mm diameter plates containing YPD Agar+200 μg/ml nourseothricin. Plates were incubated for 2-4 days at 30° C. Large colonies (8-16) were individually streaked onto a YPD Agar plate to purify. A single colony from each streak was patched to a YPD agar stock plate and incubated overnight at 30° C.

7.1.3 Genomic DNA Preparation and PCR Test for Integration of Genomic Targeting Constructs at the Desired Location in *Candida tropicalis*

Between 5 and 30 nourseothricin-resistant isolates were each inoculated into 2 ml of YP Broth and rolled overnight at 30° C. on a Rollerdrum. Genomic DNA from a 0.5 ml sample of each culture was isolated using Zymo Research's YeaStar genomic DNA isolation kit according to the manufacturer's instructions, eluting the DNA in 120 µl of TE, pH 8.0.

For PCR tests, 2.5 µl of the resulting gDNA was used in a 50 ul PCR amplification reaction. As a control for each analysis, genomic DNA was prepared from the parental strain that was transformed with the targeting construct. Oligonucleotide primers for PCR analysis were chosen to lie within the targeting construct and/or in the genomic sequence surrounding the desired integration location, as shown for example in FIG. 10. The size of amplicons was used to determine which strain(s) possessed the desired genomic structure. PCR primer sequences and diagnostic amplicon sizes are described for many of the targeting constructs in Section 7.

PCR reaction mixes were prepared containing 5 µl of 10× NEB Standard Taq Buffer, 2.5 µl of dNTP mix (6 mM of each of dATP, dCTP, dGTP, dTTP), 2.5 µl of oligonucleotide primer 1 (10 mM), 2.5 µl of oligonucleotide primer 2 (10 mM), 1 µl of NEB Taq DNA polymerase (5U of enzyme), 2.5 µl of *Candida* gDNA and water to 50 µl. PCR reactions were subjected to the following temperatures for the times indicated to amplify the target DNA:
Step 1: 1.5 min @ 95° C.
Step 2: 30 sec @ 95° C.
Step 3: 30 sec @ 48° C. (or ~5° C. lower than the calculated Tm for the primers as appropriate)
Step 4: 1 min @ 72° C. (or 1 minute per 1 kb for predicted amplicon size)
Step 5: Go to step 2 a further 29 times
Step 6: 2 min @ 72° C.
Step 7: Hold @ 4° C.
Step 8: End
The amplicon sizes were determined by running 5-10 µl of the completed PCR reaction on a 1% Agarose-TBE gel.

7.1.4 Selection and Screen for Isolates having Excised Targeting Constructs from the Genome of *Candida tropicalis*

Strains carrying a genomic targeting construct to be excised were inoculated from a YPD agar stock plate into 2 ml YP (YPD without dextrose) broth+2% maltose in a 14 ml culture tube. The culture tubes were rolled for ~48 hours at 30° C. on a rollerdrum. Growth with maltose induced production of Flp recombinase in the host strain from the integrated targeting construct. The Flp recombinase then acted at Frt sites located near the ends of the targeting construct (between the targeting sequences) to excise the sequences between the Frt sites, including the genes encoding Flp recombinase and conferring nourseothricin resistance. The culture was then diluted in serial 10-fold dilutions from 10-fold to 10,000-fold. Aliquots (100 µl) of 100, 1,000 and 10,000-fold dilutions were spread onto YPD agar plates.

Putative excisants were identified by replica-plating colonies on the YPD agar plates from the dilution series (the most useful plates for this purpose were those with 50-500 colonies) to a YPD agar+200 ug/ml nourseothricin plates and then to a YPD agar plate. Putative excisants were identified as colonies that grow on YPD agar, but not YPD agar+200 ug/ml nourseothricin following overnight incubation at room temperature. Putative excisants were streaked for single colonies to a YPD agar plate and incubated overnight at 30 C. A single isolate of each of the putative excisants is patched to a YPD agar stock plate and incubated overnight at 30° C.

Putative excisants were inoculated from the stock plate to 2 ml of YPD broth in a 14 ml culture tube and rolled overnight at 30° C. on a Rollerdrum. Genomic DNA was prepared from 0.5 ml of the overnight culture using the YeaStar Genomic DNA Isolation Kit from Zymo Research and eluted in 120 ul of TE, pH 8.0. Excision of the targeting construct was tested by PCR as described in 7.1.3.

7.2 Deletion of Cytochrome P450 Genes from *Candida*

The CYP52A type P450s are responsible for ω-hydroxylation of fatty acids in several *Candida* species. See, for example, Craft et al., 2003, Appl Environ Microbiol: 69, 5983-5991; Eschenfeldt et al., 2003, Appl Environ Microbiol 69, 5992-5999; and Ohkuma et al., 1991, DNA Cell Biol 10, 271-82; Zimmer et al., 1995, DNA Cell Biol 14, 619-628; and Zimmer et al., 1996, Biochem Biophys Res Commun 224, 784-789. They have also been implicated in the further oxidation of these ω-hydroxy fatty acids to α,ω-diacids. See Eschenfeldt et al., 2003, Appli. Environ. Microbiol. 69: 5992-5999, which is hereby incorporated by reference herein. In some embodiments it is desirable to engineer one or more CYP52A type P450s in a strain of *Candida* in order to modify the activity or specificity of the P450 enzyme. In some such embodiments it is advantageous to eliminate the activities of one or more CYP52A type P450 enzymes endogenous to the strain. Reasons to delete endogenous P450 enzymes include more accurate determination of the activity and specificity of a P450 enzyme that is being engineered and elimination of P450 enzymes whose activities may interfere with synthesis of the desired product. Strains lacking one or more of their natural CYP52A P450s are within the scope of the disclosed technology. For example in order to obtain a strain of *Candida* species of yeast including *Candida tropicalis* for the production of ω-hydroxy fatty acids, one method is to reduce or eliminate CYP52A type P450s and other enzyme activities within the cell that oxidise ω-hydroxy fatty acids to α,ω-diacids. It is then possible to re-introduce one CYP52A type P450 or other enzyme that performs the ω-hydroxylation of fatty acids, and to engineer it so that its ω-hydroxylation activity is increased relative to its oxidation of ω-hydroxy fatty acids to α,ω-diacids, thereby favoring the production of ω-hydroxy fatty acids over α,ω-diacids.

7.2.1 Deletion of CYP52A17

The sequence of a gene encoding a cytochrome P450 in *Candida tropicalis*, CYP52A17 is given as SEQ ID NO: 2. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A17 pre-targeting construct is given as SEQ ID NO: 3. Not shown in SEQ ID NO: 3 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A17 from the *Candida tropicalis* genome was prepared by digesting the SAT-1 flipper (SEQ ID NO: 1) with restriction enzymes NotI and XhoI, and ligating it into the CYP52A17 pre-targeting construct (SEQ ID NO: 3) from which the 20 bp stuffer had been removed by digestion with restriction enzymes NotI and XhoI. The sequence of the resulting targeting construct for deletion of CYP52A17 is given as SEQ ID NO: 4. This sequence is a specific example of the construct shown generically in FIG. 4: it has nearly 300 base pairs of the genomic sequence of CYP52A17 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 4 but also present in the targeting construct were a selective marker conferring resistance to kanamycin and a bacterial origin of replication, so that the targeting construct can be grown and propagated in *E coli*. The targeting sequences shown in SEQ ID NO: 4 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP65 was prepared by integration of the construct shown as SEQ ID NO: 4 into the genome of strain DP1 (Table 3) at the site of the genomic sequence of the gene for CYP52A17. *Candida tropicalis* strain DP78 was prepared by excision of the targeting construct from the genome of strain DP65, thereby deleting the gene encoding CYP52A17. Integration and deletion of targeting sequence SEQ ID NO: 4, and analysis of integrants and excisants were performed as described in Section 7.1. Sequences of oligonucleotide primers for analysis of strains were:

```
17-IN-L3:
TGGCGGAAGTGCATGTGACACAACG          (SEQ ID NO: 77)

17-IN-R2:
GTGGTTGGTTTGTCTGAGTGGAGAG          (SEQ ID NO: 78)

SAT1-R:
TGGTACTGGTTCTCGGGAGCACAGG          (SEQ ID NO: 79)

SAT1-F:
CGCTAGACAAATTCTTCCAAAAATTTTAGA     (SEQ ID NO: 80)
```

For strain DP65 (integration of SEQ ID NO: 4), PCR with primers 17-IN-L3 and SAT1-R produces a 959 base pair amplicon; PCR with primers SAT1-F and 17-IN-R2 produces a 922 base pair amplicon. PCR with primers 17-IN-L3 and 17-IN-R2 from a strain carrying a wild type copy of CYP52A17 produces a 2,372 bae pair amplicon. For strain DP78, with a deleted copy of CYP52A17, PCR with primers 17-IN-L3 and 17-IN-R2 produces a 1,478 base pair amplicon.

7.2.2 Deletion of CYP52A13

The sequence of a gene encoding a cytochrome P450 in *Candida tropicalis*, CYP52A13 is given as SEQ ID NO: 5. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A13 pre-targeting construct is given as SEQ ID NO: 6. Not shown in SEQ ID NO: 6 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A13 from the *Candida tropicalis* genome was prepared by digesting the SAT-1 flipper (SEQ ID NO: 1) with restriction enzymes NotI and XhoI, and ligating it into the CYP52A13 pre-targeting construct (SEQ ID NO: 6) from which the 20 bp stuffer had been removed by digestion with restriction enzymes NotI and XhoI. The sequence of the resulting targeting construct for deletion of CYP52A13 is given as SEQ ID NO: 7. This sequence is a specific example of the construct shown generically in FIG. 4: it has nearly 300 base pair of the genomic sequence of CYP52A13 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 7 but also present in the targeting construct were a selective marker conferring resistance to kanamycin and a bacterial origin of replication, so that the targeting construct can be grown and propagated in *E coli*. The targeting sequences shown in SEQ ID NO: 7 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP107 was prepared by integration of the construct shown as SEQ ID NO: 7 into the genome of strain DP65 (Table 3) at the site of the genomic sequence of the gene for CYP52A13. *Candida tropicalis* strain DP113 was prepared by excision of the targeting construct from the genome of strain DP107, thereby deleting the gene encoding CYP52A13. Integration and deletion of targeting sequence SEQ ID NO: 7, and analysis of integrants and excisants were performed as described in Section 7.1. Sequences of oligonucleotide primers for analysis of strains were:

```
13-IN-L2:
CATGTGGCCGCTGAATGTGGGGCA           (SEQ ID NO: 81)

13-IN-R2:
GCCATTTTGTTTTTTTTTACCCCTCTAACA     (SEQ ID NO: 82)

SAT1-R:
                                   (SEQ ID NO: 79)

SAT1-F:
                                   (SEQ ID NO: 80)
```

For strain DP107 (integration of SEQ ID NO: 7), PCR with primers 13-IN-L2 and SAT1-R produces an 874 base pair amplicon; PCR with primers SAT1-F and 13-IN-R2 produces an 879 base pair amplicon. PCR with primers 13-IN-L2 and 13-IN-R2 from a strain with wild type CYP52A13 produces a 2,259 base pair amplicon. For strain DP113 with a deleted version of CYP52A13 PCR with primers 13-IN-L2 and 13-IN-R2 produces a 1,350 base pair amplicon.

7.2.3 Deletion of CYP52A18

The sequence of a gene encoding a cytochrome P450 in *Candida tropicalis*, CYP52A18 is given as SEQ ID NO: 8. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A18 pre-targeting construct is given as SEQ ID NO: 9. The CYP52A18 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 9 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art. A targeting construct for deletion of CYP52A18 from the *Candida tropicalis* genome was prepared by digesting the SAT-1 flipper (SEQ ID NO: 1) with restriction enzymes NotI and XhoI, and ligating it into the CYP52A18 pre-targeting construct (SEQ ID NO: 9) from which the 20 base pair stuffer had been removed by digestion with restriction enzymes NotI and XhoI. The sequence of the resulting targeting construct for deletion of CYP52A18 is given as SEQ ID NO: 11. This sequence is a specific example of the construct shown generically in FIG. 4: it has nearly 300 base pairs of the genomic sequence of CYP52A18 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 11 but also present in the targeting construct were a selective marker conferring resistance to kanamycin and a bacterial origin of replication, so that the targeting construct can be grown and propagated in *E coli*. The targeting sequences shown in SEQ ID NO: 11 also include a BsmBI restriction site at each end of the construct, so that the final targeting construct can be linearized and optionally separated from the bacterial antibiotic resistance marker and origin of replication prior to transformation into *Candida tropicalis*.

Candida tropicalis strain DP140 was prepared by integration of the construct shown as SEQ ID NO: 11 into the genome of strain DP113 (Table 3) at the site of the genomic sequence of the gene for CYP52A18. *Candida tropicalis* strain DP142 was prepared by excision of the targeting construct from the genome of strain DP140, thereby deleting the gene encoding CYP52A18. Integration and deletion of targeting sequence SEQ ID NO: 11, and analysis of integrants and excisants were performed as described in Section 7.1. Oligonucleotide primers for analysis of strains were:

```
18-IN-L2:
GGAAGTGCATGTGACACAATACCCT      (SEQ ID NO: 83)

18-IN-R2:
GGTGGTTTGTCTGAGTGAGAACGTTTAATT (SEQ ID NO: 84)

SAT1-R:
                               (SEQ ID NO: 79)

SAT1-F:
                               (SEQ ID NO: 80)
```

For strain DP140 (integration of SEQ ID NO: 11), PCR with primers 18-IN-L2 and SAT1-R produces a 676 base pair amplicon; PCR with primers SAT1-F and 18-IN-R2 produces a 605 base pair amplicon. PCR from a strain with a wild type version of CYP52A18 with primers 18-IN-L2 and 18-IN-R2 produces a 2,328 base pair amplicon. For strain DP142 with a deleted version of CYP52A18, PCR with primers 18-IN-L2 and 18-IN-R2 produces an 878 base pair amplicon.

7.2.3 Deletion of CYP52A14

The sequence of a gene encoding a cytochrome P450 in *Candida tropicalis*, CYP52A14 is given as SEQ ID NO: 13. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A14 pre-targeting construct is given as SEQ ID NO: 14. The CYP52A14 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 14 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A14 from the *Candida tropicalis* genome was prepared by digesting the SAT-1 flipper (SEQ ID NO: 1) with restriction enzymes NotI and XhoI, and ligating it into the CYP52A14 pre-targeting construct (SEQ ID NO: 14) from which the 20 bp stuffer had been removed by digestion with restriction enzymes NotI and XhoI. The sequence of the resulting targeting construct for deletion of CYP52A14 is given as SEQ ID NO: 15. This sequence is a specific example of the construct shown generically in FIG. 4: it has nearly 300 base pairs of the genomic sequence of CYP52A14 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 15 but also present in the targeting construct were a selective marker conferring resistance to kanamycin and a bacterial origin of replication, so that the targeting construct can be grown and propagated in *E coli*. The targeting sequences shown in SEQ ID NO: 15 also include a BsmBI restriction site at each end of the construct, so that the final targeting construct can be linearized and optionally separated from the bacterial antibiotic resistance marker and origin of replication prior to transformation into *Candida tropicalis*.

Candida tropicalis strain DP170 was prepared by integration of the construct shown as SEQ ID NO: 15 into the genome of strain DP142 (Table 3) at the site of the genomic sequence of the gene for CYP52A14. *Candida tropicalis* strain DP174 was prepared by excision of the targeting construct from the genome of strain DP170, thereby deleting the gene encoding CYP52A14. Integration and deletion of targeting sequence SEQ ID NO: 15, and analysis of integrants and excisants were performed as described in Section 7.1. Oligonucleotide primers for analysis of strains were:

```
14-IN-L2:
GACGTAGCCGATGAATGTGGGGTGC      (SEQ ID NO: 85)
```

-continued

```
14-IN-R2:
TGCCATTTATTTTTATTACCCCTCTAAAT    (SEQ ID NO: 86)

SAT1-R:
                                 (SEQ ID NO: 79)

SAT1-F:
                                 (SEQ ID NO: 80)
```

For strain DP170 (integration of SEQ ID NO: 15), PCR with primers 14-IN-L2 and SAT1-R produces a 664 base pair amplicon; PCR with primers SAT1-F and 14-IN-R2 produces a 609 base pair amplicon. For a strain with a wild type version of CYP52A14, PCR with primers 14-IN-L2 and 14-IN-R2 produces a 2,234 base pair amplicon. For strain DP174 with a deleted version of CYP52A14, PCR with primers 14-IN-L2 and 14-IN-R2 produces an 870 base pair amplicon.

7.3 Deletion of Fatty Alcohol Oxidase Genes from Candida

As described in Section 8.2, at least one enzyme capable of oxidizing ω-hydroxy fatty acids is present in *Candida tropicalis* in addition to the cytochrome P450 genes encoding CYP52A13, CYP52A14, CYP52A17 and CYP52A18. For the production of incompletely oxidized compounds including ω-hydroxy fatty acids, it is advantageous to reduce or eliminate the further oxidation of incompletely oxidized compounds such as ω-hydroxy fatty acids. Under one aspect, this can be achieved by deleting the genes encoding the oxidizing enzymes from the *Candida tropicalis* genome. Candidate genes for this activity include fatty alcohol oxidase and dehydrogenases as shown in FIG. 14. One class of enzymes known to oxidize hydroxy fatty acids are the fatty alcohol oxidases.

7.3.1 Deletion of FAO1

The sequence of a gene encoding a fatty alcohol oxidase in *Candida tropicalis*, FAO1 is given as SEQ ID NO: 16. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the FAO1 pre-targeting construct is given as SEQ ID NO: 17. The FAO1 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 17 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO1 from the *Candida tropicalis* genome was prepared by digesting the SAT-1 flipper (SEQ ID NO: 1) with restriction enzymes NotI and XhoI, and ligating it into the FAO1 pre-targeting construct (SEQ ID NO: 17) from which the 20 base pair stuffer had been removed by digestion with restriction enzymes NotI and XhoI. The sequence of the resulting targeting construct for deletion of FAO1 is given as SEQ ID NO: 18. This sequence is a specific example of the construct shown generically in FIG. 4: it has nearly 300 base pairs of the genomic sequence of FAO1 at the 5' end and 220 base pairs of the genomic sequence of FAO1 at the 3' end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 18 but also present in the targeting construct were a selective marker conferring resistance to kanamycin and a bacterial origin of replication, so that the targeting construct can be grown and propagated in *E coli*. The targeting sequences shown in SEQ ID NO: 18 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP182 was prepared by integration of the construct shown as SEQ ID NO: 18 into the genome of strain DP174 (Table 3) at the site of the genomic sequence of the gene for FAO1. *Candida tropicalis* strain DP186 was prepared by excision of the targeting construct from the genome of strain DP182, thereby deleting the gene encoding FAO1. Integration and deletion of targeting sequence SEQ ID NO: 18, and analysis of integrants and excisants were performed as described in Section 7.1. Sequences of oligonucleotide primers for analysis of strains were:

```
FAO1-IN-L:
ATTGGCGTCGTGGCATTGGCGGCTC       (SEQ ID NO: 87)

FAO1-IN-R:
TGGGCGGAATCAAGTGGCTT            (SEQ ID NO: 88)

SAT1-R:
                                (SEQ ID NO: 79)

SAT1-F:
                                (SEQ ID NO: 80)
```

For strain DP182 (integration of SEQ ID NO: 18), PCR with primers FAO1-IN-L and SAT1-R produces a 624 base pair amplicon; PCR with primers SAT1-F and FAO1-IN-R produces a 478 base pair amplicon. For a strain with a wild type copy of FAO1, PCR with primers FAO1-IN-L and FAO1-IN-R produces a 2,709 base pair amplicon. For strain DP186 with a deleted copy of FAO1, PCR with primers FAO1-IN-L and FAO1-IN-R produces a 699 base pair amplicon.

7.3.2 Deletion of FAO1B

No sequence had been reported for a second allele for FAO1 (FAO1B) at the time of this work. To identify the allele (BAO1B) we used PCR amplification primers and sequencing primers designed to anneal to the known sequenced allele of FAO1. The primers used were:

```
FAO1_F1; CGTCGACACCCTTATGTTAT      (SEQ ID NO: 89)

FAO1_F2; CGTTGACTCCTATCAAGGACA     (SEQ ID NO: 90)

FAO1_R1; GGTCTTCTCTTCCTGGATAATG    (SEQ ID NO: 91)

FAO1_F3; CCAGCAGTTGTTTGTTCTTG      (SEQ ID NO: 92)

FAO1_R2; AATCCTGTGCTTTGTCGTAGGC    (SEQ ID NO: 93)

FAO1_F4; TCCTTAACAAGAAGGGCATCG     (SEQ ID NO: 94)

FAO1_R3; TTCTTGAATCCGGAGTTGAC      (SEQ ID NO: 95)

FAO1_F5; TCTTAGTCGTGATACCACCA      (SEQ ID NO: 96)
```

```
FAO1_R4; CTAAGGATTCTCTTGGCACC          (SEQ ID NO: 97)

FAO1_R5; GTGACCATAGGATTAGCACC          (SEQ ID NO: 98)
```

Genomic DNA was prepared from strains DP1 (which has FAO1) and DP186 (which is deleted for FAO1) as described in section 7.1.3. The FAO genes were amplified from genomic DNA by PCR using oligonucleotide primers FAO1_F1 and FAO1_R5. Genomic DNA from both strains yielded an amplicon of approximately 2 kilobases. Both amplicons were directly sequenced using the ten oligonucleotide primers listed above. The amplicon from DP1 gave sequence where there were occasionally two bases that appeared to be equally represented. The amplicon from DP186 had no such ambiguous bases but its sequence was slightly different (~95% identical) from the reported sequence of FAO1. We concluded that the sequence corresponded to a second allele of FAO1, which we refer to as FAO1B. The sequence of FAO1B is given as SEQ ID NO: 19.

This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the FAO1B pre-targeting construct is given as SEQ ID NO: 20.

A targeting construct for deletion of FAO1 from the *Candida tropicalis* genome was prepared by digesting the SAT-1 flipper (SEQ ID NO: 1) with restriction enzymes NotI and XhoI, and ligating it into the FAO1B pre-targeting construct (SEQ ID NO: 20) that had also been digested with restriction enzymes NotI and XhoI. the FAO1B pre-targeting construct (SEQ ID NO: 20) was not cloned or propagated in a bacterial host, so digestion with restriction enzymes NotI and XhoI produced two fragments which were then ligated with the digested SAT-1 flipper to produce a targeting construct for deletion of FAO1B, given as SEQ ID NO: 21. This sequence is a specific example of the construct shown generically in FIG. 4: it has nearly 300 base pairs of the genomic sequence of FAO1B at the 5' end and 220 base pairs of the genomic sequence of FAO1B at the 3' end to serve as a targeting sequence; between the targeting sequences are two frt sites that are recognized by the flp recombinase; between the two frt sites are sequences encoding the flp recombinase and a protein conferring resistance to the antibiotic nourseothricin.

*Candida tropicalis* strain DP238 was prepared by integration of the construct shown as SEQ ID NO: 21 into the genome of strain DP186 (Table 3) at the site of the genomic sequence of the gene for FAO1B. *Candida tropicalis* strain DP240 was prepared by excision of the targeting construct from the genome of strain DP238, thereby deleting the gene encoding FAO1B. Integration and deletion of targeting sequence SEQ ID NO: 21, and analysis of integrants and excisants were performed as described in Section 7.1. Sequences of oligonucleotide primers for analysis of strains were, FAO1_F1 (SEQ ID NO: 89), FAO1_R5 (SEQ ID NO: 98), SAT1-R (SEQ ID NO: 79), SAT1-F (SEQ ID NO: 80).

For strain DP182 (integration of SEQ ID NO: 18), PCR with primers FAO1_F1 and SAT1-R produces a 558 base pair amplicon; PCR with primers SAT1-F and FAO1_R5 produces a 557 base pair amplicon. For a strain with a wild type copy of FAO1B, PCR with primers FAO1_F1 and FAO1_R5 produces a 2,007 base pair amplicon. For strain DP186, with a deleted copy of FAO1B, PCR with primers FAO1_F1 and FAO1_R5 produces a 711 base pair amplicon.

7.3.3 Deletion of FAO2A

The sequence of a gene encoding a fatty alcohol oxidase in *Candida tropicalis*, FAO2A is given as SEQ ID NO: 22. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the FAO2A pre-targeting construct is given as SEQ ID NO: 23. Not shown in SEQ ID NO: 23 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO2A from the *Candida tropicalis* genome was prepared by digesting the SAT-1 flipper (SEQ ID NO: 1) with restriction enzymes NotI and XhoI, and ligating it into the FAO2A pre-targeting construct (SEQ ID NO: 23) from which the 20 bp stuffer had been removed by digestion with restriction enzymes NotI and XhoI. The sequence of the resulting targeting construct for deletion of FAO2A is given as SEQ ID NO: 24. This sequence is a specific example of the construct shown generically in FIG. 4: it has nearly 300 base pair of the genomic sequence of FAO2A at the 5' and 3' ends of the structural gene to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 24 but also present in the targeting construct were a selective marker conferring resistance to kanamycin and a bacterial origin of replication, so that the targeting construct can be grown and propagated in *E coli*. The targeting sequences shown in SEQ ID NO: 24 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP255 was prepared by integration of the construct shown as SEQ ID NO: 24 into the genome of strain DP240 (Table 3) at the site of the genomic sequence of the gene for FAO2A. *Candida tropicalis* strain DP256 was prepared by excision of the targeting construct from the genome of strain DP255, thereby deleting most of the coding portion of the gene encoding FAO2A. Integration and deletion of targeting sequence SEQ ID NO: 24, and analysis of integrants and excisants were performed as described in Section 7.1. Sequences of oligonucleotide primers for analysis of strains were:

```
FAO2A-IN-L:
CTTTTCTGATTCTTGATTTTCCCTTTTCAT         (SEQ ID NO: 99)

FAO2A-IN-R:
ATACATCTAGTATATAAGTGTCGTATTTCC         (SEQ ID NO: 100)

SAT1-R:
                                       (SEQ ID NO: 79)

SAT1-F:
                                       (SEQ ID NO: 80)
```

For strain DP255 (integration of SEQ ID NO: 24), PCR with primers FAO2A-IN-L and SAT1-R produces a 581 base pair amplicon; PCR with primers SAT1-F and FAO2A-IN-R produces a 569 base pair amplicon. For a strain with a wild type copy of FAO2A, PCR with primers FAO2A-IN-L and FAO2A-IN-R produces a 2,199 base pair amplicon. For strain DP186 with a deleted copy of FAO2A, PCR with primers FAO2A-IN-L and FAO2A-IN-R produces a 747 base pair amplicon.

7.3.4 Deletion of FAO2B

The sequence of a gene encoding a fatty alcohol oxidase in *Candida tropicalis*, FAO2B is given as SEQ ID NO: 25. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the FAO2B pre-targeting construct is given as SEQ ID NO: 26. Not shown in SEQ ID NO: 26 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO2B from the *Candida tropicalis* genome was prepared by digesting the SAT-1 flipper (SEQ ID NO: 1) with restriction enzymes NotI and XhoI, and ligating it into the FAO2B pre-targeting construct (SEQ ID NO: 26) from which the 20 base pair stuffer had been removed by digestion with restriction enzymes NotI and XhoI. The sequence of the resulting targeting construct for deletion of FAO2B is given as SEQ ID NO: 27. This sequence is a specific example of the construct shown generically in FIG. 4: it has nearly 300 base pairs of the genomic sequence of FAO2B at the 5' and 3' ends of the structural gene to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 27 but also present in the targeting construct were a selective marker conferring resistance to kanamycin and a bacterial origin of replication, so that the targeting construct can be grown and propagated in *E coli*. The targeting sequences shown in SEQ ID NO: 27 also includes a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP259 was prepared by integration of the construct shown as SEQ ID NO: 27 into the genome of strain DP256 (Table 3) at the site of the genomic sequence of the gene for FAO2BA. *Candida tropicalis* strain DP261 was prepared by excision of the targeting construct from the genome of strain DP259, thereby deleting most of the coding region of the gene encoding FAO2B. Integration and deletion of targeting sequence SEQ ID NO: 27, and analysis of integrants and excisants were performed as described in Section 7.1. Sequences of oligonucleotide primers for analysis of strains were:

```
FAO2B-IN-L:
TGCTTTTCTGATTCTTGATCATCCCCTTAG    (SEQ ID NO: 101)

FAO2B-IN-R:
ATACATCTAGTATATAAGTGTCGTATTTCT    (SEQ ID NO: 102)

SAT1-R:
                                  (SEQ ID NO: 79)

SAT1-F:
                                  (SEQ ID NO: 80)
```

For strain DP259 (integration of SEQ ID NO: 27), PCR with primers FAO2B-IN-L and SAT1-R produces a 551 base pair amplicon; PCR with primers SAT1-F and FAO2B-IN-R produces a 571 base pair amplicon. For a strain with a wild type copy of FAO2B, PCR with primers FAO2B-IN-L and FAO2B-IN-R produces a 2,198 base pair amplicon. For strain DP186 with a deleted copy of FAO2B, PCR with primers FAO2B-IN-L and FAO2B-IN-R produces a 719 base pair amplicon.

7.4 Deletion Cytochrome P450 Genes from *Candida*

As described in Section 8.3, at least one enzyme capable of oxidizing ω-hydroxy fatty acids is present in *Candida tropicalis* in addition to the cytochrome P450 genes encoding CYP52A13, CYP52A14, CYP52A17 and CYP52A18 and fatty alcohol oxidase genes FAO1, FAO1B, FAO2A and FAO2B. For the production of incompletely oxidized compounds including ω-hydroxy fatty acids, it is advantageous to reduce or eliminate the further oxidation of incompletely oxidized compounds such as ω-hydroxy fatty acids.

Under one aspect, this can be achieved by deleting the genes encoding the oxidizing enzymes from the *Candida tropicalis* genome. The CYP52A type P450s are responsible for ω-hydroxylation of fatty acids in several *Candida* species. See, for example, Craft et al., 2003, Appl Environ Microbiol 69, 5983-5991; Eschenfeldt et al., 2003, Appl Environ Microbiol 69, 5992-5999; Ohkuma et al., 1991, DNA Cell Biol 10, 271-282; Zimmer et al., 1995, DNA Cell Biol 14, 619-28; and Zimmer et al., 1996, Biochem Biophys Res Commun 224, 784-789. They have also been implicated in the further oxidation of these ω-hydroxy fatty acids to α,ω-diacids. See Eschenfeldt et al., 2003, Appli. Environ. Microbiol. 69, 5992-5999, which is hereby incorporated by reference herein. Another CYP52A type P450 whose expression is induced by fatty acids is CYP52A12.

7.4.1 Deletion of CYP52A12

The sequence of a gene encoding a cytochrome P450 in *Candida tropicalis*, CYP52A12 is given as SEQ ID NO: 28. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and a XhoI restriction site. The targeting sequences were flanked by two BsmBI restriction sites, so that the final targeting construct can be linearized prior to transformation into *Candida tropicalis*. The sequence of the CYP52A12 pre-targeting construct is given as SEQ ID NO: 29. Not shown in SEQ ID NO: 29 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A12 from the *Candida tropicalis* genome was prepared by digesting the SAT-1 flipper (SEQ ID NO: 1) with restriction enzymes NotI and XhoI, and ligating it into the CYP52A12 pre-targeting construct (SEQ ID NO: 29) from which the 20 base pair stuffer had been removed by digestion with restriction enzymes NotI and XhoI. The sequence of the resulting targeting construct for deletion of CYP52A12 is given as SEQ ID NO: 30. This sequence is a specific example of the construct shown generically in FIG. 4: it has nearly 300 base pairs of the genomic sequence of CYP52A12 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 30 but also present in the targeting construct were a selective marker conferring resistance to kanamycin and a bacterial origin of replication, so that the targeting construct can be grown and propagated in E coli. The targeting sequences shown in SEQ ID NO: 30 also include a BsmBI restriction site at each end of the construct, so that the final targeting construct can be linearized and optionally separated from the bacterial antibiotic resistance marker and origin of replication prior to transformation into Candida tropicalis.

Candida tropicalis strain DP268 was prepared by integration of the construct shown as SEQ ID NO: 30 into the genome of strain DP261 (Table 3) at the site of the genomic sequence of the gene for CYP52A12. Candida tropicalis strain DP272 was prepared by excision of the targeting construct from the genome of strain DP268, thereby deleting the gene encoding CYP52A12. Integration and deletion of targeting sequence SEQ ID NO: 30, and analysis of integrants and excisants were performed as described in Section 7.1. Sequences of oligonucleotide primers for analysis of strains were:

```
12-IN-L:
CGCCAGTCTTTCCTGATTGGGCAAG    (SEQ ID NO: 103)

12-IN-R2:
GGACGTTGTCGAGTAGAGGGATGTG    (SEQ ID NO: 104)

SAT1-R:
                             (SEQ ID NO: 79)

SAT1-F:
                             (SEQ ID NO: 80)
```

For strain DP268 (integration of SEQ ID NO: 30), PCR with primers 12-IN-L and SAT1-R produces a 596 base pair amplicon; PCR with primers SAT1-F and 12-IN-R2 produces a 650 base pair amplicon. For a strain with a wild type copy of CYP52A12, PCR with primers 12-IN-L and 12-IN-R2 produces a 2,348 base pair amplicon. For strain DP272 with a deleted copy of CYP52A12, PCR with primers 12-IN-L and 12-IN-R2 produces a 843 base pair amplicon.

7.4.2 Deletion of CYP52A12B

No sequence had been reported for a second allele for CYP52A12 at the time of this work. We reasoned that in a diploid organisms a second allele existed (CYP52A17 and CYP52A18 are an allelic pair and CYP52A13 and CYP52A14 are an allelic pair). To delete the second allele we synthesized a deletion construct based on the CYP52A12 sequence (SEQ ID NO: 28), but designed it so that the targeting sequences were homologous to regions of the CYP52A12 gene that are missing because they have been deleted in strain DP272. First we constructed a "pre-targeting" construct comprising two targeting sequences from near the 5' and 3' ends of the structural gene, but internal to the two sequences used in the design of the targeting construct for the deletion of CYP52A12. The targeting sequences were separated by a sequence, given as SEQ ID NO: 12, comprising a NotI restriction site, a 20 base pair stuffer fragment and a XhoI restriction site. The targeting sequences were flanked by two BsmBI restriction sites, so that the final targeting construct can be linearized prior to transformation into Candida tropicalis. The sequence of the CYP52A12B pre-targeting construct is given as SEQ ID NO: 31. Not shown in SEQ ID NO: 31 but also present in the pre-targeting construct were a selective marker conferring resistance to kanamycin and a bacterial origin of replication, so that the pre-targeting construct can be grown and propagated in E coli. The sequence was synthesized using standard DNA synthesis techniques well known in the art.

A targeting construct for deletion of CYP52A12B from the Candida tropicalis genome was prepared by digesting the SAT-1 flipper (SEQ ID NO: 1) with restriction enzymes NotI and XhoI, and ligating it into the CYP52A12B pre-targeting construct (SEQ ID NO: 31) from which the 20 base pair stuffer had been removed by digestion with restriction enzymes NotI and XhoI. The sequence of the resulting targeting construct for deletion of CYP52A12B is given as SEQ ID NO: 32. This sequence is a specific example of the construct shown generically in FIG. 4: it has nearly 300 base pairs of the genomic sequence of CYP52A12 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 32 but also present in the targeting construct were a selective marker conferring resistance to kanamycin and a bacterial origin of replication, so that the targeting construct can be grown and propagated in E. coli. The targeting sequences shown in SEQ ID NO: 32 also include a BsmBI restriction site at each end of the construct, so that the final targeting construct can be linearized and optionally separated from the bacterial antibiotic resistance marker and origin of replication prior to transformation into Candida tropicalis.

Candida tropicalis strain DP282 was prepared by integration of the construct shown as SEQ ID NO: 32 into the genome of strain DP272 (Table 3) at the site of the genomic sequence of the gene for CYP52A12B. Candida tropicalis strain DP284 was prepared by excision of the targeting construct from the genome of strain DP282, thereby deleting a portion of the coding region of the gene encoding CYP52A12B. Integration and deletion of targeting sequence SEQ ID NO: 32, and analysis of integrants and excisants were performed as described in Section 7.1. Sequences of oligonucleotide primers for analysis of strains were:

```
12-F1:    CTGTACTTCCGTACTTGACC    (SEQ ID NO: 105)

12-R1:    GAGACCTGGATCAGATGAGA    (SEQ ID NO: 106)

SAT1-R:                           (SEQ ID NO: 79)

SAT1-F:                           (SEQ ID NO: 80)
```

Oligonucleotides 12-F1 and 12-R1 are designed to anneal to a part of the genome that is missing in strains with deletions in CYP52A12. In such strains they will thus only be able to anneal to and amplify from the second allele CYP52A12B. For strain DP282 (integration of SEQ ID NO: 32), PCR with primers 12-F1 and SAT1-R produces a 978 base pair amplicon; PCR with primers SAT1-F and 12-R1 produces a 947 base pair amplicon. PCR from a strain with a wild type copy of CYP52A12B with primers 12-F1 and 12-R1 produces a 1,478 base pair amplicon. For strain DP272 with a deleted copy of CYP52A12B, PCR with primers 12-F1 and 12-R1 produces a 505 base pair amplicon.

7.5 Deletion of Alcohol Dehydrogenase Genes from *Candida*

As described in Section 8.4, at least one enzyme capable of oxidizing ω-hydroxy fatty acids is present in *Candida tropicalis* in addition to the cytochrome P450 genes encoding CYP52A13, CYP52A14, CYP52A17, CYP52A18, CYP52A12, CYP52A12B and the fatty alcohol oxidase genes FAO1, FAO1B, FAO2A and FAO2B. For the production of incompletely oxidized compounds including ω-hydroxy fatty acids, it is advantageous to reduce or eliminate the further oxidation of incompletely oxidized compounds such as ω-hydroxy fatty acids. Under one aspect, this can be achieved by deleting the genes encoding the oxidizing enzymes from the *Candida tropicalis* genome. One class of enzymes known to oxidize alcohols is alcohol dehydrogenases.

7.5.1 Identification of *Candida tropicalis* Alcohol Dehydrogenases

The sequences of four alcohol dehydrogenase genes were obtained from the *Candida* Geneome Database in the Department of Genetics at the School of Medicine, Stanford University, Palo Alto, Calif. The sequences of these genes are given as SEQ ID NO: 33, SEQ ID NO: 34, SEQ ID NO: 35 and SEQ ID NO: 36. These sequences were aligned and two degenerate oligonucleotide primers were designed, whose sequences are given as SEQ ID NO: 37 and SEQ ID NO: 38. These two primers were used to PCR amplify from genomic DNA from *Candida tropicalis* strain DP1. The resulting amplicon of ~1,000 base pairs was cloned and 96 independent transformants were picked, plasmid prepared and sequenced using two primers with annealing sites located in the vector reading into the cloning site and two primers designed to anneal to highly conserved sequences within the *Candida albicans* alcohol dehydrogenase sequences:

```
ADH-F:   GTTTACAAAGCCTTAAAGACT    (SEQ ID NO: 107)

ADH-R:   TTGAACGGCCAAAGAACCTAA.   (SEQ ID NO: 108)
```

Five different sequences were obtained by sequencing the 96 independent clones, called Ct_ADH-A4, Ct_ADH-A10, Ct_ADH-B2, Ct_ADH-B4 and Ct_ADH-B11. These sequences are provided as SEQ ID NO: 39, SEQ ID NO: 40, SEQ ID NO: 41, SEQ ID NO: 42 and SEQ ID NO: 43 respectively. In silico translation of Ct_ADH-B2 (SEQ ID NO: 41) yielded an amino acid sequence with multiple in-frame stop codons, so it is almost certainly a pseudogene and does not encode a functional protein. The other four sequences all encode protein sequences without stop codons. The sequence relationships of these protein sequences are shown in a phylogenetic tree in FIG. 17. Ct_ADH-A4, encoded by SEQ ID NO: 39, is most homologous to *Candida albicans* ADH1A and Ct_ADH-B4, encoded by SEQ ID NO: 42, is most homologous to *Candida albicans* ADH2A.

The four coding sequences were sufficiently dissimilar for us to conclude that they were not allelic pairs, but rather represented four different genes, each of which probably had its own allelic partner in the genome. Each of the coding sequences was thus used to design two targeting constructs, similarly to the strategy described for CYP52A12B in Section 7.4.2. The construct for the first allele of each ADH gene used ~200 base pairs at the 5' end and ~200 base pairs at the 3' end as targeting sequences (5'-ADH Out and 3'-ADH Out in FIG. 18). The construct for the second allele used two sections of ~200 base pairs between the first two targeting sequences (5'-ADH In and 3'-ADH in FIG. 18). These sequences will be eliminated by the first targeting construct from the first allele of the gene and will thus serve as a targeting sequence for the second allele of the gene. As described below, this strategy succeeded with two ADH allelic pairs: those for ADH-A4 and ADH-B4. However at the first attempt it was not successful for deletion of the second allele of ADH-A10 or ADH-B11, so the second allele of these genes were isolated, sequenced and those sequences were used to delete the second alleles of ADH-A10 or ADH-B11.

7.5.2 Deletion of ADH-A4

Sequence SEQ ID NO: 39 was used to design a "pre-targeting" construct comprising two targeting sequences from the 5' and 3' end of the ADH-A4 structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A4 pre-targeting construct is given as SEQ ID NO: 44. Not shown in SEQ ID NO: 44 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A4 from the *Candida tropicalis* genome was prepared by digesting the SAT-1 flipper (SEQ ID NO: 1) with restriction enzymes NotI and XhoI, and ligating it into the ADH-A4 pre-targeting construct (SEQ ID NO: 44) from which the 20 bp stuffer had been removed by digestion with restriction enzymes NotI and XhoI. The sequence of the resulting targeting construct for deletion of ADH-A4 is given as SEQ ID NO: 45. This sequence is a specific example of the construct shown generically in FIG. 4: it has nearly 200 base pairs of the genomic sequence of ADH-A4 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 44 but also present in the targeting construct were a selective marker conferring resistance to kanamycin and a bacterial origin of replication, so that the targeting construct can be grown and propagated in *E coli*. The targeting sequences shown in SEQ ID NO: 44 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP387 was prepared by integration of the construct shown as SEQ ID NO: 45 into the genome of strain DP283 (Table 3) at the site of the genomic sequence of the gene for ADH-A4. *Candida tropicalis* strain DP388 was prepared by excision of the targeting construct from the genome of strain DP387, thereby deleting the gene encoding ADH-A4. Integration and deletion of targeting sequence SEQ ID NO: 45, and analysis of integrants and excisants were performed as described in Section 7.1. Sequences of oligonucleotide primers for analysis of strains were:

```
A4-OUT-F:
GAATTAGAATACAAAGATATCCCAGTG      (SEQ ID NO: 109)

A4-OUT-R:
CATCAACTTGAAGACCTGTGGCAAT        (SEQ ID NO: 110)

SAT1-R:
                                 (SEQ ID NO: 79)

SAT1-F:
                                 (SEQ ID NO: 80)
```

For strain DP387 (integration of SEQ ID NO: 45), PCR with primers A4-OUT-F and SAT1-R produces a 464 base pair amplicon; PCR with primers SAT1-F and A4-OUT-R produces a 464 base pair amplicon. PCR from a strain with a wild type copy of ADH-A4 with primers A4-OUT-F and A4-OUT-R produces a 948 base pair amplicon. For strain DP388 with a deleted copy of ADH-A4, PCR with primers A4-OUT-F and A4-OUT-R produces a 525 base pair amplicon.

7.5.3 Deletion of ADH-A4B

No sequence was identified for a second allele for ADH-A4 in the initial set of 96 sequences but we reasoned that in a diploid organism, a second allele existed. To delete the second allele (ADH-A4B) we synthesized a deletion construct based on the ADH-A4 sequence (SEQ ID NO: 39), but designed it so that the targeting sequences were homologous to regions of the ADH-A4 gene that are missing because they have been deleted in strain DP388. First we constructed a "pre-targeting" construct comprising two targeting sequences internal to the two sequences used in the design of the targeting construct for the deletion of ADH-A4. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A4B pre-targeting construct is given as SEQ ID NO: 46. Not shown in SEQ ID NO: 46 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A4B from the *Candida tropicalis* genome was prepared by digesting the SAT-1 flipper (SEQ ID NO: 1) with restriction enzymes NotI and XhoI, and ligating it into the ADH-A4B pre-targeting construct (SEQ ID NO: 46) from which the 20 base pair stuffer had been removed by digestion with restriction enzymes NotI and XhoI. The sequence of the resulting targeting construct for deletion of ADH-A4B is given as SEQ ID NO: 47. This sequence is a specific example of the construct shown generically in FIG. 4: it has nearly 200 base pairs of the genomic sequence of ADH-A4B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 47 but also present in the targeting construct were a selective marker conferring resistance to kanamycin and a bacterial origin of replication, so that the targeting construct can be grown and propagated in *E coli*. The targeting sequences shown in SEQ ID NO: 47 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP389 was prepared by integration of the construct shown as SEQ ID NO: 47 into the genome of strain DP388 (Table 3) at the site of the genomic sequence of the gene for ADH-A4B. *Candida tropicalis* strain DP390 was prepared by excision of the targeting construct from the genome of strain DP389, thereby deleting a portion of the coding region of the gene encoding ADH-A4B. Integration and deletion of targeting sequence SEQ ID NO: 47, and analysis of integrants and excisants were performed as described in Section 7.1. Sequences of oligonucleotide primers for analysis of strains were:

```
A4-IN-F:
GAACGGTTCCTGTATGTCCTGTGAGTT      (SEQ ID NO: 111)

A4-IN-R:
CGGATTGGTCAATGGCTTTTTCGGAA       (SEQ ID NO: 112)

SAT1-R:
                                 (SEQ ID NO: 79)

SAT1-F:
                                 (SEQ ID NO: 80)
```

Oligonucleotides A4-IN-F and A4-IN-R are designed to anneal to a part of the genome that is missing in strains with deletions in ADH-A4. In such strains they will thus only be able to anneal to and amplify from the second allele ADH-A4B. For strain DP389 (integration of SEQ ID NO: 47), PCR with primers A4-IN-F and SAT1-R produces a 462 base pair amplicon; PCR with primers SAT1-F and A4-IN-R produces a 462 base pair amplicon. PCR from a strain with a wild-type copy of ADH-A4B with primers A4-IN-F and A4-IN-R produces a 488 base pair amplicon. For strain DP390 with a deleted copy of ADH-A4B, PCR with primers A4-IN-F and A4-IN-R produces a 521 base pair amplicon. The amplicons with primers A4-IN-F and A4-IN-R could not distinguish between a strain carrying a wild-type or a deleted copy of ADH-A4B, but digestion of the amplicon with either NotI or XhoI will cleave the amplicon derived from the deleted copy of the gene but not from the wild type, thereby distinguishing between them.

7.5.4 Deletion of ADH-B4

Sequence SEQ ID NO: 42 was used to design a "pre-targeting" construct comprising two targeting sequences from the 5' and 3' end of the ADH-B4 structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the ADH-B4 pre-targeting construct is given as SEQ ID NO: 48. Not shown in SEQ ID NO: 48 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B4 from the *Candida tropicalis* genome was prepared by digesting the SAT-1 flipper (SEQ ID NO: 1) with restriction enzymes NotI and XhoI, and ligating it into the ADH-B4 pre-targeting construct (SEQ ID NO: 48) from which the 20 bp stuffer had been removed by digestion with restriction enzymes NotI and XhoI. The sequence of the resulting targeting construct for deletion of ADH-B4 is given as SEQ ID NO: 49. This sequence is a specific example of the construct shown generically in FIG. 4: it has nearly 200 bp of the genomic sequence of ADH-B4 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 49 but also present in the targeting construct were a selective marker conferring resistance to kanamycin and a bacterial origin of replication, so that the targeting construct can be grown and propagated in E coli. The targeting sequences shown in SEQ ID NO: 49 also include a BsmBI restriction site at each end of the construct, so that the final targeting construct can be linearized and optionally separated from the bacterial antibiotic resistance marker and origin of replication prior to transformation into Candida tropicalis.

Candida tropicalis strain DP397 was prepared by integration of the construct shown as SEQ ID NO: 49 into the genome of strain DP390 (Table 3) at the site of the genomic sequence of the gene for ADH-B4. Candida tropicalis strain DP398 was prepared by excision of the targeting construct from the genome of strain DP397, thereby deleting the gene encoding ADH-B4. Integration and deletion of targeting sequence SEQ ID NO: 49, and analysis of integrants and excisants were performed as described in Section 7.1. Sequences of oligonucleotide primers for analysis of strains were:

```
B4-OUT-F:
AAATTAGAATACAAGGACATCCCAGTT    (SEQ ID NO: 113)

B4-OUT-R:
CATCAACTTGTAGACTTCTGGCAAT      (SEQ ID NO: 114)

SAT1-R:
                               (SEQ ID NO: 79)

SAT1-F:
                               (SEQ ID NO: 80)
```

For strain DP397 (integration of SEQ ID NO: 49), PCR with primers B4-OUT-F and SAT1-R produces a 464 bp amplicon; PCR with primers SAT1-F and B4-OUT-R produces a 464 base pair amplicon. PCR from a strain with a wild type copy of ADH-B4 with primers B4-OUT-F and B4-OUT-R produces a 948 base pair amplicon. For strain DP398 with a deleted copy of ADH-B4, PCR with primers B4-OUT-F and B4-OUT-R produces a 525 base pair amplicon.

7.5.5 Deletion of ADH-B4B

No sequence was identified for a second allele for ADH-B4 in the initial set of 96 sequences but we reasoned that in a diploid organisms a second allele existed. To delete the second allele (ADH-B4B) we synthesized a deletion construct based on the ADH-B4 sequence (SEQ ID NO: 42), but designed it so that the targeting sequences were homologous to regions of the ADH-B4 gene that are missing because they have been deleted in strain DP398. First we constructed a "pre-targeting" construct comprising two targeting sequences internal to the two sequences used in the design of the targeting construct for the deletion of ADH-B4. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into Candida tropicalis. The sequence of the ADH-B4B pre-targeting construct is given as SEQ ID NO: 50. Not shown in SEQ ID NO: 50 but also present in the pre-targeting construct were a selective marker conferring resistance to kanamycin and a bacterial origin of replication, so that the pre-targeting construct can be grown and propagated in E coli. The sequence was synthesized using standard DNA synthesis techniques well known in the art.

A targeting construct for deletion of ADH-B4B from the Candida tropicalis genome was prepared by digesting the SAT-1 flipper (SEQ ID NO: 1) with restriction enzymes NotI and XhoI, and ligating it into the ADH-B4B pre-targeting construct (SEQ ID NO: 50) from which the 20 base pair stuffer had been removed by digestion with restriction enzymes NotI and XhoI. The sequence of the resulting targeting construct for deletion of ADH-B4B is given as SEQ ID NO: 51. This sequence is a specific example of the construct shown generically in FIG. 4: it has nearly 200 bp of the genomic sequence of ADH-B4B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 51 but also present in the targeting construct were a selective marker conferring resistance to kanamycin and a bacterial origin of replication, so that the targeting construct can be grown and propagated in E coli. The targeting sequences shown in SEQ ID NO: 51 also include a BsmBI restriction site at each end of the construct, so that the final targeting construct can be linearized and optionally separated from the bacterial antibiotic resistance marker and origin of replication prior to transformation into Candida tropicalis.

Candida tropicalis strain DP409 was prepared by integration of the construct shown as SEQ ID NO: 51 into the genome of strain DP398 (Table 3) at the site of the genomic sequence of the gene for ADH-B4B. Candida tropicalis strain DP411 was prepared by excision of the targeting construct from the genome of strain DP409, thereby deleting a portion of the coding region of the gene encoding ADH-B4B. Integration and deletion of targeting sequence SEQ ID NO: 51, and analysis of integrants and excisants were performed as described in Section 7.1. Sequences of oligonucleotide primers for analysis of strains were:

```
B4-IN-F:
GAACGGTTCCTGTATGAACTGTGAGTA    (SEQ ID NO: 115)

B4-IN-R:
CAGATTGGTTGATGGCCTTTTCGGAG     (SEQ ID NO: 116)

SAT1-R:
                               (SEQ ID NO: 79)

SAT1-F:
                               (SEQ ID NO: 80)
```

Oligonucleotides B4-IN-F and B4-IN-R are designed to anneal to a part of the genome that is missing in strains with deletions in ADH-B4. In such strains they will thus only be able to anneal to and amplify from the second allele ADH-B4B. For strain DP409 (integration of SEQ ID NO: 51), PCR with primers B4-IN-F and SAT1-R produces a 462 base pair amplicon; PCR with primers SAT1-F and B4-IN-R produces a 462 base pair amplicon. PCR from a strain with a wild-type copy of ADH-B4B with primers B4-IN-F and B4-IN-R produces a 488 base pair amplicon. For strain DP411 with a deleted copy of ADH-B4B, PCR with primers B4-IN-F and B4-IN-R produces a 521 base pair amplicon. The amplicons with primers B4-IN-F and B4-IN-R could not distinguish between a strain carrying a wild-type or a deleted copy of ADH-B4B, but digestion of the amplicon with either NotI or XhoI will cleave the amplicon derived from the deleted copy of the gene but not from the wild type, thereby distinguishing between them.

7.5.6 Deletion of ADH-A10

Sequence SEQ ID NO: 40 was used to design a "pre-targeting" construct comprising two targeting sequences from the 5' and 3' end of the ADH-A10 structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the ADH-A10 pre-targeting construct is given as SEQ ID NO: 52. Not shown in SEQ ID NO: 52 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A10 from the *Candida tropicalis* genome was prepared by digesting the SAT-1 flipper (SEQ ID NO: 1) with restriction enzymes NotI and XhoI, and ligating it into the ADH-A10 pre-targeting construct (SEQ ID NO: 52) from which the 20 base pair stuffer had been removed by digestion with restriction enzymes NotI and XhoI. The sequence of the resulting targeting construct for deletion of ADH-A10 is given as SEQ ID NO: 53. This sequence is a specific example of the construct shown generically in FIG. 4: it has nearly 200 bp of the genomic sequence of ADH-A10 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 53 but also present in the targeting construct were a selective marker conferring resistance to kanamycin and a bacterial origin of replication, so that the targeting construct can be grown and propagated in *E coli*. The targeting sequences shown in SEQ ID NO: 53 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP415 was prepared by integration of the construct shown as SEQ ID NO: 53 into the genome of strain DP411 (Table 3) at the site of the genomic sequence of the gene for ADH-A10. *Candida tropicalis* strain DP416 was prepared by excision of the targeting construct from the genome of strain DP415, thereby deleting the gene encoding ADH-A10. Integration and deletion of targeting sequence SEQ ID NO: 53, and analysis of integrants and excisants were performed as described in Section 7.1. Sequences of oligonucleotide primers for analysis of strains were:

```
A10-OUT-F:
AAGTTAGAATACAAAGACGTGCCGGTC    (SEQ ID NO: 117)

A10-OUT-R:
CATCAAGTCAAAAATCTCTGGCACT      (SEQ ID NO: 118)
```

-continued
```
SAT1-R:
                               (SEQ ID NO: 147)
SAT1-F:
                               (SEQ ID NO: 80)
```

For strain DP415 (integration of SEQ ID NO: 49), PCR with primers A10-OUT-F and SAT1-R produces a 464 base pair amplicon; PCR with primers SAT1-F and A10-OUT-R produces a 464 base pair amplicon. PCR from a strain with a wild type copy of ADH-A10 with primers A10-OUT-F and A10-OUT-R produces a 948 base pair amplicon. For strain DP416 with a deleted copy of ADH-A10, PCR with primers A10-OUT-F and A10-OUT-R produces a 525 base pair amplicon.

7.5.6 Deletion of ADH-B11

Sequence SEQ ID NO: 43 was used to design a "pre-targeting" construct comprising two targeting sequences from the 5' and 3' end of the ADH-B11 structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-B11 pre-targeting construct is given as SEQ ID NO: 54. Not shown in SEQ ID NO: 54 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B11 from the *Candida tropicalis* genome was prepared by digesting the SAT-1 flipper (SEQ ID NO: 1) with restriction enzymes NotI and XhoI, and ligating it into the ADH-B11 pre-targeting construct (SEQ ID NO: 54) from which the 20 base pair stuffer had been removed by digestion with restriction enzymes NotI and XhoI. The sequence of the resulting targeting construct for deletion of ADH-B11 is given as SEQ ID NO: 55. This sequence is a specific example of the construct shown generically in FIG. 4: it has nearly 200 base pair of the genomic sequence of ADH-B11 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 55 but also present in the targeting construct were a selective marker conferring resistance to kanamycin and a bacterial origin of replication, so that the targeting construct can be grown and propagated in *E coli*. The targeting sequences shown in SEQ ID NO: 53 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP417 was prepared by integration of the construct shown as SEQ ID NO: 55 into the genome of strain DP416 (Table 3) at the site of the genomic sequence of the gene for ADH-B11. *Candida tropicalis* strain DP421 was prepared by excision of the targeting construct from the genome of strain DP417, thereby deleting the gene encoding ADH-B11. Integration and deletion of targeting sequence SEQ ID NO: 55 and analysis of integrants and excisants were performed as described in Section 7.1. Sequences of oligonucleotide primers for analysis of strains were:

```
B11-OUT-F:
CCATTGCAATACACCGATATCCCAGTT    (SEQ ID NO: 119)

B11-OUT-R:
CAACAATTTGAAAATCTCTGGCAAT      (SEQ ID NO: 120)

SAT1-R:
                               (SEQ ID NO: 79)

SAT1-F:
                               (SEQ ID NO: 80)
```

For strain DP417 (integration of SEQ ID NO: 49), PCR with primers B11-OUT-F and SAT1-R produces a 464 base pair amplicon; PCR with primers SAT1-F and B11-OUT-R produces a 464 base pair amplicon. PCR from a strain with a wild type copy of ADH-B11 with primers B11-OUT-F and B11-OUT-R produces a 948 base pair amplicon. For strain DP421 with a deleted copy of ADH-B11, PCR with primers B11-OUT-F and B11-OUT-R produces a 525 base pair amplicon.

7.5.7 Deletion of ADH-A10B

No sequence was identified for a second allele for ADH-A10 in the initial set of 96 sequences but we reasoned that in a diploid organism a second allele existed. At our first attempt we were unable to delete the second allele (ADH-A10B) using the strategy described for ADH-A4B and ADH-B4B. We used the primers A10-IN-F and A10-IN-R

```
A10-IN-F:
GAATGGTTCGTGTATGAACTGTGAGTT    (SEQ ID NO: 121)

A10-IN-R:
CCGACTGGTTGATTGCCTTTTCGGAC     (SEQ ID NO: 122)
``` to amplify an ~500 base pair amplicon from genomic DNA from strain DP415 which has the SAT1-flipper inserted into the first ADH-A10 allele, preventing it from amplifying with these primers. The amplicon was cloned and sequenced, the sequence is given as SEQ ID NO: 56.

We constructed a "pre-targeting" construct comprising two targeting sequences based on SEQ ID NO: 56. A single mutation was introduced into the sequence obtained as SEQ ID NO: 56: a G at position 433 was mutated to a C to destroy an unwanted BsmBI site. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A10B pre-targeting construct is given as SEQ ID NO: 57. Not shown in SEQ ID NO: 57 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A10B from the *Candida tropicalis* genome was prepared by digesting the SAT-1 flipper (SEQ ID NO: 1) with restriction enzymes NotI and XhoI, and ligating it into the ADH-A10B pre-targeting construct (SEQ ID NO: 57) from which the 20 bp stuffer had been removed by digestion with restriction enzymes NotI and XhoI. The sequence of the resulting targeting construct for deletion of ADH-A10B is given as SEQ ID NO: 58. This sequence is a specific example of the construct shown generically in FIG. 4: it has nearly 200 base pairs of the genomic sequence of ADH-A10B at each end to serve as a targeting sequence; between the targeting sequences are two frt sites that are recognized by the flp recombinase; and between the two frt sites are sequences encoding the flp recombinase and a protein conferring resistance to the antibiotic nourseothricin. Not shown in SEQ ID NO: 58 but also present in the targeting construct were a selective marker conferring resistance to kanamycin and a bacterial origin of replication, so that the targeting construct can be grown and propagated in *E coli*. The targeting sequences shown in SEQ ID NO: 58 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP424 was prepared by integration of the construct shown as SEQ ID NO: 58 into the genome of strain DP421 (Table 3) at the site of the genomic sequence of the gene for ADH-A10B. *Candida tropicalis* strain DP431 was prepared by excision of the targeting construct from the genome of strain DP424, thereby deleting a portion of the coding region of the gene encoding ADH-A10B. Integration and deletion of targeting sequence SEQ ID NO: 58, and analysis of integrants and excisants were performed as described in Section 7.1. Sequences of oligonucleotide primers for analysis of strains were A10-IN-F (SEQ ID NO: 121), A10-IN-R (SEQ ID NO: 122), SAT1-R (SEQ ID NO: 79), and SAT1-F (SEQ ID NO: 80).

Oligonucleotides A10-IN-F and A10-IN-R are designed to anneal to a part of the genome that is missing in strains with deletions in ADH-A10. In such strains they will thus only be able to anneal to and amplify from the second allele ADH-A10B. For strain DP424 (integration of SEQ ID NO: 58), PCR with primers A10-IN-F and SAT1-R produces a 462 base pair amplicon; PCR with primers SAT1-F and A10-IN-R produces a 462 base pair amplicon. PCR from a strain with a wild-type copy of ADH-A10B with primers A10-IN-F and A10-IN-R produces a 488 base pair amplicon. For strain DP431 with a deleted copy of ADH-A10B, PCR with primers A10-IN-F and A10-IN-R produces a 521 base pair amplicon. The amplicons with primers A10-IN-F and A10-IN-R could not distinguish between a strain carrying a wild-type or a deleted copy of ADH-A10B, but digestion of the amplicon with either NotI or XhoI will cleave the amplicon derived from the deleted copy of the gene but not from the wild type, thereby distinguishing between them.

7.5.8 Deletion of ADH-B11B

No sequence was identified for a second allele for ADH-B11 in the initial set of 96 sequences but we reasoned that in a diploid organism a second allele existed. At our first attempt we were unable to delete the second allele (ADH-B11B) using the strategy described for ADH-A4B and ADH-B4B. We used the primers B11-OUT-F and B11-OUT-R:

```
B11-OUT-F
GAATGGTTCGTGTATGAACTGTGAGTT    (SEQ ID NO: 121)

B11-OUT-R
CCGACTGGTTGATTGCCTTTTCGGAC     (SEQ ID NO: 122)
``` to amplify an ~950 base pair amplicon from genomic DNA from strain DP417 which has the SAT1-flipper inserted into the first ADH-B11 allele, preventing it from amplifying with these primers. The amplicon was cloned and sequenced. The sequence is given as SEQ ID NO: 59.

We constructed a "pre-targeting" construct comprising two targeting sequences based on SEQ ID NO: 59. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-B11B pre-targeting construct is given as SEQ ID NO: 60. Not shown in SEQ ID NO: 60 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B11B from the *Candida tropicalis* genome was prepared by digesting the SAT-1 flipper (SEQ ID NO: 1) with restriction enzymes NotI and XhoI, and ligating it into the ADH-B11B pre-targeting construct (SEQ ID NO: 60) from which the 20 base pair stuffer had been removed by digestion with restriction enzymes NotI and XhoI. The sequence of the resulting targeting construct for deletion of ADH-B11B is given as SEQ ID NO: 61. This sequence is a specific example of the construct shown generically in FIG. 4: it has nearly 200 base pair of the genomic sequence of ADH-B11B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 61 but also present in the targeting construct were a selective marker conferring resistance to kanamycin and a bacterial origin of replication, so that the targeting construct can be grown and propagated in *E coli*. The targeting sequences shown in SEQ ID NO: 61 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP433 was prepared by integration of the construct shown as SEQ ID NO: 61 into the genome of strain DP431 (Table 3) at the site of the genomic sequence of the gene for ADH-B11B. *Candida tropicalis* strain DP437 was prepared by excision of the targeting construct from the genome of strain DP433, thereby deleting a portion of the coding region of the gene encoding ADH-B11B. Integration and deletion of targeting sequence SEQ ID NO: 61, and analysis of integrants and excisants were performed as described in Section 7.1. Sequences of oligonucleotide primers for analysis of strains were:

```
B11-OUT-F:
                                    (SEQ ID NO: 119)

B11-IN-R:
CAGACTGGTTGATGGCTTTTTCAGAA          (SEQ ID NO: 123)

SAT1-R:
                                    (SEQ ID NO: 79)

SAT1-F:
                                    (SEQ ID NO: 80)
```

For strain DP433 (integration of SEQ ID NO: 61), PCR with primers B11-OUT-F and SAT1-R produces a 692 base pair amplicon. PCR from a strain with a wild-type copy of ADH-B11B with primers B11-OUT-F and B11-IN-R produces a 718 base pair amplicon. For strain DP437 with a deleted copy of ADH-B11B, PCR with primers B11-OUT-F and B11-IN-R produces a 751 base pair amplicon. The amplicons with primers B11-OUT-F and B11-IN-R could not distinguish between a strain carrying a wild-type or a deleted copy of ADH-B11B, but digestion of the amplicon with either NotI or XhoI will cleave the amplicon derived from the deleted copy of the gene but not from the wild type, thereby distinguishing between them.

7.6 Insertion of P450 Genes into the Genome of *Candida*

To achieve novel phenotypes of *Candida* species of yeast (e.g., *Candida tropicalis*), including (i) biotransformations of compounds by *Candida tropicalis*, (ii) chemical conversions not previously obtained, (iii) increased rates of conversion of one or more substrates to one or more products, (iv) increased specificity of conversion of one or more substrates to one or more products, (v) increased tolerance of a compound by the yeast, and/or (vi) increased uptake of a compound by the yeast, a gene encoding a cytochrome P450 polypeptide is incorporated into the genome of the yeast. Expression of the cytochrome P450 in the yeast then allows the phenotype of the yeast to be modified.

Cytochrome P450s are of particular utility in the hydroxylation of fatty acids. Different cytochrome P450s are known to have different substrate and regiospecificities and different specific activities. It is therefore useful in some embodiments to incorporate a gene encoding a cytochrome P450 into the genome of yeast in which endogenous cytochrome P450s have been disrupted. The exact P450 to be used will depend upon the substrate and the position on the substrate to be hydroxylated. A list of P450 enzymes that have utility in the hydroxylation of substrates when expressed within a yeast cell are given in Table 4. It will be appreciated that as new yeast P450 enzymes are discovered, such cytochrome P450s could be introduced into the yeast disclosed herein in order to achieve new substrate regiospecificities.

TABLE 4

| First Database Accession Number | Second Database Accession Number | Name | Species |
|---|---|---|---|
| gi 29469875 | gb AAO73958.1 | CYP52A17 | Candida tropicalis |
| gi 29469877 | gb AAO73959.1 | CYP52A18 | Candida tropicalis |
| gi 231889 | sp P30610.1 | CP52H_CANTR (Cytochrome P450 52A8) | |
| gi 3913326 | sp Q12586.1 | CP52I_CANMA (Cytochrome P450 52A9) | |
| gi 29469881 | gb AAO73961.1 | CYP52A20 | Candida tropicalis |
| gi 29469879 | gb AAO73960.1 | CYP52A19 | Candida tropicalis |
| gi 3913329 | sp Q12589.1 | CP52K_CANMA (Cytochrome P450 52A11) | |

TABLE 4-continued

| First Database Accession Number | Second Database Accession Number | Name | Species |
|---|---|---|---|
| gi 3913328 | sp Q12588.1 | CP52J_CANMA (Cytochrome P450 52A10) | |
| gi 68492087 | ref XP_710174.1 | P450 drug resistance protein | Candida albicans |
| gi 3395458 | emb CAA75058.1 | alk8 | Candida albicans |
| gi 68474594 | ref XP_718670.1 | CaO19.7513 | Candida albicans |
| gi 29469865 | gb AAO73953.1 | CYP52A13 | Candida tropicalis |
| gi 149239010 | ref XP_001525381.1 | cytochrome P450 52A11 | Lodderomyces elongisporus |
| gi 29469867 | gb AAO73954.1 | CYP52A14 | Candida tropicalis |
| gi 7548332 | gb AAA34353.2 | cytochrome P-450-alk2 | Candida tropicalis |
| gi 732622 | emb CAA39366.1 | n-alkane inducible cytochrome P-450 | Candida maltosa |
| gi 231886 | sp P30607.1 | CP52B_CANTR (Cytochrome P450 52A2) | |
| gi 68474592 | ref XP_718669.1 | CaO19.7512 | Candida albicans |
| gi 150864612 | ref XP_001383506.2 | n-alkane inducible cytochrome P-450 | Pichia stipitis |
| gi 231888 | sp P30609.1 | CP52G_CANTR (Cytochrome P450 52A7) | |
| gi 298217 | gb AAB24479.1 | cytochrome P450 monooxygenase alk4, P450 alk4 = CYP52A7 gene product {alkane-inducible} | Candida tropicalis |
| gi 149246109 | ref XP_001527524.1 | cytochrome P450 52A2 | Lodderomyces elongisporus |
| gi 29469869 | gb AAO73955.1 | CYP52A15 | Candida tropicalis |
| gi 190319368 | gb AAD22536.2 | AF103948_1 cytochrome P450 alkane hydroxylase | Debaryomyces hansenii |
| gi 146419207 | ref XP_001485567.1 | cytochrome P450 52A12 | Pichia guilliermondii |
| gi 29469863 | gb AAO73952.1 | CYP52A12 | Candida tropicalis |
| gi 50423067 | ref XP_460112.1 | DEHA0E19635g | Debaryomyces hansenii |
| gi 29469871 | gb AAO73956.1 | CYP52A16 | Candida tropicalis |
| gi 199432969 | emb CAG88381.2 | DEHA2E18612p | Debaryomyces hansenii |
| gi 170892 | gb AAA34354.1 | cytochrome P-450-alk1 | Candida tropicalis |
| gi 50423065 | ref XP_460111.1 | DEHA0E19613g | Debaryomyces hansenii |
| gi 1169075 | sp P10615.3 | CP52A_CANTR (Cytochrome P450 52A1) | |
| gi 226487 | prf 1515252A | cytochrome P450alk1 | |
| gi 732623 | emb CAA39367.1 | n-alkane inducible cytochrome P-450 | Candida maltosa |
| gi 146413358 | ref XP_001482650.1 | PGUG_05670 | Pichia guilliermondii |
| gi 117182 | sp P16141.3 | CP52D_CANMA (Cytochrome P450 52A4) | |
| gi 2608 | emb CAA36197.1 | unnamed protein product | Candida maltosa |
| gi 231887 | sp P30608.1 | CP52F_CANTR (Cytochrome P450 52A6) | |
| gi 199432970 | emb CAG88382.2 | DEHA2E18634p | Debaryomyces hansenii |
| gi 190349008 | gb EDK41572.2 | PGUG_05670 | Pichia guilliermondii |
| gi 150864699 | ref XP_001383636.2 | Cytochrome P450 52A12 (Alkane hydroxylase 1) (Alkane-inducible p450alk 1) (DH-ALK2) | Pichia stipitis |
| gi 117181 | sp P16496.3 | CP52C_CANMA (Cytochrome P450 52A3) | |
| gi 199432968 | emb CAG88380.2 | DEHA2E18590p | Debaryomyces hansenii |
| gi 50423063 | ref XP_460110.1 | DEHA0E19591g | Debaryomyces hansenii |
| gi 553118 | gb AAA34320.1 | alkane hydroxylating cytochrome P-450 | |
| gi 117183 | sp P24458.1 | CP52E_CANMA (Cytochrome P450 52A5) | |
| gi 68475852 | ref XP_717999.1 | potential alkane hydroxylating monooxygenase P450 | Candida albicans |
| gi 18203639 | sp Q9Y758.1 | CP52M_DEBHA (Cytochrome P450 52A13) | |
| gi 146412241 | ref XP_001482092.1 | cytochrome P450 52A13 | Pichia guilliermondii |
| gi 126134585 | ref XP_001383817.1 | Cytochrome P450 52A13 (Alkane hydroxylase 2) (Alkane-inducible p450alk2) (DH-ALK2) | Pichia stipitis |
| gi 50418551 | ref XP_457792.1 | DEHA0C02981g | Debaryomyces hansenii |
| gi 149236533 | ref XP_001524144.1 | cytochrome P450 52A5 | Lodderomyces elongisporus |
| gi 150864746 | ref XP_001383710.2 | Cytochrome P450 52A6 (CYPLIIA6) (Alkane-inducible P450-ALK3) | Pichia stipitis |

TABLE 4-continued

| First Database Accession Number | Second Database Accession Number | Name | Species |
|---|---|---|---|
| gi 149239404 | ref XP_001525578.1 | cytochrome P450 52A3 | Lodderomyces elongisporus |
| gi 50417817 | ref XP_457727.1 | DEHA0C01177g | Debaryomyces hansenii |
| gi 199430432 | emb CAG85755.2 | DEHA2C01100p | Debaryomyces hansenii |
| gi 149239402 | ref XP_001525577.1 | cytochrome P450 52A8 | Lodderomyces elongisporus |
| gi 29469873 | gb AAO73957.1 | CYP52D2 | Candida tropicalis |
| gi 150866745 | ref XP_001386440.2 | Cytochrome P450 52A3 (CYPLIIA3) (Alkane-inducible P450-ALK1-A) (P450-CM1) (CYP52A3-A) (Cytochrome P-450ALK) | Pichia stipitis |
| gi 190347603 | gb EDK39907.2 | PGUG_04005 | Pichia guilliermondii |
| gi 146414612 | ref XP_001483276.1 | PGUG_04005 | Pichia guilliermondii |
| gi 3913325 | sp Q12585.1 | CP52T_CANMA (Cytochrome P450 52D1) | |
| gi 50553995 | ref XP_504406.1 | YALI0E25982p | Yarrowia lipolytica |
| gi 3298289 | dbj BAA31433.1 | ALK1 | Yarrowia lipolytica |
| gi 50554897 | ref XP_504857.1 | YALI0F01320p | Yarrowia lipolytica |
| gi 50545727 | ref XP_500402.1 | YALI0B01848p | Yarrowia lipolytica |
| gi 50546066 | ref XP_500560.1 | YALI0B06248p | Yarrowia lipolytica |
| gi 50547357 | ref XP_501148.1 | YALI0B20702p | Yarrowia lipolytica |
| gi 50546771 | ref XP_500855.1 | YALI0B13816p | Yarrowia lipolytica |
| gi 50546773 | ref XP_500856.1 | YALI0B13838p | Yarrowia lipolytica |
| gi 70982077 | ref XP_746567.1 | cytochrome P450 alkane hydroxylase | Aspergillus fumigatus |
| gi 119487140 | ref XP_001262425.1 | cytochrome P450 alkane hydroxylase | Neosartorya fischeri |
| gi 50545119 | ref XP_500097.1 | YALI0A15488p | Yarrowia lipolytica |
| gi 115387741 | ref XP_001211376.1 | cytochrome P450 52A12 | Aspergillus terreus |
| gi 145248800 | ref XP_001400739.1 | An14g01110 | Aspergillus niger |
| gi 121714465 | ref XP_001274843.1 | cytochrome P450 alkane hydroxylase | Aspergillus clavatus |
| gi 50545471 | ref XP_500273.1 | YALI0A20130p | Yarrowia lipolytica |
| gi 212541280 | ref XP_002150795.1 | cytochrome P450 alkane hydroxylase | Penicillium marneffei |
| gi 169783066 | ref XP_001825995.1 | | Aspergillus oryzae |
| gi 67541935 | ref XP_664735.1 | AN7131.2 | Aspergillus nidulans |
| gi 218716670 | gb EED16091.1 | cytochrome P450 alkane hydroxylase | Talaromyces stipitatus |
| gi 211584648 | emb CAP74173.1 | Pc14g00320 | Penicillium chrysogenum |
| gi 68475719 | ref XP_718066.1 | potential alkane hydroxylating monooxygenase P450 fragment | Candida albicans |
| gi 231890 | sp P30611.1 | CP52N_CANTR (Cytochrome P450 52B1) | |
| gi 50553800 | ref XP_504311.1 | YALI0E23474p | Yarrowia lipolytica |
| gi 115391153 | ref XP_001213081.1 | ATEG_03903 | Aspergillus terreus |
| gi 1169076 | sp P43083.1 | CP52V_CANAP (Cytochrome P450 52E1) | |
| gi 212537573 | ref XP_002148942.1 | cytochrome P450 family protein | Penicillium marneffei |
| gi 119480837 | ref XP_001260447.1 | cytochrome P450 family protein | Neosartorya fischeri |
| gi 159129370 | gb EDP54484.1 | cytochrome P450 family protein | Aspergillus fumigatus |
| gi 71001214 | ref XP_755288.1 | cytochrome P450 family protein | Aspergillus fumigatus |
| gi 50548557 | ref XP_501748.1 | YALI0C12122p | Yarrowia lipolytica |
| gi 211592844 | emb CAP99212.1 | Pc22g19240 | Penicillium chrysogenum |
| gi 231891 | sp P30612.1 | CP52P_CANTR (Cytochrome P450 52C1) | |
| gi 3913327 | sp Q12587.1 | CP52Q_CANMA (Cytochrome P450 52C2) | |
| gi 50548395 | ref XP_501667.1 | YALI0C10054p | Yarrowia lipolytica |
| gi 145248373 | ref XP_001396435.1 | An13g03000 | Aspergillus niger |
| gi 169783674 | ref XP_001826299.1 | | Aspergillus oryzae |
| gi 169774249 | ref XP_001821592.1 | | Aspergillus oryzae |
| gi 212536398 | ref XP_002148355.1 | cytochrome P450 alkane hydroxylase | Penicillium marneffei |
| gi 211590140 | emb CAP96310.1 | Pc21g14130 | Penicillium chrysogenum |

TABLE 4-continued

| First Database Accession Number | Second Database Accession Number | Name | Species |
|---|---|---|---|
| gi 189200681 | ref XP_001936677.1 | cytochrome P450 52A12 | Pyrenophora tritici-repentis |
| gi 121698992 | ref XP_001267871.1 | cytochrome P450 family protein | Aspergillus clavatus |
| gi 154310961 | ref XP_001554811.1 | BC1G_06459 | Botryotinia fuckeliana |
| gi 119497443 | ref XP_001265480.1 | cytochrome P450 alkane hydroxylase | Neosartorya fischeri |
| gi 67539774 | ref XP_663661.1 | AN6057.2 | Aspergillus nidulans |
| gi 3913324 | sp Q12573.1 | CP52W_CANAP (Cytochrome P450 52E2) | |
| gi 159130401 | gb EDP55514.1 | cytochrome P450 alkane hydroxylase | Aspergillus fumigatus |
| gi 70990140 | ref XP_749919.1 | cytochrome P450 alkane hydroxylase | Aspergillus fumigatus |
| gi 212543867 | ref XP_002152088.1 | N-alkane-inducible cytochrome P450 | Penicillium marneffei ATCC 18224 |
| gi 189204508 | ref XP_001938589.1 | cytochrome P450 52A12 | Pyrenophora tritici-repentis |
| gi 67904794 | ref XP_682653.1 | AN9384.2 | Aspergillus nidulans |
| gi 115401146 | ref XP_001216161.1 | ATEG_07540 | Aspergillus terreus |
| gi 169765686 | ref XP_001817314.1 | | Aspergillus oryzae |
| gi 156034334 | ref XP_001585586.1 | SS1G_13470 | Sclerotinia sclerotiorum |
| gi 115389132 | ref XP_001212071.1 | ATEG_02893 | Aspergillus terreus |
| gi 149249004 | ref XP_001528842.1 | LELG_05768 | Lodderomyces elongisporus |
| gi 119490743 | ref XP_001263094.1 | n-alkane-inducible cytochrome P450 | Neosartorya fischeri |
| gi 169598696 | ref XP_001792771.1 | SNOG_02153 | Phaeosphaeria nodorum |
| gi 145233653 | ref XP_001400199.1 | An02g10700 | Aspergillus niger |
| gi 121703415 | ref XP_001269972.1 | cytochrome P450 alkane hydroxylase | Aspergillus clavatus |
| gi 145244813 | ref XP_001394678.1 | An11g07010 | Aspergillus niger |
| gi 115400535 | ref XP_001215856.1 | ATEG_06678 | Aspergillus terreus |
| gi 156054264 | ref XP_001593058.1 | SS1G_05980 | Sclerotinia sclerotiorum |
| gi 145235009 | ref XP_001390153.1 | An03g02570 | Aspergillus niger |
| gi 121714697 | ref XP_001274959.1 | n-alkane-inducible cytochrome P450 | Aspergillus clavatus |
| gi 115383936 | ref XP_001208515.1 | ATEG_01150 | Aspergillus terreus |
| gi 119188703 | ref XP_001244958.1 | CIMG_04399 | Coccidioides immitis |
| gi 154303347 | ref XP_001552081.1 | BC1G_09422 | Botryotinia fuckeliana |
| gi 68469246 | ref XP_721410.1 | potential n-alkane inducible cytochrome P-450 | Candida albicans |
| gi 211588353 | emb CAP86458.1 | Pc20g11290 | Penicillium chrysogenum |
| gi 218719422 | gb EED18842.1 | cytochrome P450 | Talaromyces stipitatus |
| gi 189196472 | ref XP_001934574.1 | cytochrome P450 52A11 | Pyrenophora tritici-repentis |
| gi 145228377 | ref XP_001388497.1 | An01g00510 | Aspergillus niger |
| gi 145243810 | ref XP_001394417.1 | An11g04220 | Aspergillus niger |
| gi 119467390 | ref XP_001257501.1 | n-alkane-inducible cytochrome P450 | Neosartorya fischeri |
| gi 218713692 | gb EED13116.1 | cytochrome P450 alkane hydroxylase | Talaromyces stipitatus |
| gi 156040904 | ref XP_001587438.1 | SS1G_11430 | Sclerotinia sclerotiorum |
| gi 211588608 | emb CAP86724.1 | Pc20g13950 | Penicillium chrysogenum |
| gi 189210960 | ref XP_001941811.1 | cytochrome P450 52A11 | Pyrenophora tritici-repentis |
| gi 154300280 | ref XP_001550556.1 | BC1G_11329 | Botryotinia fuckeliana |
| gi 39965179 | ref XP_365075.1 | MGG_09920 | Magnaporthe grisea |
| gi 70984521 | ref XP_747767.1 | cytochrome P450 alkane hydroxylase | Aspergillus fumigatus |
| gi 164424932 | ref XP_958030.2 | NCU09115 | Neurospora crassa |
| gi 169785321 | ref XP_001827121.1 | | Aspergillus oryzae |
| gi 171687345 | ref XP_001908613.1 | | Podospora anserina |
| gi 495225 | dbj BAA05145.1 | n-alkane-inducible cytochrome P-450 | Candida maltosa |
| gi 169778468 | ref XP_001823699.1 | | Aspergillus oryzae |
| gi 685237 | emb CAA35593.1 | cytochrome P-450-alk2 | Candida tropicalis |
| gi 115398792 | ref XP_001214985.1 | ATEG_05807 | Aspergillus terreus |
| gi 156045685 | ref XP_001589398.1 | SS1G_10037 | Sclerotinia sclerotiorum |
| gi 116181964 | ref XP_001220831.1 | CHGG_01610 | Chaetomium globosum |
| gi 212539338 | ref XP_002149824.1 | N-alkane-inducible cytochrome P450 | Penicillium marneffei |

TABLE 4-continued

| First Database Accession Number | Second Database Accession Number | Name | Species |
|---|---|---|---|
| gi 55823915 | gb AAV66104.1 | cytochrome P450 | *Fusarium heterosporum* |
| gi 169786131 | ref XP_001827526.1 | | *Aspergillus oryzae* |
| gi 67526919 | ref XP_661521.1 | AN3917.2 | *Aspergillus nidulans* |
| gi 57157397 | dbj BAD83681.1 | cytochrome P-450 | *Alternaria solani* |
| gi 39954838 | ref XP_364111.1 | MGG_08956 | *Magnaporthe grisea* |
| gi 46108804 | ref XP_381460.1 | FG01284.1 | *Gibberella zeae* |
| gi 167962420 | dbj BAG09241.1 | n-alkane inducible cytochrome P-450 | *Candida maltosa* |
| gi 119469615 | ref XP_001257962.1 | cytochrome P450 alkane hydroxylase | *Neosartorya fischeri* |
| gi 70991773 | ref XP_750735.1 | cytochrome P450 alkane hydroxylase | *Aspergillus fumigatus* |
| gi 171679185 | ref XP_001904540.1 | unnamed protein product | *Podospora anserina* |
| gi 119488606 | ref XP_001262753.1 | n-alkane-inducible cytochrome P450 | *Neosartorya fischeri* |
| gi 218722969 | gb EED22387.1 | cytochrome P450 | *Talaromyces stipitatus* |
| gi 145243244 | ref XP_001394159.1 | An11g01550 | *Aspergillus niger* |
| gi 212533853 | ref XP_002147083.1 | N-alkane-inducible cytochrome P450 | *Penicillium marneffei* |
| gi 218720976 | gb EED20395.1 | cytochrome P450 alkane hydroxylase | *Talaromyces stipitatus* |
| gi 145604320 | ref XP_362943.2 | MGG_08494 | *Magnaporthe grisea* |
| gi 154319876 | ref XP_001559255.1 | BC1G_02419 | *Botryotinia fuckeliana* |
| gi 154272319 | ref XP_001537012.1 | HCAG_08121 | *Ajellomyces capsulatus* |
| gi 39976331 | ref XP_369556.1 | MGG_05908 | *Magnaporthe grisea* |
| gi 116200125 | ref XP_001225874.1 | CHGG_08218 | *Chaetomium globosum* |
| gi 218722681 | gb EED22099.1 | cytochrome P450 alkane hydroxylase | *Talaromyces stipitatus* |
| gi 145606889 | ref XP_361347.2 | MGG_03821 | *Magnaporthe grisea* |
| gi 211592275 | emb CAP98620.1 | Pc22g13320 | *Penicillium chrysogenum* |
| gi 171688034 | ref XP_001908957.1 | unnamed protein product | *Podospora anserina* |
| gi 211587061 | emb CAP94723.1 | Pc18g04990 | *Penicillium chrysogenum* |
| gi 169612986 | ref XP_001799910.1 | SNOG_09621 | *Phaeosphaeria nodorum* |
| gi 212539354 | ref XP_002149832.1 | N-alkane-inducible cytochrome P450 | *Penicillium marneffei* |
| gi 212533239 | ref XP_002146776.1 | cytochrome P450 alkane hydroxylase | *Penicillium marneffei* |
| gi 41079162 | gb AAR99474.1 | alkane monooxygenase P-450 | *Graphium* sp. |
| gi 159122944 | gb EDP48064.1 | cytochrome P450 alkane hydroxylase | *Aspergillus fumigatus* |
| gi 67537376 | ref XP_662462.1 | AN4858.2 | *Aspergillus nidulans* |
| gi 39954738 | ref XP_364102.1 | MGG_08947 | *Magnaporthe grisea* |
| gi 39968921 | ref XP_365851.1 | MGG_10071 | *Magnaporthe grisea* |
| gi 70983886 | ref XP_747469.1 | cytochrome P450 alkane hydroxylase | *Aspergillus fumigatus* |
| gi 171691438 | ref XP_001910644.1 | unnamed protein product | *Podospora anserina* |
| gi 119193452 | ref XP_001247332.1 | CIMG_01103 | *Coccidioides immitis* |
| gi 10303293 | emb CAC10088.1 | related to n-alkane-inducible cytochrome P450 | *Neurospora crassa* |
| gi 169626152 | ref XP_001806478.1 | SNOG_16355 | *Phaeosphaeria nodorum* |
| gi 119191908 | ref XP_001246560.1 | CIMG_00331 | *Coccidioides immitis* |
| gi 154296077 | ref XP_001548471.1 | BC1G_12768 | *Botryotinia fuckeliana* |
| gi 164429645 | ref XP_964653.2 | NCU02031 | *Neurospora crassa* |
| gi 12311700 | emb CAC24473.1 | | *Candida albicans* |
| gi 154305169 | ref XP_001552987.1 | BC1G_08879 | *Botryotinia fuckeliana* |
| gi 39978177 | ref XP_370476.1 | MGG_06973 | *Magnaporthe grisea* |
| gi 70982576 | ref XP_746816.1 | cytochrome P450 alkane hydroxylase | *Aspergillus fumigatus* |
| gi 154319145 | ref XP_001558890.1 | BC1G_02524 | *Botryotinia fuckeliana* |
| gi 46127885 | ref XP_388496.1 | FG08320.1 | *Gibberella zeae* |
| gi 32330665 | gb AAP79879.1 | cytochrome P450 monooxygenase pc-3 | *Phanerochaete chrysosporium* |
| gi 116193605 | ref XP_001222615.1 | CHGG_06520 | *Chaetomium globosum* |
| gi 145241598 | ref XP_001393445.1 | An09g01270 | *Aspergillus niger* |
| gi 149210127 | ref XP_001522438.1 | MGCH7_ch7g545 | *Magnaporthe grisea* |
| gi 121699244 | ref XP_001267956.1 | cytochrome P450 alkane hydroxylase | *Aspergillus clavatus* |
| gi 156032429 | ref XP_001585052.1 | SS1G_13912 | *Sclerotinia sclerotiorum* |
| gi 159122551 | gb EDP47672.1 | cytochrome P450 alkane hydroxylase | *Aspergillus fumigatus* |
| gi 145613078 | ref XP_001412594.1 | MGG_12496 | *Magnaporthe grisea* |

TABLE 4-continued

| First Database Accession Number | Second Database Accession Number | Name | Species |
|---|---|---|---|
| gi 212531571 | ref XP_002145942.1 | N-alkane-inducible cytochrome P450 | *Penicillium marneffei* |
| gi 145252862 | ref XP_001397944.1 | An16g06420 | *Aspergillus niger* |
| gi 169855683 | ref XP_001834508.1 | CC1G_02244 | *Coprinopsis cinerea okayama* |
| gi 212530338 | ref XP_002145326.1 | N-alkane-inducible cytochrome P450 | *Penicillium marneffei* |
| gi 61657996 | gb AAX49400.1 | cytochrome P450 monooxygenase pc-2 | *Phanerochaete chrysosporium* |
| gi 170110164 | ref XP_001886288.1 | CYP63 cytochrome P450 monooxygenase-like protein | *Laccaria bicolor* |
| gi 146323950 | ref XP_748328.2 | cytochrome P450 oxidoreductase/alkane hydroxylase | *Aspergillus fumigatus* |
| gi 156042346 | ref XP_001587730.1 | SS1G_10970 | *Sclerotinia sclerotiorum* |
| gi 189196282 | ref XP_001934479.1 | cytochrome P450 71A23 | *Pyrenophora tritici-repentis* |
| gi 18369901 | gb AAL67906.1 | cytochrome P450 monooxygenase pc-2 | *Phanerochaete chrysosporium* |
| gi 218714942 | gb EED14365.1 | cytochrome P450 | *Talaromyces stipitatus* |
| gi 170106497 | ref XP_001884460.1 | cytochrome P450 | *Laccaria bicolor* |
| gi 169865534 | ref XP_001839366.1 | CC1G_08233 | *Coprinopsis cinerea okayama* |
| gi 169855669 | ref XP_001834501.1 | CC1G_02237 | *Coprinopsis cinerea okayama* |
| gi 189197495 | ref XP_001935085.1 | cytochrome P450 52A1 | *Pyrenophora tritici-repentis* |
| gi 218713646 | gb EED13070.1 | cytochrome P450 | *Talaromyces stipitatus* |
| gi 170106217 | ref XP_001884320.1 | cytochrome P450 | *Laccaria bicolor* |
| gi 116197088 | ref XP_001224356.1 | CHGG_05142 | *Chaetomium globosum* |
| gi 18369899 | gb AAL67905.1 | cytochrome P450 monooxygenase pc-1 | *Phanerochaete chrysosporium* |
| gi 154312290 | ref XP_001555473.1 | BC1G_06178 | *Botryotinia fuckeliana* |
| gi 156064223 | ref XP_001598033.1 | SS1G_00119 | *Sclerotinia sclerotiorum* |
| gi 156039263 | ref XP_001586739.1 | SS1G_11768 | *Sclerotinia sclerotiorum* |
| gi 170105206 | ref XP_001883816.1 | | *Laccaria bicolor* |
| gi 169613228 | ref XP_001800031.1 | SNOG_09744 | *Phaeosphaeria nodorum* |
| gi 169863123 | ref XP_001838184.1 | CC1G_12233 | *Coprinopsis cinerea okayama* |
| gi 67902848 | ref XP_681680.1 | AN8411.2 | *Aspergillus nidulans* |
| gi 158392452 | emb CAO91865.1 | monooxygenase | *Penicillium expansum* |
| gi 169857173 | ref XP_001835239.1 | CC1G_07782 | *Coprinopsis cinerea okayama* |
| gi 169781220 | ref XP_001825073.1 | | *Aspergillus oryzae* |
| gi 67540302 | ref XP_663925.1 | AN6321.2 | *Aspergillus nidulans* |
| gi 145234553 | ref XP_001389925.1 | An03g00180 | *Aspergillus niger* |
| gi 170106275 | ref XP_001884349.1 | | *Laccaria bicolor* |
| gi 145610012 | ref XP_366716.2 | MGG_02792 | *Magnaporthe grisea* |
| gi 119473653 | ref XP_001258702.1 | cytochrome P450 monooxygenase | *Neosartorya fischeri* |
| gi 118026355 | emb CAL69S94.1 | | *Cordyceps bassiana* |
| gi 154309945 | ref XP_001554305.1 | BC1G_06893 | *Botryotinia fuckeliana* |
| gi 211593324 | emb CAP99706.1 | Pc22g24180 | *Penicillium chrysogenum* |
| gi 170111410 | ref XP_001886909.1 | cytochrome P450 monooxygenase CYP63 | *Laccaria bicolor* |
| gi 169864610 | ref XP_001838912.1 | CC1G_05465 | *Coprinopsis cinerea okayama* |
| gi 145240007 | ref XP_001392650.1 | An08g05330 | *Aspergillus niger* |
| gi 115433302 | ref XP_001216788.1 | | *Aspergillus terreus* |
| gi 121701751 | ref XP_001269140.1 | Cytochrome P450 oxidoreductase | *Aspergillus clavatus* |
| gi 154289956 | ref XP_001545581.1 | BC1G_15919 | *Botryotinia fuckeliana* |
| gi 212527006 | ref XP_002143660.1 | cytochrome P450 alkane hydroxylase | *Penicillium marneffei* |
| gi 156054506 | ref XP_001593179.1 | SS1G_06101 | *Sclerotinia sclerotiorum* |
| gi 167962125 | dbj BAG09240.1 | n-alkane inducible cytochrome P-450 | *Candida maltosa* |
| gi 169610561 | ref XP_001798699.1 | SNOG_08385 | *Phaeosphaeria nodorum* |
| gi 154322320 | ref XP_001560475.1 | BC1G_01307 | *Botryotinia fuckeliana* |
| gi 171986596 | gb ACB59278.1 | cytochrome P450 monooxygenase | *Pseudozyma flocculosa* |
| gi 169850022 | ref XP_001831709.1 | CC1G_12229 | *Coprinopsis cinerea okayama* |

TABLE 4-continued

| First Database Accession Number | Second Database Accession Number | Name | Species |
|---|---|---|---|
| gi 84514171 | gb ABC59094.1 | cytochrome P450 monooxygenase CYP704G9 | *Medicago truncatula* |
| gi 157349259 | emb CAO24405.1 | | *Vitis vinifera* |
| gi 154322983 | ref XP_001560806.1 | BC1G_00834 | *Botryotinia fuckeliana* |
| gi 71726950 | gb AAZ39646.1 | cytochrome P450 monooxygenase | *Petunia* x *hybrida* |
| gi 2160323 | dbj BAA05146.1 | n-alkane-inducible cytochrome P-450 | *Candida maltosa* |
| gi 218717320 | gb EED16741.1 | cytochrome P450 | *Talaromyces stipitatus* |
| gi 118485860 | gb ABK94777.1 | | *Populus trichocarpa* |
| gi 71024781 | ref XP_762620.1 | UM06473.1 | *Ustilago maydis* |
| gi 58265104 | ref XP_569708.1 | | *Cryptococcus neoformans* var. *neoformans* |
| gi 169596949 | ref XP_001791898.1 | SNOG_01251 | *Phaeosphaeria nodorum* |
| gi 157355912 | emb CAO49769.1 | | *Vitis vinifera* |
| gi 134109309 | ref XP_776769.1 | CNBC2600 | *Cryptococcus neoformans* var. *neoformans* |
| gi 157349262 | emb CAO24408.1 | | *Vitis vinifera* |
| gi 147765747 | emb CAN60189.1 | | *Vitis vinifera* |
| gi 169864676 | ref XP_001838945.1 | CC1G_05498 | *Coprinopsis cinerea okayama* |
| gi 157352095 | emb CAO43102.1 | | *Vitis vinifera* |
| gi 147791153 | emb CAN63571.1 | | *Vitis vinifera* |
| gi 84514173 | gb ABC59095.1 | cytochrome P450 monooxygenase CYP704G7 | *Medicago truncatula* |
| gi 71024761 | ref XP_762610.1 | UM06463.1 | *Ustilago maydis* |
| gi 157355911 | emb CAO49768.1 | | *Vitis vinifera* |
| gi 115451645 | ref NP_001049423.1 | Os03g0223100 | *Oryza sativa* |
| gi 22748335 | gb AAN05337.1 | cytochrome P450 | *Oryza sativa* |
| gi 168059245 | ref XP_001781614.1 | | *Physcomitrella patens* subsp. *patens* |
| gi 15225499 | ref NP_182075.1 | CYP704A2 (cytochrome P450, family 704, subfamily A, polypeptide 2) oxygen binding | *Arabidopsis thaliana* |
| gi 75319885 | sp Q50EK3.1 | C04C1_PINTA (Cytochrome P450 704C1) | |
| gi 167521978 | ref XP_001745327.1 | | *Monosiga brevicollis* |
| gi 21536522 | gb AAM60854.1 | cytochrome P450-like protein | *Arabidopsis thaliana* |
| gi 15242759 | ref NP_201150.1 | CYP94B1 (cytochrome P450, family 94, subfamily B, polypeptide 1) oxygen binding | *Arabidopsis thaliana* |
| gi 168031659 | ref XP_001768338.1 | | *Physcomitrella patens* subsp. *patens* |
| gi 157339131 | emb CAO42482.1 | | *Vitis vinifera* |
| gi 30682301 | ref NP_196442.2 | cytochrome P450 family protein | *Arabidopsis thaliana* |
| gi 8346562 | emb CAB93726.1 | cytochrome P450-like protein | *Arabidopsis thaliana* |
| gi 2344895 | gb AAC31835.1 | cytochrome P450 | *Arabidopsis thaliana* |
| gi 30689861 | ref NP_850427.1 | CYP704A1 (cytochrome P450, family 704, subfamily A, polypeptide 1) oxygen binding | *Arabidopsis thaliana* |
| gi 15221776 | ref NP_173862.1 | CYP86C1 (cytochrome P450, family 86, subfamily C, polypeptide 1) oxygen binding | *Arabidopsis thaliana* |
| gi 147793015 | emb CAN77648.1 | | *Vitis vinifera* |
| gi 157356646 | emb CAO62841.1 | | *Vitis vinifera* |
| gi 147844260 | emb CAN80040.1 | | *Vitis vinifera* |
| gi 215466577 | gb EEB96517.1 | MPER_04337 | *Moniliophthora perniciosa* |
| gi 15222515 | ref NP_176558.1 | CYP86A7 (cytochrome P450, family 86, subfamily A, polypeptide 7) oxygen binding | *Arabidopsis thaliana* |
| gi 194697724 | gb ACF82946.1 | | *Zea mays* |
| gi 168021353 | ref XP_001763206.1 | | *Physcomitrella patens* subsp. *patens* |

TABLE 4-continued

| First Database Accession Number | Second Database Accession Number | Name | Species |
|---|---|---|---|
| gi 115483036 | ref NP_001065111.1 | Os10g0525000 | *Oryza sativa* (*japonica* cultivar-group) |
| gi 157338660 | emb CAO42011.1 | | *Vitis vinifera* |
| gi 147836212 | emb CAN75428.1 | | *Vitis vinifera* |
| gi 5042165 | emb CAB44684.1 | cytochrome P450-like protein | *Arabidopsis thaliana* |
| gi 79326551 | ref NP_001031814.1 | CYP96A10 (cytochrome P450, family 96, subfamily A, polypeptide 10) heme binding/iron ion binding/monooxygenase | *Arabidopsis thaliana* |
| gi 26452145 | dbj BAC43161.1 | cytochrome P450 | *Arabidopsis thaliana* |
| gi 110289450 | gb AAP54707.2 | Cytochrome P450 family protein, expressed | *Oryza sativa* |
| gi 21593258 | gb AAM65207.1 | cytochrome P450 | *Arabidopsis thaliana* |
| gi 115483034 | ref NP_001065110.1 | Os10g0524700 | *Oryza sativa* |
| gi 118486379 | gb ABK95030.1 | | *Populus trichocarpa* |
| gi 10442763 | gb AAG17470.1 | AF123610_9 cytochrome P450 | *Triticum aestivum* |
| gi 125532704 | gb EAY79269.1 | OsI_34384 | *Oryza sativa* |
| gi 15237250 | ref NP_197710.1 | CYP86B1 (cytochrome P450, family 86, subfamily B, polypeptide 1) oxygen binding | *Arabidopsis thaliana* |
| gi 125549414 | gb EAY95236.1 | OsI_17053 | *Oryza sativa* |
| gi 110289453 | gb AAP54710.2 | Cytochrome P450 family protein | *Oryza sativa* |
| gi 20146744 | gb AAM12480.1 | AC074232_7 cytochrome P450-like protein | *Oryza sativa* |
| gi 218184911 | gb EEC67338.1 | OsI_34388 | *Oryza sativa Indica* Group |
| gi 125549325 | gb EAY95147.1 | OsI_16965 | *Oryza sativa Indica* Group |
| gi 198472816 | ref XP_002133118.1 | GA29000 | *Drosophila pseudoobscura pseudoobscura* |
| gi 195574346 | ref XP_002105150.1 | GD21336 | *Drosophila simulans* |
| gi 168024173 | ref XP_001764611.1 | | *Physcomitrella patens* subsp. *patens* |
| gi 115440549 | ref NP_001044554.1 | Os01g0804400 | *Oryza sativa* (*japonica* cultivar-group) |
| gi 15223657 | ref NP_176086.1 | CYP96A15/MAH1 (MID-CHAIN ALKANE HYDROXYLASE 1) oxygen binding | *Arabidopsis thaliana* |
| gi 125540131 | gb EAY86526.1 | OsI_07906 | *Oryza sativa* |
| gi 115460030 | ref NP_001053615.1 | Os04g0573900 | *Oryza sativa* (*japonica* cultivar-group) |
| gi 157349258 | emb CAO24404.1 | | *Vitis vinifera* |
| gi 157346575 | emb CAO16644.1 | | *Vitis vinifera* |
| gi 147835182 | emb CAN76753.1 | | *Vitis vinifera* |
| gi 195613956 | gb ACG28808.1 | | *Zea mays* |
| gi 194753285 | ref XP_001958947.1 | GF12635 | *Drosophila ananassae* |
| gi 156546811 | ref XP_001606040.1 | | *Nasonia vitripennis* |
| gi 125583181 | gb EAZ24112.1 | OsJ_007595 | *Oryza sativa* (*japonica* cultivar-group) |
| gi 15229477 | ref NP_189243.1 | CYP86C2 (cytochrome P450, family 86, subfamily C, polypeptide 2) oxygen binding | *Arabidopsis thaliana* |
| gi 940446 | emb CAA62082.1 | cytochrome p450 | *Arabidopsis thaliana* |
| gi 115447789 | ref NP_001047674.1 | Os02g0666500 | *Oryza sativa* (*japonica* cultivar-group) |
| gi 15227788 | ref NP_179899.1 | CYP96A1 (cytochrome P450, family 96, subfamily A, polypeptide 1) oxygen binding | *Arabidopsis thaliana* |
| gi 195503768 | ref XP_002098791.1 | GE23738 | *Drosophila yakuba* |
| gi 147804860 | emb CAN66874.1 | | *Vitis vinifera* |
| gi 84514169 | gb ABC59093.1 | cytochrome P450 monooxygenase CYP94C9 | *Medicago truncatula* |
| gi 19698839 | gb AAL91155.1 | cytochrome P450 | *Arabidopsis thaliana* |
| gi 15237768 | ref NP_200694.1 | CYP86A1 (cytochrome P450, family 86, subfamily A, polypeptide 1) oxygen binding | *Arabidopsis thaliana* |

TABLE 4-continued

| First Database Accession Number | Second Database Accession Number | Name | Species |
|---|---|---|---|
| gi 157353969 | emb CAO46510.1 | | Vitis vinifera |
| gi 169865676 | ref XP_001839436.1 | CC1G_06649 | Coprinopsis cinerea okayama |
| gi 85001697 | gb ABC68403.1 | cytochrome P450 monooxygenase CYP86A24 | Glycine max |
| gi 115466172 | ref NP_001056685.1 | Os06g0129900 | Oryza sativa |
| gi 195637782 | gb ACG38359.1 | cytochrome P450 86A2 | Zea mays |
| gi 194704220 | gb ACF86194.1 | | Zea mays |
| gi 71006408 | ref XP_757870.1 | UM01723.1 | Ustilago maydis 521 |
| gi 195161677 | ref XP_002021689.1 | GL26642 | Drosophila persimilis |
| gi 115459886 | ref NP_001053543.1 | Os04g0560100 | Oryza sativa |
| gi 194704096 | gb ACF86132.1 | | Zea mays |
| gi 147773635 | emb CAN67559.1 | | Vitis vinifera |
| gi 125575195 | gb EAZ16479.1 | OsJ_030688 | Oryza sativa |
| gi 115482616 | ref NP_001064901.1 | Os10g0486100 | Oryza sativa |
| gi 71726942 | gb AAZ39642.1 | cytochrome P450 fatty acid omega-hydroxylase | Petunia x hybrida |
| gi 195626182 | gb ACG34921.1 | cytochrome P450 86A1 | Zea mays |
| gi 194907382 | ref XP_001981543.1 | GG11553 | Drosophila erecta |
| gi 71006688 | ref XP_758010.1 | UM01863.1 | Ustilago maydis |
| gi 157346247 | emb CAO15944.1 | | Vitis vinifera |
| gi 116830948 | gb ABK28430.1 | | Arabidopsis thaliana |
| gi 13641298 | gb AAK31592.1 | cytochrome P450 | Brassica rapa subsp. pekinensis |
| gi 2258321 | gb AAB63277.1 | cytochrome P450 | Phanerochaete chrysosporium |
| gi 15218671 | ref NP_174713.1 | CYP94D1 (cytochrome P450, family 94, subfamily D, polypeptide 1) oxygen binding | Arabidopsis thaliana |
| gi 195623910 | gb ACG33785.1 | cytochrome P450 86A1 | Zea mays |
| gi 157337152 | emb CAO21498.1 | | Vitis vinifera |

In some embodiments, one or more genes encoding a P450 enzyme are integrated into a yeast strain, a species of Candida, or a strain of Candida tropicalis in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, a cytochrome P450 is integrated into a strain of Candida tropicalis in which fatty alcohol oxidase genes FAO1, FAO1B, FAO2 and FAO2B have been disrupted.

In some embodiments, a cytochrome P450 is integrated into a strain of Candida tropicalis in which endogenous alcohol dehydrogenase genes ADH-A4, ADH-A4B, ADH-B4, ADH-B4B, ADH-A10 and ADH-B11 have been disrupted.

In some embodiments, a cytochrome P450 is integrated into a strain of Candida tropicalis in which endogenous cytochrome P450 genes CYP52A17, CYP52A18, CYP52A13, CYP52A14, CYP52A12 and CYP52A12B have been disrupted.

In some embodiments, a cytochrome P450 is integrated into a strain of Candida tropicalis in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a cytochrome P450 is integrated into a strain of Candida tropicalis in which endogenous cyocrhrome P450s have been disrupted.

In some embodiments, a cytochrome P450 is integrated into a strain of Candida in which endogenous cyocrhrome P450s have been disrupted.

In some embodiments, one or more genes, two or more genes, or three or more genes listed in Table 4 are integrated into a yeast strain, a species of Candida, or a strain of Candida tropicalis in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, one or more genes, two or more genes, or three or more genes listed in Table 4 are integrated into a strain of Candida tropicalis in which fatty alcohol oxidase genes FAO1, FAO1B, FAO2 and FAO2B have been disrupted.

In some embodiments, one or more genes, two or more genes, or three or more genes listed in Table 4 are integrated into a strain of Candida tropicalis in which endogenous alcohol dehydrogenase genes ADH-A4, ADH-A4B, ADH-B4, ADH-B4B, ADH-A10 and ADH-B11 have been disrupted.

In some embodiments, one or more genes, two or more genes, or three or more genes listed in Table 4 are integrated into a strain of Candida tropicalis in which endogenous cytochrome P450 genes CYP52A17, CYP52A18, CYP52A13, CYP52A14, CYP52A12 and CYP52A12B have been disrupted.

In some embodiments, one or more genes, two or more genes, or three or more genes listed in Table 4 are integrated into a strain of Candida tropicalis in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, one or more genes, two or more genes, or three or more genes listed in Table 4 are integrated into a strain of Candida tropicalis in which endogenous cyocrhrome P450s have been disrupted.

In some embodiments, one or more genes, two or more genes, or three or more genes listed in Table 4 are integrated into a strain of Candida in which endogenous cyocrhrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a yeast strain, a species of Candida, or a strain of Candida tropicalis in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of Candida tropicalis in which fatty alcohol oxidase genes FAO1, FAO1B, FAO2 and FAO2B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of Candida tropicalis in which endogenous alcohol dehydrogenase genes ADH-A4, ADH-A4B, ADH-B4, ADH-B4B, ADH-A10 and ADH-B11 have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of Candida tropicalis in which endogenous cytochrome P450 genes CYP52A17, CYP52A18, CYP52A13, CYP52A14, CYP52A12 and CYP52A12B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of Candida tropicalis in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of Candida tropicalis in which endogenous cyocrhrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida* in which endogenous cyocrhrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a yeast strain, a species of *Candida*, or a strain of *Candida tropicalis* in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous alcohol dehydrogenase genes ADH-A4, ADH-A4B, ADH-B4, ADH-B4B, ADH-A10 and ADH-B11 have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cytochrome P450 genes CYP52A17, CYP52A18, CYP52A13, CYP52A14, CYP52A12 and CYP52A12B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cyocrhrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida* in which endogenous cyocrhrome P450s have been disrupted.

In some embodiments, to achieve novel phenotypes of *Candida*, the activity of a polypeptide in the *Candida* is altered by altering its sequence. Then the effect of the polypeptide with altered sequence within the yeast is tested. One method for testing the effect of sequence changes in a polypeptide within yeast is to introduce a plurality of genes of known sequence, each encoding a unique modified polypeptide, into the same genomic location in a plurality of strains.

The isocitrate lyase promoter from *Candida tropicalis* has been shown to be an inducible promoter in both *Saccharomyces cerevisiae* and *E. coli*. See, for example, Atomi et al., 1995, Arch Microbiol 163, 322-328; and Umemura et al., 1995, Appl Microbiol Biotechnol 43, 489-492. When expressed in *S. cerivisiae*, the isocitrate lyase gene was found to be inducible by acetate, glycerol, lactate, ethanol, or oleate. Ethanol is interesting from the perspective that is a relatively cheap inducer and oleate for the fact that it is a potential substrate for the system for converting fatty acids to omega hydroxy fatty acids. Inducible expression of the *Candida tropicalis* ICL gene was found to be high in *S. cerivisiae* (as much as 30% of soluble protein), indicating that it may serve as a strong inducible promoter in *C. tropicalis*.

To insert genes under control of the isocitrate lyase promoter a genomic insertion construct of the form shown in FIG. 21 was synthesized. The sequence used for the sequence of promoter 1 was that of the *Candida tropicalis* isocitrate lyase promoter, given as SEQ ID NO: 62. This promoter has a BsiWI site that can be used to linearize the construct for subsequent insertion into the *Candida tropicalis* genome. The sequence used for transcription terminator 1 was that of the *Candida tropicalis* isocitrate lyase terminator, given as SEQ ID NO: 63. The sequence used for Promoter 2 was the TEF1 promoter, given as SEQ ID NO: 64. The sequence used for the bacterial promoter was the EM7 promoter, given as SEQ ID NO: 65. The sequence used for the selectable marker was the zeocin resistance gene, a version optimized for expression in *Candida tropicalis* is given as SEQ ID NO: 66. The sequence use for Transcription terminator 2 was the CYC1 transcription terminator, given as SEQ ID NO: 67. The sequence used as the bacterial origin of replication was the pUC origin, given as SEQ ID NO: 68. A genomic integration vector with these components is represented graphically as FIG. 23.

7.6.1 Insertion of CYP52A17 Under Control of the Isocitrate Lyase Promoter

A construct for expressing *Candida tropicalis* cytochrome P450 CYP52A17 under the control of the isocitrate lyase promoter was made by cloning the sequence of a gene encoding *Candida tropicalis* cytochrome P450 CYP52A17 (given as SEQ ID NO: 69) into a vector of the form shown in FIG. 23. The sequence of the complete vector is given as SEQ ID NO: 70.

The vector was prepared as described in Section 7.1.1, except that the construct was linearized with BsiWI instead of BsmBI. *Candida tropicalis* strains were transformed with the construct as described in Section 7.1.2, except that 100 µg/ml of zeocin was used instead of 200 µg/ml nourseothricin as the selective antibiotic. Genomic DNA was prepared and tested for the presence of the integrated DNA as described in Section 7.1.3.

*Candida tropicalis* strain DP201 was prepared by integration of the construct shown as SEQ ID NO: 70 into the genome of strain DP186 (Table 3) at the site of the genomic sequence of the gene for isocitrate lyase. DP428 was prepared by integration of the construct shown as SEQ ID NO: 70 into the genome of strain DP421 (Table 3) at the site of the genomic sequence of the gene for isocitrate lyase. Sequences of oligonucleotide primers for analysis of strains were:

```
ICL-IN-F1:
GGATCCGTCTGAAGAAATCAAGAACC       (SEQ ID NO: 124)

1758R2:
TGGTGTAGGCCAATAATTGCTTAATGATATACAA (SEQ ID NO: 125)
AACTGGCACCACAA

1758F2:
GAGCAATTGTTGGAATATTGGTACGTTGTGGTGC (SEQ ID NO: 126)
CAGTTTTGTATATCA

1758R34:
GAACTTAACAATAGCACCGTCTTGCAAACACATG (SEQ ID NO: 127)
GTCAAGTTAGTTAA
```

For strains DP201 and DP428 (integrants of SEQ ID NO: 70), PCR with primers ICL-IN-F1 and 1758R2 produces a 1609 base pair amplicon indicating that the construct has been integrated in the ICL promoter region; PCR with primers 1758F2 and 1758R34 produces a 1543 base pair amplicon indicating that CYP52A17 has been integrated. Neither primer pair produces an amplicon from the parental strains DP186 or DP421.

7.6.2 Insertion of CYP52A13 Under Control of the Isocitrate Lyase Promoter

A construct for expressing *Candida tropicalis* cytochrome P450 CYP52A13 under the control of the isocitrate lyase promoter was made by cloning the sequence of a gene encoding *Candida tropicalis* cytochrome P450 CYP52A13 (given as SEQ ID NO: 71) into a vector of the form shown in FIG. 23. The sequence of the complete vector is given as SEQ ID NO: 72.

The vector was prepared as described in Section 7.1.1, except that the construct was linearized with BsiWI instead of BsmBI. *Candida tropicalis* strains were transformed with the construct as described in Section 7.1.2, except that 100 µg/ml of zeocin was used instead of 200 µg/ml nourseothricin as the selective antibiotic. Genomic DNA was prepared and tested for the presence of the integrated DNA as described in Section 7.1.3.

*Candida tropicalis* strain DP522 was prepared by integration of the construct shown as SEQ ID NO: 72 into the genome of strain DP421 (Table 3) at the site of the genomic sequence of the gene for isocitrate lyase. Sequences of oligonucleotide primers for analysis of strains were:

```
ICL-IN-F1:
                                 (SEQ ID NO: 124)

4082R2:
CGATTAAGGCCAATGGAACAATGACGTACCACTT (SEQ ID NO: 128)
AGTAAAGTAGGTA

4082F2:
CATGACTGTTCACGACATTATTGCTACCTACTTT (SEQ ID NO: 129)
ACTAAGTGGTACGTC

4082R34:
ACATTTCAATATTAGCACCGTCAAATAATGACAT (SEQ ID NO: 130)
GGTCAAATGGGACA
```

For strain DP522 (integration of SEQ ID NO: 72), PCR with primers ICL-IN-F1 and 4082R2 produces a 1600 base pair amplicon indicating that the construct has been integrated in the ICL promoter region; PCR with primers 4082F2 and 4082R34 produces a 1565 base pair amplicon indicating that CYP52A13 has been integrated. Neither primer pair produces an amplicon from the parental strain DP421.

7.6.3 Insertion of CYP52A12 Under Control of the Isocitrate Lyase Promoter

A construct for expressing *Candida tropicalis* cytochrome P450 CYP52A12 under the control of the isocitrate lyase promoter was made by cloning the sequence of a gene encoding *Candida tropicalis* cytochrome P450 CYP52A12 (given as SEQ ID NO: 73) into a vector of the form shown in FIG. 23. The sequence of the complete vector is given as SEQ ID NO: 74.

The vector was prepared as described in Section 7.1.1, except that the construct was linearized with BsiWI instead of BsmBI. *Candida tropicalis* strains were transformed with the construct as described in Section 7.1.2, except that 100 µg/ml of zeocin was used instead of 200 µg/ml nourseothricin as the selective antibiotic. Genomic DNA was prepared and tested for the presence of the integrated DNA as described in Section 7.1.3.

*Candida tropicalis* strain DP526 was prepared by integration of the construct shown as SEQ ID NO: 74 into the genome of strain DP421 (Table 3) at the site of the genomic sequence of the gene for isocitrate lyase. Sequences of oligonucleotide primers for analysis of strains were:

```
ICL-IN-F1:
                                        (SEQ ID NO: 124)

CYP52A12-R2:
ATCAATAATTTCCTGGGTTGCCAT                (SEQ ID NO: 131)

CYP52A12-F1:
ATGGCAACCCAGGAAATTATTGAT                (SEQ ID NO: 132)

CYP52A12-R1:
CTACATCTTGACAAAAACACCATCATT             (SEQ ID NO: 133)
```

For strain DP526 (integration of SEQ ID NO: 74), PCR with primers ICL-IN-F1 and 4082R2 produces a 1554 base pair amplicon indicating that the construct has been integrated in the ICL promoter region; PCR with primers 4082F2 and 4082R34 produces a 1572 base pair amplicon indicating that CYP52A12 has been integrated. Neither primer pair produces an amplicon from the parental strain DP421.

7.7 Deletion of POX Genes from *Candida tropicalis*

Picataggio et al., 1991, Mol Cell Biol 11, 4333-4339 describe a system for the sequential disruption of the *Candida tropicalis* chromosomal POX4 and POX5 genes, encoding distinct isozymes of the acyl coenzyme A (acyl-CoA) oxidase, which catalyze the first reaction in the β-oxidation pathway of fatty acids. An alternative method is to use the SAT-1 flipper.

7.7.1 Deletion of POX4 Alleles

The sequence of a gene encoding an acyl-coenzyme A oxidase II (PXP-4) of *Candida tropicalis*, POX4, is given as SEQ ID NO: 136. This sequence was used to design two "pre-targeting" constructs. The first pre-targeting construct is comprised of two targeting sequences from the 5' and 3' end of the structural gene. The targeting sequences are separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the first POX4 pre-targeting construct is given as SEQ ID NO: 137. Not shown in SEQ ID NO: 137 but also present in the pre-targeting construct were a selective marker conferring resistance to kanamycin and a bacterial origin of replication, so that the pre-targeting construct can be grown and propagated in *E. coli*. The first pre-targeting sequence can be synthesized using standard DNA synthesis techniques well known in the art.

The second pre-targeting construct is comprised of two targeting sequences from the 5' and 3' end of the structural gene that lie internal to the 5' and 3' targeting sequences of the first pre-targeting construct. The targeting sequences are separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the second POX4 pre-targeting construct is given as SEQ ID NO: 138. Not shown in SEQ ID NO: 138 but also present in the pre-targeting construct is a selective marker conferring resistance to kanamycin and a bacterial origin of replication, so that the pre-targeting construct can be grown and propagated in *E. coli*. The second pre-targeting sequence can synthesized using standard DNA synthesis techniques well known in the art.

Targeting sequences for deletion of the two POX4 alleles from the *Candida tropicalis* geneome can be prepared by digesting the SAT-1 flipper (SEQ ID NO: 1) with restriction enzymes NotI and XhoI, and ligating into the POX4 pre-targeting constructs (SEQ ID NO: 137 or SEQ ID NO: 138) from which the 20 bp stuffer has been removed by digestion with restriction enzymes NotI and XhoI. The sequence of the resulting first targeting construct for the deletion of the first allele of POX4 is given as SEQ ID NO: 139. The sequence of the resulting second targeting construct for the deletion of the second allele of POX4 is given is SEQ ID NO: 140. Because the POX4 targeting sequences of the second targeting construct lie internal to the targeting sequences of the first targeting construct, use of the first targeting construct to delete the first POX4 allele assures that use of the second targeting construct is specific for the second POX4 allele since the targeting sequences of the second targeting construct no longer exist in the first deleted allele.

Analysis of integrants and excisants can be performed as described in Section 7.1. Sequences of oligonucleotide primers for the analysis of strains are:

```
POX4-IN-L:
ATGACTTTTACAAAGAAAAACGTTAGTGTATCAC   (SEQ ID NO: 141)
AAG

POX4-IN-R:
TTACTTGGACAAGATAGCAGCGGTTTC          (SEQ ID NO: 142)

SAT1-R:
TGGTACTGGTTCTCGGGAGCACAGG            (SEQ ID NO:  79)

SAT1-F:
CGCTAGACAAATTCTTCCAAAAATTTTAGA       (SEQ ID NO:  80)
```

7.7.2 Deletion of POX5 Alleles

The sequence of a gene encoding an acyl-coenzyme A oxidase I (PXP-5) of *Candida tropicalis*, POX5, is given as SEQ ID NO: 143. This sequence was used to design two "pre-targeting" constructs. The first pre-targeting construct is comprised of two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the first POX5 pre-targeting construct is given as SEQ ID NO: 144. Not shown in SEQ ID NO: 144 but also present in the pre-targeting construct were a selective marker conferring resistance to kanamycin and a bacterial origin of replication, so that the pre-targeting construct can be grown and propagated in *E. coli*. The first pre-targeting sequence can be synthesized using standard DNA synthesis techniques well known in the art.

The second pre-targeting construct is comprised of two targeting sequences from the 5' and 3' end of the structural gene that lie internal to the 5' and 3' targeting sequences of the first pre-targeting construct. The 5' targeting sequence of the second pre-targeting construct is modified at position 248 (C248T) and 294 (G294A) to remove unwanted XhoI and BsmBI sites, respectively. The targeting sequences were separated by a sequence, given as SEQ ID NO: 12, comprising a NotI restriction site, a 20 bp stuffer fragment and a XhoI restriction site. The targeting sequences are flanked by BsmBI restriction sites, so that the final targeting construct can be linearized prior to transformation into *Candida tropicalis*. The sequence of the second POX5 pre-targeting construct is given as SEQ ID NO: 145. Not shown in SEQ ID NO: 145 but also present in the pre-targeting construct were a selective marker conferring resistance to kanamycin and a bacterial origin of replication, so that the pre-targeting construct can be grown and propagated in *E. coli*. The second pre-targeting sequence can be synthesized using standard DNA synthesis techniques well known in the art.

Targeting sequences for deletion of the two POX5 alleles from the *Candida tropicalis* geneome were prepared by digesting the SAT-1 flipper (SEQ ID NO: 1) with restriction enzymes NotI and XhoI, and ligating into both of the POX5 pre-targeting constructs (SEQ ID NO 144 or 145) from which the 20 bp stuffer had been removed by digestion with restriction enzymes NotI and XhoI. The sequence of the resulting first targeting construct for the deletion of the first allele of POX5 is given as SEQ ID NO: 146. The sequence of the resulting second targeting construct for the deletion of the second allele of POX5 is given is SEQ ID NO: 147. Because the POX5 targeting sequences of the second targeting construct lie internal to the targeting sequences of the first targeting construct, use of the first targeting construct to delete the first POX5 allele assures that use of the second targeting construct is specific for the second POX5 allele since the targeting sequences of the second targeting construct no longer exist in the first deleted allele.

Analysis of integrants and excisants can be performed as described in section 7.1. Sequences of oligonucleotide primers for the analysis of strains are:

```
POX5-IN-L:
ATGCCTACCGAACTTCAAAAAGAAAGAGAA    (SEQ ID NO: 148)

POX5-IN-R:
TTAACTGGACAAGATTTCAGCAGCTTCTTC    (SEQ ID NO: 149)

SAT1-R:
TGGTACTGGTTCTCGGGAGCACAGG         (SEQ ID NO: 79)

SAT1-F:
CGCTAGACAAATTCTTCCAAAAATTTTAGA    (SEQ ID NO: 80)
```

8. CONVERSION OF FATTY ACIDS USING MODIFIED STRAINS OF CANDIDA TROPICALIS

8.1 Analytical Methods

8.1.1 GC-MS for Identification of Fatty Acids, Omega-Hydroxyfatty Acids and Diacids Gas chromatography/mass spectrometry (GC/MS) analysis was performed at 70 eV with ThermoFinnigan TraceGC Ultra gas chromatograph coupled with Trace DSQ mass spectrometer. Products were esterified with $BF_3$ in methanol (10%, w/w) at 70° C. for 20 min, and further silylation of the methyl esters with HMDS/TMCS/Pyridine at 70° C. for 10 min when needed. The experiments were carried out with injector, ion source and interface temperature of 200° C., 250° C. and 280° C., respectively. Samples in hexane (1 μl) were injected in PTV split mode and run on a capillary column (Varian CP8944 VF-5MS, 0.25 mm×0.25 um×30 m). The oven temperature was programmed at 120° C. for one minute increasing to 260° C. at the rate of 20° C./minute, and then to 280° C. at the rate of 4.0° C./minute.

8.1.2 LC-MS for Measurement of Fatty Acids, Omega-Hydroxy Fatty Acids and Diacids The concentration of omega-hydroxy fatty acids and diacids during biotransformation was measured by liquid chromatography/mass spectrometry (LC/MS) with purified products as standards. The solvent delivery system was a Waters Alliance 2795 Separation Module (Milford, Mass., USA) coupled with a Waters 2996 photodiode array detector and Waters ZQ detector with an electron spray ionization mode. The separation was carried on a reversed-phase column with a dimension of 150×4.6 mm and particle size of 5 μm. The mobile phase used for separation contained 10% $H_2O$, 5% acetonitrile, 5% Formic acid solution (1% in water) and 80% methanol.

8.1.3 NMR for Characterization of Omega-Hydroxyfatty Acids and Diacids

Proton ($^1H$) and $^{13}C$-NMR spectra were recorded on a Bruker DPX300 NMR spectrometer at 300 MHz. The chemical shifts (ppm) for $^1H$-NMR were referenced relative to tetramethylsilane (TMS, 0.00 ppm) as the internal reference.

8.2 Oxidation of Fatty Acids by *Candida tropicalis* Strains Lacking Four CYP52A P450s We compared the *Candida tropicalis* strain lacking CYP52A13, CYP52A14, CYP52A17 and CYP52A18 (DP174) constructed in Section 7.2 with the starting strain (DP1) for their abilities to oxidize fatty acids. To engineer P450s for optimal oxidation of fatty acids or other substrates it is advantageous to eliminate the endogenous P450s whose activities may mask the activities of the enzymes being engineered. We tested *Candida tropicalis* strains DP1 and DP174 (genotypes given in Table 3) to determine whether the deletion of the four CYP52 P450S had affected the ability of the yeast to oxidize fatty acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. After 16 hours 0.5 ml of culture was added to 4.5 ml fresh media F plus 60 g/l glucose in a 125 ml flask, and grown at 30° C. and 250 rpm for 12 hours. Substrates were added and shaking was continued at 30° C. and 250 rpm. We then tested the conversion of C14 fatty acid substrates as shown in FIG. 13. FIG. 13 parts A and B show that the starting strain DP1 converts methyl myristate to ω-hydroxy myristate and to the C14 diacid produced by oxidation of the ω-hydroxy myristate over a 48 hour time course, while the quadruple P450 deletion strain DP174 can effect almost no detectable conversion. FIG. 13 parts C and D show that the starting strain DP1 converts methyl myristate and sodium myristate to ω-hydroxy myristate and to the C14 diacid produced by oxidation of the ω-hydroxy myristate after 48 hours, while the quadruple P450 deletion strain DP174 effects almost no detectable conversion of these substrates.

These results confirm that at least one of the four *Candida tropicalis* cytochrome P450 genes encoding CYP52A13, CYP52A14, CYP52A17 and CYP52A18 is required for hydroxylation of fatty acids, consistent with the schematic representation of *Candida tropicalis* fatty acid metabolism pathways shown in FIG. 12. Further it shows that strain DP174 is an appropriate strain to use for testing of engineered cytochrome P450s, since it has essentially no ability to oxidize fatty acids without an added P450.

8.3 Oxidation of ω-Hydroxy Fatty Acids by *Candida tropicalis* Strains Lacking Four CYP52A P450s We compared the *Candida tropicalis* strain lacking CYP52A13, CYP52A14, CYP52A17 and CYP52A18 (DP174) constructed in Section 7.2 with the starting strain (DP1) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 280 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken at the times indicated, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). The results are shown in Table 5.

TABLE 5

Oxidation of ω-hydroxy fatty acids by *Candida tropicalis*

| Ω-HYDROXY FATTY ACID SUBSTRATE CHAIN LENGTH | REACTION TIME | DIACID PRODUCED BY DP1 (G/L) | DIACID PRODUCED BY DP174 (G/L) |
|---|---|---|---|
| C12 | 60 hours | 5.6 | 5.2 |
| C16 | 60 hours | 1.4 | 0.8 |
| C12 | 24 hours | 5.4 | 5 |
| C12 | 48 hours | 6 | 6.7 |
| C12 | 72 hours | 6.2 | 6.5 |
| C16 | 24 hours | 2.3 | 0.9 |
| C16 | 48 hours | 2.4 | 1.7 |
| C16 | 72 hours | 2.8 | 1.8 |

These results show that at least one enzyme capable of oxidizing ω-hydroxy fatty acids is present in *Candida tropicalis* in addition to the cytochrome P450 genes encoding CYP52A13, CYP52A14, CYP52A17 and CYP52A18.

8.4 Oxidation of ω-Hydroxy Fatty Acids by *Candida tropicalis* Strains Lacking Four CYP52A P450s and Four Fatty Alcohol Oxidases We compared the *Candida tropicalis* strain lacking CYP52A13, CYP52A14, CYP52A17, CYP52A18 and FAO1 (DP186) constructed in Section 7.3 with the *Candida tropicalis* strain lacking CYP52A13, CYP52A14, CYP52A17, CYP52A18, FAO1, FAO1B, FAO2A and FAO2B (DP258 and DP259) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken after 24 hours, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 15 most of the hydroxy fatty acids are converted to diacid after 24 hours. These results show that at least one enzyme capable of oxidizing ω-hydroxy fatty acids is present in *Candida tropicalis* in addition to the cytochrome P450 genes encoding CYP52A13, CYP52A14, CYP52A17, CYP52A18, FAO1, FAO1B, FAO2A and FAO2B.

8.5 Oxidation of ω-Hydroxy Fatty Acids by *Candida tropicalis* Strains Lacking Six CYP52A P450s and Four Fatty Alcohol Oxidases We compared the *Candida tropicalis* strain lacking CYP52A13, CYP52A14, CYP52A17, CYP52A18 and FAO1 (DP186) constructed in Section 7.2 with the *Candida tropicalis* strain lacking CYP52A13, CYP52A14, CYP52A17, CYP52A18, FAO1, FAO1B, FAO2A, FAO2B, CYP52A12 and CYP52A12B (DP283 and DP284) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken after 24 hours, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 16 most of the C12 hydroxy fatty acids and a substantial fraction of the C16 hydroxy fatty acids are converted to diacid after 24 hours. These results show that at least one enzyme capable of oxidizing ω-hydroxy fatty acids is present in *Candida tropicalis* in addition to the cytochrome P450 genes encoding CYP52A13, CYP52A14, CYP52A17, CYP52A18, CYP52A12, CYP52A12B, FAO1, FAO1B, FAO2A and FAO2B.

8.6 Oxidation of ω-Hydroxy Fatty Acids by *Candida tropicalis* Strains Lacking Six CYP52A P450s, Four Fatty Alcohol Oxidases and Five Alcohol Dehydrogenases We compared the *Candida tropicalis* strain DP1 with the *Candida tropicalis* strain lacking CYP52A13, CYP52A14, CYP52A17, CYP52A18, FAO1, FAO1B, FAO2A, FAO2B, CYP52A12 and CYP52A12B (DP283) and the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10 (DP415) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Samples were taken at the times indicated, cell culture was acidified to pH~1.0 by addition of 6 N HCl, products were extracted from the cell culture by diethyl ether and the concentrations of α,ω-diacids in the media were measured by LC-MS (liquid chromatography mass spectroscopy). As shown in FIG. 19 Part A, the cell growth was almost identical for the 3 strains. Strain DP415 produced much less α,ω-dicarboxy laurate than the other two strains, however, as shown in FIG. 19 part B.

These results show that a significant reduction in the ability of *Candida tropicalis* to oxidize ω-hydroxy fatty acids can be reduced by deleting genes encoding CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10.

8.7 Oxidation of ω-Hydroxy Fatty Acids by *Candida tropicalis* Strains Lacking Six CYP52A P450s, Four Fatty Alcohol Oxidases and Eight Alcohol Dehydrogenases We compared the *Candida tropicalis* strain DP1 with the *Candida tropicalis* strain lacking CYP52A13, CYP52A14, CYP52A17, CYP52A18, FAO1, FAO1B, FAO2A, FAO2B, CYP52A12, CYP52A12B, ADH-A4 and ADH-A4B (DP390), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10 (DP415), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 (DP417 and DP421), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10, ADH-A10B and ADH-B11 (DP423), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10, ADH-A10B, ADH-B11 and ADH-B11B (DP434 and DP436) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Samples were taken at the times indicated, cell culture was acidified to pH~1.0 by addition of 6 N HCl, products were extracted from the cell culture by diethyl ether and the concentrations of α,ω-diacids in the media were measured by LC-MS (liquid chromatography mass spectroscopy). As shown in FIG. 20, a significant reduction in the ability of *Candida tropicalis* to oxidize ω-hydroxy fatty acids can be obtained by deleting genes encoding alcohol dehydrogenases in strains lacking some cytochrome P450s and fatty alcohol oxidases.

8.8 Oxidation of Methyl Myristate by *Candida tropicalis* Strains Lacking Six CYP52A P450s, Four Fatty Alcohol Oxidases and Six Alcohol Dehydrogenases with a Single CYP52A P450 Added Back Under Control of the ICL Promoter We compared the *Candida tropicalis* strain DP1 with the *Candida tropicalis* strain lacking CYP52A13, CYP52A14, CYP52A17, CYP52A18 and FAO1 and with CYP52A17 added back under control of the isocitrate lyase promoter (DP201) and with the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 and with CYP52A17 added back under control of the isocitrate lyase promoter (DP428) for their abilities to oxidize methyl myristate.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glucose plus 5 g/l ethanol. After 18 hours 3 ml of preculture was added to 27 ml fresh media F plus 20 g/l glucose plus 5 g/l ethanol in a 500 ml flask, and grown at 30° C. and 250 rpm for 20 hours before addition of substrate. Biocatalytic conversion was initiated by adding 40 g/l of methyl myristate, the pH was adjusted to ~7.8 with 2M NaOH. The culture was pH controlled by adding 2 mol/l NaOH every 12 hours, glycerol was fed as cosubstrate by adding 500 g/l glycerol and ethanol was fed as a inducer by adding 50% ethanol every 12 hours. Samples were taken at the times indicated, cell culture was acidified to pH~1.0 by addition of 6 N HCl, products were extracted from the cell culture by diethyl ether and the concentrations of ω-hydroxy myristate and α,ω-dicarboxymyristate were measured by LC-MS (liquid chromatography mass spectroscopy).

As shown in FIG. 24, strains DP1 and DP201 both produce significant levels of tetradecanedioic acid (the α,ω-diacid) and negligible levels of ω-hydroxy myristic acid. In contrast, under these conditions strain DP428 produces approximately five-fold less tetradecanedioic acid, while converting nearly 70% of the methyl myristate to ω-hydroxy myristic acid after 60 hours. This shows that elimination of one or more of the genes FAO1B, FAO2A, FAO2B, CYP52A12, CYP52A12B, ADH-A4, ADH-A4B, ADH-B4, ADH-B4B, ADH-A10 and ADH-B11 prevents the over-oxidation of the fatty acid myristic acid by *Candida tropicalis*, and that the presence of CYP52A17 under control of the isocitrate lyase promoter in this strain background produces a strain that can convert methyl myristate to ω-hydroxy myristic acid, but that does not over-oxidize the product to tetradecanedioic acid.

8.9 Oxidation of Methyl Myristate by an Engineered *Candida tropicalis* Strain in a Fermentor We compared the production of ω-hydroxy myristic acid and α,ω-tetradecanoic acid by a *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 and with CYP52A17 added back under control of the isocitrate lyase promoter (DP428).

*C. tropicalis* DP428 was taken from a glycerol stock or fresh agar plate and inoculated into 500 ml shake flask containing 30 mL of YPD medium (20 g/l glucose, 20 g/l peptone and 10 g/l yeast extract) and shaken at 30° C., 250 rpm for 20 h. Cells were collected by centrifugation and re-suspended in FM3 medium for inoculation. (FM3 medium is 30 g/l glucose, 7 g/l ammonium sulfate, 5.1 g/l potassium phosphate, monobasic, 0.5 g/l magnesium sulfate, 0.1 g/l calcium chloride, 0.06 g/l citric acid, 0.023 g/l ferric chloride, 0.0002 g/l biotin and 1 ml/l of a trace elements solution. The trace elements solution contains 0.9 g/l boric acid, 0.07 g/l cupric sulfate, 0.18 g/l potassium iodide, 0.36 g/l ferric chloride, 0.72 g/l manganese sulfate, 0.36 g/l sodium molybdate, 0.72 g/l zinc sulfate.) Conversion was performed by inoculating 15 ml of preculture into 135 ml FM3 medium, methyl myristate was added to 20 g/l and the temperature was kept at 30° C. The pH was maintained at 6.0 by automatic addition of 6 M NaOH or 2 M $H_2SO_4$ solution. Dissolved oxygen was kept at 70% by agitation and $O_2$-cascade control mode. After 6 hours growth, ethanol was fed into the cell culture to 5 g/l. During the conversion phase, 80% glycerol was fed as co-substrate by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hours, ethanol was added into cell culture to 2 g/l, and methyl myristate was added to 40 g/l until the total methyl myristate added was 140 g/l (i.e. the initial 20 g/l plus 3 subsequent 40 g/l additions). Formation of products was measured at the indicated intervals by taking samples and acidifying to pH~1.0 by addition of 6 N HCl; products were extracted from the cell culture by diethyl ether and the concentrations of ω-hydroxy myristate and α,ω-dicarboxymyristate were measured by LC-MS (liquid chromatography mass spectroscopy), as shown in FIG. 26. Under these conditions the strain produced a final concentration of 91.5 g/l ω-hydroxy myristic acid, with a productivity of 1.63 g/l/hr and a w/w ratio of ω-hydroxy myristic acid: tetradecanedioic acid of 20.3:1. This shows that elimination of one or more of the genes FAO1B, FAO2A, FAO2B, CYP52A12, CYP52A12B, ADH-A4, ADH-A4B, ADH-B4, ADH-B4B, ADH-A10 and ADH-B11 prevents the over-oxidation of the fatty acid myristic acid by *Candida tropicalis*, and that the presence of CYP52A17 under control of the isocitrate lyase promoter in this strain background produces a strain that can convert methyl myristate to ω-hydroxy myristic acid, but that does not over-oxidize the product to tetradecanedioic acid.

8.10 Oxidation of Methyl Myristate, Oleic Acid and Linoleic Acid by Engineered *Candida tropicalis* Strains We compared the fatty acid oxidizing activities of two *Candida tropicalis* strains which lack CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11, one of which has CYP52A17 added back under control of the isocitrate lyase promoter (DP428) and one of which has CYP52A13 added back under control of the isocitrate lyase promoter (DP522).

Cultures of the yeast strains were grown at 30° C. in a DASGIP parallel fermentor containing 200 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. The pH was maintained at 6.0 by automatic addition of 6 M NaOH or 2 M $H_2SO_4$ solution. Dissolved oxygen was kept at 70% by agitation and $O_2$-cascade control mode. After 6 hour growth, ethanol was fed into the cell culture to 5 g/l. After 12 h growth, biocatalytic conversion was initiated by adding methyl myristate acid to 60 g/l or oleic acid to 60 g/l or linoleic acid to 30 g/l. During the conversion phase, 80% glycerol was fed as co-substrate for conversion of methyl myristate and 500 g/l glucose was fed as co-substrate for conversion of oleic acid and linoleic acid by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l. Samples were taken at various times, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 25, strains DP428 and DP522 were both able to produce ω-hydroxy fatty acids from these substrates, as well as some α,ω-diacids. FIG. 25 also shows that the different P450s had different preferences for the fatty acid substrates, and different propensities to oxidize the ω-hydroxy group.

9. DEPOSIT OF MICROORGANISMS

A living cultures of strain DP421 has been deposited with American Type Culture Collection, 12301 Parklawn Drive, Rockville, Md. 20852, on May 4, 2009, under the Budapest Treaty on the International Recognition of the Deposit of Microorganisms for the purposes of patent procedure.

10. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents, patent applications, and databases mentioned in this specification are herein incorporated by reference into the specification to the same extent as if each individual publication, patent, patent application or database was specifically and individually indicated to be incorporated herein by reference.

What is claimed:

1. A method of using a genetically modified *Candida* strain for the production of an α-carboxyl-ω-hydroxy fatty acid having a carbon chain length in the range from C6 to C22 wherein the genetically modified *Candida* strain is characterized by a first genetic modification class, a second genetic modification class, and a third genetic modification class; wherein the first genetic modification class comprises disruption of all copies of POX 4 and all copies of POX 5 in the genetically modified *Candida* strain, the second genetic modification class comprises one or more genetic modifications that collectively or individually disrupt a fatty alcohol oxidase in the genetically modified *Candida* strain, and a third genetic modification class comprising an insertion of a first gene into the *Candida* genome, wherein the first gene encodes: (i) a cytochrome P450, (ii) a desaturase, (iii) a lipase, (iv) a glycosyl transferase or (vi) a fatty alcohol oxidase that is not identical to a naturally occurring gene in *Candida*, the method comprising:

fermenting the genetically modified *Candida* strain in a culture medium comprising a nitrogen source, an organic substrate having a carbon chain length in the range from C6 to C22, and a cosubstrate thereby oxidizing the organic substrate to the α-carboxyl-ω-hydroxy fatty acid.

2. The method of claim 1, wherein the method is for the production of an α-carboxyl-ω-hydroxy fatty acid having a carbon chain length in the range from C6 to C22 and wherein the α-carboxyl-ω-hydroxy fatty acid has the formula:

$$HO-CH_2(CH_2)_{n-COOH}$$

wherein n is an integer in the range from 4 to 20.

3. The method of claim 1, wherein the method is for the production of an α-carboxyl-ω-hydroxy fatty acid having a carbon chain length in the range from C6 to C22, and the α-carboxyl-ω-hydroxy fatty acid is 12-hydroxy-dodecanoic acid, 14-hydroxy-tetradecanoic acid, 16-hydroxy-hexadecanoic acid, 17-hydroxy-heptadecanoic acid, 18-hydroxy-octadecanoic acid, 20-hydroxy-eicosanoic acid, or 22-hydroxy-docosanoic acid.

4. The method of claim 1, wherein the method is for the production of an α-carboxyl-ω-hydroxy fatty acid having a carbon chain length in the range from C6 to C22, and the α-carboxyl-ω-hydroxy fatty acid has a single carbon-carbon double bond that is in the cis or trans configuration and wherein the α-carboxyl-ω-hydroxy fatty acid has the formula:

$$HO-CH_2(CH_2)_xCH=CH(CH_2)_yCOOH$$

wherein x+y sum to an integer that is in the range from 2 to 18.

5. The method of claim 1, wherein the method is for the production of an α-carboxyl-ω-hydroxy fatty acid having a carbon chain length in the range from C6 to C22, and the α-carboxyl-ω-hydroxy fatty acid is an α-carboxyl-ω-hydroxy polyenoic fatty acid comprising a methylene-interrupted double bond, a conjugated double bond, a polymethylene-interrupted double bond, an allenic double bond, or a cumulenic double bond.

6. The method of claim 1, wherein the second genetic modification class comprises disruption of at least one fatty alcohol oxidase selected from the group consisting of FAO1, FAO1B, FAO2A and FAO2B.

7. The method of claim 1, wherein the second genetic modification class comprises disruption of all alleles of FAO1 and all alleles of FAO1B.

8. The method of claim 1, wherein the first gene is a gene listed in Table 4 other than a gene that naturally occurs in *Candida tropicalis*.

9. The method of claim 1, wherein the first gene is expressed under control of a promoter other than the promoter that controls expression of the corresponding naturally occurring gene in the *Candida* host cell.

10. The method of claim 9, wherein the promoter is the isocitrate lyase promoter, a cytochrome P450 promoter, or a fatty alcohol oxidase promoter.

11. The method of claim 1, wherein the organic substrate, having a carbon chain length in the range from C6 to C22, is enzymatically modified within the *Candida* strain.

12. The method of claim 1 wherein the *Candida* strain is *Candida tropicalis*.

* * * * *

SEQUENCE LISTING

<160> NUMBER OF SEQ ID NOS: 149

<210> SEQ ID NO 1
<211> LENGTH: 4186
<212> TYPE: DNA
<213> ORGANISM: Artificial Sequence
<220> FEATURE:
<223> OTHER INFORMATION: Contains flp recominase from Saccharomyces
      cerevisiae with flanking regions as well as the gene encoding
      resistance to the Nourseothricin resistance marker from transposon
      Tn1825

<400> SEQUENCE: 1

```
ctcgaggaag ttcctatact ttctagagaa taggaacttc ggatccaata atgattggtt      60
tgatattttt gtctagtacc atctgtacca ttacacttaa attatcttta tatctgtcta     120
actcgactgt ctggatttca ttgatgtagt cgtatgcatc gttagttcca aaaatattg      180 tcatcaattt gatattggtt tccgactcta aaatttttgg aagaatttgt ctagcgtgct     240
ctgagttgta gccactgaaa ccacggttaa taacatccaa ttttcggata tacacattct     300
gtaatgctgg atgaaagcca tactgggtac aactaaactg ggtgatggag tcaccgaaca     360
acacaaattt accgtattcc atgattgcta tggttgagaa ttttttttt  ttcttgtccc     420 acgccatttt tcaaattatg cagttgagaa tgttagtttt tgtgtacacc ccgttcgctg     480
aatatttcgg aataattcaa agattgggga gtggggagg  cgatagacga agacacggta     540
taaaaatggg caaattttc  cccaactttt tgcagtggtt taactaataa tcgtcgacat     600
gccacaattt gatatattat gtaaaacacc acctaaggtg cttgttcgtc agtttgtgga     660
aaggtttgaa agaccttcag gtgagaaaat agcattatgt gctgctgaac taacctattt     720
atgttggatg attacacata acggaacagc aatcaagaga gccacattca tgagctataa     780
tactatcata agcaattcgt tgagtttcga tattgtcaat aaatcactcc agtttaaata     840
caagacgcaa aaagcaacaa ttttggaagc ctcattaaag aaattgattc ctgcttggga     900
atttacaatt attccttact atggacaaaa acatcaatct gatatcactg atattgtaag     960
tagtttgcaa ttacagttcg aatcatcgga agaagcagat aagggaaata gccacagtaa    1020
aaaaatgctt aaagcacttc taagtgaggg tgaaagcatc tgggagatca ctgagaaaat    1080
actaaattcg tttgagtata cttcgagatt tacaaaaaca aaaactttat accaattcct    1140
cttcctagct actttcatca attgtggaag attcagcgat attaagaacg ttgatccgaa    1200
atcatttaaa ttagtccaaa ataagtattt gggagtaata atccagtgtt tagtgacaga    1260
gacaaagaca agcgttagta ggcacatata cttctttagc gcaaggggta ggatcgatcc    1320
acttgtatat ttggatgaat ttttgaggaa ttctgaacca gtcctaaaac gagtaaatag    1380
gaccggcaat tcttcaagca ataaacagga ataccaatta ttaaaagata acttagtcag    1440
atcgtacaat aaagctttga agaaaatgc  gccttattca atctttgcta taaaaaatgg    1500
cccaaaatct cacattggaa gacatttgat gacctcattt ctttcaatga agggcctaac    1560
ggagttgact aatgttgtgg gaaattggag cgataagcgt gcttctgccg tggccaggac    1620
aacgtatact catcagataa cagcaatacc tgatcactac ttcgcactag tttctcggta    1680
ctatgcatat gatccaatat caaggaaat  gatagcattg aaggatgaga ctaatccaat    1740
tgaggagtgg cagcatatag aacagctaaa gggtagtgct gaaggaagca tacgataccc    1800
cgcatggaat gggataatat cacaggaggt actagactac ctttcatcct acataaatag    1860
acgcatataa gagtgaaatt ctggaaatct ggaaatctgg ttttgtattc ttgttattct    1920
```

```
tcttttttgtt attacatata taacttgtta cttttttaaa aaaatctttg tatatttat      1980 aaatatataa aactaaattt aagaaaaaga gaaaaatgtt ttatttgaga gattgaaatt      2040
ttacttgaat ttagcttagc ttttataaag tattattatg taaaaaaaca aaacaaatat      2100
acattaaaaa gttaagacta taaaatagcc acccaaggca tttctatatc ttgttgttgt      2160
tgttttcatc ttctgtatca gaggaactta ttttattatt ttcgtcacgg gtattttctc     2220
ttgtttgatg attcatccca ttcattccat cataaaatgt cgagcgtcaa aactagagaa     2280
taataaagaa aacgatcttt tcaaaaagaa aaacctttt agttttcctt tgttgttgtt      2340
gtgggtgtgt gctatttata ttatatagtt tactcataat accataaaat attcggtttg    2400
attaggttat tttaataagc taatttgttt ctaatcgtgt aatttatgct gtgtatatta    2460
agtagtgtgt gcactgccca aaaatgtttg ttgtttatag tcggttaaag agaaaaaaga   2520 aaaaagatc catacacaca cgttaattag ttgttcaacg taatacactc atattttgtt     2580
cttatttgct ttcggtcgct gttctcacca agatttattg ccaacgaaac aattttttt     2640 tatatatttt cagatttttc tttttttcct ttcctttcct tttctaattt tcactcctgg    2700
ttttctttct ttcttagaaa cattatctcg atattaaat taaaaaaata taatcattca     2760
aaatggacgg tggtatgttt tagtttagct tcaattctaa ttgattgatt aatcagttga   2820
ttggtttcaa tatgacaaat gggtagggtg ggaaaaccttc attttcaatt cagatcaaac  2880 tttttttgttg tcgacataat atttctcgtt tgggatgtta ctgtcacatt aataatacac  2940
acacatcagc ttataatttt gaagtaatt tatcagatat gttgtgacga tcaatggaaa    3000
tggctaactt caatgtatct gttcttcccc ttttcaaag ttcacgtttt ttgattgatt    3060
gattgatctg tcggcagtgg tttcaaaacc attcggtgag taatcctatc aatcaatgtt   3120
acgacaaaag gctcaatatt caaaattgca atgttttatg ttttcctacg tgtacttgtg  3180
caaggcaatt gattcaacat tgcttttggt gtttgacgag tttctagttt ggacttgtgt   3240
tgttatctgg gctatacaga tttcccggct cactatgaat ttttttttttc gacgctcagt 3300 gcacacaact ataaacaaca caaacacaaa cacagcaaga aaaaaaaaa acgaacattg   3360 aattgaaacc aagccaactg aaaaattcct tatttaaatg actgtcatac taacccattt  3420
ttatagaaga agttgctgct ttagttatcg ataacggttc tcatatgaaa atttcggtga  3480
tccctgagca ggtggcggaa acattggatg ctgagaacca tttcattgtt cgtgaagtgt  3540
tcgatgtgca cctatccgac caaggctttg aactatctac cagaagtgtg agcccctacc 3600
ggaaggatta catctcggat gatgactctg atgaagactc tgcttgctat ggcgcattca  3660
tcgaccaaga gcttgtcggg aagattgaac tcaactcaac atggaacgat ctagcctcta  3720
tcgaacacat tgttgtgtcg cacacgcacc gaggcaaagg agtcgcgcac agtctcatcg   3780
aatttgcgaa aaagtgggca ctaagcagac agctccttgg catacgatta gagacacaaa   3840
cgaacaatgt acctgcctgc aatttgtacg caaaatgtgg ctttactctc ggcggcattg   3900
acctcttcac gtataaaact agacctcaag tctcgaacga aacagcgatg tactggtact  3960
ggttctcggg agcacaggat gacgcctaac atatgtgaag tgtgaagggg gagattttca  4020
ctttattaga tttgtatata tgtataataa ataaataaat aagttaaata aataattaga   4080
taagggtggt aattattact atttacaatc aaaggtggtc ctgcaggaag ttcctatact   4140
ttctagagaa taggaacttc agatccacta gttctagagc ggccgc                 4186
```

<210> SEQ ID NO 2
<211> LENGTH: 3826

```
<212> TYPE: DNA
<213> ORGANISM: Candida tropicalis

<400> SEQUENCE: 2
tggagtcgcc agacttgctc acttttgact cccttcgaaa ctcaaagtac gttcaggcgg    60
tgctcaacga aacgctccgt atctacccgg gggtaccacg aaacatgaag acagctacgt   120
gcaacacgac gttgccacgc ggaggaggca aagacggcaa ggaacctatc ttggtgcaga   180
agggacagtc cgttgggttg attactattg ccacgcagac ggacccagag tattttgggg   240
ccgacgctgg tgagtttaag ccggagagat ggtttgattc aagcatgaag aacttggggt   300
gtaaatactt gccgttcaat gctgggccac ggacttgctt ggggcagcag tacactttga   360
ttgaagcgag ctacttgcta gtccggttgg cccagaccta ccgggcaata gatttgcagc   420
caggatcggc gtacccacca agaaagaagt cgttgatcaa catgagtgct gccgacgggg   480
tgtttgtaaa gctttataag gatgtaacgg tagatggata gttgtgtagg aggagcggag   540
ataaattaga tttgattttg tgtaaggttt tggatgtcaa cctactccgc acttcatgca   600
gtgtgtgtga cacaagggtg tactacgtgt gcgtgtgcgc caagagacag cccaaggggg   660
tggtagtgtg tgttggcgga agtgcatgtg acacaacgcg tgggttctgg ccaatggtgg   720
actaagtgca ggtaagcagc gacctgaaac attcctcaac gcttaagaca ctggtggtag   780
agatgcggac caggctattc ttgtcgtgct acccggcgca tggaaaatca actgcgggaa   840
gaataaattt atccgtagaa tccacagagc ggataaattt gcccacctcc atcatcaacc   900
acgccgccac taactacatc actcccctat tttctctctc tctctttgtc ttactccgct   960
cccgtttcct tagccacaga tacacaccca ctgcaaacag cagcaacaat tataaagata  1020
cgccaggccc accttctttc ttttttcttca ctttttttgac tgcaactttc tacaatccac  1080
cacagccacc accacagccg ctatgattga caaactccta gaatattggt atgtcgttgt  1140
gccagtgttg tacatcatca aacaactcct tgcatacaca aagactcgcg tcttgatgaa  1200
aaagttgggt gctgctccag tcacaaacaa gttgtacgac aacgctttcg gtatcgtcaa  1260
tggatggaag gctctccagt tcaagaagaa gggcagggct caagagtaca acgattacaa  1320
gtttgaccac tccaagaacc caagcgtggg cacctacgtc agtattcttt tcggcaccag  1380
gatcgtcgtg accaaagatc cagagaatat caaagctatt ttggcaaccc agttggtga  1440 tttttctttg ggcaagaggc acactctttt taagcctttg ttaggtgatg ggatcttcac  1500
attggacggc gaaggctgga agcacagcag agccatgttg agaccacagt ttgccagaga  1560
acaagttgct catgtgacgt cgttggaacc acacttccag ttgttgaaga agcatattct  1620
taagcacaag ggtgaatact tgatatcca ggaattgttc tttagattta ccgttgattc  1680
ggccacggag ttcttatttg gtgagtccgt gcactcctta aaggacgaat ctattggtat  1740
caaccaagac gatatagatt ttgctggtag aaaggacttt gctgagtcgt tcaacaaagc  1800
ccaggaatac ttggctatta gaaccttggt gcagacgttc tactggttgg tcaacaacaa  1860
ggagtttaga gactgtacca agctggtgca caagttcacc aactactatg ttcagaaagc  1920
tttggatgct agcccagaag agcttgaaaa gcaaagtggg tatgtgttct tgtacgagct  1980
tgtcaagcag acaagagacc ccaatgtgtt gcgtgaccag tctttgaaca tcttgttggc  2040
cggaagagac accactgctg ggttgttgtc gtttgctgtc tttgagttgg ccagacaccc  2100
agagatctgg gccaagttga gagaggaaat tgaacaacag tttggtcttg gagaagactc  2160
tcgtgttgaa gagattacct tgagagcttg aagagatgt gagtacttga aagcgttcct  2220
taatgaaacc ttgcgtattt acccaagtgt cccaagaaac ttcagaatcg ccaccaagaa  2280
```

```
cacgacattg ccaagggcg gtggttcaga cggtacctcg ccaatcttga tccaaaaggg    2340
agaagctgtg tcgtatggta tcaactctac tcatttggac cctgtctatt acggccctga   2400
tgctgctgag ttcagaccag agagatggtt tgagccatca accaaaaagc tcggctgggc   2460
ttacttgcca ttcaacggtg gtccaagaat ctgtttgggt cagcagtttg ccttgacgga   2520
agctggctat gtgttggtta gattggtgca agagttctcc cacgttaggc tggacccaga   2580
cgaggtgtac ccgccaaaga ggttgaccaa cttgaccatg tgtttgcagg atggtgctat   2640
tgtcaagttt gactagcggc gtggtgaatg cgtttgattt tgtagtttct gtttgcagta   2700
atgagataac tattcagata aggcgagtgg atgtacgttt tgtaagagtt tccttacaac   2760
cttggtgggg tgtgtgaggt tgaggttgca tcttggggag attacacctt ttgcagctct   2820
ccgtatacac ttgtactctt tgtaacctct atcaatcatg tggggggggg ggttcattgt   2880
ttggccatgg tggtgcatgt taaatccgcc aactacccaa tctcacatga aactcaagca   2940
cactaaaaaa aaaaagatg ttgggggaaa actttggttt cccttcttag taattaaaca    3000
ctctcactct cactctcact ctctccactc agacaaacca accacctggg ctgcagacaa   3060
ccagaaaaaa aaagaacaaa atccagatag aaaaacaaag ggctggacaa ccataaataa   3120
acaatctagg gtctactcca tcttccactg tttcttcttc ttcagactta gctaacaaac   3180
aactcacttc accatggatt acgcaggcat cacgcgtggc tccatcagag gcgaggcctt   3240
gaagaaactc gcagaattga ccatccagaa ccagccatcc agcttgaaag aaatcaacac   3300
cggcatccag aaggacgact tgccaagtt gttgtctgcc accccgaaaa tccccaccaa    3360
gcacaagttg aacggcaacc acgaattgtc tgaggtcgcc attgccaaaa aggagtacga   3420
ggtgttgatt gccttgagcg acgccacaaa agacccaatc aaagtgacct cccagatcaa   3480
gatcttgatt gacaagttca aggtgtactt gtttgagttg cctgaccaga agttctccta   3540
ctccatcgtg tccaactccg tcaacatcgc cccctggacc ttgctcgggg agaagttgac   3600
cacgggcttg atcaacttgg ccttccagaa caacaagcag cacttggacg aggtcattga   3660
catcttcaac gagttcatcg acaagttctt tggcaacacg gagccgcaat tgaccaactt   3720
cttgaccttg tgcggtgtgt tggacggggtt gattgaccat gccaacttct tgagcgtgtc   3780
ctcgcggacc ttcaagatct tcttgaactt ggactcgtat gtggac               3826
```

<210> SEQ ID NO 3
<211> LENGTH: 640
<212> TYPE: DNA
<213> ORGANISM: Artificial Sequence
<220> FEATURE:
<223> OTHER INFORMATION: Comprises two sequences from the 5' and 3' ends of the CYP52A17 cytochrome P450 from Candida tropicalis (i) separated by a sequence comprising a NotI restriction site and a 20 bp stuffer fragment and an XhoI restriciton site and (ii) flanked by XhoI

<400> SEQUENCE: 3

```
cgtctcatga ttgaacaact cctagaatat tggtatgtcg ttgtgccagt gttgtacatc     60
atcaaacaac tccttgcata cacaaagact cgcgtcttga tgaaaaagtt gggtgctgct    120
ccagtcacaa acaagttgta cgacaacgct ttcggtatcg tcaatggatg gaaggctctc   180
cagttcaaga aagagggcag ggctcaagag tacaacgatt acaagtttga ccactccaag    240
aacccaagcg tgggcaccta cgtcagtatt cttttcggca ccaggatcgt cgtgaccaaa   300
gatgcggccg ctagatcttg cgaagctcca tctcgagatc aactctactc atttggaccc    360
tgtctattac ggccctgatg ctgctgagtt cagaccagag agatggtttg agccatcaac    420
```

```
caaaaagctc ggctgggctt acttgccatt caacggtggt ccaagaatct gtttgggtca    480
gcagtttgcc ttgacggaag ctggctatgt gttggttaga ttggtgcaag agttctccca    540
cgttaggctg gacccagacg aggtgtaccc gccaaagagg ttgaccaact tgaccatgtg    600
tttgcaggat ggtgctattg tcaagtttga ctaggagacg                          640
```

<210> SEQ ID NO 4
<211> LENGTH: 4792
<212> TYPE: DNA
<213> ORGANISM: Artificial Sequence
<220> FEATURE:
<223> OTHER INFORMATION: Targeting construct for deletion of Candida
      tropicalis CYP52A17

<400> SEQUENCE: 4

```
cgtctcatga ttgaacaact cctagaatat tggtatgtcg ttgtgccagt gttgtacatc     60
atcaaacaac tccttgcata cacaaagact cgcgtcttga tgaaaaagtt gggtgctgct    120
ccagtcacaa acaagttgta cgacaacgct ttcggtatcg tcaatggatg gaaggctctc    180
cagttcaaga aagagggcag ggctcaagag tacaacgatt acaagtttga ccactccaag    240
aacccaagcg tgggcaccta cgtcagtatt cttttcggca ccaggatcgt cgtgaccaaa    300
gatgcggccg ctctagaact agtggatctg aagttcctat tctctagaaa gtataggaac    360
ttcctgcagg accacctttg attgtaaata gtaataatta ccacccttat ctaattattt    420
atttaactta tttatttatt tattatacat atatacaaat ctaataaagt gaaaatctcc    480
cccttcacac ttcacatatg ttaggcgtca tcctgtgctc ccgagaacca gtaccagtac    540
atcgctgttt cgttcgagac ttgaggtcta gttttatacg tgaagaggtc aatgccgccg    600
agagtaaagc cacattttgc gtacaaattg caggcaggta cattgttcgt ttgtgtctct    660
aatcgtatgc caaggagctg tctgcttagt gcccactttt tcgcaaattc gatgagactg    720
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtagggctc    900 acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaatttttc agttggcttg gtttcaattc aatgttcgtt   1140
tttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat tccattgat   1500 cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaccaat caactgatta   1680 atcaatcaat tagaattgaa gctaaactaa aacataccac cgtccatttt gaatgattat   1740 attttttttaa tattaatatc gagataatgt ttctaagaaa gaaagaaaac caggagtgaa   1800
```

-continued

```
aattagaaaa ggaaaggaaa ggaaaaaaag aaaaatctga aaatatataa aaaaaaattg    1860
tttcgttggc aataaatctt ggtgagaaca gcgaccgaaa gcaaataaga acaaaatatg    1920
agtgtattac gttgaacaac taattaacgt gtgtgtatgg atcttttttt ctttttttctc   1980 tttaaccgac tataaacaac aaacattttt gggcagtgca cacactactt aatatacaca    2040
gcataaatta cacgattaga aacaaattag cttattaaaa taacctaatc aaaccgaata    2100
ttttatggta ttatgagtaa actatataat ataaatagca cacacccaca acaacaacaa    2160
aggaaaacta aaaggttttt tcttttttgaa aagatcgttt tctttattat tctctagttt   2220
tgacgctcga cattttatga tggaatgaat gggatgaatc atcaaacaag agaaaatacc    2280
cgtgacgaaa ataataaaat aagttcctct gatacagaag atgaaaacaa caacaacaag    2340
atatagaaat gccttgggtg gctattttat agtcttaact ttttaatgta tatttgtttt    2400 gttttttttac ataataatac tttataaaag ctaagctaaa ttcaagtaaa atttcaatct   2460
ctcaaataaa acattttttct cttttttctta aatttagttt tatatattta taaaatatac  2520
aaagattttt ttaaaaaagt aacaagttat atatgtaata acaaaagaa gaataacaag     2580 aatacaaaac cagatttcca gatttccaga atttcactct tatatgcgtc tatttatgta    2640
ggatgaaagg tagtctagta cctcctgtga tattatccca ttccatgcgg ggtatcgtat    2700
gcttccttca gcactaccct ttagctgttc tatatgctgc cactcctcaa ttggattagt    2760
ctcatccttc aatgctatca tttcctttga tattggatca tatgcatagt accgagaaac    2820
tagtgcgaag tagtgatcag gtattgctgt tatctgatga gtatacgttg tcctggccac    2880
ggcagaagca cgcttatcgc tccaatttcc cacaacatta gtcaactccg ttaggcccttt   2940 cattgaaaga aatgaggtca tcaaatgtct tccaatgtga gatttttgggc cattttttat   3000 agcaaagatt gaataaggcg cattttttctt caaagcttta ttgtacgatc tgactaagtt  3060
atcttttaat aattggtatt cctgtttatt gcttgaagaa ttgccggtcc tatttactcg    3120
ttttaggact ggttcagaat tcctcaaaaa ttcatccaaa tatacaagtg gatcgatcct    3180
accccttgcg ctaaagaagt atatgtgcct actaacgctt gtctttgtct ctgtcactaa    3240
acactggatt attactccca aatacttatt ttggactaat ttaaatgatt tcggatcaac    3300
gttcttaata tcgctgaatc ttccacaatt gatgaaagta gctaggaaga ggaattggta    3360
taaagttttt gttttttgtaa atctcgaagt atactcaaac gaatttagta ttttctcagt   3420
gatctcccag atgctttcac cctcacttag aagtgcttta agcatttttt tactgtggct   3480 attttcccttta tctgcttctt ccgatgattc gaactgtaat tgcaaactac ttacaatatc  3540
agtgatatca gattgatgtt tttgtccata gtaaggaata attgtaaatt cccaagcagg   3600
aatcaatttc tttaatgagg cttccaaaat tgttgctttt tgcgtcttgt atttaaactg    3660
gagtgattta ttgacaatat cgaaactcaa cgaattgctt atgatagtat tatagctcat   3720
gaatgtggct ctcttgattg ctgttccgtt atgtgtaatc atccaacata aataggttag    3780
ttcagcagca cataatgcta ttttctcacc tgaaggtctt tcaaaccttt ccacaaactg    3840
acgaacaagc accttaggtg gtgttttaca taatatatca aattgtggca tgtcgacgat    3900
tattagttaa accactgcaa aaagttgggg aaaattttgc ccatttttat accgtgtctt    3960
cgtctatcgc ctccccccact ccccaatctt tgaattattc cgaaatattc agcgaacggg   4020
gtgtacacaa aaactaacat tctcaactgc ataatttgaa aaatggcgtg ggacaagaaa    4080 aaaaaaaat tctcaaccat agcaatcatg gaatacggta aatttgtgtt gttcggtgac    4140
tccatcaccc agtttagttg tacccagtat ggctttcatc cagcattaca gaatgtgtat    4200
```

-continued

| | |
|---|---|
| atccgaaaat tggatgttat taaccgtggt ttcagtggct acaactcaga gcacgctaga | 4260 |
| caaattcttc caaaaatttt agagtcggaa accaatatca aattgatgac aatattttt | 4320 |
| ggaactaacg atgcatacga ctacatcaat gaaatccaga cagtcgagtt agacagatat | 4380 |
| aaagataatt taagtgtaat ggtacagatg gtactagaca aaaatatcaa accaatcatt | 4440 |
| attggatccg aagttcctat tctctagaaa gtataggaac ttcctcgaga tcaactctac | 4500 |
| tcatttggac cctgtctatt acggccctga tgctgctgag ttcagaccag agagatggtt | 4560 |
| tgagccatca accaaaaagc tcggctgggc ttacttgcca ttcaacggtg gtccaagaat | 4620 |
| ctgtttgggt cagcagtttg ccttgacgga agctggctat gtgttggtta gattggtgca | 4680 |
| agagttctcc cacgttaggc tggacccaga cgaggtgtac ccgccaaaga ggttgaccaa | 4740 |
| cttgaccatg tgtttgcagg atggtgctat tgtcaagttt gactaggaga cg | 4792 |

<210> SEQ ID NO 5
<211> LENGTH: 3948
<212> TYPE: DNA
<213> ORGANISM: Candida tropicalis

<400> SEQUENCE: 5

| | |
|---|---|
| gacctgtgac gcttccggtg tcttgccacc agtctccaag ttgaccgacg cccaagtcat | 60 |
| gtaccacttt atttccggtt acacttccaa gatggctggt actgaagaag gtgtcacgga | 120 |
| accacaagct actttctccg cttgtttcgg tcaaccattc ttggtgttgc acccaatgaa | 180 |
| gtacgctcaa caattgtctg acaagatctc gcaacacaag gctaacgcct ggttgttgaa | 240 |
| caccggttgg gttggttctt ctgctgctag aggtggtaag agatgctcat tgaagtacac | 300 |
| cagagccatt ttggacgcta tccactctgg tgaattgtcc aaggttgaat acgaaacttt | 360 |
| cccagtcttc aacttgaatg tcccaacctc ctgtccaggt gtcccaagtg aaatcttgaa | 420 |
| cccaaccaag gcctggaccg aaggtgttg actccttcaa caaggaaatc aagtctttgg | 480 |
| ctggtaagtt tgctgaaaac ttcaagacct atgctgacca agctaccgct gaagtgagag | 540 |
| ctgcaggtcc agaagcttaa agatatttat tcattattta gtttgcctat ttatttctca | 600 |
| ttacccatca tcattcaaca ctatatataa agttacttcg gatatcattg taatcgtgcg | 660 |
| tgtcgcaatt ggatgatttg gaactgcgct tgaaacggat tcatgcacga agcggagata | 720 |
| aaagattacg taatttatct cctgagacaa ttttagccgt gttcacacgc ccttctttgt | 780 |
| tctgagcgaa ggataaataa ttagacttcc acagctcatt ctaatttccg tcacgcgaat | 840 |
| attgaagggg ggtacatgtg gccgctgaat gtggggcag taaacgcagt ctctcctctc | 900 |
| ccaggaatag tgcaacggag gaaggataac ggatagaaag cggaatgcga ggaaaatttt | 960 |
| gaacgcgcaa gaaaagcaat atccgggcta ccaggttttg agccagggaa cacactccta | 1020 |
| tttctgctca atgactgaac atagaaaaaa caccaagacg caatgaaacg cacatggaca | 1080 |
| tttagacctc cccacatgtg atagtttgtc ttaacagaaa agtataataa gaacccatgc | 1140 |
| cgtccctttt ctttcgccgc ttcaactttt ttttttttat cttacacaca tcacgaccat | 1200 |
| gactgtacac gatattatcg ccacatactt caccaaatgg tacgtgatag taccactcgc | 1260 |
| tttgattgct tatagagtcc tcgactactt ctatggcaga tacttgatgt acaagcttgg | 1320 |
| tgctaaacca ttttttccaga aacagacaga cggctgtttc ggattcaaag ctccgcttga | 1380 |
| attgttgaag aagaagagcg acggtaccct catagacttc acactccagc gtatccacga | 1440 |
| tctcgatcgt cccgatatcc caactttcac attcccggtc ttttccatca accttgtcaa | 1500 |
| taccctttgag ccggagaaca tcaaggccat cttggccact cagttcaacg atttctcctt | 1560 |

```
gggtaccaga cactcgcact tgctcctttt gttgggtgat ggtatcttta cgttggatgg   1620
cgccggctgg aagcacagca gatctatgtt gagaccacag tttgccagag aacagatttc   1680
ccacgtcaag ttgttggagc cacacgttca ggtgttcttc aaacacgtca gaaaggcaca   1740
gggcaagact tttgacatcc aggaattgtt tttcagattg accgtcgact ccgccaccga   1800 gttttttgttt ggtgaatccg ttgagtcctt gagagatgaa tctatcggca tgtccatcaa   1860
tgcgcttgac tttgacggca aggctggctt tgctgatgct tttaactatt cgcagaatta   1920
tttggcttcg agagcggtta tgcaacaatt gtactgggtg ttgaacggga aaaagtttaa   1980
ggagtgcaac gctaaagtgc acaagtttgc tgactactac gtcaacaagg ctttggactt   2040
gacgcctgaa caattggaaa agcaggatgg ttatgtgttt ttgtacgaat ggtcaagca    2100 aaccagagac aagcaagtgt tgagagacca attgttgaac atcatggttg ctggtagaga   2160
caccaccgcc ggtttgttgt cgtttgtttt ctttgaattg ccagaaaacc cagaagttac   2220
caacaagttg agagaagaaa ttgaggacaa gtttggactc ggtgagaatg ctagtgttga   2280
agacatttcc tttgagtcgt tgaagtcctg tgaatacttg aaggctgttc tcaacgaaac   2340
cttgagatta tacccatccg tgccacagaa tttcagagtt gccaccaaga acactaccct   2400
cccaagaggt ggtggtaagg acgggttgtc tcctgttttg gtgagaaagg gtcagaccgt   2460
tatttacggt gtctacgcag cccacagaaa cccagctgtt tacggtaagg acgctcttga   2520
gtttagacca gagagatggt ttgagccaga gacaaagaag cttggctggg ccttcctccc   2580
attcaacggt ggtccaagaa tctgtttggg acagcagttt gccttgacag aagcttcgta   2640
tgtcactgtc aggttgctcc aggagtttgc acacttgtct atggacccag acaccgaata   2700
tccacctaag aaaatgtcgc atttgaccat gtcgcttttc gacggtgcca atattgagat   2760
gtattagagg gtcatgtgtt attttgattg tttagtttgt aattactgat taggttaatt   2820
catggattgt tatttattga taggggtttg cgcgtgttgc attcacttgg gatcgttcca   2880
ggttgatgtt tccttccatc ctgtcgagtc aaaaggagtt ttgttttgta actccggacg   2940
atgttttaaa tagaaggtcg atctccatgt gattgttttg actgttactg tgattatgta   3000
atctgcggac gttatacaag catgtgattg tggttttgca gccttttgca cgacaaatga   3060
tcgtcagacg attacgtaat ctttgttaga ggggtaaaaa aaaacaaaat ggcagccaga   3120
atttcaaaca ttctgcaaac aatgcaaaaa atgggaaact ccaacagaca aaaaaaaaa    3180 ctccgcagca ctccgaaccc acagaacaat ggggcgccag aattattgac tattgtgact   3240 ttttttacgct aacgctcatt gcagtgtagt gcgtcttaca cggggtattg ctttctacaa   3300
tgcaagggca cagttgaagg tttgcaccta acgttgcccc gtgtcaactc aatttgacga   3360
gtaacttcct aagctcgaat tatgcagctc gtgcgtcaac ctatgtgcag gaagaaaaa    3420 atccaaaaaa atcgaaaatg cgactttcga ttttgaataa accaaaaaga aaaatgtcgc   3480
acttttttct cgctctcgct ctctcgaccc aaatcacaac aaatcctcgc gcgcagtatt   3540
tcgacgaaac cacaacaaat aaaaaaaaca aattctacac cacttctttt tcttcaccag   3600
tcaacaaaaa acaacaaatt atacaccatt tcaacgattt ttgctcttat aaatgctata   3660
taatggttta attcaactca ggtatgttta ttttactgtt ttcagctcaa gtatgttcaa   3720
atactaacta cttttgatgt ttgtcgcttt tctagaatca aaacaacgcc cacaacacgc   3780
cgagcttgtc gaatagacgg tttgtttact cattagatgg tcccagatta cttttcaagc   3840
caaagtctct cgagttttgt ttgctgtttc cccaattcct aactatgaag ggttttttata  3900 aggtccaaag accccaaggc atagtttttt tggttccttc ttgtcgtg              3948
```

<210> SEQ ID NO 6
<211> LENGTH: 640
<212> TYPE: DNA
<213> ORGANISM: Artificial Sequence
<220> FEATURE:
<223> OTHER INFORMATION: Pre-targeting construct for Candida tropicalis CYP52A13

<400> SEQUENCE: 6

```
cgtctcatga ctgtacacga tattatcgcc acatacttca ccaaatggta cgtgatagta      60
ccactcgctt tgattgctta tagagtcctc gactacttct atggcagata cttgatgtac     120
aagcttggtg ctaaaccatt tttccagaaa cagacagacg gctgtttcgg attcaaagct     180
ccgcttgaat tgttgaagaa gaagagcgac ggtaccctca tagacttcac actccagcgt     240
atccacgatc tcgatcgtcc cgatatccca actttcacat tcccggtctt ttccatcaac     300
cttgcggccg ctagatcttg cgaagctcca tctcgaggtc tacgcagccc acagaaaccc     360
agctgtttac ggtaaggacg ctcttgagtt tagaccagag agatggtttg agccagagac     420
aaagaagctt ggctgggcct tcctcccatt caacggtggt ccaagaatct gtttgggaca     480
gcagtttgcc ttgacagaag cttcgtatgt cactgtcagg ttgctccagg agtttgcaca     540
cttgtctatg gacccagaca ccgaatatcc acctaagaaa atgtcgcatt tgaccatgtc     600
gcttttcgac ggtgccaata ttgagatgta ttaggagacg                           640
```

<210> SEQ ID NO 7
<211> LENGTH: 4792
<212> TYPE: DNA
<213> ORGANISM: Artificial Sequence
<220> FEATURE:
<223> OTHER INFORMATION: Targeting construct for deletion of Candida tropicalis CYP52A13

<400> SEQUENCE: 7

```
cgtctcatga ctgtacacga tattatcgcc acatacttca ccaaatggta cgtgatagta      60
ccactcgctt tgattgctta tagagtcctc gactacttct atggcagata cttgatgtac     120
aagcttggtg ctaaaccatt tttccagaaa cagacagacg gctgtttcgg attcaaagct     180
ccgcttgaat tgttgaagaa gaagagcgac ggtaccctca tagacttcac actccagcgt     240
atccacgatc tcgatcgtcc cgatatccca actttcacat tcccggtctt ttccatcaac     300
cttgcggccg ctctagaact agtggatctg aagttcctat tctctagaaa gtataggaac     360
ttcctgcagg accacctttg attgtaaata gtaataatta ccaccttat ctaattattt      420
atttaactta tttatttatt tattatacat atatacaaat ctaataaagt gaaaatctcc     480
cccttcacac ttcacatatg ttaggcgtca tcctgtgctc ccgagaacca gtaccagtac     540
atcgctgttt cgttcgagac ttgaggtcta gttttatacg tgaagaggtc aatgccgccg     600
agagtaaagc cacattttgc gtacaaattg caggcaggta cattgttcgt ttgtgtctct     660
aatcgtatgc caaggagctg tctgcttagt gcccactttt tcgcaaattc gatgagactg     720
tgcgcgactc ctttgcctcg gtgcgtgtgc gacacaacaa tgtgttcgat agaggctaga     780
tcgttccatg ttgagttgag ttcaatcttc ccgacaagct cttggtcgat gaatgcgcca     840
tagcaagcag agtcttcatc agagtcatca tccgagatgt aatccttccg gtagggctc     900
acacttctgg tagatagttc aaagccttgg tcggataggt gcacatcgaa cacttcacga     960
acaatgaaat ggttctcagc atccaatgtt tccgccacct gctcagggat caccgaaatt    1020
ttcatatgag aaccgttatc gataactaaa gcagcaactt cttctataaa aatgggttag    1080
```

```
tatgacagtc atttaaataa ggaattttc  agttggcttg gtttcaattc aatgttcgtt    1140 ttttttttt  cttgctgtgt tgtgttttgt gttgtttata gttgtgtgca ctgagcgtcg    1200
aaaaaaaaaa ttcatagtga gccgggaaat ctgtatagcc cagataacaa cacaagtcca    1260
aactagaaac tcgtcaaaca ccaaaagcaa tgttgaatca attgccttgc acaagtacac    1320
gtaggaaaac ataaaacatt gcaattttga atattgagcc ttttgtcgta acattgattg    1380
ataggattac tcaccgaatg gttttgaaac cactgccgac agatcaatca atcaatcaaa    1440
aaacgtgaac tttgaaaaag gggaagaaca gatacattga agttagccat ttccattgat    1500
cgtcacaaca tatctgataa attactttca aaattataag ctgatgtgtg tgtattatta    1560
atgtgacagt aacatcccaa acgagaaata ttatgtcgac aacaaaaaag tttgatctga    1620
attgaaaatg aagttttccc accctaccca tttgtcatat tgaaaccaat caactgatta    1680
atcaatcaat tagaattgaa gctaaactaa aacataccac cgtccatttt gaatgattat    1740
atttttttaa tattaatatc gagataatgt ttctaagaaa gaaagaaaac caggagtgaa    1800
aattagaaaa ggaaaggaaa ggaaaaaaag aaaaatctga aaatatataa aaaaaaattg    1860
tttcgttggc aataaatctt ggtgagaaca gcgaccgaaa gcaaataaga acaaaatatg    1920
agtgtattac gttgaacaac taattaacgt gtgtgtatgg atctttttt  cttttttctc    1980 tttaaccgac tataaacaac aaacatttt  gggcagtgca cacactactt aatatacaca    2040
gcataaatta cacgattaga aacaaattag cttattaaaa taacctaatc aaaccgaata    2100
ttttatggta ttatgagtaa actatataat ataaatagca cacacccaca acaacaacaa    2160
aggaaaacta aaaggttttt tcttttgaa  aagatcgttt tctttattat tctctagttt    2220
tgacgctcga cattttatga tggaatgaat gggatgaatc atcaaacaag agaaaatacc    2280
cgtgacgaaa ataataaaat aagttcctct gatacagaag atgaaaacaa caacaacaag    2340
atatagaaat gccttgggtg gctattttat agtcttaact ttttaatgta tatttgtttt    2400 gttttttac  ataataatac tttataaaag ctaagctaaa ttcaagtaaa atttcaatct    2460
ctcaaataaa acatttttct cttttttctta aatttagttt tatatattta taaaatatac    2520
aaagattttt ttaaaaaagt aacaagttat atatgtaata acaaaagaa  gaataacaag    2580 aatacaaaac cagatttcca gatttccaga atttcactct tatatgcgtc tatttatgta    2640
ggatgaaagg tagtctagta cctcctgtga tattatccca ttccatgcgg ggtatcgtat    2700
gcttccttca gcactaccct ttagctgttc tatatgctgc cactcctcaa ttggattagt    2760
ctcatccttc aatgctatca tttcctttga tattggatca tatgcatagt accgagaaac    2820
tagtgcgaag tagtgatcag gtattgctgt tatctgatga gtatacgttg tcctggccac    2880
ggcagaagca cgcttatcgc tccaatttcc cacaacatta gtcaactccg ttaggccctt    2940
cattgaaaga aatgaggtca tcaaatgtct tccaatgtga gattttgggc cattttttat    3000
agcaaagatt gaataaggcg cattttcctt caaagcttta ttgtacgatc tgactaagtt    3060 atctttaat  aattggtatt cctgtttatt gcttgaagaa ttgccggtcc tatttactcg    3120
ttttaggact ggttcagaat tcctcaaaaa ttcatccaaa tatacaagtg gatcgatcct    3180 acccccttgcg ctaaagaagt atatgtgcct actaacgctt gtctttgtct ctgtcactaa    3240
acactggatt attactccca aatacttatt ttggactaat ttaaatgatt tcggatcaac    3300
gttcttaata tcgctgaatc ttccacaatt gatgaaagta gctaggaaga ggaattggta    3360
taaagttttt gttttgtaa  atctcgaagt atactcaaac gaatttagta ttttctcagt    3420
gatctcccag atgctttcac cctcacttag aagtgcttta agcattttt  tactgtggct    3480
```

```
atttcccttta tctgcttctt ccgatgattc gaactgtaat tgcaaactac ttacaatatc     3540
agtgatatca gattgatgtt tttgtccata gtaaggaata attgtaaatt cccaagcagg     3600
aatcaatttc tttaatgagg cttccaaaat tgttgctttt tgcgtcttgt atttaaactg     3660
gagtgattta ttgacaatat cgaaactcaa cgaattgctt atgatagtat tatagctcat     3720
gaatgtggct ctcttgattg ctgttccgtt atgtgtaatc atccaacata aataggttag     3780
ttcagcagca cataatgcta tttctcacc tgaaggtctt tcaaaccttt ccacaaactg      3840
acgaacaagc accttaggtg gtgttttaca taatatatca aattgtggca tgtcgacgat     3900
tattagttaa accactgcaa aaagttgggg aaaattttgc ccatttttat accgtgtctt     3960
cgtctatcgc ctcccccact ccccaatctt tgaattattc cgaaatattc agcgaacggg     4020
gtgtacacaa aaactaacat tctcaactgc ataatttgaa aaatggcgtg ggacaagaaa     4080
aaaaaaaaat tctcaaccat agcaatcatg gaatacggta aatttgtgtt gttcggtgac     4140
tccatcaccc agtttagttg tacccagtat ggctttcatc cagcattaca gaatgtgtat     4200
atccgaaaat tggatgttat taaccgtggt ttcagtggct acaactcaga gcacgctaga     4260
caaattcttc caaaaatttt agagtcggaa accaatatca aattgatgac aatatttttt     4320
ggaactaacg atgcatacga ctacatcaat gaaatccaga cagtcgagtt agacagatat     4380
aaagataatt taagtgtaat ggtacagatg gtactagaca aaaatatcaa accaatcatt     4440
attggatccg aagttcctat tctctagaaa gtataggaac ttcctcgagg tctacgcagc     4500
ccacagaaac ccagctgttt acggtaagga cgctcttgag tttagaccag agagatggtt     4560
tgagccagag acaaagaagc ttggctgggc cttcctccca ttcaacggtg gtccaagaat     4620
ctgtttggga cagcagtttg ccttgacaga agcttcgtat gtcactgtca ggttgctcca     4680
ggagtttgca cacttgtcta tggacccaga caccgaatat ccacctaaga aaatgtcgca     4740
tttgaccatg tcgcttttcg acggtgccaa tattgagatg tattaggaga cg             4792
```

<210> SEQ ID NO 8
<211> LENGTH: 3910
<212> TYPE: DNA
<213> ORGANISM: Candida tropicalis

<400> SEQUENCE: 8

```
ttacaatcat ggagctcgct aggaacccag atgtctggga gaagctccgc gaagaggtca       60
acacgaactt tggcatggag tcgccagact tgctcacttt tgactctctt agaagctcaa      120
agtacgttca ggcggtgctc aacgaaacgc ttcgtatcta cccgggggtg ccacgaaaca      180
tgaagacagc tacgtgcaac acgacgttgc cgcgtggagg aggcaaagac ggtaaggaac      240
ctattttggt gcagaagggc cagtccgttg ggttgattac tattgccacg cagacggacc      300
cagagtattt tggggcagat gctggtgagt tcaaaccgga gagatggttt gattcaagca      360
tgaagaactt ggggtgtaag tacttgccgt tcaatgctgg gccccggact tgtttggggc      420
agcagtacac tttgattgaa gcgagctatt tgctagtcag gttggcgcag acctaccggg      480
taatcgattt gctgccaggg tcggcgtacc caccaagaaa gaagtcgttg atcaatatga      540
gtgctgccga tggggtggtt gtaaagtttc acaaggatct agatggatat gtaaggtgtg      600
taggaggagc ggagataaat tagatttgat tttgtgtaag gttagcacg tcaagctact       660 ccgcactttg tgtgtaggga gcacatactc cgtctgcgcc tgtgccaaga gacggcccag      720
gggtagtgtg tggtggtgga agtgcatgtg acacaatacc ctggttctgg ccaattgggg      780
atttagtgta ggtaagctgc gacctgaaac actcctcaac gcttgagaca ctggtgggta      840
```

-continued

```
gagatgcggg ccaggaggct attcttgtcg tgctacccgt gcacggaaaa tcgattgagg      900
gaagaacaaa tttatccgtg aaatccacag agcggataaa tttgtcacat tgctgcgttg      960
cccacccaca gcattctctt ttctctctct ttgtcttact ccgctcctgt ttccttatcc     1020
agaaatacac accaactcat ataaagatac gctagcccag ctgtctttct ttttcttcac     1080
ttttttttggt gtgttgcttt tttggctgct actttctaca accaccacca ccaccaccac     1140
catgattgaa caaatcctag aatattggta tattgttgtg cctgtgttgt acatcatcaa     1200
acaactcatt gcctacagca agactcgcgt cttgatgaaa cagttgggtg ctgctccaat     1260
cacaaaccag ttgtacgaca acgttttcgg tatcgtcaac ggatggaagg ctctccagtt     1320
caagaaagag ggcagagctc aagagtacaa cgatcacaag tttgacagct ccaagaaccc     1380
aagcgtcggc acctatgtca gtattctttt tggcaccaag attgtcgtga ccaaggatcc     1440
agagaatatc aaagctattt tggcaaccca gtttggcgat ttttctttgg caagagaca     1500
cgctcttttt aaacctttgt taggtgatgg gatcttcacc ttggacggcg aaggctggaa     1560
gcatagcaga tccatgttaa gaccacagtt tgccagagaa caagttgctc atgtgacgtc     1620
gttggaacca cacttccagt tgttgaagaa gcatatcctt aaacacaagg gtgagtactt     1680
tgatatccag gaattgttct ttagatttac tgtcgactcg gccacggagt tcttatttgg     1740
tgagtccgtg cactccttaa aggacgaaac tatcggtatc aaccaagacg atatagattt     1800
tgctggtaga aaggactttg ctgagtcgtt caacaaagcc caggagtatt tgtctattag     1860
aattttggtg cagaccttct actgggttgat caacaacaag gagtttagag actgtaccaa     1920
gctggtgcac aagtttacca actactatgt tcagaaagct ttggatgcta ccccagagga     1980
acttgaaaag caaggcgggt atgtgttctt gtatgagctt gtcaagcaga cgagagaccc     2040
caaggtgttg cgtgaccagt cttgaacat cttgttggca ggaagagaca ccactgctgg     2100
gttgttgtcc tttgctgtgt ttgagttggc cagaaaccca cacatctggg ccaagttgag     2160
agaggaaatt gaacagcagt ttggtcttgg agaagactct cgtgttgaag agattacctt     2220
tgagagcttg aagagatgtg agtacttgaa agcgttcctt aacgaaacct tgcgtgttta     2280
cccaagtgtc ccaagaaact tcagaatcgc caccaagaat acaacattgc caggggtgg     2340
tggtccagac ggtacccagc caatcttgat ccaaaaggga aaggtgtgt cgtatggtat     2400
caactctacc cacttagatc ctgtctatta tggccctgat gctgctgagt tcagaccaga     2460
gagatggttt gagccatcaa ccagaaagct cggctgggct tacttgccat tcaacggtgg     2520
gccacgaatc tgtttgggtc agcagtttgc cttgaccgaa gctggttacg ttttggtcag     2580
attggtgcaa gagttctccc acattaggct ggacccagat gaagtgtatc caccaaagag     2640
gttgaccaac ttgaccatgt gtttgcagga tggtgctatt gtcaagtttg actagtacgt     2700
atgagtgcgt ttgattttgt agtttctgtt tgcagtaatg agataactat tcagataagg     2760
cgggtggatg tacgttttgt aagagttcc ttacaaccct ggtgggtgtg tgaggttgca     2820
tcttagggag agatagcacc ttttgcagct ctccgtatac agttttactc tttgtaacct     2880
atgccaatca tgtgggatt cattgtttgc ccatggtggt gcatgcaaaa tcccccaac     2940
tacccaatct cacatgaaac tcaagcacac tagaaaaaaa agatgttgcg tgggttcttt     3000
tgatgttggg gaaacttc gtttccttc tcagtaatta aacgttctca ctcagacaaa     3060
ccacctgggc tgcagacaac cagaaaaaac aaaatccaga tagaagaaga aagggctgga     3120
caaccataaa taacaaccct agggtccact ccatctttca cttcttcttc ttcagactta     3180
tctaacaaac gactcacttc accatggatt acgcaggtat cacgcgtggg tccatcagag     3240
```

```
gcgaagcctt gaagaaactc gccgagttga ccatccagaa ccagccatcc agcttgaaag    3300
aaatcaacac cggcatccag aaggacgact ttgccaagtt gttgtcttcc accccgaaaa    3360
tccacaccaa gcacaagttg aatggcaacc acgaattgtc cgaagtcgcc attgccaaaa    3420
aggagtacga ggtgttgatt gccttgagcg acgccacgaa agaaccaatc aaagtcacct    3480
cccagatcaa gatcttgatt gacaagttca aggtgtactt gtttgagttg cccgaccaga    3540
agttctccta ctccatcgtg tccaactccg ttaacattgc ccctggacc ttgctcggtg     3600 agaagttgac cacgggcttg atcaacttgg cgttccagaa caacaagcag cacttggacg    3660
aagtcatcga catcttcaac gagttcatcg acaagttctt tggcaacaca gagccgcaat    3720
tgaccaactt cttgaccttg tccggtgtgt tggacgggtt gattgaccat gccaacttct    3780
tgagcgtgtc ctccaggacc ttcaagatct tcttgaactt ggactcgttt gtggacaact    3840
cggacttctt gaacgacgtg gagaactact ccgactttt gtacgacgag ccgaacgagt     3900
accagaactt                                                           3910

<210> SEQ ID NO 9
<211> LENGTH: 687
<212> TYPE: DNA
<213> ORGANISM: Artificial Sequence
<220> FEATURE:
<223> OTHER INFORMATION: Pre-targeting construct for Candida tropicalis
      CYP52A18

<400> SEQUENCE: 9
cgtctcagag atgcgggcca ggaggctatt cttgtcgtgc tacccgtgca cggaaaatcg     60
attgagggaa gaacaaattt atccgtgaaa tccacagagc ggataaattt gtcacattgc    120
tgcgttgccc acccacagca ttctctttc tctctctttg tcttactccg ctcctgtttc     180
cttatccaga aatacacacc aactcatata agatacgct agcccagctg tcttctttt     240 tcttcacttt ttttggtgtg ttgctttttt ggctgctact ttctacaacc accaccaca    300 ccaccaccat ggggcaatca gtgagtctcg caggtaccgc ggagctcgcg gccgctagat    360
cttgcgaagc tccatctcga gtcgtatgag tgcgtttgat tttgtagttt ctgtttgcag    420
taatgagata actattcaga taaggcgggt ggatgtacgt tttgtaagag tttccttaca    480
accctggtgg gtgtgtgagg ttgcatctta gggagagata gcaccttttg cagctctccg    540
tatacagttt tactctttgt aacctatgcc aatcatgtgg ggattcattg tttgcccaag    600
gtggtgcatg caaaatcccc ccaactaccc aatctcacat gaaactcaag cacactagaa    660
aaaaaagatg ttgcgtgggt tgagacg                                        687

<210> SEQ ID NO 10
<211> LENGTH: 41
<212> TYPE: DNA
<213> ORGANISM: Artificial Sequence
<220> FEATURE:
<223> OTHER INFORMATION: polylinker sequence

<400> SEQUENCE: 10
ccatggggca atcagtgagt ctcgcaggta ccgcggagct c                         41

<210> SEQ ID NO 11
<211> LENGTH: 4839
<212> TYPE: DNA
<213> ORGANISM: Artificial Sequence
<220> FEATURE:
<223> OTHER INFORMATION: Targeting construct for deletion of Candida
      tropicalis CYP52A18
```

```
<400> SEQUENCE: 11
cgtctcagag atgcgggcca ggaggctatt cttgtcgtgc tacccgtgca cggaaaatcg      60
attgagggaa gaacaaattt atccgtgaaa tccacagagc ggataaattt gtcacattgc     120
tgcgttgccc acccacagca ttctcttttc tctctctttg tcttactccg ctcctgtttc     180
cttatccaga aatacacacc aactcatata aagatacgct agcccagctg tctttctttt     240
tcttcacttt ttttggtgtg ttgctttttt ggctgctact ttctacaacc accaccacca     300
ccaccaccat ggggcaatca gtgagtctcg caggtaccgc ggagctcgcg gccgctctag     360
aactagtgga tctgaagttc ctattctcta gaaagtatag gaacttcctg caggaccacc     420
tttgattgta aatagtaata attaccaccc ttatctaatt atttatttaa cttatttatt     480
tatttattat acatatatac aaatctaata aagtgaaaat ctcccccttc acacttcaca     540
tatgttaggc gtcatcctgt gctcccgaga accagtacca gtacatcgct gtttcgttcg     600
agacttgagg tctagtttta tacgtgaaga ggtcaatgcc gccgagagta aagccacatt     660
ttgcgtacaa attgcaggca ggtacattgt tcgtttgtgt ctctaatcgt atgccaagga     720
gctgtctgct tagtgcccac tttttcgcaa attcgatgag actgtgcgcg actcctttgc     780
ctcggtgcgt gtgcgacaca acaatgtgtt cgatagaggc tagatcgttc catgttgagt     840
tgagttcaat cttcccgaca agctcttggt cgatgaatgc gccatagcaa gcagagtctt     900
catcagagtc atcatccgag atgtaatcct tccggtaggg gctcacactt ctggtagata     960
gttcaaagcc ttggtcggat aggtgcacat cgaacacttc acgaacaatg aaatggttct    1020
cagcatccaa tgtttccgcc acctgctcag ggatcaccga aattttcata tgagaaccgt    1080
tatcgataac taaagcagca acttcttcta taaaaatggg ttagtatgac agtcatttaa    1140
ataaggaatt tttcagttgg cttggtttca attcaatgtt cgttttttt ttttcttgct    1200 gtgtttgtgt ttgtgttgtt tatagttgtg tgcactgagc gtcgaaaaaa aaaattcata    1260
gtgagccggg aaatctgtat agcccagata acaacacaag tccaaactag aaactcgtca    1320
aacaccaaaa gcaatgttga atcaattgcc ttgcacaagt acacgtagga aaacataaaa    1380
cattgcaatt ttgaatattg agccttttgt cgtaacattg attgatagga ttactcaccg    1440
aatggttttg aaaccactgc cgacagatca atcaatcaat caaaaaacgt gaactttgaa    1500
aaaggggaag aacagataca ttgaagttag ccatttccat tgatcgtcac aacatatctg    1560
ataaattact ttcaaaatta taagctgatg tgtgtgtatt attaatgtga cagtaacatc    1620
ccaaacgaga aatattatgt cgacaacaaa aaagtttgat ctgaattgaa aatgaagttt    1680
tcccacccta cccatttgtc atattgaaac caatcaactg attaatcaat caattagaat    1740
tgaagctaaa ctaaaacata ccaccgtcca ttttgaatga ttatatttt ttaatattaa    1800 tatcgagata atgtttctaa gaaagaaaga aaaccaggag tgaaaattag aaaaggaaag    1860
gaaaggaaaa aaagaaaaat ctgaaaatat ataaaaaaaa attgtttcgt tggcaataaa    1920
tcttggtgag aacagcgacc gaaagcaaat aagaacaaaa tatgagtgta ttacgttgaa    1980
caactaatta acgtgtgtgt atggatcttt ttttcttttt tctctttaac cgactataaa    2040
caacaaacat ttttgggcag tgcacacact acttaatata cacagcataa attacacgat    2100
tagaaacaaa ttagcttatt aaaataacct aatcaaaccg aatattttat ggtattatga    2160
gtaaactata taatataaat agcacacacc cacaacaaca acaaggaaaa actaaaaggt    2220 ttttctttt tgaaaagatc gttttcttta ttattctcta gttttgacgc tcgacatttt    2280
atgatggaat gaatgggatg aatcatcaaa caagagaaaa taccgtgac gaaaataata    2340
```

```
aaataagttc ctctgataca gaagatgaaa acaacaacaa caagatatag aaatgccttg    2400
ggtggctatt ttatagtctt aacttttaa tgtatatttg ttttgttttt ttacataata    2460
atactttata aaagctaagc taaattcaag taaaatttca atctctcaaa taaaacattt    2520
ttctcttttt cttaaattta gttttatata tttataaaat atacaaagat ttttttaaaa    2580
aagtaacaag ttatatatgt aataacaaaa agaagaataa caagaataca aaaccagatt    2640
tccagatttc cagaatttca ctcttatatg cgtctatttta tgtaggatga aaggtagtct    2700
agtacctcct gtgatattat cccattccat gcggggtatc gtatgcttcc ttcagcacta    2760 cccctttagct gttctatatg ctgccactcc tcaattggat tagtctcatc cttcaatgct    2820
atcatttcct ttgatattgg atcatatgca tagtaccgag aaactagtgc gaagtagtga    2880
tcaggtattg ctgttatctg atgagtatac gttgtcctgg ccacggcaga agcacgctta    2940
tcgctccaat ttcccacaac attagtcaac tccgttaggc ccttcattga agaaatgag    3000 gtcatcaaat gtcttccaat gtgagatttt gggccatttt ttatagcaaa gattgaataa    3060
ggcgcatttt tcttcaaagc tttattgtac gatctgacta agttatcttt taataattgg    3120
tattcctgtt tattgcttga agaattgccg gtcctattta ctcgttttag gactggttca    3180
gaattcctca aaaattcatc caaatataca agtggatcga tcctacccct tgcgctaaag    3240
aagtatatgt gcctactaac gcttgtcttt gtctctgtca ctaaacactg gattattact    3300
cccaaatact tattttggac taatttaaat gatttcggat caacgttctt aatatcgctg    3360
aatcttccac aattgatgaa agtagctagg aagaggaatt ggtataaagt ttttgttttt    3420
gtaaatctcg aagtatactc aaacgaattt agtattttct cagtgatctc ccagatgctt    3480
tcaccctcac ttagaagtgc tttaagcatt ttttactgt ggctatttcc cttatctgct    3540
tcttccgatg attcgaactg taattgcaaa ctacttacaa tatcagtgat atcagattga    3600 tgttttgtc catagtaagg aataattgta aattcccaag caggaatcaa tttctttaat    3660
gaggcttcca aaattgttgc ttttttgcgtc ttgtatttaa actggagtga tttattgaca    3720
atatcgaaac tcaacgaatt gcttatgata gtattatagc tcatgaatgt ggctctcttg    3780
attgctgttc cgttatgtgt aatcatccaa cataaatagg ttagttcagc agcacataat    3840
gctattttct cacctgaagg tcttttcaaac cttccacaa actgacgaac aagcaccta    3900 ggtggtgttt tacataatat atcaaattgt ggcatgtcga cgattattag ttaaaccact    3960
gcaaaaagtt ggggaaaatt ttgcccattt ttataccgtg tcttcgtcta tcgcctcccc    4020
cactccccaa tctttgaatt attccgaaat attcagcgaa cggggtgtac acaaaaacta    4080
acattctcaa ctgcataatt tgaaaaatgg cgtgggacaa gaaaaaaaa aaattctcaa    4140 ccatagcaat catggaatac ggtaaatttg tgttgttcgg tgactccatc acccagttta    4200
gttgtaccca gtatggcttt catccagcat tacagaatgt gtatatccga aaattggatg    4260
ttattaaccg tggtttcagt ggctacaact cagagcacgc tagacaaatt cttccaaaaa    4320
ttttagagtc ggaaaccaat atcaaattga tgacaatatt ttttggaact aacgatgcat    4380
acgactacat caatgaaatc cagacagtcg agttagacag atataaagat aatttaagtg    4440
taatggtaca gatggtacta gacaaaaata tcaaaccaat cattattgga tccgaagttc    4500
ctattctcta gaaagtatag gaacttcctc gagtcgtatg agtgcgtttg attttgtagt    4560
ttctgtttgc agtaatgaga taactattca gataaggcgg gtggatgtac gttttgtaag    4620
agtttcctta caaccctggt gggtgtgtga ggttgcatct tagggagaga tagcaccttt    4680
tgcagctctc cgtatacagt tttactcttt gtaacctatg ccaatcatgt ggggattcat    4740
```

| | | |
|---|---|---|
| tgtttgccca aggtggtgca tgcaaaatcc ccccaactac ccaatctcac atgaaactca | 4800 |
| agcacactag aaaaaaaaga tgttgcgtgg gttgagacg | 4839 |

<210> SEQ ID NO 12
<211> LENGTH: 34
<212> TYPE: DNA
<213> ORGANISM: Artificial Sequence
<220> FEATURE:
<223> OTHER INFORMATION: NotI-XhoI and 20 base pair stuffer

<400> SEQUENCE: 12

| | |
|---|---|
| gcggccgcta gatcttgcga agctccatct cgag | 34 |

<210> SEQ ID NO 13
<211> LENGTH: 3755
<212> TYPE: DNA
<213> ORGANISM: Candida tropicalis

<400> SEQUENCE: 13

| | |
|---|---|
| gctcaacaat tgtctgacaa gatctcgcaa cacaaggcta acgcctggtt gttgaacact | 60 |
| ggttgggttg gttcttctgc tgctagaggt ggtaagagat gttcattgaa gtacaccaga | 120 |
| gccatttttgg acgctatcca ctctggtgaa ttgtccaagg ttgaatacga actttccca | 180 |
| gtcttcaact tgaatgtccc aacctcctgc ccaggtgtcc caagtgaaat cttgaaccca | 240 |
| accaaggcct ggaccgaagg tgttgactcc ttcaacaagg aaatcaagtc tttggctggt | 300 |
| aagtttgctg aaaacttcaa gacctatgct gaccaagcta ccgctgaagt tagagctgca | 360 |
| ggtccagaag cttaaagata tttattcact atttagtttg cctatttatt tctcatcacc | 420 |
| catcatcatt caacaatata tataaagtta tttcggaact catatatcat tgtaatcgtg | 480 |
| cgtgttgcaa ttgggtaatt tgaaactgta gttgaacgg attcatgcac gatgcggaga | 540 |
| taacacgaga ttatctccta agacaatttt ggcctcattc acacgccctt cttctgagct | 600 |
| aaggataaat aattagactt cacaagttca ttaaaatatc cgtcacgcga aaactgcaac | 660 |
| aataaggaag ggggggggtag acgtagccga tgaatgtggg gtgccagtaa acgcagtctc | 720 |
| tctctccccc ccccccccc ccccctcagg aatagtacaa cggggggaagg ataacgata | 780 |
| gcaagtggaa tgcgaggaaa attttgaatg cgcaaggaaa gcaatatccg ggctatcagg | 840 |
| ttttgagcca ggggacacac tcctcttctg cacaaaaact taacgtagac aaaaaaaaaa | 900 |
| aactccacca agacacaatg aatcgcacat ggacatttag acctccccac atgtgaaagc | 960 |
| ttctctggcg aaagcaaaaa aagtataata aggacccatg ccttccctct tcctgggccg | 1020 |
| tttcaacttt ttcttttttct ttgtctatca acacacacac acctcacgac catgactgca | 1080 |
| caggatatta tcgccacata catcaccaaa tggtacgtga tagtaccact cgctttgatt | 1140 |
| gcttatagggg tcctcgacta cttttacggc agatacttga tgtacaagct tggtgctaaa | 1200 |
| ccgtttttcc agaaacaaac agacggttat ttcggattca aagctccact tgaattgtta | 1260 |
| aaaaagaaga gtgacggtac cctcatagac ttcactctcg agcgtatcca agcgctcaat | 1320 |
| cgtccagata tcccaacttt tacattccca atcttttcca tcaaccttat cagcacccttt | 1380 |
| gagccggaga acatcaaggc tatcttggcc acccagttca acgatttctc cttgggcacc | 1440 |
| agacactcgc actttgctcc tttgttgggc gatggtatct ttaccttgga cggtgccggc | 1500 |
| tggaagcaca gcagatctat gttgagacca cagtttgcca gagaacagat tccccacgtc | 1560 |
| aagttgttgg agccacacat gcaggtgttc ttcaagcacg tcagaaaggc cagggcaag | 1620 |
| acttttgaca tccaagaatt gttttttcaga ttgaccgtcg actccgccac tgagttttttg | 1680 |

```
tttggtgaat ccgttgagtc cttgagagat gaatctattg ggatgtccat caatgcactt    1740
gactttgacg gcaaggctgg ctttgctgat gcttttaact actcgcagaa ctatttggct    1800
tcgagagcgg ttatgcaaca attgtactgg gtgttgaacg ggaaaaagtt taaggagtgc    1860
aacgctaaag tgcacaagtt tgctgactat tacgtcagca aggctttgga cttgacacct    1920
gaacaattgg aaaagcagga tggttatgtg ttcttgtacg agttggtcaa gcaaaccaga    1980
gacaggcaag tgttgagaga ccagttgttg aacatcatgg ttgccggtag agacaccacc    2040
gccggtttgt tgtcgtttgt tttctttgaa ttggccagaa cccagaggt gaccaacaag    2100 ttgagagaag aaatcgagga caagtttggt cttggtgaga atgctcgtgt tgaagacatt    2160
tcctttgagt cgttgaagtc atgtgaatac ttgaaggctg ttctcaacga aactttgaga    2220
ttgtacccat ccgtgccaca gaatttcaga gttgccacca aaacactac ccttccaagg    2280 ggaggtggta aggacgggtt atctcctgtt ttggtcagaa agggtcaaac cgttatgtac    2340
ggtgtctacg ctgcccacag aaacccagct gtctacggta aggacgccct tgagtttaga    2400
ccagagaggt ggtttgagcc agagacaaag aagcttggct gggccttcct tccattcaac    2460
ggtggtccaa gaattgctt gggacagcag tttgccttga cagaagcttc gtatgtcact    2520
gtcagattgc tccaagagtt tggacacttg tctatggacc ccaacaccga atatccacct    2580
aggaaaatgt cgcatttgac catgtcccct tcgacggtg ccaacattga gatgtattag    2640
aggatcatgt gttatttttg attggtttag tctgtttgta gctattgatt aggttaattc    2700
acggattgtt atttattgat aggggtgcg tgtgtgtgtg tgtgttgcat tcacatggga    2760
tcgttccagg ttgttgtttc cttccatcct gttgagtcaa aaggagtttt gttttgtaac    2820
tccggacgat gtcttagata gaaggtcgat ctccatgtga ttgtttgact gctactctga    2880
ttatgtaatc tgtaaagcct agacgttatg caagcatgtg attgtggttt ttgcaacctg    2940
tttgcacgac aaatgatcga cagtcgatta cgtaatccat attatttaga ggggtaataa    3000
aaaataaatg gcagccagaa tttcaaacat tttgcaaaca atgcaaaaga tgagaaactc    3060
caacagaaaa aataaaaaaa ctccgcagca ctccgaacca acaaaacaat gggggggcgcc    3120 agaattattg actattgtga ctttttttta ttttttccgt taactttcat tgcagtgaag    3180
tgtgttacac ggggtggtga tggtgttggt ttctacaatg caagggcaca gttgaaggtt    3240
tccacataac gttgcaccat atcaactcaa tttatcctca ttcatgtgat aaaagaagag    3300
ccaaaaggta attggcagac cccccaaggg gaacacggag tagaaagcaa tggaaacacg    3360
cccatgacag tgccatttag cccacaacac atctagtatt cttttttttt tttgtgcgca    3420
ggtgcacacc tggactttag ttattgcccc ataaagttaa caatctcacc tttggctctc    3480
ccagtgtctc cgcctccaga tgctcgtttt acaccctcga gctaacgaca acacaacacc    3540
catgagggga atgggcaaag ttaaacactt ttggtttcaa tgattcctat ttgctactct    3600
cttgttttgt gttttgattt gcaccatgtg aaataaacga caattatata tacctttcg    3660 tctgtcctcc aatgtctctt tttgctgcca ttttgctttt tgcttttgc ttttgcactc    3720 tctcccactc ccacaatcag tgcagcaaca cacaa                               3755
```

<210> SEQ ID NO 14
<211> LENGTH: 687
<212> TYPE: DNA
<213> ORGANISM: Artificial Sequence
<220> FEATURE:
<223> OTHER INFORMATION: Pre-targeting construct for Candida tropicalis
      CYP52A14

<400> SEQUENCE: 14

```
cgtctcgata acggatagca agtggaatgc gaggaaaatt ttgaatgcgc aaggaaagca      60
atatccgggc tatcaggttt tgagccaggg gacacactcc tcttctgcac aaaaacttaa     120
cgtagacaaa aaaaaaaaac tccaccaaga cacaatgaat cgcacatgga catttagacc     180
tccccacatg tgaaagcttc tctggcgaaa gcaaaaaaag tataataagg acccatgcct     240
tccctcttcc tgggccgttt caacttttc tttttctttg tctatcaaca cacacacacc      300
tcacgaccat ggggcaatca gtgagtctcg caggtaccgc ggagctcgcg gccgctagat     360
cttgcgaagc tccatctcga gaggatcatg tgttattttt gattggttta gtctgtttgt     420
agctattgat taggttaatt cacggattgt tatttattga taggggtgc gtgtgtgtgt       480 gtgtgttgca ttcacatggg atcgttccag gttgttgttt ccttccatcc tgttgagtca     540
aaaggagttt tgttttgtaa ctccggacga tgtcttagat agaaggtcga tctccatgtg     600
attgtttgac tgctactctg attatgtaat ctgtaaagcc tagacgttat gcaagcatgt     660
gattgtggtt tttgcaacct ggagacg                                         687

<210> SEQ ID NO 15
<211> LENGTH: 4839
<212> TYPE: DNA
<213> ORGANISM: Artificial Sequence
<220> FEATURE:
<223> OTHER INFORMATION: Targeting construct for deletion of Candida
      tropicalis CYP52A14

<400> SEQUENCE: 15
cgtctcgata acggatagca agtggaatgc gaggaaaatt ttgaatgcgc aaggaaagca      60
atatccgggc tatcaggttt tgagccaggg gacacactcc tcttctgcac aaaaacttaa     120
cgtagacaaa aaaaaaaaac tccaccaaga cacaatgaat cgcacatgga catttagacc     180
tccccacatg tgaaagcttc tctggcgaaa gcaaaaaaag tataataagg acccatgcct     240
tccctcttcc tgggccgttt caacttttc tttttctttg tctatcaaca cacacacacc      300
tcacgaccat ggggcaatca gtgagtctcg caggtaccgc ggagctcgcg gccgctctag     360
aactagtgga tctgaagttc ctattctcta gaaagtatag gaacttcctg caggaccacc     420
tttgattgta aatagtaata attaccaccc ttatctaatt atttatttaa cttatttatt     480
tatttattat acatatatac aaatctaata aagtgaaaat ctccccttc acacttcaca      540 tatgttaggc gtcatcctgt gctcccgaga accagtacca gtacatcgct gtttcgttcg     600
agacttgagg tctagtttta tacgtgaaga ggtcaatgcc gccgagagta aagccacatt     660
ttgcgtacaa attgcaggca ggtacattgt tcgtttgtgt ctctaatcgt atgccaagga     720
gctgtctgct tagtgcccac ttttcgcaa attcgatgag actgtgcgcg actccttgc       780 ctcggtgcgt gtgcgacaca acaatgtgtt cgatagaggc tagatcgttc catgttgagt     840
tgagttcaat cttcccgaca agctcttggt cgatgaatgc gccatagcaa gcagagtctt     900
catcagagtc atcatccgag atgtaatcct tccggtaggg gctcacactt ctggtagata     960
gttcaaagcc ttggtcggat aggtgcacat cgaacacttc acgaacaatg aaatggttct    1020
cagcatccaa tgtttccgcc acctgctcag ggatcaccga aatttcata tgagaaccgt     1080 tatcgataac taaagcagca acttcttcta taaaaatggg ttagtatgac agtcatttaa    1140
ataaggaatt tttcagttgg cttggtttca attcaatgtt cgtttttttt ttttcttgct    1200
gtgtttgtgt ttgtgttgtt tatagttgtg tgcactgagc gtcgaaaaaa aaaattcata    1260
gtgagccggg aaatctgtat agcccagata acaacacaag tccaaactag aaactcgtca    1320
```

```
aacaccaaaa gcaatgttga atcaattgcc ttgcacaagt acacgtagga aaacataaaa    1380
cattgcaatt ttgaatattg agccttttgt cgtaacattg attgatagga ttactcaccg    1440
aatggttttg aaaccactgc cgacagatca atcaatcaat caaaaaacgt gaactttgaa    1500
aaaggggaag aacagataca ttgaagttag ccatttccat tgatcgtcac aacatatctg    1560
ataaattact ttcaaaatta taagctgatg tgtgtgtatt attaatgtga cagtaacatc    1620
ccaaacgaga atattatgt cgacaacaaa aaagtttgat ctgaattgaa aatgaagttt     1680
tcccacccta cccatttgtc atattgaaac caatcaactg attaatcaat caattagaat    1740
tgaagctaaa ctaaaacata ccaccgtcca ttttgaatga ttatatttt ttaatattaa     1800 tatcgagata atgtttctaa gaaagaaaga aaaccaggag tgaaaattag aaaaggaaag    1860
gaaaggaaaa aaagaaaaat ctgaaaatat ataaaaaaaa attgtttcgt tggcaataaa    1920
tcttggtgag aacagcgacc gaaagcaaat aagaacaaaa tatgagtgta ttacgttgaa    1980
caactaatta acgtgtgtgt atggatcttt tttctttttt tctctttaac cgactataaa    2040
caacaaacat ttttgggcag tgcacacact acttaatata cacagcataa attacacgat    2100
tagaaacaaa ttagcttatt aaaataacct aatcaaaccg aatattttat ggtattatga    2160
gtaaactata taatataaat agcacacacc cacaacaaca acaaggaaa actaaaaggt     2220 tttttctttt tgaaaagatc gttttctta ttattctcta gttttgacgc tcgacatttt     2280
atgatggaat gaatgggatg aatcatcaaa caagagaaaa tacccgtgac gaaaataata    2340
aaataagttc ctctgataca gaagatgaaa acaacaacaa caagatatag aaatgccttg    2400
ggtggctatt ttatagtctt aactttttaa tgtatatttg ttttgttttt ttacataata    2460
atactttata aaagctaagc taaattcaag taaaatttca atctctcaaa taaaacatt     2520 ttctcttttt cttaaattta gttttatata tttataaaat atacaaagat tttttaaaa    2580 aagtaacaag ttatatatgt aataacaaaa agaagaataa caagaataca aaaccagatt    2640
tccagatttc cagaatttca ctcttatatg cgtctatta tgtaggatga aaggtagtct      2700
agtacctcct gtgatattat cccattccat gcggggtatc gtatgcttcc ttcagcacta    2760 cccttagct gttctatatg ctgccactcc tcaattggat tagtctcatc cttcaatgct      2820
atcatttcct ttgatattgg atcatatgca tagtaccgag aaactagtgc gaagtagtga    2880
tcaggtattg ctgttatctg atgagtatac gttgtcctgg ccacggcaga agcacgctta    2940
tcgctccaat ttcccacaac attagtcaac tccgttaggc ccttcattga aagaaatgag    3000
gtcatcaaat gtcttccaat gtgagatttt gggccatttt ttatagcaaa gattgaataa    3060
ggcgcatttt tcttcaaagc tttattgtac gatctgacta agttatcttt taataattgg    3120
tattcctgtt tattgcttga agaattgccg gtcctattta ctcgttttag gactggttca    3180
gaattcctca aaaattcatc caaatataca agtggatcga tcctaccct tgcgctaaag     3240 aagtatatgt gcctactaac gcttgtcttt gtctctgtca ctaaacactg gattattact    3300
cccaaatact tattttggac taatttaaat gatttcggat caacgttctt aatatcgctg    3360
aatcttccac aattgatgaa agtagctagg aagaggaatt ggtataaagt ttttgttttt    3420
gtaaatctcg aagtatactc aaacgaattt agtattttct cagtgatctc ccagatgctt    3480
tcaccctcac ttagaagtgc tttaagcatt ttttactgt ggctatttcc cttatctgct     3540
tcttccgatg attcgaactg taattgcaaa ctacttacaa tatcagtgat atcagattga    3600 tgttttgtc catagtaagg aataattgta aattcccaag caggaatcaa tttctttaat    3660
gaggcttcca aaattgttgc ttttttgcgtc ttgtatttaa actggagtga tttattgaca    3720
```

```
atatcgaaac tcaacgaatt gcttatgata gtattatagc tcatgaatgt ggctctcttg    3780
attgctgttc cgttatgtgt aatcatccaa cataaatagg ttagttcagc agcacataat    3840
gctattttct cacctgaagg tctttcaaac ctttccacaa actgacgaac aagcacctta    3900
ggtggtgttt tacataatat atcaaattgt ggcatgtcga cgattattag ttaaaccact    3960
gcaaaaagtt ggggaaaatt ttgcccattt ttataccgtg tcttcgtcta tcgcctcccc    4020
cactccccaa tctttgaatt attccgaaat attcagcgaa cggggtgtac acaaaaacta    4080
acattctcaa ctgcataatt tgaaaaatgg cgtgggacaa gaaaaaaaaa aaattctcaa    4140
ccatagcaat catggaatac ggtaaatttg tgttgttcgg tgactccatc acccagttta    4200
gttgtaccca gtatggcttt catccagcat tacagaatgt gtatatccga aaattggatg    4260
ttattaaccg tggtttcagt ggctacaact cagagcacgc tagacaaatt cttccaaaaa    4320
ttttagagtc ggaaaccaat atcaaattga tgacaatatt ttttggaact aacgatgcat    4380
acgactacat caatgaaatc cagacagtcg agttagacag atataaagat aatttaagtg    4440
taatggtaca gatggtacta gacaaaaata tcaaaccaat cattattgga tccgaagttc    4500
ctattctcta gaaagtatag gaacttcctc gagaggatca tgtgttattt ttgattggtt    4560
tagtctgttt gtagctattg attaggttaa ttcacggatt gttatttatt gataggggt    4620 gcgtgtgtgt gtgtgtgttg cattcacatg ggatcgttcc aggttgttgt ttccttccat    4680
cctgttgagt caaaggagt tttgtttttgt aactccggac gatgtcttag atagaaggtc    4740
gatctccatg tgattgtttg actgctactc tgattatgta atctgtaaag cctagacgtt    4800
atgcaagcat gtgattgtgg ttttgcaac ctggagacg                           4839

<210> SEQ ID NO 16
<211> LENGTH: 4296
<212> TYPE: DNA
<213> ORGANISM: Candida tropicalis

<400> SEQUENCE: 16
tgcatactcg gagcatatcg ccatcgtcca tatcgttggc actccatcca ctgagtcagc      60
caagaagcaa ttgttgttgc accacacctt aggtaatggt gactttactg ttttccacaa     120
gatctcgtca ttcatcagtg ccactactgc tgggttgacc gacccagaca ccgccgctga     180
tgaaattgat agagtgattg agtcagccta catcaaccag cgtccaacgt acttgggatt     240
cccttccaac atggttgacg ttcaagtgcc agtcagcaag ttggacaagc cattgaactt     300
aaccccacct gcaaacaatc caaagatcca gtctgaggtc ttgagcgaca ttattgcctt     360
gattgaaacc gccaaggatc cagttatcat cattgatgct tgttgtggaa ggcacaatgc     420 tacccccagag gcacagaagt tgattgagtt gacaaagttc aagtttgctg tcaccccaat     480
ggctaaaggg tctaaggaca ttgatgaaag tgatccgaag ttcattggtt gctacgttgg     540
tgacttgtct tatccaagag tcaaagagtt ggttgaaagc tcggacttgg tcttgtcctt     600
gggtgctgtc ttgtctgatt tcaacactgg ttcgttctca tactctttgg acaatgccaa     660
ggttgttgaa ttccactccg actacactca aatcaagagc gctcagtacc caggtatcag     720
aatgaaggaa ttgttgggca gttggttga ggagccagaa ttggtcaaga cgtgttccaa     780
gatcccagca aagaagttgg tcactgacaa ctttgaacca ttggtcttgc caccggacca     840
caagctcacc caatcctggt tgtggagtaa cttgggtaat tggttgaaag aaggtgatgt     900
gattgttacc gaaaccggta cttccaattt cggtattgtc cagaccaaat tcccaaagaa     960
tgctgtcggt atctcgcaag tcttgtgggg ttccattggc tactcggtcg gttctgccgc    1020
```

```
tggtgccgtt atcgccgccg aggagcttga tcccagccgt agagtcatct tgtttgttgg    1080
tgacggttct ttgcagttga ccgtgcagga aatctccacc atggccagac acaagaacaa    1140
catctacatc tttgtcttga acaacaacgg tttcaccatt gaaagattga ttcacggtcc    1200
agaagctggt tacaacagta ttcaagaatg ggagaacgct gagttattga agactttcaa    1260
ggctaccaac tacgagagtt tcaccgtcaa gactgtcggc gaacttgaca aggtgttcaa    1320
ggatgaaaag tttgccgtca acgacaagat tagattggtt gagatcatgt tagacacttt    1380
cgatgctcca gagaacttgg ttaagcaagc tgagagatct gccaacacca caagtagag    1440
tttgtctatg ttttccgttt gccttttctt tctagtacga gacgttattg aacgaagttt    1500
ttatatatct agatctaata catattccat gtctgttcat ttttgacgga gtttcataag    1560
gtggcagttt ctaatcaaag gtccgtcatt ggcgtcgtgg cattggcggc tcgcatcaac    1620
tcgtatgtca atattttctg ttaactccgc cagacatacg atcaaaacct caagcaaaa    1680
aaattccaca tgctttgttt gagatctcca caaacaacaa cggggtaaga aaatcatggg    1740
gcgattaatc atgccatctt tgtaaatttc tttgtttcaa catcaccctc tttagtcaaa    1800
ccttcacagg actgtctgct ctactttgcc acccagttca tatataaatt accaacttcc    1860
accgagcacc accaacacct caccccactc tctcccccccc ccttttttt ccagcttaga    1920
cacacacttc aaactcgaca tggctccatt ttgcccgac caggtcgact acaaacacgt    1980
cgacacccctt atgttattat gtgacgggat catccacgaa accaccgtgg acgaaatcaa    2040
agacgtcatt gccctgact tccccgccga caaatacgag gagtacgtca ggacattcac    2100
caaaccctcc gaaaccccag ggttcaggga accgtctac aacaccgtca acgcaaacac    2160
catggatgca atccaccagt tcattatctt gaccaatgtt ttgggatcaa gggtcttggc    2220
accagctttg accaactcgt tgactcctat caaggacatg agcttggaag accgtgaaaa    2280
gttgttagcc tcgtggcgtg actccctat tgctgctaaa aggaagttgt tcaggttggt    2340
ttctacgctt accttggtca cgttcacgag attggccaat gagttgcatt tgaaagccat    2400
tcattatcca ggaagagaag accgtgaaaa ggcttatgaa acccaggaga ttgacccttt    2460
taagtaccag tttttggaaa aaccgaagtt ttacggcgct gagttgtact tgccagatat    2520
tgatgtgatc attattggat ctggggccgg tgctggtgtc gtggcccaca ctttgaccaa    2580
cgacggcttc aagagtttgg tttttggaaaa gggcagatac tttagcaact ccgagttgaa    2640
ctttgatgac aaggacgggg ttcaagaatt ataccaaagt ggaggtactt tgaccaccgt    2700
caaccagcag ttgtttgttc ttgctggttc cacttttggt ggtggtacca ctgtcaattg    2760
gtcggcctgt cttaaaacgc cattcaaggt gcgtaaggaa tggtatgatg agtttggcgt    2820
tgactttgct gccgatgaag cctacgacaa agcacaggat tatgtttggc agcaaatggg    2880
agcttctacc gaaggcatca cccactcttt ggctaacgag attattattg aaggtggcaa    2940
gaaattaggt tacaaggcca aggtattaga ccaaaacagc ggtggtcatc ctcatcacag    3000
atgcggtttc tgttatttgg gttgtaagca cggtatcaag cagggctctg ttaataactg    3060
gtttagagac gcagctgccc acggttctca gttcatgcaa caggttagag ttttgcaaat    3120
ccttaacaag aagggcatcg cttatggtat cttgtgtgag gatgttgtaa ccggtgccaa    3180
gttcaccatt actggcccca aaagtttgt tgttgccgcc ggcgccttaa acactccatc    3240
tgtgttggtc aactccggat tcaagaacaa gaacatcggt aagaacttaa ctttgcatcc    3300
agtttctgtc gtgtttggtg attttggcaa agacgttcaa gcagatcact tccacaactc    3360
catcatgact gctctttgtt cagaagccgc tgatttagac ggcaagggtc atggatgcag    3420
```

```
aattgaaacc atcttgaacg ctccattcat ccaggcttca ttcttaccat ggagaggtag    3480
taacgaggct agacgagact tgttgcgtta caacaacatg gtggccatgt tacttcttag    3540
tcgtgatacc accagtggtt ccgtttcgtc ccatccaact aaacctgaag cattagttgt    3600
cgagtacgac gtgaacaagt tgacagaaa ctccatcttg caggcattgt tggtcactgc    3660
tgacttgttg tacattcaag gtgccaagag aatccttagt ccccaaccat gggtgccaat    3720
ttttgaatcc gacaagccaa aggataagag atcaatcaag gacgaggact atgtcgaatg    3780
gagagccaag gttgccaaga ttccttttga cacctacggc tcgccttatg gttcggcgca    3840
tcaaatgtct tcttgtcgta tgtcaggtaa gggtcctaaa tacggtgctg ttgataccga    3900
tggtagattg tttgaatgtt cgaatgttta tgttgctgac gctagtcttt tgccaactgc    3960
tagcggtgct aatcctatgg tcaccaccat gactcttgca agacatgttg cgttaggttt    4020
ggcagactcc ttgaagacca aggccaagtt gtagttctgt atacgtatct tataatttag    4080
attttccttt attgacggta acattcagg ataggtacta cccttgctgc aaaagcccag    4140
cacgccccaa tcgcgatgac ttgagcgaag caaacacgca cacaaaggg gtacacaaaa    4200 aataacgaga tgcccttgaa gcacacaccc aaacacgatg gaacacaaga tggccctaga    4260
aagtacaaaa aaagtaaagc cacttgattc cgccca                              4296

<210> SEQ ID NO 17
<211> LENGTH: 609
<212> TYPE: DNA
<213> ORGANISM: Artificial Sequence
<220> FEATURE:
<223> OTHER INFORMATION: Pre-targeting construct for Candida tropicalis
      FAO1

<400> SEQUENCE: 17
cgtctcctgt taactccgcc agacatacga tcaaaaccta caagcaaaaa aattccacat      60
gctttgtttg agatctccac aaacaacaac ggggtaagaa aatcatgggg cgattaatca    120
tgccatcttt gtaaatttct ttgtttcaac atcaccctct ttagtcaaac cttcacagga    180
ctgtctgctc tactttgcca cccagttcat atataaatta ccaacttcca ccgagcacca    240
ccaacacctc accccactct ctccccccc cttttttttc cagcttagac acacacttca    300
aactcgccat ggggcaatca gtgagtctcg caggtaccgc ggagctcgcg gccgctagat    360
cttgcgaagc tccatctcga gttctgtata cgtatcttat aatttagatt tccttttatt    420
gacggtaaac attcaggata ggtactaccc ttgctgcaaa agcccagcac gccccaatcg    480
cgatgacttg agcgaagcaa acacgcacac aaaagggta cacaaaaaat aacgagatgc    540
ccttgaagca cacccaaa cacgatggaa cacaagatgg ccctagaaag tacaaaaaaa    600
gtagagacg                                                            609

<210> SEQ ID NO 18
<211> LENGTH: 4761
<212> TYPE: DNA
<213> ORGANISM: Artificial Sequence
<220> FEATURE:
<223> OTHER INFORMATION: Targeting construct for deletion of Candida
      tropicalis FAO1

<400> SEQUENCE: 18
cgtctcctgt taactccgcc agacatacga tcaaaaccta caagcaaaaa aattccacat      60
gctttgtttg agatctccac aaacaacaac ggggtaagaa aatcatgggg cgattaatca    120
tgccatcttt gtaaatttct ttgtttcaac atcaccctct ttagtcaaac cttcacagga    180
```

```
ctgtctgctc tactttgcca cccagttcat atataaatta ccaacttcca ccgagcacca    240
ccaacacctc accccactct ctccccccccc cttttttttc cagcttagac acacacttca    300
aactcgccat ggggcaatca gtgagtctcg caggtaccgc ggagctcgcg gccgctctag    360
aactagtgga tctgaagttc ctattctcta gaaagtatag gaacttcctg caggaccacc    420
tttgattgta aatagtaata attaccaccc ttatctaatt atttatttaa cttatttatt    480
tatttattat acatatatac aaatctaata aagtgaaaat ctccccttc acacttcaca     540 tatgttaggc gtcatcctgt gctcccgaga accagtacca gtacatcgct gtttcgttcg    600
agacttgagg tctagtttta tacgtgaaga ggtcaatgcc gccgagagta aagccacatt    660
ttgcgtacaa attgcaggca ggtacattgt tcgtttgtgt ctctaatcgt atgccaagga    720
gctgtctgct tagtgcccac ttttcgcaa attcgatgag actgtgcgcg actccttgc      780 ctcggtgcgt gtgcgacaca acaatgtgtt cgatagaggc tagatcgttc catgttgagt    840
tgagttcaat cttcccgaca agctcttggt cgatgaatgc gccatagcaa gcagagtctt    900
catcagagtc atcatccgag atgtaatcct tccggtaggg gctcacactt ctggtagata    960
gttcaaagcc ttggtcggat aggtgcacat cgaacacttc acgaacaatg aaatggttct   1020
cagcatccaa tgtttccgcc acctgctcag ggatcaccga aattttcata tgagaaccgt   1080
tatcgataac taaagcagca acttcttcta taaaaatggg ttagtatgac agtcatttaa   1140
ataaggaatt tttcagttgg cttggtttca attcaatgtt cgttttttttt ttttcttgct   1200 gtgtttgtgt ttgtgttgtt tatagttgtg tgcactgagc gtcgaaaaaa aaaattcata   1260
gtgagccggg aaatctgtat agcccagata acaacacaag tccaaactag aaactcgtca   1320
aacaccaaaa gcaatgttga atcaattgcc ttgcacaagt acacgtagga aaacataaaa   1380
cattgcaatt ttgaatattg agccttttgt cgtaacattg attgatagga ttactcaccg   1440
aatggttttg aaaccactgc cgacagatca atcaatcaat caaaaaacgt gaactttgaa   1500
aaaggggaag aacagataca ttgaagttag ccatttccat tgatcgtcac aacatatctg   1560
ataaattact ttcaaaatta taagctgatg tgtgtgtatt attaatgtga cagtaacatc   1620
ccaaacgaga aatattatgt cgacaacaaa aaagtttgat ctgaattgaa aatgaagttt   1680
tcccacccta cccatttgtc atattgaaac caatcaactg attaatcaat caattagaat   1740
tgaagctaaa ctaaaacata ccaccgtcca ttttgaatga ttatatttt ttaatattaa    1800 tatcgagata atgtttctaa gaaagaaaga aaccaggag tgaaaattag aaaaggaaag    1860
gaaaggaaaa aagaaaaat ctgaaaatat ataaaaaaa attgtttcgt tggcaataaa    1920
tcttggtgag aacagcgacc gaaagcaaat aagaacaaaa tatgagtgta ttacgttgaa   1980
caactaatta acgtgtgtgt atggatcttt ttttcttttt tctctttaac cgactataaa   2040
caacaaacat ttttgggcag tgcacacact acttaatata cacagcataa attacacgat   2100
tagaaacaaa ttagcttatt aaaataacct aatcaaaccg aatatttat ggtattatga    2160 gtaaactata aatataaat agcacacacc cacaacaaca acaaggaaa actaaaaggt     2220 tttttctttt tgaaaagatc gttttctta ttattctcta gttttgacgc tcgacatttt    2280
atgatggaat gaatgggatg aatcatcaaa caagagaaaa tacccgtgac gaaaataata   2340
aaataagttc ctctgataca gaagatgaaa acaacaacaa caagatatag aaatgccttg   2400
ggtggctatt ttatagtctt aacttttttaa tgtatatttg ttttgttttt ttacataata   2460
atactttata aaagctaagc taaattcaag taaaatttca atctctcaaa taaaacatttt  2520 ttctcttttt cttaaattta gttttatata tttataaaat atacaaagat ttttttaaaa   2580
```

-continued

```
aagtaacaag ttatatatgt aataacaaaa agaagaataa caagaataca aaaccagatt    2640
tccagatttc cagaatttca ctcttatatg cgtctatta tgtaggatga aaggtagtct    2700
agtacctcct gtgatattat cccattccat gcggggtatc gtatgcttcc ttcagcacta    2760 cccttagct gttctatatg ctgccactcc tcaattggat tagtctcatc cttcaatgct    2820
atcatttcct ttgatattgg atcatatgca tagtaccgag aaactagtgc gaagtagtga    2880
tcaggtattg ctgttatctg atgagtatac gttgtcctgg ccacggcaga agcacgctta    2940
tcgctccaat ttcccacaac attagtcaac tccgttaggc ccttcattga agaaatgag    3000 gtcatcaaat gtcttccaat gtgagatttt gggccatttt ttatagcaaa gattgaataa    3060
ggcgcatttt tcttcaaagc tttattgtac gatctgacta agttatcttt taataattgg    3120
tattcctgtt tattgcttga agaattgccg gtcctattta ctcgttttag gactggttca    3180
gaattcctca aaaattcatc caaatataca agtggatcga tcctaccct tgcgctaaag    3240 aagtatatgt gcctactaac gcttgtcttt gtctctgtca ctaaacactg gattattact    3300
cccaaatact tattttggac taatttaaat gatttcggat caacgttctt aatatcgctg    3360
aatcttccac aattgatgaa agtagctagg aagaggaatt ggtataaagt tttgttttt    3420 gtaaatctcg aagtatactc aaacgaattt agtattttct cagtgatctc ccagatgctt    3480
tcaccctcac ttagaagtgc tttaagcatt tttttactgt ggctatttcc cttatctgct    3540
tcttccgatg attcgaactg taattgcaaa ctacttacaa tatcagtgat atcagattga    3600 tgttttgtc catagtaagg aataattgta aattcccaag caggaatcaa tttctttaat    3660
gaggcttcca aaattgttgc ttttttgcgtc ttgtatttaa actggagtga tttattgaca    3720
atatcgaaac tcaacgaatt gcttatgata gtattatagc tcatgaatgt ggctctcttg    3780
attgctgttc cgttatgtgt aatcatccaa cataaatagg ttagttcagc agcacataat    3840 gctatttct cacctgaagg tctttcaaac ctttccacaa actgacgaac aagcaccta    3900 ggtggtgttt tacataatat atcaaattgt ggcatgtcga cgattattag ttaaaccact    3960
gcaaaaagtt ggggaaaatt ttgcccattt ttataccgtg tcttcgtcta tcgcctcccc    4020
cactccccaa tctttgaatt attccgaaat attcagcgaa cggggtgtac acaaaaacta    4080
acattctcaa ctgcataatt tgaaaaatgg cgtgggacaa gaaaaaaaaa aaattctcaa    4140
ccatagcaat catggaatac ggtaaatttg tgttgttcgg tgactccatc acccagttta    4200
gttgtaccca gtatggcttt catccagcat tacagaatgt gtatatccga aaattggatg    4260
ttattaaccg tggtttcagt ggctacaact cagagcacgc tagacaaatt cttccaaaaa    4320
ttttagagtc ggaaaccaat atcaaattga tgacaatatt ttttggaact aacgatgcat    4380
acgactacat caatgaaatc cagacagtcg agttagacag atataaagat aatttaagtg    4440
taatggtaca gatggtacta gacaaaaata tcaaaccaat cattattgga tccgaagttc    4500
ctattctcta gaaagtatag gaacttcctc gagttctgta tacgtatctt ataatttaga    4560
tttcctttta ttgacggtaa acattcagga taggtactac ccttgctgca aaagcccagc    4620
acgccccaat cgcgatgact tgagcgaagc aaacacgcac acaaaagggg tacacaaaaa    4680
ataacgagat gcccttgaag cacacaccca aacacgatgg aacacaagat ggccctagaa    4740
agtacaaaaa aagtagagac g                                              4761
```

<210> SEQ ID NO 19
<211> LENGTH: 1992
<212> TYPE: DNA
<213> ORGANISM: Candida tropicalis

<400> SEQUENCE: 19

```
cttatgttat tatgtgacgg gatcatccac gaaaccaccg tcgaccaaat caaagacgtt      60
attgctcctg acttccctgc tgacaagtac gaagagtacg tcaggacatt caccaaaccc     120
tccgaaaccc cagggttcag ggaaaccgtc tacaacacag tcaacgcaaa caccacggac     180
gcaatccacc agttcattat cttgaccaat gttttggcat ccagggtctt ggctccagct     240
ttgaccaact cgttgacgcc tatcaaggac atgagcttgg aagaccgtga aaaattgttg     300
gcctcgtggc gcgactcccc aatcgctgcc aaaaggaaat tgttcaggtt ggtttccacg     360
cttaccttgg ttactttcac gagattggcc aatgagttgc atttgaaagc cattcactat     420
ccaggaagag aagaccgtga aaaggcttat gaaacccagg agattgaccc tttcaagtac     480
cagtttatgg aaaagccaaa gtttgacggc gctgagttgt acttgccaga tattgatgtt     540
atcattattg gatctggtgc cggtgctggt gttgtggccc acactttggc caacgatggc     600
ttcaagagtt tggttttgga aaagggcaaa tactttagca actccgagtt gaactttgat     660
gacaaggacg gcgttcaaga attataccaa agtggaggta ctttgactac agtcaaccaa     720
cagttgtttg ttcttgctgg ttccactttt ggtggcggta ccactgtcaa ttggtcagcc     780
tgtcttaaga cgccattcaa ggtgcgtaag gaatggtatg atgagtttgg tgttgacttt     840
gctgctgatg aagcatacga taaagcgcag gattatgttt ggcagcaaat gggagcttct     900
accgaaggca tcacccactc tttggctaac gagattatta ttgaaggtgg taagaaatta     960
ggttacaagg ccaaggtatt agaccaaaac agcggtggtc atcctcagca cagatgcggt    1020
ttctgttatt tgggctgtaa gcacggtatc aagcagggtt ctgttaataa ctggtttaga    1080
gacgcagctg cccacggttc ccagttcatg caacaggtta gagttttgca aatacttaac    1140
aagaagggga tcgcttacgg tatcttgtgt gaggatgttg taaccggcgc caagttcacc    1200
attactggcc ccaaaaagtt tgttgttgct gccggtgctt tgaacactcc atctgtgttg    1260
gtcaactccg gcttcaagaa caagaacatc ggtaagaact taactttgca cccagttttct   1320
gtcgtgtttg gtgattttgg caaagacgtt caagcagacc acttccacaa ctccatcatg    1380
actgcccttt gttcagaagc cgctgattta gacggcaagg gccatggatg cagaattgaa    1440
accatcttga acgctccatt catccaggct tcattcttac catggagagg tagtaacgag    1500
gctagacgag acttgttgcg ttacaacaac atggtggcga tgttgctcct tagtcgtgac    1560
accaccagtg gttccgtttc tgctcatcca accaaacctg aagctttggt tgtcgagtac    1620
gacgtgaaca gtttgacag aaactcgatc ttgcaggcat tgttggtcac tgctgacttg    1680
ttgtatatcc aaggtgccaa gagaatcctt agtccacagg catgggtgcc aattttttgaa   1740
tccgacaagc caaaggataa gagatcaatc aaggacgagg actatgtcga atggagagcc    1800
aaggttgcca agattccttt cgacacctac ggctcacctt atggttcggc acatcaaatg    1860
tcttcttgcc gtatgtcagg taagggtcct aaatacggtg ctgttgacac cgatggtaga    1920
ttgtttgaat gttcgaatgt ttatgttgcc gatgcaagtc ttttgccaac tgcaagcggt    1980
gctaatccta tg                                                        1992
```

<210> SEQ ID NO 20
<211> LENGTH: 603
<212> TYPE: DNA
<213> ORGANISM: Artificial Sequence
<220> FEATURE:
<223> OTHER INFORMATION: Pre-targeting construct for Candida tropicalis FAO1

<400> SEQUENCE: 20

```
cgaaaccacc gtcgaccaaa tcaaagacgt tattgctcct gacttccctg ctgacaagta      60
cgaagagtac gtcaggacat tcaccaaacc ctccgaaacc caggggttca gggaaaccgt     120
ctacaacaca gtcaacgcaa acaccacgga cgcaatccac cagttcatta tcttgaccaa     180
tgttttggca tccagggtct tggctccagc tttgaccaac tcgttgacgc ctatcaagga     240
catgagcttg gaagaccgtg aaaaattgtt ggcctcgtgg cgcgactagg cggccgctag     300
atcttgcgaa gctccatctc gagttgttgt atatccaagg tgccaagaga atccttagtc     360
cacaggcatg ggtgccaatt tttgaatccg acaagccaaa ggataagaga tcaatcaagg     420
acgaggacta tgtcgaatgg agagccaagg ttgccaagat tcctttcgac acctacggct     480
caccttatgg ttcggcacat caaatgtctt cttgccgtat gtcaggtaag ggtcctaaat     540
acggtgctgt tgacaccgat ggtagattgt ttgaatgttc gaatgtttat gttgccgatg     600
caa                                                                   603

<210> SEQ ID NO 21
<211> LENGTH: 4755
<212> TYPE: DNA
<213> ORGANISM: Artificial Sequence
<220> FEATURE:
<223> OTHER INFORMATION: Targeting construct for deletion of Candida
      tropicalis FAO1

<400> SEQUENCE: 21
cgaaaccacc gtcgaccaaa tcaaagacgt tattgctcct gacttccctg ctgacaagta      60
cgaagagtac gtcaggacat tcaccaaacc ctccgaaacc caggggttca gggaaaccgt     120
ctacaacaca gtcaacgcaa acaccacgga cgcaatccac cagttcatta tcttgaccaa     180
tgttttggca tccagggtct tggctccagc tttgaccaac tcgttgacgc ctatcaagga     240
catgagcttg gaagaccgtg aaaaattgtt ggcctcgtgg cgcgactagg cggccgctct     300
agaactagtg gatctgaagt tcctattctc tagaaagtat aggaacttcc tgcaggacca     360
cctttgattg taaatagtaa taattaccac ccttatctaa ttatttattt aacttattta     420
tttatttatt atacatatat acaaatctaa taaagtgaaa atctccccct tcacacttca     480
catatgttag gcgtcatcct gtgctcccga gaaccagtac cagtacatcg ctgtttcgtt     540
cgagacttga ggtctagttt tatacgtgaa gaggtcaatg ccgccgagag taaagccaca     600
ttttgcgtac aaattgcagg caggtacatt gttcgtttgt gtctctaatc gtatgccaag     660
gagctgtctg cttagtgccc acttttttcgc aaattcgatg agactgtgcg cgactccttt     720
gcctcggtgc gtgtgcgaca caacaatgtg ttcgatagag ctagatcgt tccatgttga     780 gttgagttca atcttcccga caagctcttg gtcgatgaat gcgccatagc aagcagagtc     840
ttcatcagag tcatcatccg agatgtaatc cttccggtag gggctcacac ttctggtaga     900
tagttcaaag cctggtcgg ataggtgcac atcgaacact tcacgaacaa tgaaatggtt     960
ctcagcatcc aatgtttccg ccacctgctc agggatcacc gaaattttca tatgagaacc    1020
gttatcgata actaaagcag caacttcttc tataaaaatg ggttagtatg acagtcattt    1080
aaataaggaa ttttttcagtt ggcttggttt caattcaatg ttcgtttttt tttttttcttg   1140 ctgtgtttgt gtttgtgttg tttatagttg tgtgcactga gcgtcgaaaa aaaaaattca    1200
tagtgagccg ggaaatctgt atagcccaga taacaacaca agtccaaact agaaactcgt    1260
caaacaccaa aagcaatgtt gaatcaattg ccttgcacaa gtacgctag gaaaacataa    1320 aacattgcaa ttttgaatat tgagcctttt gtcgtaacat tgattgatag gattactcac    1380
```

```
cgaatggttt tgaaaccact gccgacagat caatcaatca atcaaaaaac gtgaactttg   1440
aaaaagggga agaacagata cattgaagtt agccatttcc attgatcgtc acaacatatc   1500
tgataaatta ctttcaaaat tataagctga tgtgtgtgta ttattaatgt gacagtaaca   1560
tcccaaacga gaaatattat gtcgacaaca aaaagtttg atctgaattg aaaatgaagt    1620
tttcccaccc tacccatttg tcatattgaa accaatcaac tgattaatca atcaattaga   1680
attgaagcta aactaaaaca taccaccgtc cattttgaat gattatattt ttttaatatt   1740
aatatcgaga taatgtttct aagaagaaa gaaaaccagg agtgaaaatt agaaaggaa    1800 aggaaaggaa aaaagaaaa atctgaaaat atataaaaaa aaattgtttc gttggcaata    1860
aatcttggtg agaacagcga ccgaaagcaa ataagaacaa aatatgagtg tattacgttg   1920
aacaactaat taacgtgtgt gtatggatct ttttttcttt tttctcttta accgactata   1980
aacaacaaac atttttgggc agtgcacaca ctacttaata tacacagcat aaattacacg   2040
attagaaaca aattagctta ttaaaataac ctaatcaaac cgaatatttt atggtattat   2100
gagtaaacta tataatataa atagcacaca cccacaacaa caacaaagga aaactaaaag   2160
gttttttctt tttgaaaaga tcgttttctt tattattctc tagttttgac gctcgacatt   2220
ttatgatgga atgaatggga tgaatcatca aacaagagaa aatacccgtg acgaaaataa   2280
taaaataagt tcctctgata cagaagatga aacaacaac aacaagatat agaaatgcct    2340
tgggtggcta ttttatagtc ttaacttttt aatgtatatt tgttttgttt tttacataa    2400 taatacttta taaagctaa gctaaattca agtaaaattt caatctctca aataaaacat    2460
ttttctcttt ttcttaaatt tagttttata tatttataaa atatacaaag attttttaa    2520 aaaagtaaca agttatatat gtaataacaa aagaagaat aacaagaata caaaaccaga    2580
tttccagatt tccagaattt cactcttata tgcgtctatt tatgtaggat gaaaggtagt   2640
ctagtacctc ctgtgatatt atcccattcc atgcggggta tcgtatgctt ccttcagcac   2700
taccctttag ctgttctata tgctgccact cctcaattgg attagtctca tccttcaatg   2760
ctatcatttc ctttgatatt ggatcatatg catagtaccg agaaactagt gcgaagtagt   2820
gatcaggtat tgctgttatc tgatgagtat acgttgtcct ggccacggca gaagcacgct   2880
tatcgctcca atttcccaca acattagtca actccgttag gcccttcatt gaaagaaatg   2940
aggtcatcaa atgtcttcca atgtgagatt ttgggccatt ttttatagca agattgaat    3000 aaggcgcatt tttcttcaaa gctttattgt acgatctgac taagttatct tttaataatt   3060
ggtattcctg tttattgctt gaagaattgc cggtcctatt tactcgtttt aggactggtt   3120
cagaattcct caaaaattca tccaaatata caagtggatc gatcctaccc cttgcgctaa   3180
agaagtatat gtgcctacta acgcttgtct ttgtctctgt cactaaacac tggattatta   3240
ctcccaaata cttattttgg actaatttaa atgatttcgg atcaacgttc ttaatatcgc   3300
tgaatcttcc acaattgatg aaagtagcta ggaagaggaa ttggtataaa gttttgtttt   3360
ttgtaaatct cgaagtatac tcaaacgaat ttagtatttt ctcagtgatc tcccagatgc   3420
tttcaccctc acttagaagt gctttaagca tttttttact gtggctattt cccttatctg   3480
cttcttccga tgattcgaac tgtaattgca aactacttac aatatcagtg atatcagatt   3540 gatgttttg tccatagtaa ggaataattg taaattccca agcaggaatc aatttcttta   3600
atgaggcttc caaaattgtt gcttttttgcg tcttgtattt aaactggagt gatttattga   3660
caatatcgaa actcaacgaa ttgcttatga tagtattata gctcatgaat gtggctctct   3720
tgattgctgt tccgttatgt gtaatcatcc aacataaata ggttagttca gcagcacata   3780
```

-continued

| | |
|---|---|
| atgctatttt ctcacctgaa ggtctttcaa acctttccac aaactgacga acaagcacct | 3840 |
| taggtggtgt tttacataat atatcaaatt gtggcatgtc gacgattatt agttaaacca | 3900 |
| ctgcaaaaag ttggggaaaa ttttgcccat ttttataccg tgtcttcgtc tatcgcctcc | 3960 |
| cccactcccc aatctttgaa ttattccgaa atattcagcg aacggggtgt acacaaaaac | 4020 |
| taacattctc aactgcataa tttgaaaaat ggcgtgggac aagaaaaaaa aaaaattctc | 4080 |
| aaccatagca atcatggaat acggtaaatt tgtgttgttc ggtgactcca tcacccagtt | 4140 |
| tagttgtacc cagtatggct ttcatccagc attacagaat gtgtatatcc gaaaattgga | 4200 |
| tgttattaac cgtggtttca gtggctacaa ctcagagcac gctagacaaa ttcttccaaa | 4260 |
| aattttagag tcggaaacca atatcaaatt gatgacaata ttttttggaa ctaacgatgc | 4320 |
| atacgactac atcaatgaaa tccagacagt cgagttagac agatataaag ataatttaag | 4380 |
| tgtaatggta cagatggtac tagacaaaaa tatcaaacca atcattattg gatccgaagt | 4440 |
| tcctattctc tagaaagtat aggaacttcc tcgagttgtt gtatatccaa ggtgccaaga | 4500 |
| gaatccttag tccacaggca tgggtgccaa tttttgaatc cgacaagcca aaggataaga | 4560 |
| gatcaatcaa ggacgaggac tatgtcgaat ggagagccaa ggttgccaag attcctttcg | 4620 |
| acacctacgg ctcaccttat ggttcggcac atcaaatgtc ttcttgccgt atgtcaggta | 4680 |
| agggtcctaa atacggtgct gttgacaccg atggtagatt gtttgaatgt tcgaatgttt | 4740 |
| atgttgccga tgcaa | 4755 |

<210> SEQ ID NO 22
<211> LENGTH: 4158
<212> TYPE: DNA
<213> ORGANISM: Candida tropicalis

<400> SEQUENCE: 22

| | |
|---|---|
| tctcaccaag tacgagaacg agcttgttga tagagcttag acttgtcttt tgtatttgta | 60 |
| atctgacgtt gaccgtttga gttttcctg tgatatcacg taaatctggc aaccagcttt | 120 |
| ctattttttt tgcaacactt tttctcttca ccactctcag aaccaatgcc accgaagaag | 180 |
| ggtctcaacc aggaggaaaa gctctcgtca atcctcgcct ggttccaaag cagccactgc | 240 |
| ttctatacgc tcaaagaggt tgaacagaag gctagcaaag cgtgcaagat ctcgtctatg | 300 |
| cagatcaagg acttggttgc aaccttagtc aacgaaggtt tagtggaaca ggaaaaatgt | 360 |
| gggaccacca acttgtactg gtcgttcccg tactcggaac acaaacgcaa gctacagaga | 420 |
| tacgagcagc taagacaatc cgttgccaaa cttcaagcga ataaaggcaa gttggcggaa | 480 |
| gagttgcgaa acgcgtgtgg tgagcgtgac atggacagca ataggctaaa ccggatgcaa | 540 |
| cagtgcgatc agcttgttca cgaggcggca cgcctccagg aggaactaaa actgtcgagg | 600 |
| cagagagata ccattgacga gttggttcag gccattgact tcttcaacga gctgatagag | 660 |
| accgtcctca gctacatcag ccatcagtcg gggaccagca tgtcggtatt gaaaacggag | 720 |
| tttgagatac ccgcagaact agaagaggct ccccagataa acaatgccgg agttagtgcg | 780 |
| taaatcgagc atgcatacgt tggagagaaa tagagaaaca gatttccggt gaaacgctac | 840 |
| aacacagacg aggaatacag aatggaacat gacggaaata taatatccga ggaaagacga | 900 |
| aagtacgaca tggaactccg ttactgcaac atcgatcgtg ctagatacga catagaacaa | 960 |
| tgttgctatt acatggaaag ctgttgctac aatccagaat acggttgtac tcaagggaga | 1020 |
| tgaggctggg agccgagtgg tacataaata ggcatatagg accgtcactt ggtctaggat | 1080 |
| cgtgtagagg gtggaagagg taggcaagat ccattctaat ctactgagtg acggctaata | 1140 |

```
tacgatcagc gttctcaggc gagcacagtc attcctcatt tctgtacata cgttgcccct    1200
ttatgttttt tttcacagga tgctcacgcc caacatttcc ccccacattt tattacccac    1260
attgagccgt caaatgcatt ttttttatcc gtcgcttgct aagacaaaat tccacatgct    1320
ttgtctcaga gtatataaac aacggggcaa aaaacatgg ggttaatagc ttattcgtgg     1380
attgatattt ttatatttta gttcgcccct ttcgccacca agctcaattg gactatttgt    1440
cagtggtgta taagctagag attactagac tgcttttctg attcttgatt ttcccttttc    1500
attagttcca gtacctagag atgaatacct tcttgccaga cgtgctcgaa tacaaacacg    1560
tcgacaccct tttgttattg tgtgacggga tcatccacga aaccacagtc gatcagatca    1620
aggacgccat tgctcccgac ttccctgagg accagtacga ggagtatctc aagaccttca    1680
ccaagccatc tgagacccct gggttcagag aagccgtcta cgacacgatc aacgccaccc    1740
caaccgatgc cgtgcacatg tgtattgtct tgaccaccgc attggactcc agaatcttgg    1800
cccccacgtt gaccaactcg ttgacgccta tcaaggatat gaccttgaag gagcgtgaac    1860
aattgttggc ctcttggcgt gattccccga ttgcggcaaa gagaagattg ttcagattga    1920
tttcctcgct taccttgacg acgtttacga gattggccag cgaattgcac ttgaaagcca    1980
tccactaccc tggcagagac ttgcgtgaaa aggcgtatga acccaggtg gttgacccttt    2040 tcaggtacct gtttatggag aaaccaaagt ttgacggcgc cgaattgtac ttgccagata    2100
tcgacgtcat catcattgga tcaggcgccg gtgctggtgt catggcccac actctcgcca    2160
acgacgggtt caagaccttg gttttggaaa agggaaagta tttcagcaac tccgagttga    2220
actttaatga cgctgatggc gtgaaagagt tgtaccaagg taaaggtgct ttggccacca    2280
ccaatcagca gatgtttatt cttgccggtt ccactttggg cggtggtacc actgtcaact    2340
ggtctgcttg ccttaaaaca ccatttaaag tgcgtaagga gtggtacgac gagtttggtc    2400
ttgaatttgc tgccgatgaa gcctacgaca agcgcagga ttatgtttgg aaacaaatgg     2460
gtgcttcaac agatggaatc actcactcct tggccaacga agttgtggtt gaaggaggta    2520
agaagttggg ctacaagagc aaggaaattg agcagaacaa cggtggccac cctgaccacc    2580
catgtggttt ctgttacttg ggctgtaagt acggtattaa acagggttct gtgaataact    2640
ggtttagaga cgcagctgcc cacgggtcca agttcatgca acaagtcaga gttgtgcaaa    2700
tcctcaacaa gaatggcgtc gcttatggta tcttgtgtga ggatgtcgaa accggagtca    2760
ggttcactat tagtggccccc aaaaagtttg ttgtttctgc tggttctttg aacacgccaa    2820
ctgtgttgac caactccgga ttcaagaaca agcacattgg taagaacttg acgttgcacc    2880
cagtttccac cgtgtttggt gactttggca gagacgtgca agccgaccat ttccacaaat    2940
ctattatgac ttcgctttgt tacgaggttg ctgacttgga cggcaagggc cacggatgca    3000
gaatcgaaac catcttgaac gctccattca tccaagcttc tttgttgcca tggagaggaa    3060
gtgacgaggt cagaagagac ttgttgcgtt acaacaacat ggtggccatg ttgcttatca    3120
cgcgtgatac caccagtggt tcagtttctg ctgacccaaa gaagcccgac gctttgattg    3180
tcgactatga gattaacaag tttgacaaga atgccatctt gcaagctttc ttgatcactt    3240
ccgacatgtt gtacattgaa ggtgccaaga gaatcctcag tccacagcca tgggtgccaa    3300
tctttgagtc gaacaagcca aaggagcaaa gaacgatcaa ggacaaggac tatgttgagt    3360
ggagagccaa ggctgctaag ataccttttcg acacctacgg ttctgcatat gggtccgcac    3420
atcaaatgtc cacctgtcgt atgtccggaa agggtcctaa atacggtgct gttgatactg    3480
atggtagatt gtttgaatgt tcgaatgtct atgttgctga tgctagtgtt ttgcctactg    3540
```

-continued

```
ccagcggtgc caacccaatg atatccacca tgacctttgc tagacagatt gcgttaggtt    3600
tggctgactc cttgaagacc aaacccaagt tgtagagaga cggaaatacg acacttatat    3660
actagatgta tcttacaatt tatattctcg atgatggctt ttactatctc ctatgttaca    3720
ctataatgac atcaccacaa cctctactac tgtctccagt atcctccttg ctgttgaccg    3780
tacccaccag cctgttgatt gaaccctgtg aactgtggtt gctgttgagc gtacccacg    3840 ttagtgaact gcggttgttg ggcaaactgc tgtacgggct gttgctgctg ctgctgttgt    3900
tgttgttgtt gttgtcccgt gggctggttg tacaacgaca tgatgttctg cttgtttgtc    3960
tgttgggcaa ccaactgtgg gttattcatc tgcatcaact gctgctggtg ttgagggttg    4020
tttggatcca agtactcttg cccgttggcg tcgatataag aaatctgccc cgtgactggg    4080
tcagtgtact ggtatatctg tggcatgcca ccagcttgtg caggcatgcc ggttgccaat    4140
ggcacctgtg cttgcgtc                                                  4158

<210> SEQ ID NO 23
<211> LENGTH: 643
<212> TYPE: DNA
<213> ORGANISM: Artificial Sequence
<220> FEATURE:
<223> OTHER INFORMATION: Pre-targeting construct for Candida tropicalis
      FAO2A

<400> SEQUENCE: 23
cgtctcatga ataccttctt gccagacgtg ctcgaataca acacgtcga caccctttg      60 ttattgtgtg acgggatcat ccacgaaacc acagtcgatc agatcaagga cgccattgct    120
cccgacttcc ctgaggacca gtacgaggag tatctcaaga ccttcaccaa gccatctgag    180
acccctgggt tcagagaagc cgtctacgac acgatcaacg ccaccccaac cgatgccgtg    240
cacatgtgta ttgtcttgac caccgcattg gactccagaa tcttggcccc cacgttgacc    300
aactaggcgg ccgctagatc ttgcgaagct ccatctcgag aaggacaagg actatgttga    360
gtggagagcc aaggctgcta agataccttt cgacacctac ggttctgcat atgggtccgc    420
acatcaaatg tccacctgtc gtatgtccgg aaagggtcct aaatacggtg ctgttgatac    480
tgatggtaga ttgtttgaat gttcgaatgt ctatgttgct gatgctagtg ttttgcctac    540
tgccagcggt gccaacccaa tgatatccac catgaccttt gctagacaga ttgcgttagg    600
tttggctgac tccttgaaga ccaaacccaa gttgtaggag acg                      643

<210> SEQ ID NO 24
<211> LENGTH: 4795
<212> TYPE: DNA
<213> ORGANISM: Artificial Sequence
<220> FEATURE:
<223> OTHER INFORMATION: Targeting construct for deletion of Candida
      tropicalis FAO2A

<400> SEQUENCE: 24
cgtctcatga ataccttctt gccagacgtg ctcgaataca acacgtcga caccctttg      60 ttattgtgtg acgggatcat ccacgaaacc acagtcgatc agatcaagga cgccattgct    120
cccgacttcc ctgaggacca gtacgaggag tatctcaaga ccttcaccaa gccatctgag    180
acccctgggt tcagagaagc cgtctacgac acgatcaacg ccaccccaac cgatgccgtg    240
cacatgtgta ttgtcttgac caccgcattg gactccagaa tcttggcccc cacgttgacc    300
aactaggcgg ccgctctaga actagtggat ctgaagttcc tattctctag aaagtatagg    360
aacttcctgc aggaccacct ttgattgtaa atagtaataa ttaccaccct tatctaatta    420
```

```
tttatttaac ttatttattt atttattata catatataca aatctaataa agtgaaaatc    480
tcccccttca cacttcacat atgttaggcg tcatcctgtg ctcccgagaa ccagtaccag    540
tacatcgctg tttcgttcga gacttgaggt ctagttttat acgtgaagag gtcaatgccg    600
ccgagagtaa agccacattt tgcgtacaaa ttgcaggcag gtacattgtt cgtttgtgtc    660
tctaatcgta tgccaaggag ctgtctgctt agtgcccact ttttcgcaaa ttcgatgaga    720
ctgtgcgcga ctccttttgcc tcggtgcgtg tgcgacacaa caatgtgttc gatagaggct    780
agatcgttcc atgttgagtt gagttcaatc ttcccgacaa gctcttggtc gatgaatgcg    840
ccatagcaag cagagtcttc atcagagtca tcatccgaga tgtaatcctt ccggtagggg    900
ctcacacttc tggtagatag ttcaaagcct tggtcggata ggtgcacatc gaacacttca    960
cgaacaatga aatggttctc agcatccaat gtttccgcca cctgctcagg gatcaccgaa    1020
attttcatat gagaaccgtt atcgataact aaagcagcaa cttcttctat aaaaatgggt    1080
tagtatgaca gtcatttaaa taaggaattt ttcagttggc ttggtttcaa ttcaatgttc    1140 gtttttttt tttcttgctg tgtttgtgtt tgtgttgttt atagttgtgt gcactgagcg    1200
tcgaaaaaaa aaattcatag tgagccggga aatctgtata gcccagataa caacacaagt    1260
ccaaactaga aactcgtcaa acaccaaaag caatgttgaa tcaattgcct tgcacaagta    1320
cacgtaggaa aacataaaac attgcaattt tgaatattga ccttttgtc gtaacattga    1380 ttgataggat tactcaccga atggttttga aaccactgcc gacagatcaa tcaatcaatc    1440
aaaaaacgtg aactttgaaa aaggggaaga acagatacat tgaagttagc catttccatt    1500
gatcgtcaca acatatctga taaattactt tcaaaattat aagctgatgt gtgtgtatta    1560
ttaatgtgac agtaacatcc caaacgagaa atattatgtc gacaacaaaa aagtttgatc    1620
tgaattgaaa atgaagtttt cccaccctac ccatttgtca tattgaaacc aatcaactga    1680
ttaatcaatc aattagaatt gaagctaaac taaaacatac caccgtccat tttgaatgat    1740 tatattttt taatattaat atcgagataa tgtttctaag aaagaaagaa aaccaggagt    1800
gaaaattaga aaaggaaagg aaaggaaaaa aagaaaaatc tgaaaatata taaaaaaaaa    1860
ttgtttcgtt ggcaataaat cttggtgaga acagcgaccg aaagcaaata agaacaaaat    1920
atgagtgtat tacgttgaac aactaattaa cgtgtgtgta tggatctttt ttctttttt    1980 ctctttaacc gactataaac aacaaacatt tttgggcagt gcacacacta cttaatatac    2040
acagcataaa ttacacgatt agaaacaaat tagcttatta aaataaccta atcaaaccga    2100 atatttatg gtattatgag taaactatat aatataaata gcacacaccc acaacaacaa    2160
caaaggaaaa ctaaaaggtt ttttcttttt gaaaagatcg ttttctttat tattctctag    2220
ttttgacgct cgacattta tgatggaatg aatgggatga atcatcaaac aagagaaaat    2280
acccgtgacg aaaataataa aataagttcc tctgatacag aagatgaaaa caacaacaac    2340
aagatataga aatgccttgg gtggctattt tatagtctta acttttaat gtatatttgt    2400 tttgtttttt tacataataa tacttataa aagctaagct aaattcaagt aaaatttcaa    2460
tctctcaaat aaaacatttt tctcttttc ttaaatttag ttttatatat ttataaaata    2520
tacaaagatt ttttaaaaa agtaacaagt tatatatgta ataacaaaaa gaagaataac    2580
aagaatacaa aaccagattt ccagatttcc agaatttcac tcttatatgc gtctatttat    2640
gtaggatgaa aggtagtcta gtacctcctg tgatattatc ccattccatg cggggtatcg    2700
tatgcttcct tcagcactac cctttagctg ttctatatgc tgccactcct caattggatt    2760
agtctcatcc ttcaatgcta tcatttcctt tgatattgga tcatatgcat agtaccgaga    2820
```

-continued

```
aactagtgcg aagtagtgat caggtattgc tgttatctga tgagtatacg ttgtcctggc   2880
cacggcagaa gcacgcttat cgctccaatt tcccacaaca ttagtcaact ccgttaggcc   2940
cttcattgaa agaaatgagg tcatcaaatg tcttccaatg tgagattttg ggccattttt   3000
tatagcaaag attgaataag gcgcattttt cttcaaagct ttattgtacg atctgactaa   3060
gttatctttt aataattggt attcctgttt attgcttgaa gaattgccgg tcctatttac   3120
tcgtttttagg actggttcag aattcctcaa aaattcatcc aaatatacaa gtggatcgat   3180
cctacccctt gcgctaaaga agtatatgtg cctactaacg cttgtctttg tctctgtcac   3240
taaacactgg attattactc ccaaatactt attttggact aatttaaatg atttcggatc   3300
aacgttctta atatcgctga atcttccaca attgatgaaa gtagctagga agaggaattg   3360
gtataaagtt tttgttttg taaatctcga agtatactca aacgaattta gtattttctc   3420
agtgatctcc cagatgcttt caccctcact tagaagtgct ttaagcattt ttttactgtg   3480
gctatttccc ttatctgctt cttccgatga ttcgaactgt aattgcaaac tacttacaat   3540
atcagtgata tcagattgat gttttttgtcc atagtaagga ataattgtaa attcccaagc   3600
aggaatcaat ttctttaatg aggcttccaa aattgttgct ttttgcgtct tgtatttaaa   3660
ctggagtgat ttattgacaa tatcgaaact caacgaattg cttatgatag tattatagct   3720
catgaatgtg gctctcttga ttgctgttcc gttatgtgta atcatccaac ataaataggt   3780
tagttcagca gcacataatg ctatttctc acctgaaggt ctttcaaacc tttccacaaa   3840
ctgacgaaca agcaccttag gtggtgtttt acataatata tcaaattgtg gcatgtcgac   3900
gattattagt taaaccactg caaaaagttg gggaaaattt tgcccatttt tataccgtgt   3960
cttcgtctat cgcctccccc actccccaat ctttgaatta ttccgaaata ttcagcgaac   4020
ggggtgtaca caaaaactaa cattctcaac tgcataattt gaaaaatggc gtgggacaag   4080
aaaaaaaaaa aattctcaac catagcaatc atggaatacg gtaaatttgt gttgttcggt   4140
gactccatca cccagtttag ttgtacccag tatggctttc atccagcatt acagaatgtg   4200
tatatccgaa aattggatgt tattaaccgt ggtttcagtg gctacaactc agagcacgct   4260
agacaaattc ttccaaaaat tttagagtcg gaaaccaata tcaaattgat gacaatattt   4320
tttggaacta acgatgcata cgactacatc aatgaaatcc agacagtcga gttagacaga   4380
tataaagata atttaagtgt aatggtacag atggtactag acaaaaatat caaaccaatc   4440
attattggat ccgaagttcc tattctctag aaagtatagg aacttcctcg agaaggacaa   4500
ggactatgtt gagtggagag ccaaggctgc taagatacct ttcgacacct acggttctgc   4560
atatgggtcc gcacatcaaa tgtccacctg tcgtatgtcc ggaaagggtc ctaaatacgg   4620
tgctgttgat actgatggta gattgttga atgttcgaat gtctatgttg ctgatgctag   4680
tgttttgcct actgccagcg gtgccaaccc aatgatatcc accatgacct tgctagaca   4740
gattgcgtta ggtttggctg actccttgaa gaccaaaccc aagttgtagg agacg         4795
```

<210> SEQ ID NO 25
<211> LENGTH: 3753
<212> TYPE: DNA
<213> ORGANISM: Candida tropicalis

<400> SEQUENCE: 25

```
tgttgataga gcttagactt gtgttttgta tttgtaatct gacgttgatc gtttgatatt     60
ttcctgtgat atcacgtaaa ttcggcaacc aacttttac ttttttgcaac actttctctt    120
caccactctc agaaccaatg ccaccgaaga agggtctcag ccaggaggaa aagctctcgg    180
```

```
cactcctcac ctggttccaa gccagtcatt gcttctacac actcaaggag gttgaacaga    240
aggcgagcaa agcgtgcaag atctcgtcta tgcagatcaa ggacttggtt gcaagcttag    300
tcaacgaagg tttggtagaa caggaaaagt gtgggaccac aaacttgtac tggtcgttcc    360
agtactcgga attcaaacgg aagctacaga gatacgggca gctaagacaa tcagccgcca    420
aacttcaagc ggataaaggc aagttggcgg aagagttgcg aaacgcatgt ggtgaacggg    480
acatggacaa caataggcaa gaccggatgc aacaatacga tcaccttgtt aacgaggcgg    540
cacgtctcca ggaggaacta aaactgtcaa ggcagataga taccattgac gagttagttc    600
aggccattga tttcttcaac gagctgatag agaccgtcct cagctacatc agccatcagt    660
cagggaccag cgtgtcgata ttgaaaacgg agtttgagat acccgcagaa ctagaagagg    720 cccccccagat aagcaatgcc ggagttagtg cgtaaatcga gcaggcatac attgcccctt   780 tgtattttt cacaggatgc tcaccccacc acgcccaaca tttcccccca cattttatta    840
cccacattga gccgtcaaat gcattttttt atccgtcgct agctaaacca aaattccaca    900
tgcgttgcct cagagtatat aaacaacggg gcaaaaaaca tgggattaat agcttatttg    960
tggattgata ttttatatt ttagttcgcc ccttctacga ccaagctcaa ttggactatt      1020
tgtcagtggt gtataagcta gagattacta gactgctttt ctgattcttg atcatcccct    1080
tagttccagt gcctagagat gaataccttc ttgccagacg tgctcgaata caaacacgtc    1140
gatacccttt tgttattatg tgacgggatc atccacgaaa ccacagtcga ccagatcagg    1200
gacgccattg ctcccgactt ccctgaagac cagtacgagg agtatctcaa gaccttcacc    1260
aagccatctg agacccctgg gttcagagaa gccgtctacg cacgatcaa cagcaccccca   1320 accgaggctg tgcacatgtg tattgtattg accaccgcat tggactcgag aatcttggcc    1380
cccacgttga ccaactcgtt gacgcctatc aaggatatga ccttgaaaga gcgtgaacaa    1440
ttgttggctg cctggcgtga ttccccgatc gcggccaaga gaagattgtt cagattgatt    1500
tcctcactta ccttgacgac ctttacgaga ttggccagcg acttgcactt gagagccatc    1560
cactaccctg gcagagactt gcgtgaaaag gcatatgaaa cccaggtggt tgacccttc     1620 aggtacctgt ttatggaaaa accaaagttt gacggcaccg agttgtactt gccagatatc    1680
gacgtcatca tcattggatc cggtgccggt gctggtgtca tggcccacac tttagccaac    1740
gacgggtaca agaccttggt tttggaaaag ggaaagtatt tcagcaactc cgagttgaac    1800
tttaatgatg ccgatggtat gaaagagttg taccaaggta aatgtgcgtt gaccaccacg    1860
aaccagcaga tgtttattct tgccggttcc actttgggcg tggtaccac tgttaactgg    1920 tctgcttgtc ttaaaacacc atttaaagtg cgtaaggagt ggtacgacga gtttggtctt    1980
gaatttgctg ccgacgaagc ctacgacaaa gcacaagact atgtttggaa acaaatgggc    2040
gcttctaccg aaggaatcac tcactctttg gcgaacgcgg ttgtggttga aggaggtaag    2100
aagtggggtt acaagagcaa ggaaatcgag cagaacaatg gtggccatcc tgaccacccc    2160
tgtggtttct gttacttggg ctgtaagtac ggtattaagc agggttctgt gaataactgg    2220
tttagagacg cagctgccca cgggtccaag ttcatgcaac aagtcagagt tgtgcaaatc    2280
ctccacaata aaggcgtcgc ttatggcatc ttgtgtgagg atgtcgagac cggagtcaaa    2340
ttcactatca gtgccccaa aaagtttgtt gtttctgcag gttcttttgaa cacgccaacg    2400 gtgttgacca actccggatt caagaacaaa cacatcggta agaacttgac gttgcaccca    2460
gtttcgaccg tgtttggtga ctttggcaga gacgtgcaag ccgaccattt ccacaaatct    2520
attatgactt cgctctgtta cgaagtcgct gacttggacg gcaaggggcca cggatgcaga    2580
```

```
atcgagacca tcttgaacgc tccattcatc caagcttctt tgttgccatg gagaggaagc    2640
gacgaggtca gaagagactt gttgcgttac aacaacatgg tggccatgtt gcttatcacc    2700
cgtgacacca ccagtggttc agtttctgct gacccaaaga agcccgacgc tttgattgtc    2760
gactatgaca tcaacaagtt tgacaagaat gccatcttgc aagctttctt gatcacctcc    2820
gacatgttgt acatcgaagg tgccaagaga atcctcagtc acaggcatg ggtgccaatc    2880 tttgagtcga acaagccaaa ggagcaaaga acaatcaagg acaaggacta tgtcgaatgg    2940
agagccaagg ctgccaagat acctttcgac acctacggtt ctgcctatgg gtccgcacat    3000
caaatgtcca cctgtcgtat gtccggaaag ggtcctaaat acggcgccgt tgataccgat    3060
ggtagattgt ttgaatgttc gaatgtctat gttgctgatg ctagtgtttt gcctactgcc    3120
agcggtgcca acccaatgat ctccaccatg acgtttgcta gacagattgc gttaggtttg    3180
gctgactctt tgaagaccaa acccaagttg tagagagaga cagaaatacg acacttatat    3240
actagatgta tcttacaatt tatattttcg atgatggct ttactatctc ctatgttaca    3300
ctataatgac atcaccacat cttctactac tgtctccagt atcctccttg ctgttgaccg    3360
tatccaccag cctgttggtt gaaccccgtg aactgtggtt gctgttgagc gtaccccacg    3420
ttagtgaact gcggttgttg ggtaaactgc tgtacgggct gttgttgctg ttgctgttgt    3480
tgctgttgtt gctgttgttg ctgttgttgc tgttgttgtt gttgtcccgt tggctggttg    3540
tacaacgaca tgatgttctg cttgtttgtc tgctgggcaa ccaactgtgg gttattcatc    3600
tgcatcaact gctgctggtg ctgagggttg tttggatcca agtactcctg cccgttggcg    3660
tcgatataag aaatctgccc cgtgactggg tcagtgtact ggtatatctg tggcatgcca    3720
cccgcttgtg caggcatgcc ggttgccaat ggc                                 3753

<210> SEQ ID NO 26
<211> LENGTH: 616
<212> TYPE: DNA
<213> ORGANISM: Artificial Sequence
<220> FEATURE:
<223> OTHER INFORMATION: Pre-targeting construct for Candida tropicalis
      FAO2B

<400> SEQUENCE: 26
cgtctcatga ataccttctt gccagacgtg ctcgaataca aacacgtcga tacccttttg      60
ttattatgtg acgggatcat ccacgaaacc acagtcgacc agatcaggga cgccattgct     120
cccgacttcc ctgaagacca gtacgaggag tatctcaaga ccttcaccaa gccatctgag     180 accccctgggt tcagagaagc cgtctacgac acgatcaaca gcaccccaac cgaggctgtg     240
cacatgtgta ttgtattgac caccgcattg gactcgtagg cggccgctag atcttgcgaa     300
gctccatctc gagaaggaca aggactatgt cgaatggaga gccaaggctg ccaagatacc     360
tttcgacacc tacggttctg cctatgggtc cgcacatcaa atgtccacct gtcgtatgtc     420
cggaaagggt cctaaatacg gcgccgttga taccgatggt agattgtttg aatgttcgaa     480
tgtctatgtt gctgatgcta gtgttttgcc tactgccagc ggtgccaacc caatgatctc     540
caccatgacg tttgctagac agattgcgtt aggtttggct gactctttga agaccaaacc     600
caagttgtag gagacg                                                    616

<210> SEQ ID NO 27
<211> LENGTH: 4768
<212> TYPE: DNA
<213> ORGANISM: Artificial Sequence
<220> FEATURE:
<223> OTHER INFORMATION: Targeting construct for deletion of Candida
``` tropicalis FAO2B

<400> SEQUENCE: 27

```
cgtctcatga ataccttctt gccagacgtg ctcgaataca aacacgtcga tacccttttg      60
ttattatgtg acgggatcat ccacgaaacc acagtcgacc agatcaggga cgccattgct     120
cccgacttcc ctgaagacca gtacgaggag tatctcaaga ccttcaccaa gccatctgag     180
accctgggt tcagagaagc cgtctacgac acgatcaaca gcaccccaac cgaggctgtg      240
cacatgtgta ttgtattgac caccgcattg gactcgtagg cggccgctct agaactagtg     300
gatctgaagt tcctattctc tagaaagtat aggaacttcc tgcaggacca cctttgattg     360
taaatagtaa taattaccac ccttatctaa ttatttattt aacttattta tttatttatt     420
atacatatat acaaatctaa taaagtgaaa atctccccct tcacacttca catatgttag     480
gcgtcatcct gtgctcccga gaaccagtac cagtacatcg ctgtttcgtt cgagacttga     540
ggtctagttt tatacgtgaa gaggtcaatg ccgccgagag taaagccaca ttttgcgtac     600
aaattgcagg caggtacatt gttcgtttgt gtctctaatc gtatgccaag gagctgtctg     660
cttagtgccc acttttttcgc aaattcgatg agactgtgcg cgactccttt gcctcggtgc     720
gtgtgcgaca caacaatgtg ttcgatagag gctagatcgt tccatgttga gttgagttca     780
atcttcccga caagctcttg gtcgatgaat gcgccatagc aagcagagtc ttcatcagag     840
tcatcatccg agatgtaatc cttccggtag gggctcacac ttctggtaga tagttcaaag     900
ccttggtcgg ataggtgcac atcgaacact tcacgaacaa tgaaatggtt ctcagcatcc     960
aatgtttccg ccacctgctc agggatcacc gaaattttca tatgagaacc gttatcgata    1020
actaaagcag caacttcttc tataaaaatg ggttagtatg acagtcattt aaataaggaa    1080
ttttcagtt ggcttggttt caattcaatg ttcgtttttt tttttcttg ctgtgtttgt      1140
gtttgtgttg tttatagttg tgtgcactga gcgtcgaaaa aaaaattca tagtgagccg     1200
ggaaatctgt atagcccaga taacaacaca agtccaaact agaaactcgt caaacaccaa    1260
aagcaatgtt gaatcaattg ccttgcacaa gtacacgtag gaaaacataa aacattgcaa    1320
ttttgaatat tgagcctttt gtcgtaacat tgattgatag gattactcac cgaatggttt    1380
tgaaaccact gccgacagat caatcaatca atcaaaaaac gtgaactttg aaaaggggga    1440
agaacagata cattgaagtt agccatttcc attgatcgtc acaacatatc tgataaatta    1500
ctttcaaaat tataagctga tgtgtgtgta ttattaatgt gacagtaaca tcccaaacga    1560
gaaatattat gtcgacaaca aaaaagtttg atctgaattg aaaatgaagt tttcccaccc    1620
tacccatttg tcatattgaa accaatcaac tgattaatca atcaattaga attgaagcta    1680
aactaaaaca taccaccgtc cattttgaat gattatattt ttttaatatt aatatcgaga    1740
taatgtttct aagaaagaaa gaaaaccagg agtgaaaatt agaaaaggaa aggaaaggaa    1800
aaaaagaaaa atctgaaaat atataaaaaa aaattgtttc gttggcaata atcttggtg     1860
agaacagcga ccgaaagcaa ataagaacaa aatatgagtg tattacgttg aacaactaat    1920
taacgtgtgt gtatggatct ttttttcttt tttctcttta accgactata aacaacaaac    1980
attttttgggc agtgcacaca ctacttaata tacacagcat aaattacacg attagaaaca    2040
aattagctta ttaaaataac ctaatcaaac cgaatatttt atggtattat gagtaaacta    2100
tataatataa atagcacaca cccacaacaa caacaaagga aaactaaaag gttttttctt    2160
tttgaaaaga tcgttttctt tattattctc tagttttgac gctcgacatt ttatgatgga    2220
atgaatggga tgaatcatca aacaagagaa aatacccgtg acgaaaataa taaaataagt    2280
```

```
tcctctgata cagaagatga aaacaacaac aacaagatat agaaatgcct tgggtggcta    2340
ttttatagtc ttaactttt  aatgtatatt tgttttgttt ttttacataa taatacttta    2400
taaaagctaa gctaaattca agtaaaattt caatctctca aataaaacat ttttctcttt    2460
ttcttaaatt tagttttata tatttataaa atatacaaag attttttaa  aaaagtaaca    2520 agttatatat gtaataacaa aagaagaat  aacaagaata caaaaccaga tttccagatt    2580
tccagaattt cactcttata tgcgtctatt tatgtaggat gaaaggtagt ctagtacctc    2640
ctgtgatatt atcccattcc atgcggggta tcgtatgctt ccttcagcac tacccttag    2700 ctgttctata tgctgccact cctcaattgg attagtctca tccttcaatg ctatcatttc    2760
ctttgatatt ggatcatatg catagtaccg agaaactagt gcgaagtagt gatcaggtat    2820
tgctgttatc tgatgagtat acgttgtcct ggccacggca gaagcacgct tatcgctcca    2880
atttcccaca acattagtca actccgttag gcccttcatt gaaagaaatg aggtcatcaa    2940
atgtcttcca atgtgagatt tgggccatt  ttttatagca agattgaat  aaggcgcatt    3000 tttcttcaaa gctttattgt acgatctgac taagttatct tttaataatt ggtattcctg    3060
tttattgctt gaagaattgc cggtcctatt tactcgtttt aggactggtt cagaattcct    3120
caaaaattca tccaaatata caagtggatc gatcctaccc cttgcgctaa agaagtatat    3180
gtgcctacta acgcttgtct ttgtctctgt cactaaacac tggattatta ctcccaaata    3240
cttattttgg actaatttaa atgatttcgg atcaacgttc ttaatatcgc tgaatcttcc    3300
acaattgatg aaagtagcta ggaagaggaa ttggtataaa gttttgttt  ttgtaaatct    3360 cgaagtatac tcaaacgaat ttagtatttt ctcagtgatc tcccagatgc tttcacccct    3420
acttagaagt gctttaagca ttttttttact gtggctattt cccttatctg cttcttccga    3480
tgattcgaac tgtaattgca aactacttac aatatcagtg atatcagatt gatgtttttg    3540
tccatagtaa ggaataattg taaattccca agcaggaatc aatttcttta atgaggcttc    3600
caaaattgtt gcttttgcg  tcttgtattt aaactggagt gatttattga caatatcgaa    3660
actcaacgaa ttgcttatga tagtattata gctcatgaat gtggctctct tgattgctgt    3720
tccgttatgt gtaatcatcc aacataaata ggttagttca gcagcacata atgctatttt    3780
ctcacctgaa ggtctttcaa accttttccac aaactgacga acaagcacct taggtggtgt    3840
tttacataat atatcaaatt gtggcatgtc gacgattatt agttaaacca ctgcaaaaag    3900
ttggggaaaa ttttgcccat ttttataccg tgtcttcgtc tatcgcctcc cccactcccc    3960
aatctttgaa ttattccgaa atattcagcg aacgggtgt  acacaaaaac taacattctc    4020
aactgcataa tttgaaaaat ggcgtgggac aagaaaaaaa aaaaattctc aaccatagca    4080
atcatggaat acgtaaatt  tgtgttgttc ggtgactcca tcacccagtt tagttgtacc    4140
cagtatggct ttcatccagc attacagaat gtgtatatcc gaaaattgga tgttattaac    4200
cgtggtttca gtggctacaa ctcagagcac gctagacaaa ttcttccaaa aattttagag    4260
tcggaaacca atatcaaatt gatgacaata tttttggaa  ctaacgatgc atacgactac    4320
atcaatgaaa tccagacagt cgagttagac agatataaag ataatttaag tgtaatggta    4380
cagatggtac tagacaaaaa tatcaaacca atcattattg gatccgaagt tcctattctc    4440
tagaaagtat aggaacttcc tcgagaagga caaggactat gtcgaatgga gagccaaggc    4500
tgccaagata cctttcgaca cctacggttc tgcctatggg tccgcacatc aaatgtccac    4560
ctgtcgtatg tccggaaagg gtcctaaata cggcgccgtt gataccgatg gtagattgtt    4620
tgaatgttcg aatgtctatg ttgctgatgc tagtgttttg cctactgcca gcggtgccaa    4680
```

```
cccaatgatc tccaccatga cgtttgctag acagattgcg ttaggtttgg ctgactcttt   4740
gaagaccaaa cccaagttgt aggagacg                                     4768

<210> SEQ ID NO 28
<211> LENGTH: 4115
<212> TYPE: DNA
<213> ORGANISM: Candida tropicalis

<400> SEQUENCE: 28
catatgcgct aatcttcttt ttcttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctccttta ggcaatagaa aaagactaag    300
agaacagcgt ttttacaggt tgcattggtt aatgtagtat tttttagtc ccagcattct     360 gtgggttgct ctgggtttct agaataggaa atcacaggag aatgcaaatt cagatggaag    420
aacaaagaga taaaaacaa aaaaaaactg agttttgcac aatagaatg tttgatgata      480 tcatccactc gctaaacgaa tcatgtgggt gatcttctct ttagttttgg tctatcataa    540
aacacatgaa agtgaaatcc aaatacacta cactccgggt attgtccttc gttttacaga    600
tgtctcattg tcttactttt gaggtcatag gagttgcctg tgagagatca cagagattat    660
cacactcaca tttatcgtag tttcctatct catgctgtgt gtctctggtt ggttcatgag    720
tttggattgt tgtacattaa aggaatcgct ggaaagcaaa gctaactaaa ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900 acaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcacttct    1080 cttttgctct tctttactt agtcaggttt gataacttcc ttttttatta ccctatctta   1140
tttatttatt tattcattta taccaaccaa ccaaccatgg ccacacaaga aatcatcgat   1200
tctgtacttc cgtacttgac caaatggtac actgtgatta ctgcagcagt attagtcttc   1260
cttatctcca caaacatcaa gaactacgtc aaggcaaaga aattgaaatg tgtcgatcca   1320
ccatacttga aggatgccgg tctcactggt attctgtctt tgatcgccgc catcaaggcc   1380
aagaacgacg gtagattggc taactttgcc gatgaagttt cgacgagta cccaaaccac   1440 accttctact tgtctgttgc cggtgctttg aagattgtca tgactgttga cccagaaaac   1500
atcaaggctg tcttggccac ccaattcact gacttctcct tgggtaccag acacgcccac   1560
tttgctcctt tgtgggtga cggtatcttc accttggacg gagaaggttg gaagcactcc   1620
agagctatgt tgagaccaca gtttgctaga gaccagattg gacacgttaa agccttggaa   1680
ccacacatcc aaatcatggc taagcagatc aagttgaacc agggaaagac tttcgatatc   1740
caagaattgt tctttagatt taccgtcgac accgctactg agttcttgtt tggtgaatcc   1800
gttcactcct tgtacgatga aaattgggc atcccaactc aaacgaaat cccaggaaga    1860 gaaaactttg ccgctgcttt caacgtttcc caacactact tggccaccag aagttactcc   1920 cagactttt acttttttgac caacccctaag gaattcagag actgtaacgc caaggtccac   1980
cacttggcca agtactttgt caacaaggcc ttgaacttta ctcctgaaga actcgaagag   2040
```

```
aaatccaagt ccggttacgt tttcttgtac gaattggtta agcaaaccag agatccaaag    2100
gtcttgcaag atcaattgtt gaacattatg gttgccggaa gagacaccac tgccggtttg    2160
ttgtcctttg ctttgtttga attggctaga cacccagaga tgtggtccaa gttgagagaa    2220
gaaatcgaag ttaactttgg tgttggtgaa gactcccgcg ttgaagaaat taccttcgaa    2280
gccttgaaga gatgtgaata cttgaaggct atccttaacg aaaccttgcg tatgtaccca    2340
tctgttcctg tcaactttag aaccgccacc agagacacca ctttgccaag aggtggtggt    2400
gctaacggta ccgacccaat ctacattcct aaaggctcca ctgttgctta cgttgtctac    2460
aagacccacc gtttggaaga atactacggt aaggacgcta acgacttcag accagaaaga    2520
tggtttgaac catctactaa gaagttgggc tgggcttatg ttccattcaa cggtggtcca    2580
agagtctgct tgggtcaaca attcgccttg actgaagctt cttatgtgat cactagattg    2640
gcccagatgt ttgaaactgt ctcatctgat ccaggtctcg aataccctcc accaaagtgt    2700
attcacttga ccatgagtca caacgatggt gtctttgtca agatgtaaag tagtcgatgc    2760
tgggtattcg attacatgtg tataggaaga ttttggtttt ttattcgttc ttttttttaa    2820
tttttgttaa attagtttag agatttcatt aatacataga tgggtgctat ttccgaaact    2880
ttacttctat cccctgtatc ccttattatc cctctcagtc acatgattgc tgtaattgtc    2940
gtgcaggaca caaactccct aacggactta aaccataaac aagctcagaa ccataagccg    3000
acatcactcc ttcttctctc ttctccaacc aatagcatgg acagacccac cctcctatcc    3060
gaatcgaaga cccttattga ctccataccc acctggaagc ccctcaagcc acacacgtca    3120
tccagcccac ccatcaccac atccctctac tcgacaacgt ccaaagacgg cgagttctgg    3180
tgtgcccgga aatcagccat cccggccaca tacaagcagc cgttgattgc gtgcatactc    3240
ggcgagccca caatgggagc cacgcattcg gaccatgaag caaagtacat tcacgagatc    3300
acgggtgttt cagtgtcgca gattgagaag ttcgacgatg gtggaagtac cgatctcgtt    3360
gcggattacg acttcggtgg gttgttatct aaacgaagat tctatgagac gcagcatgtg    3420
tttcggttcg aggattgtgc gtacgtcatg agtgtgcctt ttgatggacc caaggaggaa    3480
ggttacgtgg ttgggacgta cagatccatt gaaaggttga gctggggtaa agacggggac    3540
gtggagtgga ccatggcgac gacgtcggat cctggtgggt ttatcccgca atggataact    3600
cgattgagca tccctggagc aatcgcaaaa gatgtgccta gtgtattaaa ctacatacag    3660
aaataaaaac gtgtcttgat tcattggttt ggttcttgtt gggttccgag ccaatatttc    3720
acatcatctc ctaaattctc caagaatccc aacgtagcgt agtccagcac gccctctgag    3780
atcttattta atatcgactt ctcaaccacc ggtggaatcc cgttcagacc attgttacct    3840
gtagtgtgtt tgctcttgtt cttgatgaca atgatgtatt tgtcacgata cctgaaataa    3900 taaacatcc agtcattgag cttattactc gtgaacttat gaaagaactc attcaagccg    3960
ttcccaaaaa acccagaatt gaagatcttg ctcaactggt catgcaagta gtagatcgcc    4020
atgatctgat actttaccaa gctatcctct ccaagttctc ccacgtacgg caagtacggc    4080
aacgagctct ggaagctttg ttgtttgggg tcata                              4115
```

<210> SEQ ID NO 29
<211> LENGTH: 649
<212> TYPE: DNA
<213> ORGANISM: Artificial Sequence
<220> FEATURE:
<223> OTHER INFORMATION: Pre-targeting construct for Candida tropicalis
      CYP52A12

<400> SEQUENCE: 29

```
cgtctctcac aggttgtctc ctctcaacca acaaaaaaat aagattaaac tttctttgct      60
catgcatcaa tcggagttat ctctgaaaga gttgcctttg tgtaatgtgt gccaaactca     120
aactgcaaaa ctaaccacag aatgattccc ctcacaatta tataaactca cccacatttc     180
cacagaccgt aatttcatgt ctcactttct cttttgctct tcttttactt agtcaggttt     240
gataacttcc tttttatta ccctatctta tttatttatt tattcattta taccaaccaa      300
ccaacctagg cggccgctag atcttgcgaa gctccatctc gagagtagtc gatgctgggt     360
attcgattac atgtgtatag gaagattttg gttttttatt cgttcttttt tttaattttt     420
gttaaattag tttagagatt tcattaatac atagatgggt gctatttccg aaactttact     480
tctatcccct gtatcccta ttatccctct cagtcacatg attgctgtaa ttgtcgtgca     540
ggacacaaac tccctaacgg acttaaacca taaacaagtc cagaaccata agccgacatc     600
actccttctt ctctcttctc caaccaatag catggacaga cccgagacg                649

<210> SEQ ID NO 30
<211> LENGTH: 4801
<212> TYPE: DNA
<213> ORGANISM: Artificial Sequence
<220> FEATURE:
<223> OTHER INFORMATION: Targeting construct for deletion of Candida
      tropicalis CYP52A12

<400> SEQUENCE: 30
cgtctctcac aggttgtctc ctctcaacca acaaaaaaat aagattaaac tttctttgct      60
catgcatcaa tcggagttat ctctgaaaga gttgcctttg tgtaatgtgt gccaaactca     120
aactgcaaaa ctaaccacag aatgattccc ctcacaatta tataaactca cccacatttc     180
cacagaccgt aatttcatgt ctcactttct cttttgctct tcttttactt agtcaggttt     240
gataacttcc tttttatta ccctatctta tttatttatt tattcattta taccaaccaa      300
ccaacctagg cggccgctct agaactagtg gatctgaagt tcctattctc tagaaagtat     360
aggaacttcc tgcaggacca cctttgattg taaatagtaa taattaccac ccttatctaa     420
ttatttattt aacttattta tttatttatt atacatatat acaaatctaa taagtgaaa      480 atctcccct tcacacttca catatgttag gcgtcatcct gtgctcccga gaaccagtac      540
cagtacatcg ctgtttcgtt cgagactgga ggtctagttt tatacgtgaa gaggtcaatg     600
ccgccgagag taaagccaca ttttgcgtac aaattgcagg caggtacatt gttcgtttgt     660
gtctctaatc gtatgccaag gagctgtctg cttagtgccc acttttttcgc aaattcgatg    720 agactgtgcg cgactccttt gcctcggtgc gtgtgcgaca caacaatgtg ttcgatagag     780
gctagatcgt tccatgttga gttgagttca atcttcccga caagctcttg gtcgatgaat     840
gcgccatagc aagcagagtc ttcatcagag tcatcatccg agatgtaatc cttccggtag     900
gggctcacac ttctggtaga tagttcaaag ccttggtcgg ataggtgcac atcgaacact     960
tcacgaacaa tgaaatggtt ctcagcatcc aatgtttccg ccacctgctc agggatcacc    1020
gaaattttca tatgagaacc gttatcgata actaaagcag caacttcttc tataaaaatg    1080
ggttagtatg acagtcattt aaataaggaa ttttttcagtt ggcttggttt caattcaatg    1140
ttcgtttttt ttttttcttg ctgtgttttgt gtttgtgttg tttatagttg tgtgcactga    1200
gcgtcgaaaa aaaaaattca tagtgagccg ggaaatctgt atagcccaga taacaacaca    1260
agtccaaact agaactcgt caaacaccaa aagcaatgtt gaatcaattg ccttgcacaa     1320
gtacacgtag gaaaacataa aacattgcaa ttttgaatat tgagcctttt gtcgtaacat    1380
```

-continued

```
tgattgatag gattactcac cgaatggttt tgaaaccact gccgacagat caatcaatca    1440
atcaaaaaac gtgaactttg aaaaggggga agaacagata cattgaagtt agccatttcc    1500
attgatcgtc acaacatatc tgataaatta ctttcaaaat tataagctga tgtgtgtgta    1560
ttattaatgt gacagtaaca tcccaaacga gaaatattat gtcgacaaca aaaaagtttg    1620
atctgaattg aaaatgaagt tttcccaccc tacccatttg tcatattgaa accaatcaac    1680
tgattaatca atcaattaga attgaagcta aactaaaaca taccaccgtc cattttgaat    1740
gattatattt ttttaatatt aatatcgaga taatgtttct aagaaagaaa gaaaaccagg    1800
agtgaaaatt agaaaggaa aggaaaggaa aaaagaaaa atctgaaaat atataaaaaa    1860
aaattgtttc gttggcaata atcttggtg agaacagcga ccgaaagcaa ataagaacaa    1920
aatatgagtg tattacgttg aacaactaat taacgtgtgt gtatggatct ttttttcttt    1980
tttctcttta accgactata aacaacaaac attttttggc agtgcacaca ctacttaata    2040
tacacagcat aaattacacg attagaaaca aattagctta ttaaaataac ctaatcaaac    2100
cgaatatttt atggtattat gagtaaacta tataatataa atagcacaca cccacaacaa    2160
caacaaagga aaactaaaag gttttttctt tttgaaaaga tcgttttctt tattattctc    2220
tagttttgac gctcgacatt ttatgatgga atgaatggga tgaatcatca aacaagagaa    2280
aatacccgtg acgaaaataa taaaataagt tcctctgata cagaagatga aaacaacaac    2340
aacaagatat agaaatgcct tgggtggcta ttttatagtc ttaactttt aatgtatatt    2400 tgttttgttt ttttacataa taatacttta taaaagctaa gctaaattca agtaaaattt    2460
caatctctca aataaaacat ttttctcttt ttcttaaatt tagttttata tatttataaa    2520
atatacaaag attttttttaa aaagtaaca agttatatat gtaataacaa aaagaagaat    2580
aacaagaata caaaaccaga tttccagatt tccagaattt cactcttata tgcgtctatt    2640
tatgtaggat gaaaggtagt ctagtacctc ctgtgatatt atcccattcc atgcggggta    2700
tcgtatgctt ccttcagcac tacccttag ctgttctata tgctgccact cctcaattgg    2760
attagtctca tccttcaatg ctatcatttc ctttgatatt ggatcatatg catagtaccg    2820
agaaactagt gcgaagtagt gatcaggtat tgctgttatc tgatgagtat acgttgtcct    2880
ggccacggca gaagcacgct tatcgctcca atttcccaca acattagtca actccgttag    2940
gcccttcatt gaaagaaatg aggtcatcaa atgtcttcca atgtgagatt ttgggccatt    3000
ttttatagca aagattgaat aaggcgcatt tttcttcaaa gctttattgt acgatctgac    3060
taagttatct tttaataatt ggtattcctg tttattgctt gaagaattgc cggtcctatt    3120
tactcgtttt aggactggtt cagaattcct caaaaattca tccaaatata caagtggatc    3180
gatcctaccc cttgcgctaa agaagtatat gtgcctacta acgcttgtct ttgtctctgt    3240
cactaaacac tggattatta ctcccaaata cttatttgg actaatttaa atgatttcgg    3300
atcaacgttc ttaatatcgc tgaatcttcc acaattgatg aaagtagcta ggaagaggaa    3360
ttggtataaa gttttttgttt ttgtaaatct cgaagtatac tcaaacgaat ttagtatttt    3420
ctcagtgatc tcccagatgc tttcaccctc acttagaagt gctttaagca tttttttact    3480 gtggctatt ccccttatctg cttcttccga tgattcgaac tgtaattgca aactacttac    3540
aatatcagtg atatcagatt gatgttttg tccatagtaa ggaataattg taaattccca    3600
agcaggaatc aatttcttta atgaggcttc caaaattgtt gcttttgcg tcttgtattt    3660 aaactggagt gatttattga caatatcgaa actcaacgaa ttgcttatga tagtattata    3720
gctcatgaat gtggctctct tgattgctgt tccgttatgt gtaatcatcc aacataaata    3780
```

```
ggttagttca gcagcacata atgctatttt ctcacctgaa ggtctttcaa acctttccac    3840
aaactgacga acaagcacct taggtggtgt tttacataat atatcaaatt gtggcatgtc    3900
gacgattatt agttaaacca ctgcaaaaag ttggggaaaa ttttgcccat ttttataccg    3960
tgtcttcgtc tatcgcctcc cccactcccc aatctttgaa ttattccgaa atattcagcg    4020
aacggggtgt acacaaaaac taacattctc aactgcataa tttgaaaaat ggcgtgggac    4080
aagaaaaaaa aaaattctc aaccatagca atcatggaat acgtaaatt tgtgttgttc    4140 ggtgactcca tcacccagtt tagttgtacc cagtatggct ttcatccagc attacagaat    4200
gtgtatatcc gaaaattgga tgttattaac cgtggtttca gtggctacaa ctcagagcac    4260
gctagacaaa ttcttccaaa aattttagag tcggaaacca atatcaaatt gatgacaata    4320
ttttttggaa ctaacgatgc atacgactac atcaatgaaa tccagacagt cgagttagac    4380
agatataaag ataatttaag tgtaatggta cagatggtac tagacaaaaa tatcaaacca    4440
atcattattg gatccgaagt tcctattctc tagaaagtat aggaacttcc tcgagagtag    4500
tcgatgctgg gtattcgatt acatgtgtat aggaagattt tggttttta ttcgttcttt    4560 tttttaattt ttgttaaatt agtttagaga tttcattaat acatagatgg gtgctatttc    4620
cgaaacttta cttctatccc ctgtatccct tattatccct ctcagtcaca tgattgctgt    4680
aattgtcgtg caggacacaa actccctaac ggacttaaac cataaacaag ctcagaacca    4740
taagccgaca tcactccttc ttctctcttc tccaaccaat agcatggaca gacccgagac    4800
g                                                                   4801
```

<210> SEQ ID NO 31
<211> LENGTH: 643
<212> TYPE: DNA
<213> ORGANISM: Artificial Sequence
<220> FEATURE:
<223> OTHER INFORMATION: Pre-targeting construct for Candida tropicalis CYP52A12B

<400> SEQUENCE: 31

```
cgtctcatgg ccacacaaga aatcatcgat tctgtacttc cgtacttgac caaatggtac     60
actgtgatta ctgcagcagt attagtcttc cttatctcca caaacatcaa gaactacgtc    120
aaggcaaaga aattgaaatg tgtcgatcca ccatacttga aggatgccgg tctcactggt    180
attctgtctt tgatcgccgc catcaaggcc aagaacgacg gtagattggc taactttgcc    240
gatgaagttt tcgacgagta cccaaaccac accttctact tgtctgttgc cggtgctttg    300
aagtaggcgg ccgctagatc ttgcgaagct ccatctcgag gttgtctaca agacccaccg    360
tttggaagaa tactacggta aggacgctaa cgacttcaga ccagaaagat ggtttgaacc    420
atctactaag aagttgggct gggcttatgt tccattcaac ggtggtccaa gagtctgctt    480
gggtcaacaa ttcgccttga ctgaagcttc ttatgtgatc actagattgg cccagatgtt    540
tgaaactgtc tcatctgatc caggtctcga ataccctcca ccaaagtgta ttcacttgac    600
catgagtcac aacgatggtg tctttgtcaa gatgtaagag acg                      643
```

<210> SEQ ID NO 32
<211> LENGTH: 4795
<212> TYPE: DNA
<213> ORGANISM: Artificial Sequence
<220> FEATURE:
<223> OTHER INFORMATION: Targeting construct for deletion of Candida tropicalis CYP52A12B

<400> SEQUENCE: 32

```
cgtctcatgg ccacacaaga aatcatcgat tctgtacttc cgtacttgac caaatggtac    60
actgtgatta ctgcagcagt attagtcttc cttatctcca caaacatcaa gaactacgtc   120
aaggcaaaga aattgaaatg tgtcgatcca ccatacttga aggatgccgg tctcactggt   180
attctgtctt tgatcgccgc catcaaggcc aagaacgacg gtagattggc taactttgcc   240
gatgaagttt tcgacgagta cccaaaccac accttctact tgtctgttgc cggtgctttg   300
aagtaggcgg ccgctctaga actagtggat ctgaagttcc tattctctag aaagtatagg   360
aacttcctgc aggaccacct tgattgtaa atagtaataa ttaccaccct tatctaatta   420
tttatttaac ttatttattt atttattata catatataca aatctaataa agtgaaaatc   480 tccccttca cacttcacat atgttaggcg tcatcctgtg ctcccgagaa ccagtaccag   540
tacatcgctg tttcgttcga gacttgaggt ctagttttat acgtgaagag gtcaatgccg   600
ccgagagtaa agccacattt tgcgtacaaa ttgcaggcag gtacattgtt cgtttgtgtc   660
tctaatcgta tgccaaggag ctgtctgctt agtgcccact ttttcgcaaa ttcgatgaga   720
ctgtgcgcga ctcctttgcc tcggtgcgtg tgcgacacaa caatgtgttc gatagaggct   780
agatcgttcc atgttgagtt gagttcaatc ttcccgacaa gctcttggtc gatgaatgcg   840
ccatagcaag cagagtcttc atcagagtca tcatccgaga tgtaatcctt ccggtagggg   900
ctcacacttc tggtagatag ttcaaagcct tggtcggata ggtgcacatc gaacacttca   960
cgaacaatga aatggttctc agcatccaat gtttccgcca cctgctcagg gatcaccgaa  1020
attttcatat gagaaccgtt atcgataact aaagcagcaa cttcttctat aaaaatgggt  1080
tagtatgaca gtcatttaaa taaggaattt ttcagttggc ttggtttcaa ttcaatgttc  1140
gttttttttt tttcttgctg tgtttgtgtt tgtgttgttt atagtgtgt gcactgagcg  1200 tcgaaaaaaa aaattcatag tgagccggga aatctgtata gcccagataa caacacaagt  1260
ccaaactaga aactcgtcaa acaccaaaag caatgttgaa tcaattgcct tgcacaagta  1320
cacgtaggaa aacataaaac attgcaattt tgaatattga gccttttgtc gtaacattga  1380
ttgataggat tactcaccga atggttttga aaccactgcc gacagatcaa tcaatcaatc  1440
aaaaaacgtg aactttgaaa aaggggaaga acagatacat tgaagttagc catttccatt  1500
gatcgtcaca acatatctga taaattactt tcaaaattat aagctgatgt gtgtgtatta  1560
ttaatgtgac agtaacatcc caaacgagaa atattatgtc gacaacaaaa aagtttgatc  1620
tgaattgaaa atgaagtttt cccaccctac ccatttgtca tattgaaacc aatcaactga  1680
ttaatcaatc aattagaatt gaagctaaac taaaacatac caccgtccat tttgaatgat  1740 tatattttt taatattaat atcgagataa tgtttctaag aaagaaagaa aaccaggagt  1800
gaaaattaga aaaggaaagg aaaggaaaaa aagaaaatc tgaaaatata taaaaaaaaa  1860
ttgtttcgtt ggcaataaat cttggtgaga acagcgaccg aaagcaaata agaacaaaat  1920
atgagtgtat tacgttgaac aactaattaa cgtgtgtgta tggatctttt tttcttttt   1980 ctctttaacc gactataaac aacaaacatt tttgggcagt gcacacacta cttaatatac  2040
acagcataaa ttacacgatt agaaacaaat tagcttatta aaataaccta atcaaaccga  2100
atattttatg gtattatgag taaactatat aatataaata gcacacaccc acaacaacaa  2160
caaaggaaaa ctaaaaggtt ttttcttttt gaaaagatcg ttttctttat tattctctag  2220
ttttgacgct cgacattta tgatggaatg aatgggatga atcatcaaac aagagaaaat  2280
acccgtgacg aaaataataa aataagttcc tctgatacag aagatgaaaa caacaacaac  2340
aagatataga aatgccttgg gtggctattt tatagtctta acttttaat gtatatttgt   2400
```

```
tttgtttttt tacataataa tactttataa aagctaagct aaattcaagt aaaatttcaa    2460
tctctcaaat aaaacatttt tctcttttc  ttaaatttag ttttatatat ttataaaata    2520
tacaaagatt tttttaaaaa agtaacaagt tatatatgta ataacaaaaa gaagaataac    2580
aagaatacaa aaccgattt  ccagatttcc agaatttcac tcttatatgc gtctatttat    2640
gtaggatgaa aggtagtcta gtacctcctg tgatattatc ccattccatg cggggtatcg    2700
tatgcttcct tcagcactac cctttagctg ttctatatgc tgccactcct caattggatt    2760
agtctcatcc ttcaatgcta tcatttcctt tgatattgga tcatatgcat agtaccgaga    2820
aactagtgcg aagtagtgat caggtattgc tgttatctga tgagtatacg ttgtcctggc    2880
cacggcagaa gcacgcttat cgctccaatt tcccacaaca ttagtcaact ccgttaggcc    2940
cttcattgaa agaaatgagg tcatcaaatg tcttccaatg tgagattttg ggccattttt    3000
tatagcaaag attgaataag gcgcattttt cttcaaagct ttattgtacg atctgactaa    3060
gttatctttt aataattggt attcctgttt attgcttgaa gaattgccgg tcctatttac    3120
tcgttttagg actggttcag aattcctcaa aaattcatcc aaatatacaa gtggatcgat    3180
cctacccctt gcgctaaaga agtatatgtg cctactaacg cttgtctttg tctctgtcac    3240
taaacactgg attattactc ccaaatactt atttttggact aatttaaatg atttcggatc    3300
aacgttctta atatcgctga atcttccaca attgatgaaa gtagctagga agaggaattg    3360
gtataaagtt tttgttttg  taaatctcga agtatactca aacgaattta gtattttctc    3420
agtgatctcc cagatgcttt caccctcact tagaagtgct ttaagcattt ttttactgtg    3480
gctatttccc ttatctgctt cttccgatga ttcgaactgt aattgcaaac tacttacaat    3540
atcagtgata tcagattgat gttttttgtcc atagtaagga ataattgtaa attcccaagc    3600
aggaatcaat ttcttaatg  aggcttccaa aattgttgct ttttgcgtct tgtatttaaa    3660
ctggagtgat ttattgacaa tatcgaaact caacgaattg cttatgatag tattatagct    3720
catgaatgtg gctctcttga ttgctgttcc gttatgtgta atcatccaac ataaataggt    3780
tagttcagca gcacataatg ctattttctc acctgaaggt cttcaaacc  tttccacaaa    3840
ctgacgaaca agcaccttag gtggtgtttt acataatata tcaaattgtg gcatgtcgac    3900
gattattagt taaccactg  caaaaagttg gggaaaattt tgcccatttt tataccgtgt    3960
cttcgtctat cgcctccccc actccccaat ctttgaatta ttccgaaata ttcagcgaac    4020
ggggtgtaca caaaaactaa cattctcaac tgcataattt gaaaaatggc gtgggacaag    4080
aaaaaaaaaa aattctcaac catagcaatc atggaatacg gtaaatttgt gttgttcggt    4140
gactccatca cccagtttag ttgtacccag tatggctttc atccagcatt acagaatgtg    4200
tatatccgaa aattggatgt tattaaccgt ggtttcagtg gctacaactc agagcacgct    4260
agacaaattc ttccaaaaat tttagagtcg gaaaccaata tcaaattgat gacaatattt    4320
tttgaaacta acgatgcata cgactacatc aatgaaatcc agacagtcga gttagacaga    4380
tataaagata atttaagtgt aatggtacag atggtactag acaaaaatat caaaccaatc    4440
attattggat ccgaagttcc tattctctag aaagtatagg aacttcctcg aggttgtcta    4500
caagacccac cgtttggaag aatactacgg taaggacgct aacgacttca gaccagaaag    4560
atggtttgaa ccatctacta agaagttggg ctgggcttat gttccattca acggtggtcc    4620
aagagtctgc ttgggtcaac aattcgcctt gactgaagct tcttatgtga tcactagatt    4680
ggcccagatg tttgaaactg tctcatctga tccaggtctc gaatacctc  caccaaagtg    4740
tattcacttg accatgagtc acaacgatgg tgtctttgtc aagatgtaag agacg         4795
```

<210> SEQ ID NO 33
<211> LENGTH: 1305
<212> TYPE: DNA
<213> ORGANISM: Candida albicans

<400> SEQUENCE: 33

```
atgcaagcaa gcttattcag aattttcaga ggtgcgagtc tcaccactac cactgcagct      60
gcatctttta cagcaacagc aacagcaggt gccaccacgg caaagacatt gtctggatcc     120
actgtgctcc gaaaactgta taaaggacc tattcatccc tggtcttatc ttctccagaa      180
ttatttttttt ttcatcagtt taacaacaac aaacgttatt gtcatacaac aacaacaaca    240
aatacaaaaa caattatgtc tgaacaaatc ccaaaaactc aaaaagccgt tgtctttgat     300
accaatggtg gtcaattagt ctacaaggat tacccagttc caactccaaa gccaaatgaa     360
ttgttgattc acgtcaaata ctctggtgtc tgtcacactg atttacatgc ttggaaaggt     420
gactggccat ggctactaa attgccatta gttggtggtc acgaaggtgc cggtgtcgtt      480
gtcggtatgg gtgaaaacgt caaggatgg aaaatcggtg actttgccgg tatcaaatgg     540
ttgaacggtt cttgtatgag ttgtgaattc tgtcaacaag gtgctgaacc aaactgtggt     600
gaagctgact tgtctggtta cactcacgat ggttcattcg aacaatacgc tactgctgat     660
gctgtccaag ccgctaaaat tccagctggt actgatttag ccaatgtcgc accaatctta     720
tgtgctggtg ttactgtttta caaagcctta agactgctg acttagcagc tggccaatgg    780
gttgctatct ccggtgctgg tggtggttta ggttctttgg ccgttcaata cgccagagcc    840
atgggtttga gagttgttgc tattgacggt ggtgacgaaa aggtgaatt tgtcaaatca     900
ttgggtgctg aagcttacgt tgatttcacc aaagataag atattgttga agctgttaag     960
aaggctactg atggtggtcc acacggtgct atcaatgtct ctgtttctga aaaagctatt    1020
gaccaatctg ttgaatatgt tagaccatta ggtaaagttg ttttggttgg tttaccagct   1080
cacgctaaag tcactgctcc agttttcgat gctgttgtca atccattga atcaaaggt     1140
tcttacgttg gtaacagaaa agatactgct gaagctattg acttcttctc cagaggttta   1200
atcaaatgcc caatcaagat tgtcggttta tctgacttgc cagaagtctt caaattgatg   1260
gaagaaggta aaatcttgag tagatacgta ttggacacca gttga                   1305
```

<210> SEQ ID NO 34
<211> LENGTH: 1308
<212> TYPE: DNA
<213> ORGANISM: Candida albicans

<400> SEQUENCE: 34

```
atggaagcaa ggttttcag aattttcaag gggggagtc tcaccactac cactgcagct       60
gcatctttta cagcaacagc aacagcaggt gccaccacgg caaagacatt gtctggatcc    120
actgtgctcc gaaaactgta taaaggacc tattcatccc tggtcttatc ttctccagaa     180
ttatttttttt ttcatcagtt taacaacaac aaacgttatt gtcatacaac aacaacaaca   240
aatacaaaaa caattatgtc tgaacaaatc ccaaaaactc aaaaagccgt tgtctttgat    300
accaatggtg gtcaattagt ctacaaggat tacccagttc caactccaaa gccaaatgaa    360
ttgttaatca acgtcaaata ctctggtgtc tgtcacactg atttacacgc ttggaaaggt    420
gactggccat ggctaccaa attgccatta gttggtggtc acgaaggtgc cggtgtcgtt     480
gtcggtatgg gtgaaaacgt caaggatgg aaaatcggtg actttgccgg tatcaaatgg    540
ttgaacggtt cttgtatgag ctgtgaattc tgtcaacaag gtgctgaacc aaactgtggt    600
```

```
gaagctgact tgtctggtta cactcacgat ggttcattcg aacaatacgc tactgctgat      660
gctgtccaag ccgctaaaat tccagctggt actgatttag ccaatgtcgc accaatctta      720
tgtgctggtg ttactgttta caaagcctta aagactgctg acttagcagc tggccaatgg      780
gttgctatct ccggtgctgg tggtggttta ggttctttgg ccgttcaata cgccagagcc      840
atgggtttga gagttgttgc tattgacggt ggtgacgaaa aggtgaattt tgttaaatca      900
ttgggtgctg aagcttacgt tgatttcacc aaagataaag atattgttga agctgtcaag      960
aaagctactg atggtggtcc acacggtgct atcaatgtct ctgtttctga aaaagccatt     1020
gaccaatctg ttgaatatgt tagaccatta ggtaaagttg ttttggttgg tttaccagct     1080
cacgctaaag tcactgctcc agttttcgat gctgttgtca aatccattga aatcaaaggt     1140
tcttacgttg gtaacagaaa agacactgct gaagctattg acttcttctc cagaggttta     1200
atcaaatgtc caatcaagat tgtcggttta tctgacttgc cagaagtctt caaattgatg     1260
gaagaaggta aaatcttggg tagatacgtc ttggacacca gtaaataa                  1308

<210> SEQ ID NO 35
<211> LENGTH: 1047
<212> TYPE: DNA
<213> ORGANISM: Candida albicans

<400> SEQUENCE: 35
atgtctgtcc caactactca aaaagctgtt attttcgaaa ccaacggtgg taagttggaa       60
tacaaagata tcccagtccc aaaaccaaaa gcaaatgaat tgttaatcaa cgttaaatac      120
tctggtgtct gtcacactga tttacacgct tggaaaggtg actggccatt ggctactaaa      180
ttgccattgg ttggtggtca cgaaggtgct ggtgttgttg tcgccttggg tgaaaacgtt      240
aaaggctgga agttggtgga ttacgctggt gttaaatggt tgaacggctc ttgtttgaac      300
tgtgaatact gtcaatcagg tgctgaacca aactgtgctg aagctgattt atccggttac      360
acccacgatg gttctttcca acaatatgct actgctgacg ctgttcaagc tgccagaatc      420
ccagctggta ccgacttagc caatgttgca ccaatcttat gtgctggtgt caccgtctac      480
aaagctttaa agactgctga attagaagcc ggtcaatggg ttgctatttc cggtgccgct      540
ggtggtttag gttctttagc tgttcaatac gccaaggcca tgggttacag agttcttgcc      600
atcgatggtg gtgaagacaa gggtgaattc gtcaaatcct gggtgctgaa acctttatt      660 gattttacca agaaaaaga cgttgtcgaa gctgtcaaga aggccaccaa tggtggtcca      720
catggtgtta tcaatgtctc tgtctcagaa agagccattg gtcaatccac tgaatatgtc      780
agaactttag gtaaagttgt tttggttggt ttgccagctg gtgctaaaat tagtaccccca     840 gtctttgatg ctgttatcaa gaccattcaa attaaaggtt cttatgtcgg taacagaaaa      900
gatactgctg aagccgttga tttcttcaca agaggtttga tcaaatgtcc aatcaagatt      960
gttggcttat ccgaattacc agaagttttac aaattgatgg aagaaggtaa aatcttgggt     1020
agatatgtct tggacaacga caaataa                                         1047

<210> SEQ ID NO 36
<211> LENGTH: 1047
<212> TYPE: DNA
<213> ORGANISM: Candida albicans

<400> SEQUENCE: 36
atgtctgtcc caactactca aaaagctgtt attttcgaaa ccaacggtgg taagttggaa       60
tacaaagata tcccagtccc aaaaccaaaa gcaaatgaat tgttaatcaa cgtcaaatac      120
```

```
tctggtgtct gtcacactga tttacacgct tggaaaggtg actggccatt ggctactaaa    180
ttgccattgg ttggtggtca cgaaggtgct ggtgttgttg tcgccttggg tgaaaacgtt    240
aaaggctgga agttggtga ttacgctggt gttaatggt tgaacggttc ttgtttgaac      300
tgtgaatact gtcaatcagg tgctgaacca aactgtgctg aagctgattt atccggttac    360
acccacgatg gttctttcca acaatatgct actgctgacg ctgttcaagc tgccagaatc    420
ccagctggta ccgacttagc caatgttgca ccaatcttat gtgctggtgt caccgtctac    480
aaagctttaa agactgctga attagaagcc ggtcaatggg ttgctatttc cggtgccgct    540
ggtggtttag gttcttttagc tgttcaatac gccaaggcca tgggttacag agttcttgcc    600
atcgatggtg gtgaagacaa gggtgaattc gtcaaatcct ggggtgctga aacctttatt    660
gattttacca agaaaaaga cgttgtcgaa gctgtcaaga aggccaccaa tggtggtcca    720
catggtgtta tcaatgtctc tgtctcagaa agagccattg gtcaatccac tgaatatgtc    780
agaactttag gtaaagttgt tttggttggt ttgccagctg gtgctaaaat tagtaccccca    840 gtctttgatg ctgttatcaa gaccattcaa attaaaggtt cttatgtcgg taacagaaaa    900
gatactgctg aagccgttga tttcttcaca gaggtttga tcaaatgtcc aatcaagatt    960
gttggcttat ccgaattacc agaagtttac aaattgatgg aagaaggtaa aatcttgggt   1020
agatatgtct tggacaacga caaataa                                        1047
```

<210> SEQ ID NO 37
<211> LENGTH: 35
<212> TYPE: DNA
<213> ORGANISM: Artificial Sequence
<220> FEATURE:
<223> OTHER INFORMATION: Degenerate 5' oligonucleotide for PCR
      amplification of Candida tropicalis alcohol dehydrogenase genes

<400> SEQUENCE: 37

```
actcaaaaag cygttrtytt ygawaccaay ggtgg                                 35
```

<210> SEQ ID NO 38
<211> LENGTH: 36
<212> TYPE: DNA
<213> ORGANISM: Artificial Sequence
<220> FEATURE:
<223> OTHER INFORMATION: Degenerate 3' oligonucleotide for PCR
      amplification of Candida tropicalis alcohol dehydrogenase genes

<400> SEQUENCE: 38

```
gtccaakacr tatctacyca agattttacc ttcttc                                36
```

<210> SEQ ID NO 39
<211> LENGTH: 948
<212> TYPE: DNA
<213> ORGANISM: Candida tropicalis

<400> SEQUENCE: 39

```
gaattagaat acaaagatat cccagtgcca accccaaagg ccaacgaatt gctcatcaac     60
gtcaaatact cgggtgtctg ccacactgat ttgcacgcct ggaagggtga ctggccattg    120
gccaccaagt tgccattggt tggtggtcac gaaggtgctg gtgtcgttgt cggcatgggt    180
gaaaacgtca agggctggaa gattggtgac ttcgccggta tcaaatggtt gaacggttcc    240
tgtatgtcct gtgagttctg tcaacaaggt gctgaaccaa actgtggtga ggccgacttg    300
tctggttaca cccacgatgg ttctttcgaa caatacgcca ctgctgatgc tgttcaagcc    360
gccagaatcc cagctggtac tgatttggcc gaagttgccc caatcttgtg tgcgggtgtc    420
```

```
accgtctaca aagccttgaa gactgccgac ttggccgctg gtcaatgggt cgctatctcc    480
ggtgctggtg gtggtttggg ttccttggct gtccaatacg ccgtcgccat gggcttgaga    540
gtcgttgcca ttgacggtgg tgacgaaaag ggtgcctttg tcaagtcctt gggtgctgaa    600
gcctacattg atttcctcaa ggaaaaggac attgtctctg ctgtcaagaa ggccaccgat    660
ggaggtccac acggtgctat caatgtttcc gtttccgaaa aagccattga ccaatccgtc    720
gagtacgtta gaccattggg taaggttgtt ttggttggtt gccagctgg ctccaaggtc     780
actgctggtg ttttcgaagc cgttgtcaag tccattgaaa tcaagggttc ctatgtcggt    840
aacagaaagg ataccgccga agccgttgac tttttctcca gaggcttgat caagtgtcca    900
atcaagattg ttggcttgag tgaattgcca caggtcttca agttgatg               948
```

<210> SEQ ID NO 40
<211> LENGTH: 948
<212> TYPE: DNA
<213> ORGANISM: Candida tropicalis

<400> SEQUENCE: 40

```
aagttagaat acaaagacgt gccggtccct gtccctaaac ccaacgaatt gcttgtcaac     60
gtcaagtact cgggtgtgtg tcattctgac ttgcatgtct ggaaaggcga ctggcccatt    120
cctgccaagt tgcccttggt gggaggtcac gaaggtgctg gtgtcgttgt cggcatgggt    180
gacaacgtca agggctggaa ggtgggggac ttggctggta tcaagtggtt gaatggttcg    240
tgtatgaact gtgagttttg ccaacagggc gcagaaccta actgttcaag agccgacatg    300
tctgggtata cccacgatgg aactttccaa caatacgcca ctgctgatgc tgtccaagct    360
gccaagatcc cagaaggcgc cgacatggct agtatcgccc cgatcttgtg cgctggtgtg    420
accgtgtaca aggctttgaa gaacgccgac ttgttggctg ccaatgggt ggctatctct     480
ggtgctggtg gtggtttggg ctccttgggt gtgcagtacg ctaaagccat gggttacaga    540
gtgttggcta tcgacggtgg tgacgagaga ggagagtttg tcaagtcctt gggcgccgaa    600
gtgtacattg acttcctcaa ggaacaggac atcgttagtg ctatcagaaa gcaactggt     660
ggtggtccac acggtgttat taacgtgtca gtgtccgaaa aggcaatcaa ccagtcggtg    720
gagtacgtca gaacttttggg gaaagtggtt ttagttagct tgccggcagg tggtaaactc   780
actgctcctc ttttcgagtc tgttgctaga tcaatccaga ttagaactac gtgtgttggc    840
aacagaaagg atactactga agctattgat ttctttgtta gagggttgat cgattgccca    900
attaaagtcg ctggtttaag tgaagtgcca gagatttttg acttgatg                948
```

<210> SEQ ID NO 41
<211> LENGTH: 948
<212> TYPE: DNA
<213> ORGANISM: Candida tropicalis

<400> SEQUENCE: 41

```
ccattgcaat acatcgatat tccagtccca gtccctaagc caaacgattt gctcgtcaat     60
gtcaaatact ccggtctttg tcactcagat atacacctct ggaagggtga ctgattccca    120
gcatcaaaat tgccagttgt tggtggtcac gaaggtgcca gtgttgtcgt tgctattggt    180
gaaaacgtcc agggctggaa agtaggtgcc ttggcgggca taagatgtt gaatggttcc     240
tgtatgaact gtgaattctg tcaacaaagt gcttaaccaa gctgtcccca tgctgatgtc    300
tcgggttact cccacgacgg cactttccaa cagtacgcta ccgctgatgc tgctcaagct    360
gctaaattcc cagctggttc tgatttagct agcatcgcac ctatatcctg tgccggtgtt    420
```

```
actgtttaca aagcattgaa gactgctggc ttgcatccgg gccaatgggt tgccatctcc    480
gatgctggtg gtggtttggg ttctttggcc gtgcaatacg ccaaggccat gggctacaga    540
gtggtggcca ttgactgcgg cggcgaaaat ggagtgtttg tcagatcgtt gggtactgaa    600
gctttcgttg attccaccaa ggaggccaat gtctctgagg ctatcatcaa ggctaccgac    660
ggtggtgtcc atggtgtcat caacgtttcc atttctgaaa aagccatcaa ccagtctgtt    720
gaaaatgtca gaacttttggg tactgttgtc ttggttggtt tgccagctgg tgccaagctc    780
gaagcaccta tcttcaatgc cgttgccaaa tccatctaaa tcaaggattc ttacgtgggt    840
aaccgaagag acactgctga ggctgttgat ttcttcgcga aaggtttggt caagtgtcca    900
attaaggttg ttgagttgag tgaattgcca gagattttca aattgttg                 948

<210> SEQ ID NO 42
<211> LENGTH: 948
<212> TYPE: DNA
<213> ORGANISM: Candida tropicalis

<400> SEQUENCE: 42
aaattagaat acaaggacat cccagttcca aagccaaagc caaacgaatt gctcatcaac     60
gtcaagtact ccggtgtctg ccacactgat ttacacgcct ggaagggtga ctggccattg    120
gacaccaagt tgccattggt gggtggtcac gaaggtgctg gtgttgttgt tgccattggt    180
gacaatgtca agggatggaa ggtcggtgat ttggccggtg tcaagtggtt gaacggttcc    240
tgtatgaact gtgagtactg tcaacagggt gccgaaccaa actgtccaca ggctgacttg    300
tctggttaca cccacgacgg ttcttttccag caatacgcca ctgcagatgc cgtgcaagcc    360
gctagaattc cagctggtac tgatttagcc aacgttgccc ccatcttgtg tgctggtgtc    420
actgtttaca aggccttgaa gaccgccgac ttgcagccag gtcaatgggt cgccatttcc    480
ggtgccgctg gtggtttggg ttctttggcc gttcaatacg ccaaggccat gggctacaga    540
gttgtcgcca tcgatggtgg tgccgacaag ggtgagttcg tcaagtcttt gggcgctgag    600
gtctttgttg atttcctcaa ggaaaaggac attgttggtg ctgtcaagaa ggcaaccgat    660
ggtggcccac acggtgccgt taacgtttcc atctccgaaa aggccatcaa ccaatctgtc    720
gactacgtta gaaccttggg taaggttgtc ttggtcggtt tgccagctgg ctccaaggtt    780
tctgctccag tctttgactc cgtcgtcaag tccatccaaa tcaagggttc ctatgtcggt    840
aacagaaagg acactgccga agctgttgac ttttttctcca gaggcttgat caagtgtcca    900
atcaaggttg tcggtttgag tgaattgcca gaagtctaca gtttgatg                 948

<210> SEQ ID NO 43
<211> LENGTH: 948
<212> TYPE: DNA
<213> ORGANISM: Candida tropicalis

<400> SEQUENCE: 43
ccattgcaat acaccgatat cccagttcca gtccctaagc caaacgaatt gctcgtccac     60
gtcaaatact ccggtgtttg tcactcagat atacacgtct ggaagggtga ctggttccca    120
gcatcgaaat tgcccgttgt tggtggtcac gaaggtgccg gtgttgtcgt tgccattggt    180
gaaaacgtcc aaggctggaa agtaggtgac ttggcaggta aagatgtt gaatggttcc    240 tgtatgaact gtgaatactg tcaacaaggt gctgaaccaa actgtcccca cgctgatgtc    300
tcgggttact cccacgacgg tacttttccaa cagtacgcta ccgccgatgc tgttcaagct    360
gctaaattcc cagctggttc tgatttagct agcatcgcac ctatatcctg cgccggtgtt    420
```

| | |
|---|---|
| actgtttaca aagcattgaa aactgcaggc ttgcagccag gtcaatgggt tgccatctct | 480 |
| ggtgcagctg gtggtttggg ttctttggct gtgcaatacg ccaaggccat gggtttgaga | 540 |
| gtcgtggcca ttgacggtgg tgacgaaaga ggagtgtttg tcaaatcgtt gggtgctgaa | 600 |
| gttttcgttg atttcaccaa agaggccaat gtctctgagg ctatcatcaa ggctaccgac | 660 |
| ggtggtgccc atggcgtcat caacgtttcc atttctgaaa aagccatcaa ccagtctgtt | 720 |
| gaatatgtta gaactttggg aactgttgtc ttggttggtt tgccagctgg tgcaaagctc | 780 |
| gaagctccta tcttcaatgc cgttgccaaa tccatccaaa tcaaaggttc ttacgtggga | 840 |
| aacagaagag acactgctga ggctgttgat ttcttcgcta gaggtttggt caaatgtcca | 900 |
| attaaggttg ttgggttgag tgaattgcca gagattttca aattgttg | 948 |

<210> SEQ ID NO 44
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A4

<400> SEQUENCE: 44

| | |
|---|---|
| cgtctcaccc caaaggccaa cgaattgctc atcaacgtca atactcgggt tgtctgccac | 60 |
| actgatttgc acgcctggaa gggtgactgg ccattggcca ccaagttgcc attggttggt | 120 |
| ggtcacgaag gtgctggtgt cgttgtcggc atgggtgaaa acgtcaaggg ctggaagatt | 180 |
| ggtgacttcg ccggtatcaa atggtaggcg gccgctagat cttgcgaagc tccatctcga | 240 |
| ggagtacgtt agaccattgg gtaaggttgt tttggttggt ttgccagctg gctccaaggt | 300 |
| cactgctggt gttttcgaag ccgttgtcaa gtccattgaa atcaagggtt cctatgtcgg | 360 |
| taacagaaag gataccgccg aagccgttga cttttttctcc agaggcttga tcaagtgtcc | 420 |
| aatcaagatt gttggcttgg agacg | 445 |

<210> SEQ ID NO 45
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-A4

<400> SEQUENCE: 45

| | |
|---|---|
| cgtctcaccc caaaggccaa cgaattgctc atcaacgtca atactcgggt tgtctgccac | 60 |
| actgatttgc acgcctggaa gggtgactgg ccattggcca ccaagttgcc attggttggt | 120 |
| ggtcacgaag gtgctggtgt cgttgtcggc atgggtgaaa acgtcaaggg ctggaagatt | 180 |
| ggtgacttcg ccggtatcaa atggtaggcg gccgctctag aactagtgga tctgaagttc | 240 |
| ctattctcta gaaagtatag gaacttcctg caggaccacc tttgattgta aatagtaata | 300 |
| attaccaccc ttatctaatt atttatttaa cttatttatt tatttattat acatatatac | 360 |
| aaatctaata aagtgaaaat ctcccccttc acacttcaca tatgttaggc gtcatcctgt | 420 |
| gctcccgaga accagtacca gtacatcgct gtttcgttcg agacttgagg tctagtttta | 480 |
| tacgtgaaga ggtcaatgcc gccgagagta aagccacatt ttgcgtacaa attgcaggca | 540 |
| ggtacattgt tcgtttgtgt ctctaatcgt atgccaagga gctgtctgct tagtgcccac | 600 |
| tttttcgcaa attcgatgag actgtgcgcg actccttttgc ctcggtgcgt gtgcgacaca | 660 |
| acaatgtgtt cgatagaggc tagatcgttc catgttgagt tgagttcaat cttcccgaca | 720 |

```
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgttttttt ttttcttgct gtgtttgtgt ttgtgttgtt    1080
tatagttgtg tgcactgagc gtcgaaaaaa aaaattcata gtgagccggg aaatctgtat   1140
agcccagata caacacaag tccaaactag aaactcgtca acaccaaaa gcaatgttga     1200 atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccaccctc cccatttgtc   1560
atattgaaac caatcaactg attaatcaat caattagaat tgaagctaaa ctaaaacata   1620
ccaccgtcca ttttgaatga ttatatttt ttaatattaa tatcgagata atgtttctaa    1680
gaaagaaaga aaaccaggag tgaaaattag aaaaggaaag gaaggaaaa aagaaaaat     1740 ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980 aaaataaccct aatcaaaccg aatatttat ggtattatga gtaaactata taatataaat   2040
agcacacacc cacaacaaca acaaaggaaa actaaaaggt ttttctttt tgaaaagatc    2100 gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280 aacttttaa tgtatatttg ttttgttttt ttacataata atactttata aaagctaagc    2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aggtagtct agtacctcct gtgatattat    2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga agaaatgag gtcatcaaat gtcttccaat    2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctaccccct tgcgctaaag aagtatatgt gcctactaac   3120
```

```
gcttgtctttt gtctctgtca ctaaacactg gattattact cccaaatact tattttggac    3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt tttttactgt ggctatttcc cttatctgct tcttccgatg attcgaactg    3420
taattgcaaa ctacttacaa tatcagtgat atcagattga tgtttttgtc catagtaagg    3480
aataattgta aattcccaag caggaatcaa tttctttaat gaggcttcca aaattgttgc    3540
tttttgcgtc ttgtatttaa actggagtga tttattgaca atatcgaaac tcaacgaatt    3600
gcttatgata gtattatagc tcatgaatgt ggctctcttg attgctgttc cgttatgtgt    3660
aatcatccaa cataaatagg ttagttcagc agcacataat gctattttct cacctgaagg    3720
tctttcaaac ctttccacaa actgacgaac aagcaccttaa ggtggtgttt tacataatat    3780
atcaaattgt ggcatgtcga cgattattag ttaaaccact gcaaaaagtt ggggaaaatt    3840
ttgcccattt ttataccgtg tcttcgtcta tcgcctcccc cactcccaa tctttgaatt    3900 attccgaaat attcagcgaa cggggtgtac acaaaaacta acattctcaa ctgcataatt    3960 tgaaaatgg cgtgggacaa gaaaaaaaaa aaattctcaa ccatagcaat catggaatac    4020
ggtaaatttg tgttgttcgg tgactccatc acccagttta gttgtaccca gtatggcttt    4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gaggagtacg ttagaccatt gggtaaggtt gttttggttg gtttgccagc    4440
tggctccaag gtcactgctg gtgttttcga agccgttgtc aagtccattg aaatcaaggg    4500
ttcctatgtc ggtaacagaa aggataccgc cgaagccgtt gactttttct ccagaggctt    4560
gatcaagtgt ccaatcaaga ttgttggctt ggagacg                             4597
```

<210> SEQ ID NO 46
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A4B

<400> SEQUENCE: 46

```
cgtctctgtc aacaaggtgc tgaaccaaac tgtggtgagg ccgacttgtc tggttacacc      60
cacgatggtt ctttcgaaca atacgccact gctgatgctg ttcaagccgc cagaatccca     120
gctggtactg atttggccga agttgcccca atcttgtgtg cgggtgtcac cgtctacaaa     180
gccttgaaga ctgccgactt ggcctaggcg gccgctagat cttgcgaagc tccatctcga     240
gggtttgggt tccttggctg tccaatacgc cgtcgccatg gcttgagag tcgttgccat     300 tgacggtggt gacgaaaagg gtgccttttgt caagtccttg ggtgctgaag cctacattga     360
tttcctcaag gaaaaggaca ttgtctctgc tgtcaagaag gccaccgatg aggtccaca     420 cggtgctatc aatgtttccg agacg                                           445
```

<210> SEQ ID NO 47
<211> LENGTH: 4597

<212> TYPE: DNA
<213> ORGANISM: Artificial Sequence
<220> FEATURE:
<223> OTHER INFORMATION: Targeting construct for deletion of Candida tropicalis ADH-A4B

<400> SEQUENCE: 47

```
cgtctctgtc aacaaggtgc tgaaccaaac tgtggtgagg ccgacttgtc tggttacacc      60
cacgatggtt ctttcgaaca atacgccact gctgatgctg ttcaagccgc cagaatccca     120
gctggtactg atttggccga agttgcccca atcttgtgtg cgggtgtcac cgtctacaaa     180
gccttgaaga ctgccgactt ggcctaggcg gccgctctag aactagtgga tctgaagttc     240
ctattctcta gaaagtatag gaacttcctg caggaccacc tttgattgta aatagtaata     300
attaccaccc ttatctaatt atttatttaa cttatttatt tatttattat acatatatac     360
aaatctaata aagtgaaaat ctcccccttc acacttcaca tatgttaggc gtcatcctgt     420
gctcccgaga accagtacca gtacatcgct gtttcgttcg agacttgagg tctagtttta     480
tacgtgaaga ggtcaatgcc gccgagagta aagccacatt ttgcgtacaa attgcaggca     540
ggtacattgt tcgtttgtgt ctctaatcgt atgccaagga gctgtctgct tagtgcccac     600
tttttcgcaa attcgatgag actgtgcgcg actcctttgc ctcggtgcgt gtgcgacaca     660
acaatgtgtt cgatagaggc tagatcgttc catgttgagt tgagttcaat cttcccgaca     720
agctcttggt cgatgaatgc gccatagcaa gcagagtctt catcagagtc atcatccgag     780
atgtaatcct tccggtaggg gctcacactt ctggtagata gttcaaagcc ttggtcggat     840
aggtgcacat cgaacacttc acgaacaatg aaatggttct cagcatccaa tgtttccgcc     900
acctgctcag ggatcaccga aattttcata tgagaaccgt tatcgataac taaagcagca     960
acttcttcta taaaaatggg ttagtatgac agtcatttaa ataaggaatt tttcagttgg    1020
cttggtttca attcaatgtt cgttttttt ttttcttgct gtgtttgtgt ttgtgttgtt    1080
tatagttgtg tgcactgagc gtcgaaaaaa aaaattcata gtgagccggg aaatctgtat    1140
agcccagata acaacacaag tccaaactag aaactcgtca aacaccaaaa gcaatgttga    1200
atcaattgcc ttgcacaagt acacgtagga aaacataaaa cattgcaatt ttgaatattg    1260
agccttttgt cgtaacattg attgatagga ttactcaccg aatggttttg aaaccactgc    1320
cgacagatca atcaatcaat caaaaaacgt gaacttgaa aaaggggaag aacagataca    1380
ttgaagttag ccatttccat tgatcgtcac aacatatctg ataaattact ttcaaaatta    1440
taagctgatg tgtgtgtatt attaatgtga cagtaacatc ccaaacgaga atatattgt    1500
cgacaacaaa aaagtttgat ctgaattgaa aatgaagttt cccacccta cccatttgtc    1560
atattgaaac caatcaactg attaatcaat caattagaat tgaagctaaa ctaaaacata    1620
ccaccgtcca ttttgaatga ttatattttt ttaatattaa tatcgagata atgtttctaa    1680
gaaagaaaga aaaccaggag tgaaaattag aaaaggaaag gaaaggaaaa aagaaaaat    1740
ctgaaaatat ataaaaaaaa attgtttcgt tggcaataaa tcttggtgag aacagcgacc    1800
gaaagcaaat aagaacaaaa tatgagtgta ttacgttgaa caactaatta acgtgtgtgt    1860
atggatcttt ttttcttttt tctctttaac cgactataaa caacaaacat ttttgggcag    1920
tgcacacact acttaatata cacagcataa attacacgat tagaaacaaa ttagcttatt    1980
aaaataacct aatcaaaccg aatatttat ggtattatga gtaaactata taatataaat    2040
agcacacacc cacaacaaca acaaaggaaa actaaaaggt ttttctttt tgaaaagatc    2100
gttttcttta ttattctcta gttttgacgc tcgacatttt atgatggaat gaatgggatg    2160
```

```
aatcatcaaa caagagaaaa tacccgtgac gaaaataata aaataagttc ctctgataca    2220
gaagatgaaa acaacaacaa caagatatag aaatgccttg ggtggctatt ttatagtctt    2280 aacttttaa tgtatatttg ttttgttttt ttacataata atactttata aaagctaagc     2340
taaattcaag taaaatttca atctctcaaa taaaacattt ttctcttttt cttaaattta    2400
gttttatata tttataaaat atacaaagat ttttttaaaa aagtaacaag ttatatatgt    2460
aataacaaaa agaagaataa caagaataca aaaccagatt tccagatttc cagaatttca    2520
ctcttatatg cgtctatta tgtaggatga aaggtagtct agtacctcct gtgatattat    2580
cccattccat gcggggtatc gtatgcttcc ttcagcacta ccctttagct gttctatatg    2640
ctgccactcc tcaattggat tagtctcatc cttcaatgct atcatttcct ttgatattgg    2700
atcatatgca tagtaccgag aaactagtgc gaagtagtga tcaggtattg ctgttatctg    2760
atgagtatac gttgtcctgg ccacggcaga agcacgctta tcgctccaat ttcccacaac    2820
attagtcaac tccgttaggc ccttcattga aagaaatgag gtcatcaaat gtcttccaat    2880
gtgagatttt gggccatttt ttatagcaaa gattgaataa ggcgcatttt tcttcaaagc    2940
tttattgtac gatctgacta agttatcttt taataattgg tattcctgtt tattgcttga    3000
agaattgccg gtcctattta ctcgttttag gactggttca gaattcctca aaaattcatc    3060
caaatataca agtggatcga tcctacccct tgcgctaaag aagtatatgt gcctactaac    3120
gcttgtcttt gtctctgtca ctaaacactg gattattact cccaaatact tattttggac    3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt tttttactgt ggctatttcc cttatctgct tcttccgatg attcgaactg    3420
taattgcaaa ctacttacaa tatcagtgat atcagattga tgttttgtc catagtaagg     3480 aataattgta aattcccaag caggaatcaa tttctttaat gaggcttcca aaattgttgc    3540 ttttgcgtc ttgtatttaa actggagtga tttattgaca atatcgaaac tcaacgaatt    3600
gcttatgata gtattatagc tcatgaatgt ggctctcttg attgctgttc cgttatgtgt    3660
aatcatccaa cataaatagg ttagttcagc agcacataat gctattttct cacctgaagg    3720
tctttcaaac ctttccacaa actgacgaac aagcacctta ggtggtgttt tacataatat    3780
atcaaattgt ggcatgtcga cgattattag ttaaaccact gcaaaaagtt ggggaaaatt    3840
ttgcccattt ttataccgtg tcttcgtcta tcgcctcccc cactcccaa tctttgaatt    3900 attccgaaat attcagcgaa cggggtgtac acaaaaacta acattctcaa ctgcataatt    3960
tgaaaaatgg cgtgggacaa gaaaaaaaaa aaattctcaa ccatagcaat catgaataac    4020
ggtaaatttg tgttgttcgg tgactccatc acccagttta gttgtaccca gtatggcttt    4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gagggtttgg gttccttggc tgtccaatac gccgtcgcca tgggcttgag    4440
agtcgttgcc attgacggtg gtgacgaaaa gggtgccttt gtcaagtcct ggggtgctga    4500
agcctacatt gatttcctca aggaaaagga cattgtctct gctgtcaaga aggccaccga    4560
```

-continued tggaggtcca cacggtgcta tcaatgtttc cgagacg        4597

<210> SEQ ID NO 48
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B4

<400> SEQUENCE: 48
cgtctcaagc caaagccaaa cgaattgctc atcaacgtca agtactccgg tgtctgccac        60
actgatttac acgcctggaa gggtgactgg ccattggaca ccaagttgcc attggtgggt        120
ggtcacgaag gtgctggtgt tgttgttgcc attggtgaca atgtcaaggg atggaaggtc        180
ggtgatttgg ccggtgtcaa gtggtaggcg ccgctagat cttgcgaagc tccatctcga        240
ggactacgtt agaaccttgg gtaaggttgt cttggtcggt ttgccagctg gctccaaggt        300
ttctgctcca gtctttgact ccgtcgtcaa gtccatccaa atcaagggtt cctatgtcgg        360
taacagaaag gacactgccg aagctgttga cttttctcc agaggcttga tcaagtgtcc        420
aatcaaggtt gtcggtttgg agacg        445

<210> SEQ ID NO 49
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-B4

<400> SEQUENCE: 49
cgtctcaagc caaagccaaa cgaattgctc atcaacgtca agtactccgg tgtctgccac        60
actgatttac acgcctggaa gggtgactgg ccattggaca ccaagttgcc attggtgggt        120
ggtcacgaag gtgctggtgt tgttgttgcc attggtgaca atgtcaaggg atggaaggtc        180
ggtgatttgg ccggtgtcaa gtggtaggcg ccgctctag aactagtgga tctgaagttc        240
ctattctcta gaaagtatag gaacttcctg caggaccacc tttgattgta atagtaata        300
attaccaccc ttatctaatt atttatttaa cttatttatt tatttattat acatatatac        360
aaatctaata aagtgaaaat ctcccccttc acacttcaca tatgttaggc gtcatcctgt        420
gctcccgaga accagtacca gtacatcgct gtttcgttcg agacttgagg tctagtttta        480
tacgtgaaga ggtcaatgcc gccgagagta aagccacatt ttgcgtacaa attgcaggca        540
ggtacattgt tcgtttgtgt ctctaatcgt atgccaagga gctgtctgct tagtgcccac        600
ttttcgcaa attcgatgag actgtgcgcg actcctttgc ctcggtgcgt gtgcgacaca        660
acaatgtgtt cgatagaggc tagatcgttc catgttgagt tgagttcaat cttcccgaca        720
agctcttggt cgatgaatgc gccatagcaa gcagagtctt catcagagtc atcatccgag        780
atgtaatcct tccggtaggg gctcacactt ctggtagata gttcaaagcc ttggtcggat        840
aggtgcacat cgaacacttc acgaacaatg aaatggttct cagcatccaa tgtttccgcc        900
acctgctcag ggatcaccga aattttcata tgagaaccgt tatcgataac taaagcagca        960
acttcttcta taaaaatggg ttagtatgac agtcatttaa ataaggaatt tttcagttgg        1020
cttggtttca attcaatgtt cgttttttttt ttttcttgct gtgtttgtgt ttgtgttgtt        1080
tatagttgtg tgcactgagc gtcgaaaaaa aaaattcata gtgagccggg aaatctgtat        1140
agcccagata acaacacaag tccaaactag aaactcgtca aacaccaaaa gcaatgttga        1200

```
atcaattgcc ttgcacaagt acacgtagga aaacataaaa cattgcaatt ttgaatattg    1260
agccttttgt cgtaacattg attgatagga ttactcaccg aatggttttg aaaccactgc    1320
cgacagatca atcaatcaat caaaaaacgt gaactttgaa aaaggggaag aacagataca    1380
ttgaagttag ccatttccat tgatcgtcac aacatatctg ataaattact ttcaaaatta    1440
taagctgatg tgtgtgtatt attaatgtga cagtaacatc ccaaacgaga aatattatgt    1500
cgacaacaaa aaagtttgat ctgaattgaa aatgaagttt tcccacccta cccatttgtc    1560
atattgaaac caatcaactg attaatcaat caattagaat tgaagctaaa ctaaaacata    1620
ccaccgtcca ttttgaatga ttatattttt ttaatattaa tatcgagata atgtttctaa    1680
gaaagaaaga aaaccaggag tgaaaattag aaaaggaaag gaaaggaaaa aagaaaaat    1740 ctgaaaatat ataaaaaaaa attgtttcgt tggcaataaa tcttggtgag aacagcgacc    1800
gaaagcaaat aagaacaaaa tatgagtgta ttacgttgaa caactaatta acgtgtgtgt    1860
atggatcttt ttttcttttt tctcttaac cgactataaa caacaaacat ttttgggcag     1920
tgcacacact acttaatata cacagcataa attacacgat tagaaacaaa ttagcttatt    1980 aaaataaccct aatcaaaccg aatattttat ggtattatga gtaaactata taatataaat    2040
agcacacacc cacaacaaca acaaaggaaa actaaaaggt ttttttcttt tgaaaagatc   2100
gttttcttta ttattctcta gttttgacgc tcgacatttt atgatggaat gaatgggatg    2160
aatcatcaaa caagagaaaa tacccgtgac gaaaataata aaataagttc ctctgataca    2220
gaagatgaaa acaacaacaa caagatatag aaatgcctttg ggtggctatt ttatagtctt    2280 aacttttttaa tgtatatttg ttttgttttt ttacataata atactttata aaagctaagc   2340
taaattcaag taaaatttca atctctcaaa taaaacattt ttctcttttt cttaaattta    2400
gttttatata tttataaaat atacaaagat tttttttaaaa aagtaacaag ttatatatgt   2460
aataacaaaa agaagaataa caagaataca aaaccagatt tccagatttc cagaatttca    2520
ctcttatatg cgtctatta tgtaggatga aaggtagtct agtacctcct gtgatattat     2580
cccattccat gcggggtatc gtatgcttcc ttcagcacta ccctttagct gttctatatg    2640
ctgccactcc tcaattggat tagtctcatc cttcaatgct atcattttcct ttgatattgg    2700 atcatatgca tagtaccgag aaactagtgc gaagtagtga tcaggtattg ctgttatctg    2760
atgagtatac gttgtcctgg ccacggcaga agcacgctta tcgctccaat ttcccacaac    2820
attagtcaac tccgttaggc ccttcattga aagaatgag gtcatcaaat gtcttccaat     2880
gtgagatttt gggccatttt ttatagcaaa gattgaataa ggcgcatttt tcttcaaagc    2940
tttattgtac gatctgacta agttatcttt taataattgg tattcctgtt tattgcttga    3000
agaattgccg gtcctattta ctcgttttag gactggttca gaattcctca aaaattcatc    3060
caaatataca agtggatcga tcctacccct tgcgctaaag aagtatatgt gcctactaac    3120
gcttgtcttt gtctctgtca ctaaacactg gattattact cccaaatact tattttggac    3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt ttttactgt ggctatttcc cttatctgct tcttccgatg attcgaactg     3420
taattgcaaa ctacttacaa tatcagtgat atcagattga tgtttttgtc catagtaagg    3480
aataattgta aattcccaag caggaatcaa tttctttaat gaggcttcca aaattgttgc    3540
tttttgcgtc ttgtatttaa actggagtga tttattgaca atatcgaaac tcaacgaatt    3600
```

-continued

```
gcttatgata gtattatagc tcatgaatgt ggctctcttg attgctgttc cgttatgtgt    3660
aatcatccaa cataaatagg ttagttcagc agcacataat gctattttct cacctgaagg    3720
tctttcaaac ctttccacaa actgacgaac aagcacctta ggtggtgttt tacataatat    3780
atcaaattgt ggcatgtcga cgattattag ttaaaccact gcaaaaagtt ggggaaaatt    3840
ttgcccattt ttataccgtg tcttcgtcta tcgcctcccc cactcccccaa tctttgaatt    3900 attccgaaat attcagcgaa cggggtgtac acaaaaacta acattctcaa ctgcataatt    3960 tgaaaatgg cgtgggacaa gaaaaaaaaa aaattctcaa ccatagcaat catggaatac    4020
ggtaaatttg tgttgttcgg tgactccatc acccagttta gttgtaccca gtatggcttt    4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gaggactacg ttagaacctt gggtaaggtt gtcttggtcg gtttgccagc    4440
tggctccaag gtttctgctc cagtctttga ctccgtcgtc aagtccatcc aaatcaaggg    4500
ttcctatgtc ggtaacagaa aggacactgc cgaagctgtt gacttttct ccagaggctt    4560 gatcaagtgt ccaatcaagg ttgtcggttt ggagacg                            4597
```

<210> SEQ ID NO 50
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B4B

<400> SEQUENCE: 50

```
cgtctctgtc aacagggtgc cgaaccaaac tgtccacagg ctgacttgtc tggttacacc     60
cacgacggtt ctttccagca atacgccact gcagatgccg tgcaagccgc tagaattcca    120
gctggtactg atttagccaa cgttgccccc atcttgtgtg ctggtgtcac tgtttacaag    180
gccttgaaga ccgccgactt gcagtaggcg gccgctagat cttgcgaagc tccatctcga    240
gggtttgggt tctttggccg ttcaatacgc caaggccatg ggctacagag ttgtcgccat    300
cgatggtggt gccgacaagg gtgagttcgt caagtctttg ggcgctgagg tctttgttga    360
tttcctcaag gaaaaggaca ttgttggtgc tgtcaagaag gcaaccgatg gtggcccaca    420
cggtgccgtt aacgtttccg agacg                                          445
```

<210> SEQ ID NO 51
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-B4B

<400> SEQUENCE: 51

```
cgtctctgtc aacagggtgc cgaaccaaac tgtccacagg ctgacttgtc tggttacacc     60
cacgacggtt ctttccagca atacgccact gcagatgccg tgcaagccgc tagaattcca    120
gctggtactg atttagccaa cgttgccccc atcttgtgtg ctggtgtcac tgtttacaag    180
gccttgaaga ccgccgactt gcagtaggcg gccgctctag aactagtgga tctgaagttc    240
```

```
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctccccttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggttttca attcaatgtt cgttttttt ttttcttgct gtgtttgtgt ttgtgttgtt   1080
tatagttgtg tgcactgagc gtcgaaaaaa aaaattcata gtgagccggg aaatctgtat   1140
agcccagata caacacaag tccaaactag aaactcgtca acaccaaaa gcaatgttga    1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacgcgat tagaaacaaa ttagcttatt   1980
aaaataaccct aatcaaaccg aatatttat ggtattatga gtaaactata taatataaat   2040
agcacacacc cacaacaaca acaaaggaaa actaaaaggt ttttcttt tgaaaagatc    2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aacttttaa tgtatatttg ttttgttttt ttacataata atactttata aaagctaagc    2340
taaattcaag taaaatttca atctctcaaa taaaacattt ttctcttttt cttaaattta   2400
gttttatata tttataaaat atacaaagat tttttaaaa aagtaacaag ttatatatgt    2460
aataacaaaa agaagaataa caagaataca aaaccagatt tccagatttc cagaatttca   2520
ctcttatatg cgtctatttta tgtaggatga aaggtagtct agtacctcct gtgatattat   2580
cccattccat gcggggtatc gtatgcttcc ttcagcacta ccctttagct gttctatatg   2640
```

```
ctgccactcc tcaattggat tagtctcatc cttcaatgct atcatttcct ttgatattgg    2700
atcatatgca tagtaccgag aaactagtgc gaagtagtga tcaggtattg ctgttatctg    2760
atgagtatac gttgtcctgg ccacggcaga agcacgctta tcgctccaat ttcccacaac    2820
attagtcaac tccgttaggc ccttcattga agaaatgag gtcatcaaat gtcttccaat     2880
gtgagatttt gggccatttt ttatagcaaa gattgaataa ggcgcatttt tcttcaaagc    2940
tttattgtac gatctgacta agttatcttt taataattgg tattcctgtt tattgcttga    3000
agaattgccg gtcctattta ctcgttttag gactggttca gaattcctca aaaattcatc    3060
caaatataca agtggatcga tcctacccct tgcgctaaag aagtatatgt gcctactaac    3120
gcttgtcttt gtctctgtca ctaaacactg gattattact cccaaatact tattttggac    3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt ttttactgt ggctatttcc cttatctgct tcttccgatg attcgaactg      3420
taattgcaaa ctacttacaa tatcagtgat atcagattga tgttttgtc catagtaagg     3480 aataattgta aattcccaag caggaatcaa tttctttaat gaggcttcca aaattgttgc    3540
tttttgcgtc ttgtatttaa actggagtga tttattgaca atatcgaaac tcaacgaatt    3600
gcttatgata gtattatagc tcatgaatgt ggctctcttg attgctgttc cgttatgtgt    3660
aatcatccaa cataaatagg ttagttcagc agcacataat gctatttct cacctgaagg     3720 tctttcaaac ctttccacaa actgacgaac aagcaccta ggtggtgttt tacataatat      3780
atcaaattgt ggcatgtcga cgattattag ttaaaccact gcaaaagtt ggggaaaatt     3840 ttgcccattt ttataccgtg tcttcgtcta tcgcctcccc cactcccaa tctttgaatt     3900 attccgaaat attcagcgaa cggggtgtac acaaaaacta acattctcaa ctgcataatt    3960
tgaaaaatgg cgtgggacaa gaaaaaaaaa aaattctcaa ccatagcaat catggaatac    4020
ggtaaatttg tgttgttcgg tgactccatc acccagttta gttgtaccca gtatggcttt   4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gagggtttgg gttctttggc cgttcaatac gccaaggcca tgggctacag    4440
agttgtcgcc atcgatggtg gtgccgacaa gggtgagttc gtcaagtctt gggcgctga    4500 ggtctttgtt gatttcctca aggaaaagga cattgttggt gctgtcaaga aggcaaccga    4560
tggtggccca cacggtgccg ttaacgtttc cgagacg                             4597
```

<210> SEQ ID NO 52
<211> LENGTH: 445
<212> TYPE: DNA
<213> ORGANISM: Artificial Sequence
<220> FEATURE:
<223> OTHER INFORMATION: Pre-targeting construct for Candida tropicalis
      ADH-A10

<400> SEQUENCE: 52

```
cgtctcgtcc ctaaacccaa cgaattgctt gtcaacgtca agtactcggg tgtgtgtcat       60
tctgacttgc atgtctggaa aggcgactgg cccattcctg ccaagttgcc cttggtggga      120
```

```
ggtcacgaag gtgctggtgt cgttgtcggc atgggtgaca acgtcaaggg ctggaaggtg      180
ggggacttgg ctggtatcaa gtggtaggcg gccgctagat cttgcgaagc tccatctcga      240
ggagtacgtc agaactttgg ggaaagtggt tttagttagc ttgccggcag gtggtaaact      300
cactgctcct cttttcgagt ctgttgctag atcaatccag attagaacta cgtgtgttgg      360
caacagaaag gatactactg aagctattga tttctttgtt agagggttga tcgattgccc      420
aattaaagtc gctggtttag agacg                                           445
```

<210> SEQ ID NO 53
<211> LENGTH: 4597
<212> TYPE: DNA
<213> ORGANISM: Artificial Sequence
<220> FEATURE:
<223> OTHER INFORMATION: Targeting construct for deletion of Candida
      tropicalis ADH-A10

<400> SEQUENCE: 53

```
cgtctcgtcc ctaaacccaa cgaattgctt gtcaacgtca agtactcggg tgtgtgtcat       60
tctgacttgc atgtctggaa aggcgactgg cccattcctg ccaagttgcc cttggtggga      120
ggtcacgaag gtgctggtgt cgttgtcggc atgggtgaca acgtcaaggg ctggaaggtg      180
ggggacttgg ctggtatcaa gtggtaggcg gccgctctag aactagtgga tctgaagttc      240
ctattctcta gaaagtatag gaacttcctg caggaccacc tttgattgta aatagtaata      300
attaccaccc ttatctaatt atttatttaa cttatttatt tatttattat acatatatac      360
aaatctaata aagtgaaaat ctccccctc acacttcaca tatgttaggc gtcatcctgt      420
gctcccgaga accagtacca gtacatcgct gtttcgttcg agacttgagg tctagtttta      480
tacgtgaaga ggtcaatgcc gccgagagta aagccacatt ttgcgtacaa attgcaggca      540
ggtacattgt tcgtttgtgt ctctaatcgt atgccaagga gctgtctgct tagtgcccac      600
tttttcgcaa attcgatgag actgtgcgcg actcctttgc ctcggtgcgt gtgcgacaca      660
acaatgtgtt cgatagaggc tagatcgttc catgttgagt tgagttcaat cttcccgaca      720
agctcttggt cgatgaatgc gccatagcaa gcagagtctt catcagagtc atcatccgag      780
atgtaatcct tccggtaggg gctcacactt ctggtagata gttcaaagcc ttggtcggat      840
aggtgcacat cgaacacttc acgaacaatg aaatggttct cagcatccaa tgtttccgcc      900
acctgctcag ggatcaccga aattttcata tgagaaccgt tatcgataac taaagcagca      960
acttcttcta taaaaatggg ttagtatgac agtcattta ataaggaatt tttcagttgg     1020
cttggtttca attcaatgtt cgttttttt tttttcttgct gtgtttgtgt ttgtgttgtt     1080
tatagttgtg tgcactgagc gtcgaaaaaa aaaattcata gtgagccggg aaatctgtat     1140
agcccagata caacacaag tccaaactag aaactcgtca acaccaaaa gcaatgttga     1200 atcaattgcc ttgcacaagt acacgtagga aaacataaaa cattgcaatt ttgaatattg     1260
agccttttgt cgtaacattg attgatagga ttactcaccg aatggttttg aaaccactgc     1320
cgacagatca atcaatcaat caaaaaacgt gaactttgaa aaaggggaag aacagataca     1380
ttgaagttag ccatttccat tgatcgtcac aacatatctg ataaattact ttcaaaatta     1440
taagctgatg tgtgtgtatt attaatgtga cagtaacatc ccaaacgaga atatattgt     1500 cgacaacaaa aaagtttgat ctgaattgaa aatgaagttt ccccacccta cccatttgtc     1560
atattgaaac caatcaactg attaatcaat caattagaat tgaagctaaa ctaaaacata     1620
ccaccgtcca ttttgaatga ttatattttt ttaatattaa tatcgagata atgtttctaa     1680
```

```
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctcttttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt ttttctttt tgaaaagatc    2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aacttttttaa tgtatatttg ttttgttttt ttacataata atactttata aaagctaagc   2340
taaattcaag taaaatttca atctctcaaa taaaacattt ttctctttt cttaaattta    2400
gttttatata tttataaaat atacaaagat tttttttaaaa aagtaacaag ttatatatgt   2460
aataacaaaa agaagaataa caagaataca aaaccagatt tccagatttc cagaatttca   2520
ctcttatatg cgtctatttta tgtaggatga aggtagtct agtacctcct gtgatattat    2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctatttta ctcgttttag gactggttca gaattcctca aaaattcatc   3060
caaatataca agtggatcga tcctaccccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt ttttactgt ggctatttcc cttatctgct tcttccgatg attcgaactg    3420
taattgcaaa ctacttacaa tatcagtgat atcagattga tgttttttgtc catagtaagg  3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctatttttct cacctgaagg   3720
tctttcaaac ctttccacaa actgacgaac aagcaccttaa ggtggtgttt tacataatat  3780
atcaaattgt ggcatgtcga cgattattag ttaaaccact gcaaaaagtt ggggaaaatt   3840
ttgcccattt ttataccgtg tcttcgtcta tcgcctcccc cactcccaa tctttgaatt    3900
attccgaaat attcagcgaa cggggtgtac acaaaaacta acattctcaa ctgcataatt   3960
tgaaaaatgg cgtgggacaa gaaaaaaaaa aaattctcaa ccatagcaat catggaatac   4020
ggtaaatttg tgttgttcgg tgactccatc acccagttta gttgtaccca gtatggcttt   4080
```

-continued

```
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gaggagtacg tcagaacttt ggggaaagtg gttttagtta gcttgccggc    4440
aggtggtaaa ctcactgctc ctcttttcga gtctgttgct agatcaatcc agattagaac    4500
tacgtgtgtt ggcaacagaa aggatactac tgaagctatt gatttctttg ttagagggtt    4560
gatcgattgc ccaattaaag tcgctggttt agagacg                            4597
```

<210> SEQ ID NO 54
<211> LENGTH: 445
<212> TYPE: DNA
<213> ORGANISM: Artificial Sequence
<220> FEATURE:
<223> OTHER INFORMATION: Pre-targeting construct for Candida tropicalis
      ADH-B11

<400> SEQUENCE: 54

```
cgtctcgtcc ctaagccaaa cgaattgctc gtccacgtca atactccgg tgtttgtcac      60 tcagatatac acgtctggaa gggtgactgg ttcccagcat cgaaattgcc cgttgttggt    120
ggtcacgaag gtgccggtgt tgtcgttgcc attggtgaaa acgtccaagg ctggaaagta    180
ggtgacttgg caggtataaa gatgtaggcg gccgctagat cttgcgaagc tccatctcga    240
ggaatatgtt agaactttgg gaactgttgt cttggttggt ttgccagctg gtgcaaagct    300
cgaagctcct atcttcaatg ccgttgccaa atccatccaa atcaaggtt cttacgtggg    360 aaacagaaga gacactgctg aggctgttga tttcttcgct agaggtttgg tcaaatgtcc    420
aattaaggtt gttgggttgg agacg                                         445
```

<210> SEQ ID NO 55
<211> LENGTH: 4597
<212> TYPE: DNA
<213> ORGANISM: Artificial Sequence
<220> FEATURE:
<223> OTHER INFORMATION: Targeting construct for deletion of Candida
      tropicalis ADH-B11

<400> SEQUENCE: 55

```
cgtctcgtcc ctaagccaaa cgaattgctc gtccacgtca atactccgg tgtttgtcac      60 tcagatatac acgtctggaa gggtgactgg ttcccagcat cgaaattgcc cgttgttggt    120
ggtcacgaag gtgccggtgt tgtcgttgcc attggtgaaa acgtccaagg ctggaaagta    180
ggtgacttgg caggtataaa gatgtaggcg gccgctctag aactagtgga tctgaagttc    240
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctccccctttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
```

```
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgttttttt ttttcttgct gtgtttgtgt ttgtgttgtt   1080
tatagttgtg tgcactgagc gtcgaaaaaa aaaattcata gtgagccggg aaatctgtat   1140
agcccagata caacacaag tccaaactag aaactcgtca acaccaaaa gcaatgttga    1200 atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaggggaag aacagataca    1380 ttgaagttag ccatttccat tgatcgtcac aacatatctg ataaattact ttcaaaatta   1440
taagctgatg tgtgtgtatt attaatgtga cagtaacatc ccaaacgaga atattatgt    1500 cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatatttt ttaatattaa tatcgagata atgtttctaa    1680
gaaagaaaga aaaccaggag tgaaaattag aaaaggaaag gaaaggaaaa aagaaaaat    1740 ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttctttt tctctttaac cgactataaa caacaaacat ttttgggcag    1920
tgcacacact acttaatata cacagcataa attacacgat tagaaacaaa ttagcttatt   1980 aaaataaccct aatcaaaccg aatatttat ggtattatga gtaaactata taatataaat    2040
agcacacacc cacaacaaca acaaaggaaa actaaaaggt tttttcttt tgaaaagatc    2100 gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280 aacttttaa tgtatatttg ttttgttttt ttacataata atactttata aaagctaagc    2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta cccttagct gttctatatg    2640 ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga agaaatgag gtcatcaaat gtcttccaat    2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctatta ctcgttttag gactggttca gaattcctca aaaattcatc    3060
caaatataca agtggatcga tcctaccccct tgcgctaaag aagtatatgt gcctactaac   3120
```

-continued

```
gcttgtcttt gtctctgtca ctaaacactg gattattact cccaaatact tattttggac    3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt ttttactgt ggctatttcc cttatctgct tcttccgatg attcgaactg     3420
taattgcaaa ctacttacaa tatcagtgat atcagattga tgtttttgtc catagtaagg    3480
aataattgta aattcccaag caggaatcaa tttctttaat gaggcttcca aaattgttgc    3540
tttttgcgtc ttgtatttaa actggagtga tttattgaca atatcgaaac tcaacgaatt    3600
gcttatgata gtattatagc tcatgaatgt ggctctcttg attgctgttc cgttatgtgt    3660
aatcatccaa cataaatagg ttagttcagc agcacataat gctattttct cacctgaagg    3720
tctttcaaac ctttccacaa actgacgaac aagcaccttg ggtggtgttt tacataatat    3780
atcaaattgt ggcatgtcga cgattattag ttaaaccact gcaaaagtt ggggaaaatt     3840 ttgcccattt ttataccgtg tcttcgtcta tcgcctcccc cactcccaa tctttgaatt     3900 attccgaaat attcagcgaa cggggtgtac acaaaaacta acattctcaa ctgcataatt    3960 tgaaaatgg cgtgggacaa gaaaaaaaaa aaattctcaa ccatagcaat catggaatac    4020
ggtaaatttg tgttgttcgg tgactccatc acccagttta gttgtaccca gtatggcttt    4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gaggaatatg ttagaacttt gggaactgtt gtcttggttg gtttgccagc    4440
tggtgcaaag ctcgaagctc ctatcttcaa tgccgttgcc aaatccatcc aaatcaaagg    4500
ttcttacgtg ggaaacagaa gagacactgc tgaggctgtt gatttcttcg ctagaggttt    4560
ggtcaaatgt ccaattaagg ttgttgggtt ggagacg                             4597
```

<210> SEQ ID NO 56
<211> LENGTH: 460
<212> TYPE: DNA
<213> ORGANISM: Candida tropicalis

<400> SEQUENCE: 56

```
tgaactgtga gttttgccaa cagggcgctg aacctaattg tccaagagcc gacatgtctg     60 gatatacccca cgatgggact ttccaacaat atgctaccgc cgatgccgtc caagctgcca   120
agatcccaga aggcgcagac atggctagta tcgccccgat cttgtgtgct ggtgtgaccg    180
tgtacaaggc tttgaagaac gccgacttgt tggctggcca atgggtggct atctctggtg    240
ctggtggtgg tttgggctcc ttgggtgtgc agtacgctaa agccatgggt tacagagtgt    300
tagccatcga tggtggtgat gagagaggag agtttgtcaa gtcattgggc gccgaagtgt    360
acattgactt ccttaaggaa caggacattg ttagtgccat tagaaaggca actggtggtg    420
gcccacacgg tgttattaac gtctcggtgt ccgaaaaggc                          460
```

<210> SEQ ID NO 57
<211> LENGTH: 445
<212> TYPE: DNA
<213> ORGANISM: Artificial Sequence
<220> FEATURE:

<223> OTHER INFORMATION: Pre-targeting construct for Candida tropicalis
ADH-A10B

<400> SEQUENCE: 57

| | | | | | |
|---|---|---|---|---|---|
| cgtctctgcc | aacagggcgc | tgaacctaat | tgtccaagag | ccgacatgtc | tggatatacc | 60 |
| cacgatggga | ctttccaaca | atatgctacc | gccgatgccg | tccaagctgc | caagatccca | 120 |
| gaaggcgcag | acatggctag | tatcgccccg | atcttgtgtg | ctggtgtgac | cgtgtacaag | 180 |
| gctttgaaga | acgccgactt | gttgtaggcg | gccgctagat | cttgcgaagc | tccatctcga | 240 |
| gggtttgggc | tccttgggtg | tgcagtacgc | taaagccatg | ggttacagag | tgttagccat | 300 |
| cgatggtggt | gatgagagag | gagagtttgt | caagtcattg | ggcgccgaag | tgtacattga | 360 |
| cttccttaag | gaacaggaca | ttgttagtgc | cattagaaag | gcaactggtg | gtggcccaca | 420 |
| cggtgttatt | aacgtgtcgg | agacg | | | | 445 |

<210> SEQ ID NO 58
<211> LENGTH: 4597
<212> TYPE: DNA
<213> ORGANISM: Artificial Sequence
<220> FEATURE:
<223> OTHER INFORMATION: Targeting construct for deletion of Candida
tropicalis ADH-A10B

<400> SEQUENCE: 58

| | | | | | |
|---|---|---|---|---|---|
| cgtctctgcc | aacagggcgc | tgaacctaat | tgtccaagag | ccgacatgtc | tggatatacc | 60 |
| cacgatggga | ctttccaaca | atatgctacc | gccgatgccg | tccaagctgc | caagatccca | 120 |
| gaaggcgcag | acatggctag | tatcgccccg | atcttgtgtg | ctggtgtgac | cgtgtacaag | 180 |
| gctttgaaga | acgccgactt | gttgtaggcg | gccgctctag | aactagtgga | tctgaagttc | 240 |
| ctattctcta | gaaagtatag | gaacttcctg | caggaccacc | tttgattgta | aatagtaata | 300 |
| attaccaccc | ttatctaatt | atttatttaa | cttattttatt | tatttattat | acatatatac | 360 |
| aaatctaata | aagtgaaaat | ctccccttc | acacttcaca | tatgttaggc | gtcatcctgt | 420 |
| gctcccgaga | accagtacca | gtacatcgct | gtttcgttcg | agacttgagg | tctagtttta | 480 |
| tacgtgaaga | ggtcaatgcc | gccgagagta | aagccacatt | ttgcgtacaa | attgcaggca | 540 |
| ggtacattgt | tcgtttgtgt | ctctaatcgt | atgccaagga | gctgtctgct | tagtgcccac | 600 |
| ttttttcgcaa | attcgatgag | actgtgcgcg | actcctttgc | ctcggtgcgt | gtgcgacaca | 660 |
| acaatgtgtt | cgatagaggc | tagatcgttc | catgttgagt | tgagttcaat | cttcccgaca | 720 |
| agctcttggt | cgatgaatgc | gccatagcaa | gcagagtctt | catcagagtc | atcatccgag | 780 |
| atgtaatcct | tccggtaggg | gctcacactt | ctggtagata | gttcaaagcc | ttggtcggat | 840 |
| aggtgcacat | cgaacacttc | acgaacaatg | aaatggttct | cagcatccaa | tgtttccgcc | 900 |
| acctgctcag | ggatcaccga | aattttcata | tgagaaccgt | tatcgataac | taaagcagca | 960 |
| acttcttcta | taaaaatggg | ttagtatgac | agtcatttaa | ataaggaatt | tttcagttgg | 1020 |
| cttggtttca | attcaatgtt | cgttttttt | ttttcttgct | gtgtttgtgt | ttgtgttgtt | 1080 |
| tatagttgtg | tgcactgagc | gtcgaaaaaa | aaaattcata | gtgagccggg | aaatctgtat | 1140 |
| agcccagata | acaacacaag | tccaaactag | aaactcgtca | acaccaaaa | gcaatgttga | 1200 |
| atcaattgcc | ttgcacaagt | acacgtagga | aaacataaaa | cattgcaatt | ttgaatattg | 1260 |
| agccttttgt | cgtaacattg | attgatagga | ttactcaccg | aatggttttg | aaaccactgc | 1320 |
| cgacagatca | atcaatcaat | caaaaaacgt | gaactttgaa | aaaggggaag | aacagataca | 1380 |
| ttgaagttag | ccatttccat | tgatcgtcac | aacatatctg | ataaattact | ttcaaaatta | 1440 |

```
taagctgatg tgtgtgtatt attaatgtga cagtaacatc ccaaacgaga aatattatgt    1500
cgacaacaaa aaagtttgat ctgaattgaa aatgaagttt tcccacccta cccatttgtc    1560
atattgaaac caatcaactg attaatcaat caattagaat tgaagctaaa ctaaaacata    1620
ccaccgtcca ttttgaatga ttatatttt ttaatattaa tatcgagata atgtttctaa     1680
gaaagaaaga aaaccaggag tgaaaattag aaaaggaaag gaaaggaaaa aagaaaaat    1740 ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctcttaac cgactataaa caacaaacat ttttgggcag    1920
tgcacacact acttaatata cacagcataa attacacgat tagaaacaaa ttagcttatt   1980 aaaataaccct aatcaaaccg aatattttat ggtattatga gtaaactata taatataaat  2040
agcacacacc cacaacaaca acaaaggaaa actaaaaggt ttttctttt tgaaaagatc    2100 gttttcttta ttattctcta gttttgacgc tcgacatttt atgatggaat gaatgggatg    2160
aatcatcaaa caagagaaaa tacccgtgac gaaaataata aaataagttc ctctgataca    2220
gaagatgaaa acaacaacaa caagatatag aaatgccttg ggtggctatt ttatagtctt    2280 aacttttaa tgtatatttg ttttgttttt ttacataata atactttata aaagctaagc    2340
taaattcaag taaaatttca atctctcaaa taaaacattt ttctctttt cttaaattta    2400 gttttatata tttataaaat atacaaagat tttttaaaa aagtaacaag ttatatatgt    2460
aataacaaaa agaagaataa caagaataca aaaccagatt tccagatttc cagaatttca    2520
ctcttatatg cgtctattta tgtaggatga aggtagtct agtacctcct gtgatattat    2580
cccattccat gcggggtatc gtatgcttcc ttcagcacta ccctttagct gttctatatg    2640
ctgccactcc tcaattggat tagtctcatc cttcaatgct atcatttcct ttgatattgg    2700
atcatatgca tagtaccgag aaactagtgc gaagtagtga tcaggtattg ctgttatctg    2760
atgagtatac gttgtcctgg ccacggcaga agcacgctta tcgctccaat ttcccacaac    2820
attagtcaac tccgttaggc ccttcattga aagaaatgag gtcatcaaat gtcttccaat    2880
gtgagatttt gggccatttt ttatagcaaa gattgaataa ggcgcatttt tcttcaaagc    2940
tttattgtac gatctgacta agttatcttt taataattgg tattcctgtt tattgcttga    3000
agaattgccg gtcctattta ctcgttttag gactggttca gaattcctca aaaattcatc    3060
caaatataca agtggatcga tcctacccct tgcgctaaag aagtatatgt gcctactaac    3120
gcttgtcttt gtctctgtca ctaaacactg gattattact cccaaatact tattttggac   3180
taatttaaat gatttcggat caacgttctt aatatcgctg aatcttccac aattgatgaa    3240
agtagctagg aagaggaatt ggtataaagt ttttgttttt gtaaatctcg aagtatactc    3300
aaacgaattt agtattttct cagtgatctc ccagatgctt tcaccctcac ttagaagtgc    3360
tttaagcatt ttttactgt ggctatttcc cttatctgct tcttccgatg attcgaactg     3420
taattgcaaa ctacttacaa tatcagtgat atcagattga tgttttgtc catagtaagg    3480 aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctatttct cacctgaagg    3720 tctttcaaac ctttccacaa actgacgaac aagcaccta ggtggtgttt tacataatat    3780
atcaaattgt ggcatgtcga cgattattag ttaaaccact gcaaaaagtt ggggaaaatt    3840
```

```
ttgcccattt ttataccgtg tcttcgtcta tcgcctcccc cactcccaa tctttgaatt    3900 attccgaaat attcagcgaa cggggtgtac acaaaaacta acattctcaa ctgcataatt    3960
tgaaaaatgg cgtgggacaa gaaaaaaaaa aaattctcaa ccatagcaat catggaatac    4020
ggtaaatttg tgttgttcgg tgactccatc acccagttta gttgtaccca gtatggcttt    4080
catccagcat tacagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gagggtttgg gctccttggg tgtgcagtac gctaaagcca tgggttacag    4440
agtgttagcc atcgatggtg gtgatgagag aggagagttt gtcaagtcat gggcgccga    4500 agtgtacatt gacttcctta aggaacagga cattgttagt gccattagaa aggcaactgg    4560
tggtggccca cacggtgtta ttaacgtgtc ggagacg                             4597
```

<210> SEQ ID NO 59
<211> LENGTH: 948
<212> TYPE: DNA
<213> ORGANISM: Candida tropicalis

<400> SEQUENCE: 59

```
ccattgcaat acaccgatat cccagttcca gtccctaagc caaacgattt gctcgtcaat     60
gtcaaatact ccggtctttg tcactcagat atacacctct ggaagggtga ctgattccca    120
gcatcaaaat tgccagttgt tggtggtcac gaaggtgcca gtgttgtcgt tgctattggt    180
gaaaacgtcc agggctggaa agtaggtgcc ttggcgggca taaagatgtt gaatggttcc    240
tgtatgaact gtgaattctg tcaacaaagt gcttaaccaa gctgtcccca tgctgatgtc    300
tcgggttact cccacgacgg cactttccaa cagtacgcta ccgctgatgc tgctcaagct    360
gctaaattcc cagctggttc tgatttagct agcatcgcac ctatatcctg tgccggtgtt    420
actgtttaca aagcattgaa gactgctggc ttgcatccgg ccaatgggt tgccatctcc     480 gatgctggtg gtggtttggg ttcttttggcc gtgcaatacg ccaaggccat gggctacaga    540
gtggtggcca ttgactgcgg cggcgaaaat ggagtgtttg tcagatcgtt gggtactgaa    600
gctttcgttg attccaccaa ggaggccaat gtctctgagg ctatcatcaa ggctaccgac    660
ggtggtgtcc atggtgtcat caacgtttcc atttctgaaa aagccatcaa ccagtctgtt    720
gaaaatgtca gaactttggg tactgttgtc ttggttggtt tgccagctgg tgccaagctc    780
gaagcaccta tcttcaatgc cgttgccaaa tccatctaaa tcaaggattc ttacgtgggt    840
aaccgaagag acactgctga ggctgttgat ttcttcgcga aaggtttggt caagtgtcca    900
attaaggttg ttgagttgag tgaattgcca gagattttca aattgttg                  948
```

<210> SEQ ID NO 60
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B11B

<400> SEQUENCE: 60

```
cgtctctgtc aacaaagtgc ttaaccaagc tgtccccatg ctgatgtctc gggttactcc     60
cacgacggca ctttccaaca gtacgctacc gctgatgctg ctcaagctgc taaattccca    120
```

```
gctggttctg atttagctag catcgcacct atatcctgtg ccggtgttac tgtttacaaa    180
gcattgaaga ctgctggctt gcattaggcg gccgctagat cttgcgaagc tccatctcga    240
gggtttgggt tctttggccg tgcaatacgc caaggccatg gctacagag tggtggccat     300 tgactgcggc ggcgaaaatg gagtgtttgt cagatcgttg ggtactgaag ctttcgttga    360
ttccaccaag gaggccaatg tctctgaggc tatcatcaag gctaccgacg gtggtgtcca    420
tggtgtcatc aacgtttccg agacg                                          445

<210> SEQ ID NO 61
<211> LENGTH: 4597
<212> TYPE: DNA
<213> ORGANISM: Artificial Sequence
<220> FEATURE:
<223> OTHER INFORMATION: Targeting construct for deletion of Candida
      tropicalis ADH-B11B

<400> SEQUENCE: 61
cgtctctgtc aacaaagtgc ttaaccaagc tgtccccatg ctgatgtctc gggttactcc    60
cacgacggca ctttccaaca gtacgctacc gctgatgctg ctcaagctgc taaattccca    120
gctggttctg atttagctag catcgcacct atatcctgtg ccggtgttac tgtttacaaa    180
gcattgaaga ctgctggctt gcattaggcg gccgctctag aactagtgga tctgaagttc    240
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctcccccttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600 ttttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgttttttt tttttcttgct gtgtttgtgt ttgtgttgtt   1080
tatagttgtg tgcactgagc gtcgaaaaaa aaaattcata gtgagccggg aaatctgtat   1140
agcccagata caacacaag tccaaactag aaactcgtca acaccaaaa gcaatgttga    1200 atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga atatattgt    1500 cgacaacaaa aaagtttgat ctgaattgaa aatgaagttt tcccaccta cccatttgtc    1560 atattgaaac caatcaactg attaatcaat caattagaat tgaagctaaa ctaaaacata   1620
ccaccgtcca ttttgaatga ttatatttt ttaatattaa tatcgagata atgtttctaa   1680
```

```
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctcttttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt ttttctttt tgaaaagatc    2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aacttttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctatttta tgtaggatga aggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctatttta ctcgttttag gactggttca gaattcctca aaaattcatc   3060
caaatataca agtggatcga tcctaccccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgttttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataatat   3780
atcaaattgt ggcatgtcga cgattattag ttaaaccact gcaaaagtt ggggaaaatt    3840
ttgcccattt ttataccgtg tcttcgtcta tcgcctcccc cactcccaa tctttgaatt    3900
attccgaaat attcagcgaa cggggtgtac acaaaaacta acattctcaa ctgcataatt   3960
tgaaaaatgg cgtgggacaa gaaaaaaaaa aaatttctcaa ccatagcaat catgggaatac  4020
ggtaaatttg tgttgttcgg tgactccatc acccagttta gttgtaccca gtatggcttt   4080
```

```
catccagcat acagaatgt gtatatccga aaattggatg ttattaaccg tggtttcagt    4140
ggctacaact cagagcacgc tagacaaatt cttccaaaaa ttttagagtc ggaaaccaat    4200
atcaaattga tgacaatatt ttttggaact aacgatgcat acgactacat caatgaaatc    4260
cagacagtcg agttagacag atataaagat aatttaagtg taatggtaca gatggtacta    4320
gacaaaaata tcaaaccaat cattattgga tccgaagttc ctattctcta gaaagtatag    4380
gaacttcctc gagggtttgg gttctttggc cgtgcaatac gccaaggcca tgggctacag    4440
agtggtggcc attgactgcg gcggcgaaaa tggagtgttt gtcagatcgt tgggtactga    4500
agctttcgtt gattccacca aggaggccaa tgtctctgag gctatcatca aggctaccga    4560
cggtggtgtc catggtgtca tcaacgtttc cgagacg                             4597
```

<210> SEQ ID NO 62
<211> LENGTH: 1484
<212> TYPE: DNA
<213> ORGANISM: Candida tropicalis

<400> SEQUENCE: 62

```
tattaggcga agaggcatct agtagtagtg gcagtggtga gaacgtgggc gctgctatag      60
tgaacaatct ccagtcgatg gttaagaaga agagtgacaa accagcagtg aatgacttgt     120
ctgggtccgt gaggaaaaga aagaagcccg acacaaagga cagtaacgtc aagaaaccca     180 agaaatagggg gggacctgtt tagatgtata ggaataaaaa ctccgagatg atctcaatgt    240
gtaatggagt tgtaatattg caaggggga aaatcaagac tcaaacgtgt gtatgagtga      300
gcgtacgtat atctccgaga gtagtatgac ataatgatga ctgtgaatca tcgtaatctc     360
acacaaaaac cccattgtcg gccatatacc acaccaagca acaccacata tcccccggaa     420
aaaaaaacgt gaaaaaaaga aacaatcaaa actacaacct actccttgat cacacagtca     480
ttgatcaagt tacagttcct gctagggaat gaccaaggta caaatcagca ccttaatggt     540
tagcacgctc tcttactctc tctcacagtc ttccggcccc tattcaaaat tctgcacttc     600
catttgaccc cagggttggg aaacagggcc acaaaagaaa acccgacgt gaatgaaaaa      660 actaagaaaa gaaaaaaaat tatcacacca gaaatttacc taattgggta attcccatcg     720 gtgttttcc tggattgtcg cacgcacgca tgctgaaaaa agtgttcgag ttttgctttt       780
gcctcggagt ttcacgcaag ttttcgatc tcggaaccgg agggcggtcg ccttgttgtt      840
tgtgatgtcg tgctttgggt gttctaatgt gctgttattg tgctcttttt ttttcttctt      900
tttttggtga tcatatgata ttgctcggta gattactttc gtgtgtaggt attcttttag      960
acgtttggtt attgggtaga tatgagagag agagagtggg tggggagga gttggttgta      1020 ggagggaccc ctgggaggaa gtgtagttga gttttccctg acgaatgaaa atacgttttt     1080
gagaagataa tacaggaaag gtgtgtcggt gaatttccat ctatccgagg atatgagtgg     1140
aggagagtcg tgtgcgtgtg gttaatttag gatcagtgga acacacaaag taactaagac     1200
agagagacag agagaaaaat ctggggaaga gacaaagagt cagagtgtgt gagttattct     1260
gtattgtgaa atttttttgc ccaactacat aatattgctg aaactaattt tacttaaaaa     1320
gaaaagccaa caacgtcccc agtaaaactt ttctataaat atcagcagtt ttcccttttcc    1380 tccattcctc ttcttgtctt ttttcttact ttccctttt tataccttt cattatcatc      1440 ctttataatt gtctaaccaa caactatata tctatcaacc atgg                      1484
```

<210> SEQ ID NO 63
<211> LENGTH: 319
<212> TYPE: DNA

<213> ORGANISM: Candida tropicalis

<400> SEQUENCE: 63

```
aagaaaaaag aaaaggtaaa gaacttcatt tgagatgaac ttttgtatat gacttttagt      60
ttctactttt ttttttattt attgcttaat tttcttattt tcaatccccc atagtttgtg     120
tagaatatat ttattcattc tggtaactca aacacgtagc aagctcgttg catctcgcct     180
cgtcacgggt acagctctgg aaccaaagac aaaaaaaaaa gttgatccga accctctcgc     240
tattccttgc tatgctatcc acgagatggg gtttatcagc ccaggcaagt cactaaagag     300
acaaagaccc agaaagaat                                                  319
```

<210> SEQ ID NO 64
<211> LENGTH: 412
<212> TYPE: DNA
<213> ORGANISM: Saccharomyces cerevisiae

<400> SEQUENCE: 64

```
cccacacacc atagcttcaa aatgtttcta ctccttttt actcttccag attttctcgg      60
actccgcgca tcgccgtacc acttcaaaac acccaagcac agcatactaa attttccctc    120
tttcttcctc tagggtgtcg ttaattaccc gtactaaagg tttggaaaag aaaaaagaga    180
ccgcctcgtt tcttttttctt cgtcgaaaaa ggcaataaaa attttatca cgtttctttt    240
tcttgaaatt ttttttttta gttttttttct ctttcagtga cctccattga tatttaagtt    300
aataaacggt cttcaatttc tcaagtttca gtttcatttt tcttgttcta ttacaacttt    360
ttttacttct tgttcattag aaagaaagca tagcaatcta atctaagggg cg            412
```

<210> SEQ ID NO 65
<211> LENGTH: 68
<212> TYPE: DNA
<213> ORGANISM: Artificial sequence
<220> FEATURE:
<223> OTHER INFORMATION: EM7 promoter

<400> SEQUENCE: 65

```
gtgttgacaa ttaatcatcg gcatagtata tcggcatagt ataatacgac aaggtgagga     60
actaaacc                                                              68
```

<210> SEQ ID NO 66
<211> LENGTH: 375
<212> TYPE: DNA
<213> ORGANISM: Artificial Sequence
<220> FEATURE:
<223> OTHER INFORMATION: Zeocin-resistance gene optimized for Candida
      tropicali

<400> SEQUENCE: 66

```
atgtctaaat taacctctgc tgttccagtg ttaaccgccc gtgatgttgc cggtgcagtg     60
gaattttgga ctgaccgttt gggtttctca cgtgactttg tcgaagatga ttttgctggc    120
gttgtgcgtg atgacgtcac tttgttcatc tctgctgttc aggatcaggt cgtcccagac    180
aacactttgg cctgggtctg ggttcgtggt ttggacgaat gtacgctga gtggagtgaa    240
gttgtgtcta caaactttcg tgatgcatca ggtccagcta tgaccgaaat tggcgaacaa    300
ccttggggcc gtgagttcgc tttacgtgat ccagccggta attgcgtgca cttcgttgct    360
gaggagcaag attag                                                     375
```

<210> SEQ ID NO 67
<211> LENGTH: 230

```
<212> TYPE: DNA
<213> ORGANISM: Artificial Sequence
<220> FEATURE:
<223> OTHER INFORMATION: CYC1 transcription terminator

<400> SEQUENCE: 67
cacgtccgac ggcggcccac gggtcccagg cctcggagat ccgtccccct tttcctttgt      60
cgatatcatg taattagtta tgtcacgctt acattcacgc cctccccca catccgctct      120 aaccgaaaag gaaggagtta gacaacctga agtctaggtc cctatttatt tttttatagt     180
tatgttagta ttaagaacgt tatttatatt tcaaattttt cttttttttc                230

<210> SEQ ID NO 68
<211> LENGTH: 805
<212> TYPE: DNA
<213> ORGANISM: Artificial Sequence
<220> FEATURE:
<223> OTHER INFORMATION: pUC bacterial origin of replication

<400> SEQUENCE: 68
ctcatgacca aaatccctta acgtgagtta cgcgcgcgtc gttccactga gcgtcagacc      60
ccgtagaaaa gatcaaagga tcttcttgag atcctttttt tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg gctgctgcca gtggcgataa gtcgtgtctt accgggttgg     360
actcaagacg atagttaccg gataaggcgc agcggtcggg ctgaacgggg ggttcgtgca     420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc     600
ctgtcgggtt tcgccaccct tgacttgagc gtcgattttt gtgatgctcg tcagggggc     660 ggagcctatg gaaaaacgcc agcaacgcgg ccttttacg gttcctggcc ttttgctggc     720
cttttgctca catgttcttt cctgcgttat cccctgattc tgtggataac cgtattaccg     780
cctttgagtg agctgatacc gctcg                                           805

<210> SEQ ID NO 69
<211> LENGTH: 1554
<212> TYPE: DNA
<213> ORGANISM: Candida tropicalis

<400> SEQUENCE: 69
atggctgagc aattgttgga atattggtac gttgtggtgc cagttttgta tatcattaag      60
caattattgg cctacaccaa gaccagagtc ttaatgaaga agttgggtgc cgccccagtt    120
actaacaaat tgtacgacaa cgctttcgga attgtcaacg gatggaaggc tttgcaattt    180
aagaaggagg gtagagccca agaatacaat gattataagt ttgatcacag taaaaaccct    240
tccgtcggta cttacgtgtc cattttgttt ggcactagaa ttgtcgtcac caaagaccca    300
gaaaatatca aagctatctt ggctacacaa tttggtgact ctccttgggg caaaagacac    360 accttatttta agccattgtt gggagatggt attttcacct tagacggcga aggttggaaa    420
cactccagag ccatgttgcg tccacaattt gcaagagaac aggttgctca cgttacctct    480
ttggaaccac attttcaatt attgaagaaa cacatttgac aacacaaggg tgagtacttc    540
gacatccaag aattattctt tagattcacc gttgactccg ccactgagtt tttgtttggt    600
```

```
gagtccgttc attccttgaa agacgaaagt attggtatta accaagacga catcgacttc      660
gctggaagaa aggacttcgc tgaatccttt aataaggccc aggaatactt ggctatcaga      720
actttggtcc agacctttta ctggttggtg aacaataagg aatttagaga ctgtaccaaa      780
agtgtccata aattcaccaa ttattacgtc caaaaggcct tagacgcttc accagaggaa      840
ttagaaaagc aatccggtta cgtgttctta tatgagttgg tgaagcaaac acgtgatcca      900
aacgtcttga gagatcaaag tttaaacatt ttattggctg gtagagatac tactgctggc      960
ttgttgtctt ttgctgtttt tgaattggcc agacatccag agatttgggc taaattgaga     1020
gaagaaattg agcaacagtt cggtttgggt gaagattctc gtgttgagga gatcactttc     1080
gaatcattga gagatgtgaa atatttgaag gctttcttga acgaaacctt gagaatttat     1140
ccatctgttc aagaaacttt agaatcgcaa ccaaaaaca caacattgcc aagaggaggt     1200
ggaagtgatg gcacctctcc aatttttgatt caaaaaggtg aagctgtctc ttatggtatt     1260
aattccactc acttggaccc agtttattat ggtccagatg ccgccgaatt tagaccagaa     1320
agatggtttg aaccatctac caagaagttg ggatgggctt atttgccatt caacggtggt     1380
cctagaatct gcttgggtca acaattcgct ttgaccgaag ctggctacgt tttggttaga     1440
ttggtccagg agttctcaca cgtgagatcc gacccagacg aggtttatcc accaaagaga     1500
ttaactaact tgaccatgtg tttgcaagac ggtgctattg ttaagttcga ctag           1554

<210> SEQ ID NO 70
<211> LENGTH: 5268
<212> TYPE: DNA
<213> ORGANISM: Artificial Sequence
<220> FEATURE:
<223> OTHER INFORMATION: Genomic integration vector for integrating
      CYP52A17 under control of the isocitrate lyase promoter

<400> SEQUENCE: 70
agatctgaat tctattaggc gaagaggcat ctagtagtag tggcagtggt gagaacgtgg       60
gcgctgctat agtgaacaat ctccagtcga tggttaagaa gaagagtgac aaaccagcag      120
tgaatgactt gtctgggtcc gtgaggaaaa gaaagaagcc cgacacaaag gacagtaacg      180
tcaagaaacc caagaaatag gggggacctg tttagatgta taggaataaa aactccgaga      240
tgatctcaat gtgtaatgga gttgtaatat tgcaaagggg gaaaatcaag actcaaacgt      300
gtgtatgagt gagcgtacgt atatctccga gagtagtatg acataatgat gactgtgaat      360
catcgtaatc tcacacaaaa accccattgt cggccatata ccacaccaag caacaccaca      420
tatccccggg aaaaaaaaac gtgaaaaaaa gaaacaatca aaactacaac ctactccttg      480
atcacacagt cattgatcaa gttacagttc ctgctaggga tgaccaagg tacaaatcag      540 caccttaatg gttagcacgc tctcttactc tctctcacag tcttccggcc cctattcaaa      600
attctgcact tccatttgac cccagggttg gaaacaggg ccacaaaaga aaacccgac      660 gtgaatgaaa aaactaagaa agaaaaaaaa attatcacac cagaaattta cctaattggg      720
taattcccat cggtgttttt cctggattgt cgcacgcacg catgctgaaa aaagtgttcg      780
agttttgctt ttgcctcgga gtttcacgca gttttttcga tctcggaacc ggagggcggt      840
cgccttgttt tttgtgatgt cgtgctttgg gtgttctaat gtgctgttat tgtgctcttt      900 tttttcttc ttttttttggt gatcatatga tattgctcgg tagattactt tcgtgtgtag      960
gtattctttt agacgtttgg ttattgggta gatatgagag agagagagtg ggtggggag     1020 gagttggttg taggagggac ccctgggagg aagtgtagtt gagttttccc tgacgaatga     1080
```

-continued

```
aaatacgttt ttgagaagat aatacaggaa aggtgtgtcg gtgaatttcc atctatccga  1140
ggatatgagt ggaggagagt cgtgtgcgtg tggttaattt aggatcagtg gaacacacaa  1200
agtaactaag acagagagac agagagaaaa atctggggaa gagacaaaga gtcagagtgt  1260
gtgagttatt ctgtattgtg aaattttttt gcccaactac ataatattgc tgaaactaat  1320
tttacttaaa aagaaaagcc aacaacgtcc ccagtaaaac ttttctataa atatcagcag  1380
ttttcccttt cctccattcc tcttcttgtc tttttttctta ctttcccttt tttatacctt  1440
ttcattatca tcctttataa ttgtctaacc aacaactata tatctatcaa ccatggctga  1500
gcaattgttg gaatattggt acgttgtggt gccagttttg tatatcatta agcaattatt  1560
ggcctacacc aagaccagag tcttaatgaa gaagttgggt gccgcccag ttactaacaa   1620
attgtacgac aacgctttcg gaattgtcaa cggatggaag gctttgcaat ttaagaagga  1680
gggtagagcc caagaataca atgattataa gtttgatcac agtaaaaacc cttccgtcgg  1740
tacttacgtg tccattttgt ttggcactag aattgtcgtc accaaagacc cagaaaatat  1800
caaagctatc ttggctacac aatttggtga cttctccttg ggcaaaagac acaccttatt  1860
taagccattg ttgggagatg gtattttcac cttagacggc gaaggttgga acactccag   1920
agccatgttg cgtccacaat ttgcaagaga acaggttgct cacgttacct ctttggaacc  1980
acattttcaa ttattgaaga aacacatttt gaaacacaag ggtgagtact tcgacatcca  2040
agaattattc tttagattca ccgttgactc cgccactgag ttttttgtttg gtgagtccgt  2100
tcattccttg aaagacgaaa gtattggtat taaccaagac gacatcgact tcgctggaag  2160
aaaggacttc gctgaatcct ttaataaggc ccaggaatac ttggctatca gaactttggt  2220
ccagaccttt tactggttgg tgaacaataa ggaatttaga gactgtacca aaagtgtcca  2280
taaattcacc aattattacg tccaaaaggc cttagacgct tcaccagagg aattagaaaa  2340
gcaatccggt tacgtgttct tatatgagtt ggtgaagcaa acacgtgatc caaacgtctt  2400
gagagatcaa agtttaaaca ttttattggc tggtagagat actactgctg gcttgttgtc  2460
ttttgctgtt tttgaattgg ccagacatcc agagatttgg gctaaattga gagaagaaat  2520
tgagcaacag ttcggtttgg gtgaagattc tcgtgttgag gagatcactt tcgaatcatt  2580
gaagagatgt gaatatttga aggctttctt gaacgaaacc ttgagaattt atccatctgt  2640
tccaagaaac tttagaatcg caaccaaaaa cacaacattg ccaagaggag gtggaagtga  2700
tggcacctct ccaatttttga ttcaaaaagg tgaagctgtc tcttatggta ttaattccac  2760
tcacttggac ccagttttatt atggtccaga tgccgccgaa tttagaccag aaagatggtt  2820
tgaaccatct accaagaagt gggatgggc ttatttgcca ttcaacggtg gtcctagaat   2880
ctgcttgggc caacaattcg ctttgaccga agctggctac gttttggtta gattggtcca  2940
ggagttctca cacgtgagat ccgacccaga cgaggtttat ccaccaaaga gattaactaa  3000
cttgaccatg tgtttgcaag acggtgctat tgttaagttc gactaggcgg ccgcaagaaa  3060
aaagaaaagg taagaacttt catttgagat gaactttgtt atatgacttt agtttctac   3120
tttttttttt atttattgct taatttttctt tatttcaatc ccccatagtt tgtgtagaat  3180
atatttattc attctggtaa ctcaaacacg tagcaagctc gttgcatctc gcctcgtcac  3240
gggtacagct ctgaaccaa agacaaaaaa aaaagttgat ccgaaccctc tcgctattcc   3300
ttgctatgct atccacgaga tggggttat cagcccaggc aagtcactaa aggatccccc    3360
acacaccata gcttcaaaat gtttctactc cttttttact cttccagatt ttctcggact  3420
ccgcgcatcg ccgtaccact tcaaaacacc caagcacagc atactaaatt ttccctcttt  3480
```

-continued

```
cttcctctag ggtgtcgtta attacccgta ctaaaggttt ggaaaagaaa aaagagaccg    3540 cctcgttttct tttcttcgt cgaaaaaggc aataaaaatt tttatcacgt ttcttttct    3600 tgaaattttt tttttagtt tttttctctt tcagtgacct ccattgatat ttaagttaat    3660
aaacggtctt caatttctca gtttcagtt tcattttct tgttctatta caactttttt    3720
tacttcttgt tcattagaaa gaaagcatag caatctaatc taaggggcgg tgttgacaat    3780
taatcatcgg catagtatat cggcatagta taatacgaca aggtgaggaa ctaaaccatg    3840
tctaaattaa cctctgctgt tccagtgtta accgcccgtg atgttgccgg tgcagtggaa    3900
ttttggactg accgtttggg tttctcacgt gactttgtcg aagatgattt tgctggcgtt    3960
gtgcgtgatg acgtcacttt gttcatctct gctgttcagg atcaggtcgt cccagacaac    4020
actttggcct gggtctgggt tcgtggtttg gacgaattgt acgctgagtg gagtgaagtt    4080
gtgtctacaa actttcgtga tgcatcaggt ccagctatga ccgaaattgg cgaacaacct    4140
tggggccgtg agttcgcttt acgtgatcca gccggtaatt gcgtgcactt cgttgctgag    4200
gagcaagatt agcacgtccg acggcggccc acgggtccca ggcctcggag atccgtcccc    4260
cttttccttt gtcgatatca tgtaattagt tatgtcacgc ttacattcac gccctccccc    4320
cacatccgct ctaaccgaaa aggaaggagt tagacaacct gaagtctagg tccctattta    4380 ttttttata gttatgttag tattaagaac gttatttata tttcaaattt ttctttttt    4440 tctgtacaga cgcgtgtacg catgtaacat tatactgaaa accttgcttg agaaggtttt    4500
gggacgctcg aaggctttaa tttgcaagct ggagaccaac atgtgagcaa aaggccagca    4560
aaaggccagg aaccgtaaaa aggccgcgtt gctggcgttt ttccataggc tccgcccccc    4620
tgacgagcat cacaaaaatc gacgctcaag tcagaggtgg cgaaacccga caggactata    4680
aagataccag gcgtttcccc ctggaagctc cctcgtgcgc tctcctgttc cgaccctgcc    4740
gcttaccgga tacctgtccg cctttctccc ttcgggaagc gtggcgcttt ctcaatgctc    4800
acgctgtagg tatctcagtt cggtgtaggt cgttcgctcc aagctgggct gtgtgcacga    4860
accccccgtt cagcccgacc gctgcgcctt atccggtaac tatcgtcttg agtccaaccc    4920
ggtaagacac gacttatcgc cactggcagc agccactggt aacaggatta gcagagcgag    4980
gtatgtaggc ggtgctacag agttcttgaa gtggtggcct aactacggct acactagaag    5040
gacagtattt ggtatctgcg ctctgctgaa gccagttacc ttcggaaaaa gagttggtag    5100
ctcttgatcc ggcaaacaaa ccaccgctgg tagcggtggt tttttgttt gcaagcagca    5160 gattacgcgc agaaaaaaag gatctcaaga agatcctttg atcttttcta cggggtctga    5220
cgctcagtgg aacgaaaact cacgttaagg gattttggtc atgagatc                 5268
```

<210> SEQ ID NO 71
<211> LENGTH: 1569
<212> TYPE: DNA
<213> ORGANISM: Candida tropicalis

<400> SEQUENCE: 71

```
atgactgttc acgacattat tgctacctac tttactaagt ggtacgtcat tgttccattg      60
gccttaatcg cctatagagt tttggattac ttttacggta gatacttgat gtacaaattg     120
ggtgctaaac cattctttca gaaacaaact gacggttgtt ttggttttaa ggccccttta     180
gaattattga agaaaaagtc tgacggtaca ttgatcgatt ttaccttgca agaatccac      240 gacttggaca gaccagatat cccaaccttt acctttcctg ttttctcaat caatttggtg     300
aatactttgg aacctgaaaa catcaaggct atcttggcta cccagttcaa tgattttagt     360
```

-continued

```
ttgggcacca gacactcaca ttttgcacca ttgttgggag atggtatctt tacattggat    420
ggtgctggtt ggaagcattc aagatccatg ttaagaccac aatttgcaag agagcagatt    480
tcccatgtta agttgttgga accacatgtt caagtcttct tcaagcatgt tagaaaagcc    540
caaggtaaga cttttgatat tcaggagttg ttctttagat tgactgttga ttctgccacc    600 gaattttttgt ttggtgaatc cgtcgaatcc ttgagagacg aatctattgg tatgtctatt    660
aacgctttgg attttgatgg taaggctgga tttgcagatg catttaacta ttcccaaaac    720
tatttagctt ctagagctgt catgcaacaa ttatactggg ttttaaatgg taaaaagttc    780
aaggaatgta atgctaaggt ccacaagttc gctgactatt atgtcaacaa ggctttagac    840
ttaactccag agcaattaga aaagcaggat ggttacgtct tcttatatga attggtcaaa    900
cagactagag ataagcaagt tttgagagat cagttattga atatcatggt cgctggtaga    960
gacacaactg ctggtttgtt gtcctttgtc ttctttgaat tggccagaaa cccagaagtc   1020
accaacaaat taagagagga aatcgaagat aaatttggat taggcgaaaa tgcaagtgtc   1080
gaggacattt ccttttgagtc tttgaagtct tgtgaatatt tgaaagctgt tttgaacgag   1140
acattgcgtt tgtaccccttc agttccacag aactttagag ttgcaaccaa gaacaccaca   1200
ttgcctagag gcggtggtaa agatggtttg tctcctgttt tggtgagaaa gggtcaaacc   1260
gttatttacg tgtctacgc cgcccacaga acccagcag tctatggtaa agatgctttg   1320
gaattcagac cagagcgttg gttcgaacct gaaaccaaaa agttgggttg ggccttctta   1380
cctttcaacg gaggtccaag aatctgtttg ggtcagcaat tcgccttgac agaagcctca   1440
tatgtgactg tgagattgtt gcaagaattc gctcacttgt ctatggaccc tgacactgaa   1500
taccctccta aaaagatgtc ccatttgacc atgtcattat ttgacggtgc taatattgaa   1560
atgtattag                                                            1569
```

<210> SEQ ID NO 72
<211> LENGTH: 5283
<212> TYPE: DNA
<213> ORGANISM: Artificial Sequence
<220> FEATURE:
<223> OTHER INFORMATION: Genomic integration vector for integrating CYP52A13 under control of the isocitrate lyase promoter

<400> SEQUENCE: 72

```
agatctgaat tctattaggc gaagaggcat ctagtagtag tggcagtggt gagaacgtgg     60
gcgctgctat agtgaacaat ctccagtcga tggttaagaa gaagagtgac aaaccagcag    120
tgaatgactt gtctgggtcc gtgaggaaaa gaaagaagcc cgacacaaag gacagtaacg    180
tcaagaaacc caagaaatag gggggaccctg tttagatgta taggaataaa actccgaga    240 tgatctcaat gtgtaatgga gttgtaatat tgcaaggggg gaaaatcaag actcaaacgt    300
gtgtatgagt gagcgtacgt atatctccga gagtagtatg acataatgat gactgtgaat    360
catcgtaatc tcacacaaaa acccccattgt cggccatata ccacaccaag caacaccaca    420 tatccccccgg aaaaaaaaac gtgaaaaaaaa gaaacaatca aaactacaac ctactccttg    480
atcacacagt cattgatcaa gttacagttc ctgctaggga atgaccaagg tacaaatcag    540
caccttaatg gttagcacgc tctcttactc tctctcacag tcttccggcc cctattcaaa    600
attctgcact tccatttgac cccagggttg gaaacaggg ccacaaaaga aaacccgac    660 gtgaatgaaa aaactaagaa aagaaaaaaaa attatcacac cagaaattta cctaattggg    720
taattcccat cggtgttttt cctggattgt cgcacgcacg catgctgaaa aaagtgttcg    780
agttttgctt tgcctcgga gtttcacgca agttttttcga tctcggaacc ggagggcggt    840
```

```
cgccttgttg tttgtgatgt cgtgctttgg gtgttctaat gtgctgttat tgtgctcttt    900
ttttttcttc ttttttttggt gatcatatga tattgctcgg tagattactt tcgtgtgtag    960
gtattctttt agacgtttgg ttattgggta gatatgagag agagagagtg ggtggggggag   1020
gagttggttg taggagggac ccctgggagg aagtgtagtt gagttttccc tgacgaatga   1080
aaatacgttt ttgagaagat aatacaggaa aggtgtgtcg gtgaatttcc atctatccga   1140
ggatatgagt ggaggagagt cgtgtgcgtg tggttaattt aggatcagtg gaacacacaa   1200
agtaactaag acagagagac agagagaaaa atctggggaa gagacaaaga gtcagagtgt   1260
gtgagttatt ctgtattgtg aaattttttt gcccaactac ataatattgc tgaaactaat   1320
tttacttaaa aagaaaagcc aacaacgtcc ccagtaaaac ttttctataa atatcagcag   1380
ttttcccttt cctccattcc tcttcttgtc tttttttctta ctttcccttt tttataccttt  1440
ttcattatca tcctttataa ttgtctaacc aacaactata tatctatcaa ccatgactgt   1500
tcacgacatt attgctacct actttactaa gtggtacgtc attgttccat tggccttaat   1560
cgcctataga gttttggatt acttttacgg tagatacttg atgtacaaat tgggtgctaa   1620
accattcttt cagaaacaaa ctgacggttg ttttggtttt aaggcccctt tagaattatt   1680
gaagaaaaag tctgacggta cattgatcga ttttaccttg caaagaatcc acgacttgga   1740
cagaccagat atcccaacct ttaccttttcc tgttttctca atcaatttgg tgaatacttt   1800
ggaacctgaa aacatcaagg ctatcttggc tacccagttc aatgatttta gtttgggcac   1860
cagacactca cattttgcac cattgttggg agatggtatc tttacattgg atggtgctgg   1920
ttggaagcat tcaagatcca tgttaagacc acaatttgca agagagcaga tttcccatgt   1980
taagttgttg gaaccacatg ttcaagtctt cttcaagcat gttagaaaag cccaaggtaa   2040
gacttttgat attcaggagt tgttctttag attgactgtt gattctgcca ccgaattttt   2100
gtttggtgaa tccgtcgaat ccttgagaga cgaatctatt ggtatgtcta ttaacgcttt   2160
ggattttgat ggtaaggctg gatttgcaga tgcatttaac tattcccaaa actatttagc   2220
ttctagagct gtcatgcaac aattatactg gttttaaat ggtaaaaagt tcaaggaatg   2280
taatgctaag gtccacaagt tcgctgacta ttatgtcaac aaggctttag acttaactcc   2340
agagcaatta gaaaagcagg atggttacgt cttcttatat gaattggtca aacagactag   2400
agataagcaa gttttgagag atcagttatt gaatatcatg gtcgctggta gagacacaac   2460
tgctggtttg ttgtcctttg tcttctttga attggccaga aacccagaag tcaccaacaa   2520
attaagagag gaaatcgaag ataaatttgg attaggcgaa aatgcaagtg tcgaggacat   2580
ttcctttgag tctttgaagt cttgtgaata tttgaaagct gttttgaacg agacattgcg   2640
tttgtaccct tcagttccac agaactttag agttgcaacc aagaacacca cattgcctag   2700
aggcggtggt aaagatggtt tgtctcctgt tttggtgaga aagggtcaaa ccgttattta   2760
cggtgtctac gccgcccaca gaaacccagc agtctatggt aaagatgctt tggaattcag   2820
accagagcgt tggttcgaac ctgaaaccaa aaagttgggt tgggccttct tacctttcaa   2880
cggaggtcca agaatctgtt tgggtcagca attcgccttg acagaagcct catatgtgac   2940
tgtgagattg ttgcaagaat tcgctcactt gtctatggac cctgacactg aatacccctcc   3000
taaaaagatg tcccatttga ccatgtcatt atttgacggt gctaatattg aaatgtatta   3060
ggcggccgca agaaaaaaga aaaggtaaag aacttcattt gagatgaact tttgtatatg   3120
acttttagtt tctactttt ttttatttta ttgcttaatt ttcttatttt caatccccca    3180
tagtttgtgt agaatatatt tattcattct ggtaactcaa acacgtagca agctcgttgc   3240
```

| | |
|---|---|
| atctcgcctc gtcacgggta cagctctgga accaaagaca aaaaaaaaag ttgatccgaa | 3300 |
| ccctctcgct attccttgct atgctatcca cgagatgggg tttatcagcc caggcaagtc | 3360 |
| actaaaggat cccccacaca ccatagcttc aaaatgtttc tactccttttt ttactcttcc | 3420 |
| agattttctc ggactccgcg catcgccgta ccacttcaaa acacccaagc acagcatact | 3480 |
| aaattttccc tctttcttcc tctagggtgt cgttaattac ccgtactaaa ggtttggaaa | 3540 |
| agaaaaaaga gaccgcctcg tttcttttc ttcgtcgaaa aaggcaataa aaatttttat | 3600 |
| cacgtttctt tttcttgaaa ttttttttt tagttttttt ctctttcagt gacctccatt | 3660 |
| gatatttaag ttaataaacg gtcttcaatt tctcaagttt cagtttcatt tttcttgttc | 3720 |
| tattacaact ttttttactt cttgttcatt agaaagaaag catagcaatc taatctaagg | 3780 |
| ggcggtgttg acaattaatc atcggcatag tatatcggca tagtataata cgacaaggtg | 3840 |
| aggaactaaa ccatgtctaa attaacctct gctgttccag tgttaaccgc ccgtgatgtt | 3900 |
| gccggtgcag tggaattttg gactgaccgt ttgggtttct cacgtgactt tgtcgaagat | 3960 |
| gattttgctg gcgttgtgcg tgatgacgtc actttgttca tctctgctgt tcaggatcag | 4020 |
| gtcgtcccag acaacacttt ggcctgggtc tgggttcgtg gtttggacga attgtacgct | 4080 |
| gagtggagtg aagttgtgtc tacaaacttt cgtgatgcat caggtccagc tatgaccgaa | 4140 |
| attggcgaac aaccttgggg ccgtgagttc gctttacgtg atccagccgg taattgcgtg | 4200 |
| cacttcgttg ctgaggagca agattagcac gtccgacggc ggcccacggg tcccaggcct | 4260 |
| cggagatccg tccccctttt cctttgtcga tatcatgtaa ttagttatgt cacgcttaca | 4320 |
| ttcacgccct ccccccacat ccgctctaac cgaaaaggaa ggagttagac aacctgaagt | 4380 |
| ctaggtccct atttattttt ttatagttat gttagtatta agaacgttat ttatatttca | 4440 |
| aattttctt ttttttctgt acagacgcgt gtacgcatgt aacattatac tgaaaacctt | 4500 |
| gcttgagaag gtttttgggac gctcgaaggc tttaatttgc aagctggaga ccaacatgtg | 4560 |
| agcaaaaggc cagcaaaagg ccaggaaccg taaaaaggcc gcgttgctgg cgttttttcca | 4620 |
| taggctccgc cccctgacg agcatcacaa aaatcgacgc tcaagtcaga ggtggcgaaa | 4680 |
| cccgacagga ctataaagat accaggcgtt tcccctgga agctccctcg tgcgctctcc | 4740 |
| tgttccgacc ctgccgctta ccggatacct gtccgccttt ctcccttcgg gaagcgtggc | 4800 |
| gctttctcaa tgctcacgct gtaggtatct cagttcggtg taggtcgttc gctccaagct | 4860 |
| gggctgtgtg cacgaacccc ccgttcagcc cgaccgctgc gccttatccg gtaactatcg | 4920 |
| tcttgagtcc aacccggtaa gacacgactt atcgccactg gcagcagcca ctggtaacag | 4980 |
| gattagcaga gcgaggtatg taggcggtgc tacagagttc ttgaagtggt ggcctaacta | 5040 |
| cggctacact agaaggacag tatttggtat ctgcgctctg ctgaagccag ttaccttcgg | 5100 |
| aaaaagagtt ggtagctctt gatccggcaa acaaaccacc gctggtagcg gtggtttttt | 5160 |
| tgtttgcaag cagcagatta cgcgcagaaa aaaaggatct caagaagatc ctttgatctt | 5220 |
| ttctacgggg tctgacgctc agtggaacga aaactcacgt taagggattt tggtcatgag | 5280 |
| atc | 5283 |

<210> SEQ ID NO 73
<211> LENGTH: 1572
<212> TYPE: DNA
<213> ORGANISM: Candida tropicalis

<400> SEQUENCE: 73

| | |
|---|---|
| atggcaaccc aggaaattat tgattctgtt ttaccttact tgaccaagtg gtatactgtc | 60 |

```
attaccgccg ctgtgttggt gttcttgatt tctacaaaca ttaagaacta cgttaaagcc    120
aagaagttga agtgtgttga cccaccatac ttaaaagacg ctggtttgac cggtatttct    180
tcattgatcg ctgctattaa ggccaagaat gacggtcgtt tggccaactt tgccgacgag    240
gttttcgatg aataccctaa ccacaccttc tacttgtctg tggcaggagc tttgaagatt    300
gttatgaccg ttgacccaga aaatatcaaa gctgttttgg caacacagtt cacagacttt    360
tcattgggta ctcgtcatgc ccattttgct ccattgttgg gtgatggtat ttttacttta    420
gacggtgaag gttggaagca ttcaagagcc atgttgcgtc cacagtttgc cagagatcaa    480
atcggtcatg tgaaagcctt agaaccacat atccaaatta tggccaagca aatcaagttg    540
aaccaaggaa agactttcga tatccaagaa ttgttcttca gatttacagt tgacacagct    600
actgaattct tgtttggtga atctgttcac agtttatatg acgaaaagtt gggtattcca    660
accccaaatg aaatcccagg tagagaaaat ttcgctgctg cattcaatgt ctctcaacac    720
tacttggcta caagatctta cagtcaaact ttctactttt tgactaaccc aaaggaattt    780
agagactgta acgccaaggt tcaccatttg gccaagtact ttgtgaataa agctttgaat    840
ttcaccccag aggaattaga agaaaagtct aaatccggct atgtttcttt atacgaatta    900
gttaaacaaa caagagatcc taaggttttg caagaccaat tgttgaacat tatggtcgct    960
ggtagagaca ctactgctgg tttattgtcc tttgctttgt ttgaattggc tagacatcca   1020
gaaatgtggt caaagttgag agaggaaatc gaagttaact ttggcgtggg tgaagattca   1080
agagttgaag agattacctt tgaggccttg aaaagatgtg aatacttgaa ggctatcttg   1140
aacgagacat tgagaatgta tccatctgtt cctgttaact ttagaacagc cactagagat   1200
acaaccttgc caagaggtgg tggtgccaac ggtacagatc caatttacat tcctaagggt   1260
tccaccgtcg cttacgtcgt gtacaaaacc caccgtttgg aggaatatta cggtaaggac   1320
gctaacgatt tccgtcctga aagatggttt gaaccaagta ctaagaagtt gggatgggcc   1380
tatgttcctt ttaacggtgg tccaagagtt tgtttgggtc agcagtttgc tttgactgaa   1440
gccagttacg ttatcaccag attagcccaa atgttcgaaa ccgtttcatc tgacccagga   1500
ttggagtatc caccaccaaa gtgtattcat ttgacaatgt cccataatga tggtgttttt   1560
gtcaagatgt ag                                                       1572
```

<210> SEQ ID NO 74
<211> LENGTH: 5286
<212> TYPE: DNA
<213> ORGANISM: Artificial Sequence
<220> FEATURE:
<223> OTHER INFORMATION: Genomic integration vector for integrating CYP52A12 under control of the isocitrate lyase promoter

<400> SEQUENCE: 74

```
agatctgaat tctattaggc gaagaggcat ctagtagtag tggcagtggt gagaacgtgg     60
gcgctgctat agtgaacaat ctccagtcga tggttaagaa gaagagtgac aaaccagcag    120
tgaatgactt gtctgggtcc gtgaggaaaa gaaagaagcc cgacacaaag gacagtaacg    180
tcaagaaacc caagaaatag gggggacctg tttagatgta taggaataaa aactccgaga    240
tgatctcaat gtgtaatgga gttgtaatat tgcaaagggg gaaaatcaag actcaaacgt    300
gtgtatgagt gagcgtacgt atatctccga gagtagtatg acataatgat gactgtgaat    360
catcgtaatc tcacacaaaa accccattgt cggccatata ccacaccaag caacaccaca    420
tatcccccgg aaaaaaaaac gtgaaaaaaa gaaacaatca aaactacaac ctactccttg    480
```

```
atcacacagt cattgatcaa gttacagttc ctgctaggga atgaccaagg tacaaatcag    540
caccttaatg gttagcacgc tctcttactc tctctcacag tcttccggcc cctattcaaa    600
attctgcact tccatttgac cccagggttg ggaaacaggg ccacaaaaga aaacccgac     660 gtgaatgaaa aaactaagaa aagaaaaaaa attatcacac cagaaattta cctaattggg   720
taattcccat cggtgttttt cctggattgt cgcacgcacg catgctgaaa aaagtgttcg    780
agttttgctt ttgcctcgga gtttcacgca agttttcga tctcggaacc ggagggcggt    840
cgccttgttg tttgtgatgt cgtgctttgg gtgttctaat gtgctgttat tgtgctcttt    900
ttttttcttc tttttttggt gatcatatga tattgctcgg tagattactt tcgtgtgtag    960
gtattctttt agacgtttgg ttattgggta gatatgagag agagagagtg ggtgggggag   1020
gagttggttg taggagggac ccctgggagg aagtgtagtt gagttttccc tgacgaatga   1080
aaatacgttt ttgagaagat aatacaggaa aggtgtgtcg gtgaatttcc atctatccga   1140
ggatatgagt ggaggagagt cgtgtgcgtg tggttaattt aggatcagtg gaacacacaa    1200
agtaactaag acagagagac agagagaaaa atctgggaa gagacaaaga gtcagagtgt    1260
gtgagttatt ctgtattgtg aaattttttt gcccaactac ataatattgc tgaaactaat   1320
tttacttaaa aagaaaagcc aacaacgtcc ccagtaaaac ttttctataa atatcagcag   1380
ttttcccttt cctccattcc tcttcttgtc tttttttctta ctttcccttt tttatacctt   1440
ttcattatca tcctttataa ttgtctaacc aacaactata tatctatcaa ccatggcaac   1500
ccaggaaatt attgattctg ttttacctta cttgaccaag tggtatactg tcattaccgc   1560
cgctgtgttg gtgttcttga tttctacaaa cattaagaac tacgttaaag ccaagaagtt   1620
gaagtgtgtt gacccaccat acttaaaaga cgctggtttg accggtatttt cttcattgat   1680 cgctgctatt aaggccaaga atgacggtcg tttggccaac tttgccgacg aggttttcga   1740
tgaataccct aaccacacct tctacttgtc tgtggcagga gctttgaaga ttgttatgac   1800
cgttgaccca gaaaatatca aagctgtttt ggcaacacag ttcacagact tttcattggg   1860
tactcgtcat gcccattttg ctccattgtt gggtgatggt attttttactt tagacggtga   1920 aggttggaag cattcaagag ccatgttgcg tccacagttt gccagagatc aaatcggtca   1980
tgtgaaagcc ttagaaccac atatccaaat tatggccaag caaatcaagt tgaaccaagg   2040
aaagactttc gatatccaag aattgttctt cagatttaca gttgacacag ctactgaatt   2100
cttgtttggt gaatctgttc acagtttata tgacgaaaag ttgggtattc caaccccaaa   2160
tgaaatccca ggtagagaaa atttcgctgc tgcattcaat gtctctcaac actacttggc   2220
tacaagatct tacagtcaaa ctttctactt tttgactaac ccaaaggaat ttagagactg   2280
taacgccaag gttcaccatt tggccaagta ctttgtgaat aaagctttga atttcacccc   2340
agaggaatta aagaaaagt ctaaatccgg ctatgttttc ttatacgaat tagttaaaca    2400
aacaagagat cctaaggttt tgcaagacca attgttgaac attatggtcg ctggtagaga   2460
cactactgct ggtttattgt cctttgcttt gtttgaattg gctagacatc cagaaatgtg   2520
gtcaaagttg agagaggaaa tcgaagttaa cttggcgtg ggtgaagatt caagagttga    2580
agagattacc tttgaggcct tgaaaagatg tgaatacttg aaggctatct tgaacgagac   2640
attgagaatg tatccatctg ttcctgttaa ctttagaaca gccactagag atacaacctt   2700
gccaagaggt ggtggtgcca acggtacaga tccaatttac attcctaagg gttccaccgt   2760
cgcttacgtc gtgtacaaaa cccaccgttt ggaggaatat tacggtaagg acgctaacga   2820
tttccgtcct gaaagatggt ttgaaccaag tactaagaag ttgggatggg cctatgttcc   2880
```

```
ttttaacggt ggtccaagag tttgtttggg tcagcagttt gctttgactg aagccagtta    2940
cgttatcacc agattagccc aaatgttcga aaccgtttca tctgacccag gattggagta    3000
tccaccacca aagtgtattc atttgacaat gtcccataat gatggtgttt tgtcaagat    3060 gtaggcggcc gcaagaaaaa agaaaaggta aagaacttca tttgagatga acttttgtat    3120 atgacttta gttctactt ttttttttat ttattgctta attttcttta tttcaatccc    3180
ccatagtttg tgtagaatat atttattcat tctggtaact caaacacgta gcaagctcgt    3240
tgcatctcgc ctcgtcacgg gtacagctct ggaaccaaag acaaaaaaaa aagttgatcc    3300
gaaccctctc gctattcctt gctatgctat ccacgagatg gggtttatca gcccaggcaa    3360
gtcactaaag gatccccac acaccatagc ttcaaaatgt ttctactcct tttttactct    3420
tccagatttt ctcggactcc gcgcatcgcc gtaccacttc aaaacaccca agcacagcat    3480
actaaatttt ccctctttct tcctctaggg tgtcgttaat tacccgtact aaaggtttgg    3540
aaaagaaaaa agagaccgcc tcgtttcttt ttcttcgtcg aaaaaggcaa taaaaatttt    3600
tatcacgttt cttttcttg aaatttttt tttagtttt tttctcttc agtgacctcc    3660 attgatattt aagttaataa acggtcttca atttctcaag tttcagtttc attttcttg    3720 ttctattaca acttttttta cttcttgttc attagaaaga aagcatagca atctaatcta    3780
aggggcggtg ttgacaatta atcatcggca tagtatatcg gcatagtata atacgacaag    3840
gtgaggaact aaaccatgtc taaattaacc tctgctgttc cagtgttaac cgcccgtgat    3900
gttgccggtg cagtggaatt ttggactgac cgtttgggtt tctcacgtga ctttgtcgaa    3960
gatgattttg ctggcgttgt gcgtgatgac gtcactttgt tcatctctgc tgttcaggat    4020
caggtcgtcc cagacaacac tttggcctgg gtctgggttc gtggtttgga cgaattgtac    4080
gctgagtgga gtgaagttgt gtctacaaac tttcgtgatg catcaggtcc agctatgacc    4140
gaaattggcg aacaaccttg gggccgtgag ttcgctttac gtgatccagc cggtaattgc    4200
gtgcacttcg ttgctgagga gcaagattag cacgtccgac ggcggcccac gggtcccagg    4260
cctcggagat ccgtccccct tttccttgt cgatatcatg taattagtta tgtcacgctt    4320
acattcacgc cctcccccca catccgctct aaccgaaaag gaaggagtta gacaacctga    4380
agtctaggtc cctatttatt tttttatagt tatgttagta ttaagaacgt tatttatatt    4440 tcaaatttt ctttttttc tgtacagacg cgtgtacgca tgtaacatta tactgaaaac    4500
cttgcttgag aaggttttgg gacgctcgaa ggctttaatt tgcaagctgg agaccaacat    4560
gtgagcaaaa ggccagcaaa aggccaggaa ccgtaaaaag gccgcgttgc tggcgttttt    4620
ccataggctc cgcccccctg acgagcatca caaaaatcga cgctcaagtc agaggtggcg    4680
aaacccgaca ggactataaa gataccaggc gtttccccct ggaagctccc tcgtgcgctc    4740
tcctgttccg accctgccgc ttaccggata cctgtccgcc tttctccctt cgggaagcgt    4800
ggcgctttct caatgctcac gctgtaggta tctcagttcg gtgtaggtcg ttcgctccaa    4860
gctgggctgt gtgcacgaac cccccgttca gcccgaccgc tgcgccttat ccggtaacta    4920
tcgtcttgag tccaacccgg taagacacga cttatcgcca ctggcagcag ccactggtaa    4980
caggattagc agagcgaggt atgtaggcgg tgctacagag ttcttgaagt ggtggcctaa    5040
ctacggctac actagaagga cagtatttgg tatctgcgct ctgctgaagc cagttacctt    5100
cggaaaaaga gttggtagct cttgatccgg caaacaaacc accgctggta gcggtggttt    5160
ttttgtttgc aagcagcaga ttacgcgcag aaaaaaagga tctcaagaag atcctttgat    5220 ctttttctacg gggtctgacg ctcagtggaa cgaaaactca cgttaaggga ttttggtcat    5280
```

-continued

| gagatc | 5286 |

<210> SEQ ID NO 75
<211> LENGTH: 711
<212> TYPE: DNA
<213> ORGANISM: Artificial Sequence
<220> FEATURE:
<223> OTHER INFORMATION: Cloned into genomic integration and expression
constructs to express mCherry

<400> SEQUENCE: 75

| atggtttcta agggtgaaga agacaacatg gcaatcatca aggaatttat gcgttttaag | 60 |
| gtccatatgg aaggctccgt taacggccac gagttcgaga tcgagggaga aggtgagggt | 120 |
| agaccatacg aaggtactca aaccgccaag ttgaaagtta caagggtgg tccattgcca | 180 |
| tttgcttggg atatcttgtc cccacaattt atgtacggat caaaggcata tgtcaagcat | 240 |
| cctgccgaca tcccagatta cttgaagtta tcctttccag aaggttttaa gtgggagaga | 300 |
| gttatgaact tgaagatgg cggagttgtt actgttactc aggactcttc cttgcaagat | 360 |
| ggtgaattta tctataaagt gaaattgaga ggtactaact ttccatccga cggtccagtc | 420 |
| atgcaaaaga agacaatggg ttgggaggct cttccgaaa gaatgtaccc agaagacggt | 480 |
| gcattgaaag gtgaaatcaa gcaacgttta agttgaagg acggtggtca ctacgatgcc | 540 |
| gaggtcaaga ccacttataa ggctaagaag ccagtccaat tgccaggtgc ttataacgtt | 600 |
| aacatcaagt tagatattac ttcacacaac gaagactaca caatcgttga acaatatgaa | 660 |
| agagccgaag gtagacattc taccggcggc atggacgagt tatataagta g | 711 |

<210> SEQ ID NO 76
<211> LENGTH: 4425
<212> TYPE: DNA
<213> ORGANISM: Artificial Sequence
<220> FEATURE:
<223> OTHER INFORMATION: Genomic integration vector for integrating
mCherry under control of the isocitrate lyase promoter

<400> SEQUENCE: 76

| agatctgaat tctattaggc gaagaggcat ctagtagtag tggcagtggt gagaacgtgg | 60 |
| gcgctgctat agtgaacaat ctccagtcga tggttaagaa gaagagtgac aaaccagcag | 120 |
| tgaatgactt gtctgggtcc gtgaggaaaa gaaagaagcc cgacacaaag gacagtaacg | 180 |
| tcaagaaacc caagaaatag gggggacctg tttagatgta taggaataaa aactccgaga | 240 |
| tgatctcaat gtgtaatgga gttgtaatat tgcaaagggg gaaaatcaag actcaaacgt | 300 |
| gtgtatgagt gagcgtacgt atatctccga gagtagtatg acataatgat gactgtgaat | 360 |
| catcgtaatc tcacacaaaa accccattgt cggccatata ccacaccaag caacaccaca | 420 |
| tatcccccgg aaaaaaaaac gtgaaaaaaa gaaacaatca aaactacaac ctactccttg | 480 |
| atcacacagt cattgatcaa gttacagttc ctgctaggga atgaccaagg tacaaatcag | 540 |
| caccttaatg gttagcacgc tctcttactc tctctcacag tcttccggcc cctattcaaa | 600 |
| attctgcact tccatttgac cccagggttg ggaaacaggg ccacaaaaga aaaacccgac | 660 |
| gtgaatgaaa aaactaagaa aagaaaaaaa attatcacac cagaaattta cctaattggg | 720 |
| taattcccat cggtgttttt cctggattgt cgcacgcacg catgctgaaa aaagtgttcg | 780 |
| agttttgctt ttgcctcgga gtttcacgca agtttttcga tctcggaacc ggagggcggt | 840 |
| cgccttgttg tttgtgatgt cgtgctttgg gtgttctaat gtgctgttat tgtgctcttt | 900 |
| tttttttcttc tttttttggt gatcatatga tattgctcgg tagattactt tcgtgtgtag | 960 |

```
gtattctttt agacgtttgg ttattgggta gatatgagag agagagagtg ggtgggggag    1020
gagttggttg taggagggac ccctgggagg aagtgtagtt gagttttccc tgacgaatga    1080
aaatacgttt ttgagaagat aatacaggaa aggtgtgtcg gtgaatttcc atctatccga    1140
ggatatgagt ggaggagagt cgtgtgcgtg tggttaattt aggatcagtg gaacacacaa    1200
agtaactaag acagagagac agagagaaaa atctgggaa gagacaaaga gtcagagtgt     1260
gtgagttatt ctgtattgtg aaattttttt gcccaactac ataatattgc tgaaactaat    1320
tttacttaaa aagaaaagcc aacaacgtcc ccagtaaaac ttttctataa atatcagcag    1380
ttttcccttt cctccattcc tcttcttgtc ttttttctta ctttcccttt tttatacctt    1440
ttcattatca tcctttataa ttgtctaacc aacaactata tatctatcaa ccatggtttc    1500
taagggtgaa gaagacaaca tggcaatcat caaggaattt atgcgtttta aggtccatat    1560
ggaaggctcc gttaacggcc acgagttcga gatcgaggga gaaggtgagg gtagaccata    1620
cgaaggtact caaaccgcca agttgaaagt tacaaagggt ggtccattgc catttgcttg    1680
ggatatcttg tccccacaat ttatgtacgg atcaaaggca tatgtcaagc atcctgccga    1740
catcccagat tacttgaagt tatcctttcc agaaggtttt aagtgggaga gagttatgaa    1800
cttttgaagat ggcggagttg ttactgttac tcaggactct tccttgcaag atggtgaatt   1860
tatctataaa gtgaaattga gaggtactaa ctttccatcc gacggtccag tcatgcaaaa    1920
gaagacaatg ggttgggagg cttcttccga aagaatgtac ccagaagacg gtgcattgaa    1980
aggtgaaatc aagcaacgtt taagttgaa ggacggtggt cactacgatg ccgaggtcaa     2040
gaccacttat aaggctaaga agccagtcca attgccaggt gcttataacg ttaacatcaa    2100
gttagatatt acttcacaca acgaagacta cacaatcgtt gaacaatatg aaagagccga    2160
aggtagacat tctaccggcg gcatggacga gttatataag taggcggccg caagaaaaaa    2220
gaaaaggtaa agaacttcat ttgagatgaa cttttgtata tgacttttag tttctacttt    2280
tttttttatt tattgcttaa ttttctttat ttcaatcccc catagtttgt gtagaatata    2340
tttattcatt ctggtaactc aaacacgtag caagctcgtt gcatctcgcc tcgtcacggg    2400
tacagctctg gaaccaaaga caaaaaaaaa agttgatccg aaccctctcg ctattccttg    2460
ctatgctatc cacgagatgg ggtttatcag cccaggcaag tcactaaagg atcccccaca    2520
caccatagct tcaaaatgtt tctactcctt tttactctt ccagatttc tcggactccg      2580
cgcatcgccg taccacttca aaacacccaa gcacagcata ctaaattttc cctctttctt    2640
cctctagggt gtcgttaatt acccgtacta aaggtttgga aaagaaaaaa gagaccgcct    2700
cgtttctttt tcttcgtcga aaaaggcaat aaaaattttt atcacgtttc ttttcttga    2760
aattttttt tttagtttt ttctctttca gtgacctcca ttgatattta agttaataaa     2820
cggtcttcaa tttctcaagt ttcagtttca ttttttcttgt tctattacaa cttttttac    2880
ttcttgttca ttagaaagaa agcatagcaa tctaatctaa ggggcggtgt tgacaattaa    2940
tcatcggcat agtatatcgg catagtataa tacgacaagg tgaggaacta aaccatgtct    3000
aaattaaccct ctgctgttcc agtgttaacc gcccgtgatg ttgccggtgc agtggaattt   3060
tggactgacc gtttgggttt ctcacgtgac tttgtcgaag atgattttgc tggcgttgtg    3120
cgtgatgacg tcacttttgtt catctctgct gttcaggatc aggtcgtccc agacaacact   3180
ttggcctggg tctgggttcg tggtttggac gaattgtacg ctgagtggag tgaagttgtg    3240
tctacaaact tcgtgatgc atcaggtcca gctatgaccg aaattggcga acaaccttgg     3300
ggccgtgagt tcgctttacg tgatccagcc ggtaattgcg tgcacttcgt tgctgaggag    3360
```

-continued

```
caagattagc acgtccgacg gcggcccacg ggtcccaggc ctcggagatc cgtccccctt      3420
ttcctttgtc gatatcatgt aattagttat gtcacgctta cattcacgcc ctcccccac      3480 atccgctcta accgaaaagg aaggagttag acaacctgaa gtctaggtcc ctatttattt      3540
ttttatagtt atgttagtat taagaacgtt atttatattt caaattttc tttttttct       3600 gtacagacgc gtgtacgcat gtaacattat actgaaaacc ttgcttgaga aggttttggg     3660
acgctcgaag gctttaattt gcaagctgga gaccaacatg tgagcaaaag gccagcaaaa     3720
ggccaggaac cgtaaaaagg ccgcgttgct ggcgtttttc cataggctcc gcccccctga     3780
cgagcatcac aaaaatcgac gctcaagtca gaggtggcga acccgacag gactataaag      3840 ataccaggcg tttccccctg gaagctccct cgtgcgctct cctgttccga ccctgccgct     3900
taccggatac ctgtccgcct ttctcccttc gggaagcgtg gcgctttctc aatgctcacg     3960
ctgtaggtat ctcagttcgg tgtaggtcgt tcgctccaag ctgggctgtg tgcacgaacc     4020
ccccgttcag cccgaccgct gcgccttatc cggtaactat cgtcttgagt ccaacccggt    4080
aagacacgac ttatcgccac tggcagcagc cactggtaac aggattagca gagcgaggta    4140
tgtaggcggt gctacagagt tcttgaagtg gtggcctaac tacggctaca ctagaaggac    4200
agtatttggt atctgcgctc tgctgaagcc agttaccttc ggaaaaagag ttggtagctc    4260
ttgatccggc aaacaaacca ccgctggtag cggtggtttt tttgtttgca agcagcagat    4320
tacgcgcaga aaaaaggat ctcaagaaga tcctttgatc ttttctacgg ggtctgacgc     4380
tcagtggaac gaaaactcac gttaagggat tttggtcatg agatc                    4425
```

<210> SEQ ID NO 77
<211> LENGTH: 25
<212> TYPE: DNA
<213> ORGANISM: Candida Tropicalis

<400> SEQUENCE: 77
tggcggaagt gcatgtgaca caacg                                             25

<210> SEQ ID NO 78
<211> LENGTH: 25
<212> TYPE: DNA
<213> ORGANISM: Candida Tropicalis

<400> SEQUENCE: 78
gtggttggtt tgtctgagtg gagag                                             25

<210> SEQ ID NO 79
<211> LENGTH: 25
<212> TYPE: DNA
<213> ORGANISM: Artificial Sequence
<220> FEATURE:
<223> OTHER INFORMATION: Primer for analysis of strains

<400> SEQUENCE: 79
tggtactggt tctcgggagc acagg                                             25

<210> SEQ ID NO 80
<211> LENGTH: 30
<212> TYPE: DNA
<213> ORGANISM: Candida tropicalis

<400> SEQUENCE: 80
cgctagacaa attcttccaa aaatttaga                                         30

<210> SEQ ID NO 81

```
<211> LENGTH: 25
<212> TYPE: DNA
<213> ORGANISM: Candida tropicalis

<400> SEQUENCE: 81
catgtggccg ctgaatgtgg gggca                                         25

<210> SEQ ID NO 82
<211> LENGTH: 30
<212> TYPE: DNA
<213> ORGANISM: Artificial sequence
<220> FEATURE:
<223> OTHER INFORMATION: Primer for analysis of strains

<400> SEQUENCE: 82
gccattttgt ttttttttac ccctctaaca                                    30

<210> SEQ ID NO 83
<211> LENGTH: 25
<212> TYPE: DNA
<213> ORGANISM: Candida tropicalis

<400> SEQUENCE: 83
ggaagtgcat gtgacacaat accct                                         25

<210> SEQ ID NO 84
<211> LENGTH: 30
<212> TYPE: DNA
<213> ORGANISM: Artificial Sequence
<220> FEATURE:
<223> OTHER INFORMATION: Oligonucleotide primer for analysis of strains

<400> SEQUENCE: 84
ggtggtttgt ctgagtgaga acgtttaatt                                    30

<210> SEQ ID NO 85
<211> LENGTH: 25
<212> TYPE: DNA
<213> ORGANISM: Candida tropicalis

<400> SEQUENCE: 85
gacgtagccg atgaatgtgg ggtgc                                         25

<210> SEQ ID NO 86
<211> LENGTH: 30
<212> TYPE: DNA
<213> ORGANISM: Artificial Sequence
<220> FEATURE:
<223> OTHER INFORMATION: Oligonucleotide primer for analysis of strains

<400> SEQUENCE: 86
tgccatttat tttttattac ccctctaaat                                    30

<210> SEQ ID NO 87
<211> LENGTH: 25
<212> TYPE: DNA
<213> ORGANISM: Candidida tropicalis

<400> SEQUENCE: 87
attggcgtcg tggcattggc ggctc                                         25

<210> SEQ ID NO 88
<211> LENGTH: 20
<212> TYPE: DNA
<213> ORGANISM: Artificial Sequence
<220> FEATURE:
```

```
<223> OTHER INFORMATION: Oligonucleotide primers for analysis of strains

<400> SEQUENCE: 88
tgggcggaat caagtggctt                                              20

<210> SEQ ID NO 89
<211> LENGTH: 20
<212> TYPE: DNA
<213> ORGANISM: Candida tropicalis

<400> SEQUENCE: 89
cgtcgacacc cttatgttat                                              20

<210> SEQ ID NO 90
<211> LENGTH: 21
<212> TYPE: DNA
<213> ORGANISM: Candida tropicalis

<400> SEQUENCE: 90
cgttgactcc tatcaaggac a                                            21

<210> SEQ ID NO 91
<211> LENGTH: 22
<212> TYPE: DNA
<213> ORGANISM: Artificial Sequence
<220> FEATURE:
<223> OTHER INFORMATION: Primer used for analysis of strains

<400> SEQUENCE: 91
ggtcttctct tcctggataa tg                                           22

<210> SEQ ID NO 92
<211> LENGTH: 20
<212> TYPE: DNA
<213> ORGANISM: Candida tropicalis

<400> SEQUENCE: 92
ccagcagttg tttgttcttg                                              20

<210> SEQ ID NO 93
<211> LENGTH: 22
<212> TYPE: DNA
<213> ORGANISM: Artificial Sequence
<220> FEATURE:
<223> OTHER INFORMATION: Primer used for analysis of strains

<400> SEQUENCE: 93
aatcctgtgc tttgtcgtag gc                                           22

<210> SEQ ID NO 94
<211> LENGTH: 21
<212> TYPE: DNA
<213> ORGANISM: Candida tropicalis

<400> SEQUENCE: 94
tccttaacaa gaagggcatc g                                            21

<210> SEQ ID NO 95
<211> LENGTH: 20
<212> TYPE: DNA
<213> ORGANISM: Artificial Sequence
<220> FEATURE:
<223> OTHER INFORMATION: TTCTTGAATCCGGAGTTGAC

<400> SEQUENCE: 95
```

```
ttcttgaatc cggagttgac                                          20
```

<210> SEQ ID NO 96
<211> LENGTH: 20
<212> TYPE: DNA
<213> ORGANISM: Candida tropicalis

<400> SEQUENCE: 96

```
tcttagtcgt gataccacca                                          20
```

<210> SEQ ID NO 97
<211> LENGTH: 20
<212> TYPE: DNA
<213> ORGANISM: Artificial Sequence
<220> FEATURE:
<223> OTHER INFORMATION: Primer used for analysis of strains

<400> SEQUENCE: 97

```
ctaaggattc tcttggcacc                                          20
```

<210> SEQ ID NO 98
<211> LENGTH: 20
<212> TYPE: DNA
<213> ORGANISM: Artificial Sequence
<220> FEATURE:
<223> OTHER INFORMATION: Primer used for analysis of strains

<400> SEQUENCE: 98

```
gtgaccatag gattagcacc                                          20
```

<210> SEQ ID NO 99
<211> LENGTH: 30
<212> TYPE: DNA
<213> ORGANISM: Candida tropicalis

<400> SEQUENCE: 99

```
cttttctgat tcttgatttt ccctttttcat                              30
```

<210> SEQ ID NO 100
<211> LENGTH: 30
<212> TYPE: DNA
<213> ORGANISM: Artificial Sequence
<220> FEATURE:
<223> OTHER INFORMATION: Primer for analysis of strains

<400> SEQUENCE: 100

```
atacatctag tatataagtg tcgtatttcc                               30
```

<210> SEQ ID NO 101
<211> LENGTH: 30
<212> TYPE: DNA
<213> ORGANISM: Candida tropicalis

<400> SEQUENCE: 101

```
tgcttttctg attcttgatc atccccttag                               30
```

<210> SEQ ID NO 102
<211> LENGTH: 30
<212> TYPE: DNA
<213> ORGANISM: Artificial Sequence
<220> FEATURE:
<223> OTHER INFORMATION: Primer for analysis of strains

<400> SEQUENCE: 102

```
atacatctag tatataagtg tcgtatttct                               30
```

-continued

```
<210> SEQ ID NO 103
<211> LENGTH: 25
<212> TYPE: DNA
<213> ORGANISM: Candida tropicalis

<400> SEQUENCE: 103
cgccagtctt tcctgattgg gcaag                                    25

<210> SEQ ID NO 104
<211> LENGTH: 25
<212> TYPE: DNA
<213> ORGANISM: Artificial Sequence
<220> FEATURE:
<223> OTHER INFORMATION: Analysis of constructs

<400> SEQUENCE: 104
ggacgttgtc gagtagaggg atgtg                                    25

<210> SEQ ID NO 105
<211> LENGTH: 20
<212> TYPE: DNA
<213> ORGANISM: Candida tropicalis

<400> SEQUENCE: 105
ctgtacttcc gtacttgacc                                          20

<210> SEQ ID NO 106
<211> LENGTH: 19
<212> TYPE: DNA
<213> ORGANISM: Artificial Sequence
<220> FEATURE:
<223> OTHER INFORMATION: Analysis of strains

<400> SEQUENCE: 106
gagacctgga tcagatgag                                           19

<210> SEQ ID NO 107
<211> LENGTH: 21
<212> TYPE: DNA
<213> ORGANISM: Candida albicans

<400> SEQUENCE: 107
gtttacaaag ccttaaagac t                                        21

<210> SEQ ID NO 108
<211> LENGTH: 21
<212> TYPE: DNA
<213> ORGANISM: Artificial Sequence
<220> FEATURE:
<223> OTHER INFORMATION: Analysis of strains

<400> SEQUENCE: 108
ttgaacggcc aaagaaccta a                                        21

<210> SEQ ID NO 109
<211> LENGTH: 27
<212> TYPE: DNA
<213> ORGANISM: Candida tropicalis

<400> SEQUENCE: 109
gaattagaat acaaagatat cccagtg                                  27

<210> SEQ ID NO 110
<211> LENGTH: 25
<212> TYPE: DNA
```

```
<213> ORGANISM: Artificial Sequence
<220> FEATURE:
<223> OTHER INFORMATION: Primer for analysis of strains

<400> SEQUENCE: 110
catcaacttg aagacctgtg gcaat                                              25

<210> SEQ ID NO 111
<211> LENGTH: 27
<212> TYPE: DNA
<213> ORGANISM: Candida tropicalis

<400> SEQUENCE: 111
gaacggttcc tgtatgtcct gtgagtt                                            27

<210> SEQ ID NO 112
<211> LENGTH: 26
<212> TYPE: DNA
<213> ORGANISM: Artificial sequence
<220> FEATURE:
<223> OTHER INFORMATION: Probe for analysis of strains

<400> SEQUENCE: 112
cggattggtc aatggctttt tcggaa                                             26

<210> SEQ ID NO 113
<211> LENGTH: 27
<212> TYPE: DNA
<213> ORGANISM: Candida tropicalis

<400> SEQUENCE: 113
aaattagaat acaaggacat cccagtt                                            27

<210> SEQ ID NO 114
<211> LENGTH: 25
<212> TYPE: DNA
<213> ORGANISM: Artificial sequence
<220> FEATURE:
<223> OTHER INFORMATION: Probe for analysis of strains

<400> SEQUENCE: 114
catcaacttg tagacttctg gcaat                                              25

<210> SEQ ID NO 115
<211> LENGTH: 27
<212> TYPE: DNA
<213> ORGANISM: Candida tropicalis

<400> SEQUENCE: 115
gaacggttcc tgtatgaact gtgagta                                            27

<210> SEQ ID NO 116
<211> LENGTH: 26
<212> TYPE: DNA
<213> ORGANISM: Artificial Sequence
<220> FEATURE:
<223> OTHER INFORMATION: Probe for analysis of strains

<400> SEQUENCE: 116
cagattggtt gatggccttt tcggag                                             26

<210> SEQ ID NO 117
<211> LENGTH: 27
<212> TYPE: DNA
<213> ORGANISM: Candida tropicalis
```

```
<400> SEQUENCE: 117
aagttagaat acaaagacgt gccggtc                                          27

<210> SEQ ID NO 118
<211> LENGTH: 25
<212> TYPE: DNA
<213> ORGANISM: Artificial Sequence
<220> FEATURE:
<223> OTHER INFORMATION: Primer for analysis of probes

<400> SEQUENCE: 118
catcaagtca aaatctctg gcact                                             25

<210> SEQ ID NO 119
<211> LENGTH: 27
<212> TYPE: DNA
<213> ORGANISM: Candida tropicalis

<400> SEQUENCE: 119
ccattgcaat acaccgatat cccagtt                                          27

<210> SEQ ID NO 120
<211> LENGTH: 25
<212> TYPE: DNA
<213> ORGANISM: Artificial sequence
<220> FEATURE:
<223> OTHER INFORMATION: Primer for analysis of genes

<400> SEQUENCE: 120
caacaatttg aaaatctctg gcaat                                            25

<210> SEQ ID NO 121
<211> LENGTH: 27
<212> TYPE: DNA
<213> ORGANISM: Candida tropicalis

<400> SEQUENCE: 121
gaatggttcg tgtatgaact gtgagtt                                          27

<210> SEQ ID NO 122
<211> LENGTH: 26
<212> TYPE: DNA
<213> ORGANISM: Artificial Sequence
<220> FEATURE:
<223> OTHER INFORMATION: Probe for analysis of strains

<400> SEQUENCE: 122
ccgactggtt gattgccttt tcggac                                           26

<210> SEQ ID NO 123
<211> LENGTH: 26
<212> TYPE: DNA
<213> ORGANISM: Artificial Sequence
<220> FEATURE:
<223> OTHER INFORMATION: Probe for analysis of primers

<400> SEQUENCE: 123
cagactggtt gatggctttt tcagaa                                           26

<210> SEQ ID NO 124
<211> LENGTH: 26
<212> TYPE: DNA
<213> ORGANISM: Artificial sequence
<220> FEATURE:
<223> OTHER INFORMATION: Probe for analysis of strains
```

<400> SEQUENCE: 124
ggatccgtct gaagaaatca agaacc                                    26

<210> SEQ ID NO 125
<211> LENGTH: 48
<212> TYPE: DNA
<213> ORGANISM: Artificial sequence
<220> FEATURE:
<223> OTHER INFORMATION: Probe for analysis of strains

<400> SEQUENCE: 125
tggtgtaggc aataattgc ttaatgatat acaaaactgg caccacaa              48

<210> SEQ ID NO 126
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 126
gagcaattgt tggaatattg gtacgttgtg gtgccagttt tgtatatca            49

<210> SEQ ID NO 127
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 127
cgaacttaac aatagcaccg tcttgcaaac acatggtcaa gttagttaa            49

<210> SEQ ID NO 128
<211> LENGTH: 47
<212> TYPE: DNA
<213> ORGANISM: Artificial Sequence
<220> FEATURE:
<223> OTHER INFORMATION: Probe for analysis of strains

<400> SEQUENCE: 128
cgattaaggc caatggaaca atgacgtacc acttagtaaa gtaggta              47

<210> SEQ ID NO 129
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 129
catgactgtt cacgacatta ttgctaccta ctttactaag tggtacgtc            49

<210> SEQ ID NO 130
<211> LENGTH: 48
<212> TYPE: DNA
<213> ORGANISM: Artificial Sequence
<220> FEATURE:
<223> OTHER INFORMATION: Probe for analysis of strains

<400> SEQUENCE: 130
acatttcaat attagcaccg tcaaataatg acatggtcaa atgggaca             48

<210> SEQ ID NO 131
<211> LENGTH: 24
<212> TYPE: DNA

-continued

```
<213> ORGANISM: Artificial sequence
<220> FEATURE:
<223> OTHER INFORMATION: Analysis of probes

<400> SEQUENCE: 131
atcaataatt tcctgggttg ccat                                              24

<210> SEQ ID NO 132
<211> LENGTH: 24
<212> TYPE: DNA
<213> ORGANISM: Artificial sequence
<220> FEATURE:
<223> OTHER INFORMATION: Analysis of probes

<400> SEQUENCE: 132
atggcaaccc aggaaattat tgat                                              24

<210> SEQ ID NO 133
<211> LENGTH: 27
<212> TYPE: DNA
<213> ORGANISM: Artificial sequence
<220> FEATURE:
<223> OTHER INFORMATION: CTACATCTTGACAAAAACACCATCATT

<400> SEQUENCE: 133
ctacatcttg acaaaaacac catcatt                                           27

<210> SEQ ID NO 134
<211> LENGTH: 709
<212> TYPE: PRT
<213> ORGANISM: Candida tropicalis

<400> SEQUENCE: 134
```

Met Thr Phe Thr Lys Lys Asn Val Ser Val Ser Gln Gly Pro Asp Pro
1               5                   10                  15

Arg Ser Ser Ile Gln Lys Glu Arg Asp Ser Ser Lys Trp Asn Pro Gln
            20                  25                  30

Gln Met Asn Tyr Phe Leu Glu Gly Ser Val Glu Arg Ser Glu Leu Met
        35                  40                  45

Lys Ala Leu Ala Gln Gln Met Glu Arg Asp Pro Ile Leu Phe Thr Asp
    50                  55                  60

Gly Ser Tyr Tyr Asp Leu Thr Lys Asp Gln Gln Arg Glu Leu Thr Ala
65                  70                  75                  80

Val Lys Ile Asn Arg Ile Ala Arg Tyr Arg Glu Gln Glu Ser Ile Asp
                85                  90                  95

Thr Phe Asn Lys Arg Leu Ser Leu Ile Gly Ile Phe Asp Pro Gln Val
            100                 105                 110

Gly Thr Arg Ile Gly Val Asn Leu Gly Leu Phe Leu Ser Cys Ile Arg
        115                 120                 125

Gly Asn Gly Thr Thr Ser Gln Leu Asn Tyr Trp Ala Asn Glu Lys Glu
    130                 135                 140

Thr Ala Asp Val Lys Gly Ile Tyr Gly Cys Phe Gly Met Thr Glu Leu
145                 150                 155                 160

Ala His Gly Ser Asn Val Ala Gly Leu Glu Thr Thr Ala Thr Phe Asp
                165                 170                 175

Lys Glu Ser Asp Glu Phe Val Ile Asn Thr Pro His Ile Gly Ala Thr
            180                 185                 190

Lys Trp Trp Ile Gly Gly Ala Ala His Ser Ala Thr His Cys Ser Val
        195                 200                 205

Tyr Ala Arg Leu Ile Val Asp Gly Gln Asp Tyr Gly Val Lys Thr Phe

-continued

```
               210                 215                 220
Val Val Pro Leu Arg Asp Ser Asn His Asp Leu Met Pro Gly Val Thr
225                 230                 235                 240

Val Gly Asp Ile Gly Pro Lys Met Gly Arg Asp Gly Ile Asp Asn Gly
                245                 250                 255

Trp Ile Gln Phe Ser Asn Val Arg Ile Pro Arg Phe Phe Met Leu Gln
                260                 265                 270

Lys Phe Cys Lys Val Ser Ala Glu Gly Glu Val Thr Leu Pro Pro Leu
                275                 280                 285

Glu Gln Leu Ser Tyr Ser Ala Leu Leu Gly Gly Arg Val Met Met Val
                290                 295                 300

Leu Asp Ser Tyr Arg Met Leu Ala Arg Met Ser Thr Ile Ala Leu Arg
305                 310                 315                 320

Tyr Ala Ile Gly Arg Arg Gln Phe Lys Gly Asp Asn Val Asp Pro Asn
                325                 330                 335

Asp Pro Asn Ala Leu Glu Thr Gln Leu Ile Asp Tyr Pro Leu His Gln
                340                 345                 350

Lys Arg Leu Phe Pro Tyr Phe Val Pro Pro Met Ser Ser Pro Ser Val
                355                 360                 365

Pro Ser Arg Leu Asn Thr Pro Ser Arg Pro Pro Trp Ser Asn Trp Thr
                370                 375                 380

Ser Pro Leu Lys Arg Thr Thr Pro Arg Leu Ile Phe Lys Ser Ile Asp
385                 390                 395                 400

Asp Met Lys Ser Leu Phe Val Asp Ser Gly Ser Leu Lys Ser Thr Ala
                405                 410                 415

Thr Trp Leu Gly Ala Glu Ala Ile Asp Gln Cys Arg Gln Ala Cys Gly
                420                 425                 430

Gly His Gly His Ser Ser Tyr Asn Gly Phe Gly Lys Ala Tyr Asn Asp
                435                 440                 445

Trp Val Val Gln Cys Thr Trp Glu Gly Asp Asn Asn Val Leu Gly Met
                450                 455                 460

Ser Val Gly Lys Pro Ile Val Lys Gln Val Ile Ser Ile Glu Asp Ala
465                 470                 475                 480

Gly Lys Thr Val Arg Gly Ser Thr Ala Phe Leu Asn Gln Leu Lys Glu
                485                 490                 495

Tyr Thr Gly Ser Asn Ser Ser Lys Val Val Leu Asn Thr Val Ala Asp
                500                 505                 510

Leu Asp Asp Ile Lys Thr Val Ile Lys Ala Ile Glu Val Ala Ile Ile
                515                 520                 525

Arg Leu Ser Gln Glu Ala Ala Ser Ile Val Lys Lys Glu Ser Phe Asp
530                 535                 540

Tyr Val Gly Ala Glu Leu Val Gln Leu Ser Lys Leu Lys Ala His His
545                 550                 555                 560

Tyr Leu Leu Thr Glu Tyr Ile Arg Arg Ile Asp Thr Phe Asp Gln Lys
                565                 570                 575

Glu Leu Ala Pro Tyr Leu Ile Thr Leu Gly Lys Leu Tyr Ala Ala Thr
                580                 585                 590

Ile Val Leu Asp Arg Phe Ala Gly Val Phe Leu Thr Phe Asn Val Ala
                595                 600                 605

Ser Thr Glu Ala Ile Thr Ala Leu Ala Ser Val Gln Ile Pro Lys Leu
                610                 615                 620

Cys Ala Glu Val Arg Pro Asn Val Val Ala Tyr Thr Asp Ser Phe Gln
625                 630                 635                 640
```

```
Gln Ser Asp Met Ile Val Asn Ser Ala Ile Gly Arg Tyr Asp Gly Asp
                645                 650                 655

Ile Tyr Glu Asn Tyr Phe Asp Leu Val Lys Leu Gln Asn Pro Pro Ser
            660                 665                 670

Lys Thr Lys Ala Pro Tyr Ser Asp Ala Leu Glu Ala Met Leu Asn Arg
        675                 680                 685

Pro Thr Leu Asp Glu Arg Glu Arg Phe Gln Lys Ser Asp Glu Thr Ala
    690                 695                 700

Ala Ile Leu Ser Lys
705

<210> SEQ ID NO 135
<211> LENGTH: 662
<212> TYPE: PRT
<213> ORGANISM: Candida tropicalis

<400> SEQUENCE: 135

Met Pro Thr Glu Leu Gln Lys Glu Arg Glu Leu Thr Lys Phe Asn Pro
1               5                   10                  15

Lys Glu Leu Asn Tyr Phe Leu Glu Gly Ser Gln Glu Arg Ser Glu Ile
            20                  25                  30

Ile Ser Asn Met Val Glu Gln Met Gln Lys Asp Pro Ile Leu Lys Val
        35                  40                  45

Asp Ala Ser Tyr Tyr Asn Leu Thr Lys Asp Gln Gln Arg Glu Val Thr
    50                  55                  60

Ala Lys Lys Ile Ala Arg Leu Ser Arg Tyr Phe Glu His Glu Tyr Pro
65                  70                  75                  80

Asp Gln Gln Ala Gln Arg Leu Ser Ile Leu Gly Val Phe Asp Pro Gln
                85                  90                  95

Val Phe Thr Arg Ile Gly Val Asn Leu Gly Leu Phe Val Ser Cys Val
            100                 105                 110

Arg Gly Asn Gly Thr Asn Ser Gln Phe Phe Tyr Trp Thr Ile Asn Lys
        115                 120                 125

Gly Ile Asp Lys Leu Arg Gly Ile Tyr Gly Cys Phe Gly Met Thr Glu
    130                 135                 140

Leu Ala His Gly Ser Asn Val Gln Gly Ile Glu Thr Thr Ala Thr Phe
145                 150                 155                 160

Asp Glu Asp Thr Asp Glu Phe Val Ile Asn Thr Pro His Ile Gly Ala
                165                 170                 175

Thr Lys Trp Trp Ile Gly Gly Ala Ala His Ser Ala Thr His Cys Ser
            180                 185                 190

Val Tyr Ala Arg Leu Lys Val Lys Gly Lys Asp Tyr Gly Val Lys Thr
        195                 200                 205

Phe Val Val Pro Leu Arg Asp Ser Asn His Asp Leu Glu Pro Gly Val
    210                 215                 220

Thr Val Gly Asp Ile Gly Ala Lys Met Gly Arg Asp Gly Ile Asp Asn
225                 230                 235                 240

Gly Trp Ile Gln Phe Ser Asn Val Arg Ile Pro Arg Phe Phe Met Leu
                245                 250                 255

Gln Lys Tyr Cys Lys Val Ser Arg Ser Gly Glu Val Thr Met Pro Pro
            260                 265                 270

Ser Glu Gln Leu Ser Tyr Ser Ala Leu Ile Gly Gly Arg Val Thr Met
        275                 280                 285

Met Met Asp Ser Tyr Arg Met Thr Ser Arg Phe Ile Thr Ile Ala Leu
    290                 295                 300
```

```
Arg Tyr Ala Ile His Arg Arg Gln Phe Lys Lys Asp Thr Asp Thr
305                 310                 315                 320

Ile Glu Thr Lys Leu Ile Asp Tyr Pro Leu His Gln Lys Arg Leu Phe
            325                 330                 335

Pro Phe Leu Ala Ala Tyr Leu Phe Ser Gln Gly Ala Leu Tyr Leu
                340                 345                 350

Glu Gln Thr Met Asn Ala Thr Asn Asp Lys Leu Asp Glu Ala Val Ser
            355                 360                 365

Ala Gly Glu Lys Glu Ala Ile Asp Ala Ile Val Glu Ser Lys Lys
        370                 375                 380

Leu Phe Val Ala Ser Gly Cys Leu Lys Ser Thr Cys Thr Trp Leu Thr
385                 390                 395                 400

Ala Glu Ala Ile Asp Glu Ala Arg Gln Ala Cys Gly Gly His Gly Tyr
                405                 410                 415

Ser Ser Tyr Asn Gly Phe Gly Lys Ala Tyr Ser Asp Trp Val Val Gln
            420                 425                 430

Cys Thr Trp Glu Gly Asp Asn Asn Ile Leu Ala Met Asn Val Ala Lys
            435                 440                 445

Pro Met Val Arg Asp Leu Leu Lys Glu Pro Glu Gln Lys Gly Leu Val
        450                 455                 460

Leu Ser Ser Val Ala Asp Leu Asp Asp Pro Ala Lys Leu Val Lys Ala
465                 470                 475                 480

Phe Asp His Ala Leu Ser Gly Leu Ala Arg Asp Ile Gly Ala Val Ala
                485                 490                 495

Glu Asp Lys Gly Phe Asp Ile Thr Gly Pro Ser Leu Val Leu Val Ser
            500                 505                 510

Lys Leu Asn Ala His Arg Phe Leu Ile Asp Gly Phe Phe Lys Arg Ile
            515                 520                 525

Thr Pro Glu Trp Ser Glu Val Leu Arg Pro Leu Gly Phe Leu Tyr Ala
        530                 535                 540

Asp Trp Ile Leu Thr Asn Phe Gly Ala Thr Phe Leu Gln Tyr Gly Ile
545                 550                 555                 560

Ile Thr Pro Asp Val Ser Arg Lys Ile Ser Ser Glu His Phe Pro Ala
                565                 570                 575

Leu Cys Ala Lys Val Arg Pro Asn Val Val Gly Leu Thr Asp Gly Phe
            580                 585                 590

Asn Leu Thr Asp Met Met Thr Asn Ala Ala Ile Gly Arg Tyr Asp Gly
            595                 600                 605

Asn Val Tyr Glu His Tyr Phe Glu Thr Val Lys Ala Leu Asn Pro Pro
        610                 615                 620

Glu Asn Thr Lys Ala Pro Tyr Ser Lys Ala Leu Glu Asp Met Leu Asn
625                 630                 635                 640

Arg Pro Asp Leu Glu Val Arg Glu Arg Gly Glu Lys Ser Glu Glu Ala
                645                 650                 655

Ala Glu Ile Leu Ser Ser
            660

<210> SEQ ID NO 136
<211> LENGTH: 2845
<212> TYPE: DNA
<213> ORGANISM: Candida tropicalis

<400> SEQUENCE: 136
gagctccaat tgtaatattt cgggagaaat atcgttgggg taaaacaaca gagagagaga      60
gggagagatg gttctggtag aattataatc tggttgttgc aaatgctact gatcgactct     120
```

```
ggcaatgtct gtagctcgct agttgtatgc aacttaggtg ttatgcatac acacggttat    180
tcggttgaat tgtggagtaa aaattgtctg agttgtgtct tagctactgg ctggcccccc    240
gcgaaagata atcaaaatta cacttgtgaa ttttgcaca cacaccgatt aacatttccc     300
ttttttgtcc accgatacac gcttgcctct tcttttttt ctctgtgctt cccctcctg      360 tgacttttc caccattgat ataaaatcaa ctccatttcc ctaaaatctc ccagattct      420 aaaaacaact tcttctcttc tgcttttcct tttttttgt tatatttatt taccatccct    480
tttttttgaa tagttattcc ccactaacat tgttcaaatc ttcacgacat aatgactttt   540 acaagaaaa acgttagtgt atcacaaggt cctgaccta gatcatccat ccaaaaggaa     600
agagacagct ccaaatggaa ccctcaacaa atgaactact tcttggaagg ctccgtcgaa   660
agaagtgagt tgatgaaggc tttggcccaa caaatggaaa gagacccaat cttgttcaca   720
gacggctcct actacgactt gaccaaggac caacaaagag aattgaccgc cgtcaagatc   780
aacagaatcg ccagatacag agaacaagaa tccatcgaca ctttcaacaa gagattgtcc   840
ttgattggta tctttgaccc acaggtcggt accagaattg tgtcaacct cggtttgttc    900 cttctcttgta tcagaggtaa cggtaccact tcccaattga actactgggc taacgaaaag   960
gaaaccgctg acgttaaagg tatctacggt tgtttcggta tgaccgaatt ggcccacggt   1020
tccaacgttg ctggttttgga aaccaccgcc acatttgaca aggaatctga cgagtttgtc   1080
atcaacaccc cacacattgg tgccaccaag tggtggattg tggtgctgc tcactccgcc   1140 acccactgtt ctgtctacgc cagattgatt gttgacggtc aagattacgg tgtcaagact   1200
tttgttgtcc cattgagaga ctccaaccac gacctcatgc caggtgtcac tgttggtgac   1260
attggtgcca agatgggtag agatggtatc gataacggtt ggatccaatt ctccaacgtc   1320
agaatcccaa gattctttat gttgcaaaag ttctgtaagg ttttctgctga aggtgaagtc   1380 accttgccac ctttggaaca attgtcttac tccgccttgt tgggtggtag agtcatgatg   1440
gttttggact cctacagaat gttggctaga atgtccacca ttgccttgag atacgccatt   1500
ggtagaagac aattcaaggg tgacaatgtc gatccaaaag atccaaacgc tttggaaacc   1560
caattgatag attacccatt gcaccaaaag agattgttcc catacttggc tgctgcctac   1620
gtcatctccg ctggtgccct caaggttgaa gacaccatcc ataacacctt ggctgaattg   1680
gacgctgccg ttgaaaagaa cgacaccaag gctatcttta gtctattga cgacatgaag   1740 tcattgtttg ttgactctgg ttccttgaag tccactgcca cttggttggg tgctgaagcc   1800
attgaccaat gtagacaagc ctgtggtggt cacggttact cgtcctacaa cggcttcggt   1860
aaagcctaca acgattgggt tgtccaatgt acttgggaag gtgacaacaa tgtcttggcc   1920
atgagtgttg gtaagccaat tgtcaagcaa gttatcagca ttgaagatgc cggcaagacc   1980
gtcagaggtt ccaccgcttt cttgaaccaa ttgaaggact acactggttc caacagctcc   2040
aaggttgttt tgaacactgt tgctgacttg gacgacatca agactgtcat caaggctatt   2100
gaagttgcca tcatcagatt gtcccaagaa gctgcttcta ttgtcaagaa ggaatctttc   2160
gactatgtcg gcgctgaatt ggttcaactc tccaagttga aggctcacca ctacttgttg   2220
actgaataca tcagaagaat tgacacctt gaccaaaagg acttggttcc atacttgatc   2280
accctcggta agttgtacgc tgccactatt gtcttggaca gatttgccgg tgtcttcttg   2340
actttcaacg ttgcctccac cgaagccatc actgctttgg cctctgtgca aattccaaag   2400
ttgtgtgctg aagtcagacc aaacgttgtt gcttacaccg actccttcca acaatccgac   2460
atgattgtca attctgctat tggtagatac gatggtgaca tctatgagaa ctactttgac   2520
```

```
ttggtcaagt tgcagaaccc accatccaag accaaggctc cttactctga tgctttggaa    2580
gccatgttga acagaccaac cttggacgaa agagaaagat ttgaaaagtc tgatgaaacc    2640
gctgctatct tgtccaagta agaatagaag agagtgactc ttttgataag agtcgcaaat    2700
ttgatttcat aagtatatat tcattatgta aagtagtaaa tggaaaattc attaaaaaaa    2760
aagcaaattt ccgttgtatg catactccga acacaaaact agccccggaa aaacccttag    2820
ttgatagttg cgaatttagg tcgac                                          2845
```

<210> SEQ ID NO 137
<211> LENGTH: 640
<212> TYPE: DNA
<213> ORGANISM: Artificial Sequence
<220> FEATURE:
<223> OTHER INFORMATION: Pre-targeting construct for transformation of
    POX4 into Candida tropicalis

<400> SEQUENCE: 137

```
cgtctccaaa aggaaagaga cagctccaaa tggaaccctc aacaaatgaa ctacttcttg     60
gaaggctccg tcgaaagaag tgagttgatg aaggctttgg cccaacaaat ggaaagagac    120
ccaatcttgt tcacagacgg ctcctactac gacttgacca aggaccaaca aagagaattg    180
accgccgtca agatcaacag aatcgccaga tacagaaaac aagaatccat cgacactttc    240
aacaagagat tgtccttgat tggtatcttt gacccacagg tcggtaccag aattggtgtc    300
aacgcggccg ctagatcttg cgaagctcca tctcgagact attgtcttgg acagatttgc    360
cggtgtcttc ttgactttca acgttgcctc caccgaagcc atcactgctt tggcctctgt    420
gcaaattcca aagttgtgtg ctgaagtcag accaaacgtt gttgcttaca ccgactcctt    480
ccaacaatcc gacatgattg tcaattctgc tattggtaga tacgatggtg acatctatga    540
gaactacttt gacttggtca agttgcagaa cccaccatcc aagaccaagg ctccttactc    600
tgatgctttg gaagccatgt tgaacagacc aaccgagacg                          640
```

<210> SEQ ID NO 138
<211> LENGTH: 640
<212> TYPE: DNA
<213> ORGANISM: Artificial Sequence
<220> FEATURE:
<223> OTHER INFORMATION: pre-targeting construct for targeting POX4 in
    Candida tropicalis

<400> SEQUENCE: 138

```
cgtctcgcta acgaaaagga aaccgctgac gttaaaggta tctacggttg tttcggtatg     60
accgaattgg cccacggttc caacgttgct ggtttggaaa ccaccgccac atttgacaag    120
gaatctgacg agtttgtcat caacacccca cacattggtg ccaccaagtg gtggattggt    180
ggtgctgctc actccgccac ccactgttct gtctacgcca gattgattgt tgacggtcaa    240
gattacggtg tcaagacttt tgttgtccca ttgagagact ccaaccacga cctcatgcca    300
ggtgcggccg ctagatcttg cgaagctcca tctcgagcaa gttatcagca ttgaagatgc    360
cggcaagacc gtcagaggtt ccaccgcttt cttgaaccaa ttgaaggact acactggttc    420
caacagctcc aaggttgttt tgaacactgt tgctgacttg gacgacatca agactgtcat    480
caaggctatt gaagttgcca tcatcagatt gtcccaagaa gctgcttcta ttgtcaagaa    540
ggaatctttc gactatgtcg gcgctgaatt ggttcaactc tccaagttga aggctcacca    600
ctacttgttg actgaataca tcagaagaat tgacgagacg                          640
```

<210> SEQ ID NO 139
<211> LENGTH: 4792
<212> TYPE: DNA
<213> ORGANISM: Artificial Sequence
<220> FEATURE:
<223> OTHER INFORMATION: Sequence of a first targeting construct for the deletion of a first allele of POX4 in Candida tropicalis

<400> SEQUENCE: 139

| | | | | | |
|---|---|---|---|---|---|
| cgtctccaaa | aggaaagaga | cagctccaaa | tggaaccctc | aacaaatgaa ctacttcttg | 60 |
| gaaggctccg | tcgaaagaag | tgagttgatg | aaggctttgg | cccaacaaat ggaaagagac | 120 |
| ccaatcttgt | tcacagacgg | ctcctactac | gacttgacca | aggaccaaca agagaattg | 180 |
| accgccgtca | agatcaacag | aatcgccaga | tacagagaac | aagaatccat cgacactttc | 240 |
| aacaagagat | tgtccttgat | tggtatcttt | gacccacagg | tcggtaccag aattggtgtc | 300 |
| aacgcggccg | ctctagaact | agtggatctg | aagttcctat | tctctagaaa gtataggaac | 360 |
| ttcctgcagg | accaccttg | attgtaaata | gtaataatta | ccacccttat ctaattattt | 420 |
| atttaactta | tttatttatt | tattatacat | atatacaaat | ctaataaagt gaaaatctcc | 480 |
| cccttcacac | ttcacatatg | ttaggcgtca | tcctgtgctc | ccgagaacca gtaccagtac | 540 |
| atcgctgttt | cgttcgagac | ttgaggtcta | gttttatacg | tgaagaggtc aatgccgccg | 600 |
| agagtaaagc | cacattttgc | gtacaaattg | caggcaggta | cattgttcgt ttgtgtctct | 660 |
| aatcgtatgc | caaggagctg | tctgcttagt | gcccactttt | tcgcaaattc gatgagactg | 720 |
| tgcgcgactc | ctttgcctcg | gtgcgtgtgc | gacacaacaa | tgtgttcgat agaggctaga | 780 |
| tcgttccatg | ttgagttgag | ttcaatcttc | ccgacaagct | cttggtcgat gaatgcgcca | 840 |
| tagcaagcag | agtcttcatc | agagtcatca | tccgagatgt | aatccttccg gtaggggctc | 900 |
| acacttctgg | tagatagttc | aaagccttgg | tcggataggt | gcacatcgaa cacttcacga | 960 |
| acaatgaaat | ggttctcagc | atccaatgtt | tccgccacct | gctcagggat caccgaaatt | 1020 |
| ttcatatgag | aaccgttatc | gataactaaa | gcagcaactt | cttctataaa aatgggttag | 1080 |
| tatgacagtc | atttaaataa | ggaatttttc | agttggcttg | gtttcaattc aatgttcgtt | 1140 |
| tttttttttt | cttgctgtgt | ttgtgtttgt | gttgtttata | gttgtgtgca ctgagcgtcg | 1200 |
| aaaaaaaaaa | ttcatagtga | gccgggaaat | ctgtatagcc | cagataacaa cacaagtcca | 1260 |
| aactagaaac | tcgtcaaaca | ccaaaagcaa | tgttgaatca | attgccttgc acaagtacac | 1320 |
| gtaggaaaac | ataaaacatt | gcaatttgta | atattgagcc | ttttgtcgta acattgattg | 1380 |
| ataggattac | tcaccgaatg | gttttgaaac | cactgccgac | agatcaatca atcaatcaaa | 1440 |
| aaacgtgaac | tttgaaaaag | gggaagaaca | gatacattga | agttagccat ttccattgat | 1500 |
| cgtcacaaca | tatctgataa | attactttca | aaattataag | ctgatgtgtg tgtattatta | 1560 |
| atgtgacagt | aacatcccaa | acgagaaata | ttatgtcgac | aacaaaaaag tttgatctga | 1620 |
| attgaaaatg | aagttttccc | accctaccca | tttgtcatat | tgaaccaat caactgatta | 1680 |
| atcaatcaat | tagaattgaa | gctaaactaa | aacataccac | cgtccatttt gaatgattat | 1740 |
| attttttaa | tattaatatc | gagataatgt | ttctaagaaa | gaaagaaaac caggagtgaa | 1800 |
| aattagaaaa | ggaaaggaaa | ggaaaaaaag | aaaaatctga | aatatataa aaaaaaattg | 1860 |
| tttcgttggc | aataaatctt | ggtgagaaca | gcgaccgaaa | gcaaataaga acaaatatg | 1920 |
| agtgtattac | gttgaacaac | taattaacgt | gtgtgtatgg | atcttttttt cttttttctc | 1980 |
| tttaaccgac | tataacaac | aaacattttt | gggcagtgca | cacactactt aatatacaca | 2040 |
| gcataaatta | cacgattaga | aacaaattag | cttattaaaa | taacctaatc aaaccgaata | 2100 |

```
ttttatggta ttatgagtaa actatataat ataaatagca cacacccaca acaacaacaa    2160
aggaaaacta aaaggttttt tctttttgaa aagatcgttt tctttattat tctctagttt    2220
tgacgctcga catttatga tggaatgaat gggatgaatc atcaaacaag agaaaatacc    2280
cgtgacgaaa ataataaaat aagttcctct gatacagaag atgaaaacaa caacaacaag    2340
atatagaaat gccttgggtg gctatttat agtcttaact ttttaatgta tatttgtttt    2400
gttttttac ataataatac tttataaaag ctaagctaaa ttcaagtaaa atttcaatct    2460
ctcaaataaa acatttttct cttttctta aatttagttt tatatattta taaaatatac    2520
aaagattttt ttaaaaaagt aacaagttat atatgtaata acaaaaagaa gaataacaag    2580
aatacaaaac cagatttcca gatttccaga atttcactct tatatgcgtc tatttatgta    2640
ggatgaaagg tagtctagta cctcctgtga tattatccca ttccatgcgg ggtatcgtat    2700
gcttccttca gcactaccct ttagctgttc tatatgctgc cactcctcaa ttggattagt    2760
ctcatccttc aatgctatca tttcctttga tattggatca tatgcatagt accgagaaac    2820
tagtgcgaag tagtgatcag gtattgctgt tatctgatga gtatacgttg tcctggccac    2880
ggcagaagca cgcttatcgc tccaatttcc cacaacatta gtcaactccg ttaggccctt    2940
cattgaaaga aatgaggtca tcaaatgtct tccaatgtga gattttgggc catttttat    3000
agcaaagatt gaataaggcg catttttctt caaagcttta ttgtacgatc tgactaagtt    3060
atctttaat aattggtatt cctgtttatt gcttgaagaa ttgccggtcc tatttactcg    3120
ttttaggact ggttcagaat tcctcaaaaa ttcatccaaa tatacaagtg gatcgatcct    3180
accccttgcg ctaagaagt atatgtgcct actaacgctt gtctttgtct ctgtcactaa    3240
acactggatt attactccca aatacttatt ttggactaat ttaaatgatt tcggatcaac    3300
gttcttaata tcgctgaatc ttccacaatt gatgaaagta gctaggaaga ggaattggta    3360
taaagttttt gtttttgtaa atctcgaagt atactcaaac gaatttagta ttttctcagt    3420
gatctcccag atgctttcac cctcacttag aagtgcttta agcattttt tactgtggct    3480
atttcccta tctgcttctt ccgatgattc gaactgtaat tgcaaactac ttacaatatc    3540
agtgatatca gattgatgtt tttgtccata gtaaggaata attgtaaatt cccaagcagg    3600
aatcaatttc tttaatgagg cttccaaaat tgttgctttt tgcgtcttgt atttaaactg    3660
gagtgattta ttgacaatat cgaaactcaa cgaattgctt atgatagtat tatagctcat    3720
gaatgtggct ctcttgattg ctgttccgtt atgtgtaatc atccaacata aataggttag    3780
ttcagcagca cataatgcta ttttctcacc tgaaggtctt tcaaaccttt ccacaaactg    3840
acgaacaagc accttaggtg gtgttttaca taatatatca aattgtggca tgtcgacgat    3900
tattagttaa accactgcaa aaagttgggg aaaattttgc ccatttttat accgtgtctt    3960
cgtctatcgc ctccccact ccccaatctt tgaattattc cgaaatattc agcgaacggg    4020
gtgtacacaa aaactaacat tctcaactgc ataatttgaa aaatggcgtg ggacaagaaa    4080
aaaaaaaaat tctcaaccat agcaatcatg gaatacggta aatttgtgtt gttcggtgac    4140
tccatcaccc agtttagttg tacccagtat ggctttcatc cagcattaca gaatgtgtat    4200
atccgaaaat tggatgttat taaccgtggt ttcagtggct acaactcaga gcacgctaga    4260
caaattcttc caaaatttt agagtcggaa accaatatca aattgatgac aatattttt    4320
ggaactaacg atgcatacga ctacatcaat gaaatccaga cagtcgagtt agacagatat    4380
aaagataatt taagtgtaat ggtacagatg gtactagaca aaaatatcaa accaatcatt    4440
attggatccg aagttcctat tctctagaaa gtataggaac ttcctcgaga ctattgtctt    4500
```

-continued

```
ggacagattt gccggtgtct tcttgacttt caacgttgcc tccaccgaag ccatcactgc    4560
tttggcctct gtgcaaattc caaagttgtg tgctgaagtc agaccaaacg ttgttgctta    4620
caccgactcc ttccaacaat ccgacatgat tgtcaattct gctattggta gatacgatgg    4680
tgacatctat gagaactact ttgacttggt caagttgcag aacccaccat ccaagaccaa    4740
ggctccttac tctgatgctt tggaagccat gttgaacaga ccaaccgaga cg            4792
```

<210> SEQ ID NO 140
<211> LENGTH: 4792
<212> TYPE: DNA
<213> ORGANISM: Artificial Sequence
<220> FEATURE:
<223> OTHER INFORMATION: Sequence of a resulting second targeting construct for the deletion of the second allele of POX4 in Candida tropicalis

<400> SEQUENCE: 140

```
cgtctcgcta acgaaaagga aaccgctgac gttaaaggta tctacggttg tttcggtatg      60
accgaattgg cccacggttc caacgttgct ggtttggaaa ccaccgccac atttgacaag     120
gaatctgacg agtttgtcat caacacccca cacattggtg ccaccaagtg gtggattggt     180
ggtgctgctc actccgccac ccactgttct gtctacgcca gattgattgt tgacggtcaa     240
gattacggtg tcaagacttt tgttgtccca ttgagagact ccaaccacga cctcatgcca     300
ggtgcggccg ctctagaact agtggatctg aagttcctat tctctagaaa gtataggaac     360
ttcctgcagg accacctttg attgtaaata gtaataatta ccacccttat ctaattattt     420
atttaactta tttatttatt tattatacat atatacaaat ctaataaagt gaaaatctcc     480
cccttcacac ttcacatatg ttaggcgtca tcctgtgctc ccgagaacca gtaccagtac     540
atcgctgttt cgttcgagac ttgaggtcta gttttatacg tgaagaggtc aatgccgccg     600
agagtaaagc cacattttgc gtacaaattg caggcaggta cattgttcgt ttgtgtctct     660
aatcgtatgc caaggagctg tctgcttagt gcccactttt tcgcaaattc gatgagactg     720
tgcgcgactc ctttgcctcg gtgcgtgtgc gacacaacaa tgtgttcgat agaggctaga     780
tcgttccatg ttgagttgag ttcaatcttc ccgacagct cttggtcgat gaatgcgcca     840
tagcaagcag agtcttcatc agagtcatca tccgagatgt aatccttccg gtaggggctc     900
acacttctgg tagatagttc aaagccttgg tcggataggt gcacatcgaa cacttcacga     960
acaatgaaat ggttctcagc atccaatgtt tccgccacct gctcagggat caccgaaatt    1020
ttcatatgag aaccgttatc gataactaaa gcagcaactt cttctataaa atgggttag     1080 tatgacagtc atttaaataa ggaattttt agttggcttg gtttcaattc aatgttcgtt     1140 ttttttttt cttgctgtgt tgtgtttgt gttgtttata gttgtgtgca ctgagcgtcg     1200
aaaaaaaaaa ttcatagtga gccgggaaat ctgtatagcc cagataacaa cacaagtcca    1260
aactagaaac tcgtcaaaca ccaaaagcaa tgttgaatca attgccttgc acaagtacac    1320
gtaggaaaac ataaaacatt gcaattttga atattgagcc ttttgtcgta acattgattg    1380
ataggattac tcaccgaatg gttttgaaac cactgccgac agatcaatca atcaatcaaa    1440
aaacgtgaac tttgaaaaag gggaagaaca gatacattga agttagccat ttccattgat    1500
cgtcacaaca tatctgataa attactttca aaattataag ctgatgtgtg tgtattatta    1560
atgtgacagt aacatcccaa acgagaaata ttatgtcgac aacaaaaaag tttgatctga    1620
attgaaaatg aagtttttccc accctaccca tttgtcatat tgaaaccaat caactgatta    1680
atcaatcaat tagaattgaa gctaaactaa aacataccac cgtccatttt gaatgattat    1740
```

-continued

```
attttttttaa tattaatatc gagataatgt ttctaagaaa gaaagaaaac caggagtgaa    1800
aattagaaaa ggaaaggaaa ggaaaaaaag aaaaatctga aaatatataa aaaaaaattg    1860
tttcgttggc aataaatctt ggtgagaaca gcgaccgaaa gcaaataaga acaaaatatg    1920
agtgtattac gttgaacaac taattaacgt gtgtgtatgg atcttttttt cttttttctc    1980
tttaaccgac tataaacaac aaacattttt gggcagtgca cacactactt aatatacaca    2040
gcataaatta cacgattaga aacaaattag cttattaaaa taacctaatc aaaccgaata    2100
ttttatggta ttatgagtaa actatataat ataaatagca cacacccaca acaacaacaa    2160
aggaaaacta aaaggttttt tcttttttgaa aagatcgttt tctttattat tctctagttt    2220
tgacgctcga catttttatga tggaatgaat gggatgaatc atcaaacaag agaaaatacc    2280
cgtgacgaaa ataataaaat aagttcctct gatacagaag atgaaaacaa caacaacaag    2340
atatagaaat gccttgggtg gctatttttat agtcttaact ttttaatgta tatttgtttt    2400 gttttttttac ataataatac tttataaaag ctaagctaaa ttcaagtaaa atttcaatct    2460
ctcaaataaa acattttttct cttttttctta aatttagttt tatatattta taaaatatac    2520 aaagatttttt ttaaaaaagt aacaagttat atatgtaata acaaaaagaa gaataacaag    2580
aatacaaaac cagatttcca gatttccaga atttcactct tatatgcgtc tatttatgta    2640
ggatgaaagg tagtctagta cctcctgtga tattatccca ttccatgcgg ggtatcgtat    2700
gcttccttca gcactaccct ttagctgttc tatatgctgc cactcctcaa ttggattagt    2760
ctcatccttc aatgctatca tttcctttga tattggatca tatgcatagt accgagaaac    2820
tagtgcgaag tagtgatcag gtattgctgt tatctgatga gtatacgttg tcctggccac    2880
ggcagaagca cgcttatcgc tccaatttcc cacaacatta gtcaactccg ttaggccctt    2940
cattgaaaga aatgaggtca tcaaatgtct tccaatgtga gattttgggc catttttat    3000 agcaaagatt gaataaggcg catttttctt caaagcttta ttgtacgatc tgactaagtt    3060 atctttttaat aattggtatt cctgtttatt gcttgaagaa ttgccggtcc tatttactcg    3120
ttttaggact ggttcagaat tcctcaaaaa ttcatccaaa tatacaagtg gatcgatcct    3180
accccttgcg ctaaagaagt atatgtgcct actaacgctt gtctttgtct ctgtcactaa    3240
acactggatt attactccca aatacttatt ttggactaat ttaaatgatt tcggatcaac    3300
gttcttaata tcgctgaatc ttccacaatt gatgaaagta gctaggaaga ggaattggta    3360
taaagttttt gttttttgtaa atctcgaagt atactcaaac gaatttagta ttttctcagt    3420
gatctcccag atgctttcac cctcacttag aagtgcttta agcattttttt tactgtggct    3480 atttcccttaa tctgcttctt ccgatgattc gaactgtaat tgcaaactac ttacaatatc    3540
agtgatatca gattgatgtt tttgtccata gtaaggaata attgtaaatt ccaagcagg    3600 aatcaatttc tttaatgagg cttccaaaat tgttgctttt tgcgtcttgt atttaaactg    3660
gagtgattta ttgacaatat cgaaactcaa cgaattgctt atgatagtat tatagctcat    3720
gaatgtggct ctcttgattg ctgttccgtt atgtgtaatc atccaacata aataggttag    3780
ttcagcagca cataatgcta ttttctcacc tgaaggtctt tcaaaccttt ccacaaactg    3840
acgaacaagc accttaggtg gtgttttaca taatatatca aattgtggca tgtcgacgat    3900
tattagttaa accactgcaa aaagttgggg aaaattttgc ccatttttat accgtgtctt    3960
cgtctatcgc ctccccccact ccccaatctt tgaattattc cgaaatattc agcgaacggg    4020
gtgtacacaa aaactaacat tctcaactgc ataatttgaa aaatggcgtg ggacaagaaa    4080
aaaaaaaaat tctcaaccat agcaatcatg gaatacggta aatttgtgtt gttcggtgac    4140
```

-continued

```
tccatcaccc agtttagttg tacccagtat ggctttcatc cagcattaca gaatgtgtat    4200
atccgaaaat tggatgttat taaccgtggt ttcagtggct acaactcaga gcacgctaga    4260
caaattcttc caaaaatttt agagtcggaa accaatatca aattgatgac aatattttt     4320 ggaactaacg atgcatacga ctacatcaat gaaatccaga cagtcgagtt agacagatat    4380
aaagataatt taagtgtaat ggtacagatg gtactagaca aaaatatcaa accaatcatt    4440
attggatccg aagttcctat tctctagaaa gtataggaac ttcctcgagc aagttatcag    4500
cattgaagat gccggcaaga ccgtcagagg ttccaccgct ttcttgaacc aattgaagga    4560
ctacactggt tccaacagct ccaaggttgt tttgaacact gttgctgact ggacgacat    4620 caagactgtc atcaaggcta ttgaagttgc catcatcaga ttgtcccaag aagctgcttc    4680
tattgtcaag aaggaatctt tcgactatgt cggcgctgaa ttggttcaac tctccaagtt    4740
gaaggctcac cactacttgt tgactgaata catcagaaga attgacgaga cg            4792
```

<210> SEQ ID NO 141
<211> LENGTH: 37
<212> TYPE: DNA
<213> ORGANISM: Candida tropicalis

<400> SEQUENCE: 141

```
atgactttta caaagaaaaa cgttagtgta tcacaag                              37
```

<210> SEQ ID NO 142
<211> LENGTH: 27
<212> TYPE: DNA
<213> ORGANISM: Artificial Sequence
<220> FEATURE:
<223> OTHER INFORMATION: Oligonucleotide primer for evaluating contructs

<400> SEQUENCE: 142

```
ttacttggac aagatagcag cggtttc                                         27
```

<210> SEQ ID NO 143
<211> LENGTH: 2624
<212> TYPE: DNA
<213> ORGANISM: Candida tropicalis

<400> SEQUENCE: 143

```
gaattcacat ggctaatttg gcctcggttc cacaacgcac tcagcattaa aaaaaaaata    60
cgcaatggca gctcggtcga cgcagcagaa gcgccgacgt accgtcgcgt tgccccgccc    120
atgcctcgcc gacccctcca ccgccatcgt ttgcccattg tttgtggtag tgcgccgtga    180
cacaaaaact tgtcctgtca catgctgaag ttacaccaac ataactacta tgggattacg    240
taatcaaaaa tttcacagtt ttaacaaaaa aaaatcata caatcaacat tgggacatct    300
tgccctcccc cacaaaactt gcttctgcat caatcatata taaacatcat gaaataagcc    360
taaactcact tcttttttt tcatccttcc tacttcttct ttcatagtaa ctactttttt    420
tttattacca cacttattca ttcataccac gctatcatgc ctaccgaact tcaaaagaa    480 agagaactca ccaagttcaa cccaaaggag ttgaactact tcttggaagg ttcccaagaa    540
agatccgaga tcatcagcaa catggtcgaa caaatgcaaa agaccctat cttgaaggtc    600 gacgcttcat actacaactt gaccaaagac caacaaagag aagtcaccgc caagaagatt    660
gccagactct ccagatactt tgagcacgag tacccagacc aacaggccca gagattgtcg    720
atcctcggtg tctttgaccc acaagtcttc accagaatcg gtgtcaactt gggttttgttt    780 gtttcctgtg tccgtggtaa cggtaccaac tcccagttct tctactggac cataaataag    840
```

-continued

```
ggtatcgaca agttgagagg tatctatggt tgttttggta tgactgagtt ggcccacggt      900
tccaacgtcc aaggtattga accaccgcc acttttgacg aagacactga cgagtttgtc      960
atcaacaccc cacacattgg tgccaccaag tggtggatcg gtggtgctgc gcactccgcc     1020
acccactgct ccgtctacgc cagattgaag gtcaaaggaa aggactacgg tgtcaagacc     1080
tttgttgtcc cattgagaga ctccaaccac gacctcgagc caggtgtgac tgttggtgac     1140
attggtgcca agatgggtag agacggtatc gataacggtt ggatccagtt ctccaacgtc     1200
agaatcccaa gattctttat gttgcaaaag tactgtaagg tttcccgtct gggtgaagtc     1260
accatgccac catctgaaca attgtcttac tcggctttga ttggtggtag agtcaccatg     1320
atgatggact cctacagaat gaccagtaga ttcatcacca ttgccttgag atacgccatc     1380
cacagaagac aattcaagaa gaaggacacc gataccattg aaaccaagtt gattgactac     1440
ccattgcatc aaaagagatt gttcccattc ttggctgccg cttacttgtt ctcccaaggt     1500
gccttgtact tagaacaaac catgaacgca accaacgaca agttggacga agctgtcagt     1560
gctggtgaaa aggaagccat tgacgctgcc attgtcgaat ccaagaaatt gttcgtcgct     1620
tccggttgtt tgaagtccac ctgtacctgg ttgactgctg aagccattga cgaagctcgt     1680
caagcttgtg gtggtcacgg ttactcgtct tacaacggtt tcggtaaagc ctactccgac     1740
tgggttgtcc aatgtacctg ggaaggtgac aacaacatct tggccatgaa cgttgccaag     1800
ccaatggtta gagacttgtt gaaggagcca gaacaaaagg gattggttct ctccagcgtt     1860
gccgacttgg acgacccagc caagttggtt aaggctttcg accacgccct ttccggcttg     1920
gccagagaca ttggtgctgt tgctgaagac aagggtttcg acattaccgg tccaagtttg     1980
gttttggttt ccaagttgaa cgctcacaga ttcttgattg acggtttctt caagcgtatc     2040
accccagaat ggtctgaagt cttgagacct ttgggtttct tgtatgccga ctggatcttg     2100
accaactttg gtgccacctt cttgcagtac ggtatcatta ccccagatgt cagcagaaag     2160
atttcctccg agcacttccc agccttgtgt gccaaggtta gaccaaacgt tgttggtttg     2220
actgatggtt tcaacttgac tgacatgatg accaatgctg ctattggtag atatgatggt     2280
aacgtctacg aacactactt cgaaactgtc aaggctttga accccaccaga aaacaccaag     2340
gctccatact ccaaggcttt ggaagacatg ttgaaccgtc cagaccttga agtcagagaa     2400
agaggtgaaa agtccgaaga agctgctgaa atccttgtcca gttaatagag cactaggttt     2460
tgataatttg gttcttacag tttatgtatt ttgattcttc cttttttaga tactttttt      2520
tatatttat tattccttat tgatgtaacg acagtcccac tataattaac ttaaactttg     2580
ctgtaaatca gatgacaagt gttcccctgt ttgcagggga gctc                       2624
```

<210> SEQ ID NO 144
<211> LENGTH: 640
<212> TYPE: DNA
<213> ORGANISM: Artificial Sequence
<220> FEATURE:
<223> OTHER INFORMATION: Pretargeting construct for deletion of POX5
      allele from Candida tropicalis

<400> SEQUENCE: 144

```
cgtctctact tcttggaagg ttcccaagaa agatccgaga tcatcagcaa catggtcgaa       60
caaatgcaaa aagaccctat cttgaaggtc gacgcttcat actacaactt gaccaaagac      120
caacaaagag aagtcaccgc caagaagatt gccagactct ccagatactt tgagcacgag      180
tacccagacc aacaggccca gagattgtcg atcctcggtg tctttgaccc acaagtcttc      240
accagaatcg gtgtcaactt gggtttgttt gtttcctgtg tccgtggtaa cggtaccaac      300
```

```
tccgcggccg ctagatcttg cgaagctcca tctcgaggac tggatcttga ccaactttgg      360
tgccaccttc ttgcagtacg gtatcattac cccagatgtc agcagaaaga tttcctccga      420
gcacttccca gccttgtgtg ccaaggttag accaaacgtt gttggtttga ctgatggttt      480
caacttgact gacatgatga ccaatgctgc tattggtaga tatgatggta acgtctacga      540
acactacttc gaaactgtca aggctttgaa cccaccagaa aacaccaagg ctccatactc      600
caaggctttg gaagacatgt tgaaccgtcc agacgagacg                            640
```

<210> SEQ ID NO 145
<211> LENGTH: 640
<212> TYPE: DNA
<213> ORGANISM: Artificial Sequence
<220> FEATURE:
<223> OTHER INFORMATION: Second POX5 Pre-Targeting Sequence for deletion
      of POX5 allele from Candida tropicalis

<400> SEQUENCE: 145

```
cgtctctttg gtatgactga gttggcccac ggttccaacg tccaaggtat tgaaaccacc      60
gccacttttg acgaagacac tgacgagttt gtcatcaaca ccccacacat tggtgccacc     120
aagtggtgga tcggtggtgc tgcgcactcc gccacccact gctccgtcta cgccagattg     180
aaggtcaaag gaaaggacta cggtgtcaag acctttgttg tcccattgag agactccaac     240
cacgacttcg agccaggtgt gactgttggt gacattggtg ccaagatggg taaagacggt     300
atcgcggccg ctagatcttg cgaagctcca tctcgagtac tccgactggg ttgtccaatg     360
tacctgggaa ggtgacaaca acatcttggc catgaacgtt gccaagccaa tggttagaga     420
cttgttgaag gagccagaac aaaagggatt ggttctctcc agcgttgccg acttggacga     480
cccagccaag ttggttaagg ctttcgacca cgcccttttcc ggcttggcca gagacattgg     540
tgctgttgct gaagacaagg gtttcgacat taccggtcca agtttggttt tggtttccaa     600
gttgaacgct cacagattct tgattgacgg tttcgagacg                            640
```

<210> SEQ ID NO 146
<211> LENGTH: 4792
<212> TYPE: DNA
<213> ORGANISM: Artificial Sequence
<220> FEATURE:
<223> OTHER INFORMATION: Sequence of resulting first targeting construct
      for deletion of a first allele of POX5 in Candida tropicalis

<400> SEQUENCE: 146

```
cgtctctact tcttggaagg ttcccaagaa agatccgaga tcatcagcaa catggtcgaa      60
caaatgcaaa aagaccctat cttgaaggtc gacgcttcat actacaactt gaccaaagac     120
caacaaagag aagtcaccgc caagaagatt gccagactct ccagatactt tgagcacgag     180
tacccagacc aacaggccca gagattgtcg atcctcggtg tctttgaccc acaagtcttc     240
accagaatcg gtgtcaactt gggtttgttt gtttcctgtg tccgtggtaa cggtaccaac     300
tccgcggccg ctctagaact agtggatctg aagttcctat tctctagaaa gtataggaac     360
ttcctgcagg accaccttg attgtaaata gtaataatta ccacccttat ctaattattt     420
atttaactta tttatttatt tattatacat atatacaaat ctaataaagt gaaaatctcc     480
cccttcacac ttcacatatg ttaggcgtca tcctgtgctc ccgagaacca gtaccagtac     540
atcgctgttt cgttcgagac ttgaggtcta gttttatacg tgaagaggtc aatgccgccg     600
agagtaaagc cacattttgc gtacaaattg caggcaggta cattgttcgt ttgtgtctct     660
aatcgtatgc caaggagctg tctgcttagt gcccactttt tcgcaaattc gatgagactg     720
```

```
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtagggctc     900
acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaattttc agttggcttg gtttcaattc aatgttcgtt    1140
tttttttttt cttgctgtgt tgtgtttgt gttgtttata gttgtgtgca ctgagcgtcg    1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagtttttccc accctaccca tttgtcatat tgaaaccaat caactgatta   1680
atcaatcaat tagaattgaa gctaaactaa acataccac cgtccatttt gaatgattat    1740
attttttaa tattaatatc gagataatgt ttctaagaaa gaaagaaaac caggagtgaa    1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt cttttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tcttttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctatttat agtcttaact ttttaatgta tatttgtttt    2400
gttttttac ataataatac tttataaaag ctaagctaaa ttcaagtaaa atttcaatct    2460
ctcaaataaa acattttct ctttttctta aatttagttt tatatattta taaaatatac    2520
aaagattttt ttaaaaagt aacaagttat atatgtaata acaaaagaa gaataacaag     2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc cattttttat   3000
agcaaagatt gaataaggcg cattttctt caaagcttta ttgtacgatc tgactaagtt    3060
atcttttaat aattggtatt cctgtttatt gcttgaagaa ttgccggtcc tatttactcg   3120
```

```
ttttaggact ggttcagaat tcctcaaaaa ttcatccaaa tatacaagtg gatcgatcct    3180 acccctttgcg ctaagaagt atatgtgcct actaacgctt gtctttgtct ctgtcactaa    3240
acactggatt attactccca aatacttatt ttggactaat ttaaatgatt tcggatcaac    3300
gttcttaata tcgctgaatc ttccacaatt gatgaaagta gctaggaaga ggaattggta    3360
taaagttttt gttttgtaa atctcgaagt atactcaaac gaatttagta ttttctcagt    3420
gatctcccag atgctttcac cctcacttag aagtgcttta agcattttt tactgtggct    3480 atttccctta tctgcttctt ccgatgattc gaactgtaat tgcaaactac ttacaatatc    3540
agtgatatca gattgatgtt tttgtccata gtaaggaata attgtaaatt cccaagcagg    3600
aatcaatttc tttaatgagg cttccaaaat tgttgctttt tgcgtcttgt atttaaactg    3660
gagtgattta ttgacaatat cgaaactcaa cgaattgctt atgatagtat tatagctcat    3720
gaatgtggct ctcttgattg ctgttccgtt atgtgtaatc atccaacata aataggttag    3780
ttcagcagca cataatgcta ttttctcacc tgaaggtctt caaacctttt ccacaaactg    3840
acgaacaagc accttaggtg gtgttttaca taatatatca aattgtggca tgtcgacgat    3900
tattagttaa accactgcaa aaagttgggg aaaattttgc ccatttttat accgtgtctt    3960
cgtctatcgc ctccccccact ccccaatctt tgaattattc cgaaatattc agcgaacggg    4020
gtgtacacaa aaactaacat tctcaactgc ataatttgaa aaatggcgtg ggacaagaaa    4080 aaaaaaaat tctcaaccat agcaatcatg gaatacggta aatttgtgtt gttcggtgac    4140
tccatcaccc agtttagttg tacccagtat ggctttcatc cagcattaca gaatgtgtat    4200
atccgaaaat tggatgttat taaccgtggt ttcagtggct acaactcaga gcacgctaga    4260
caaattcttc caaaaatttt agagtcggaa accaatatca aattgatgac aatatttttt    4320
ggaactaacg atgcatacga ctacatcaat gaaatccaga cagtcgagtt agacagatat    4380
aaagataatt taagtgtaat ggtacagatg gtactagaca aaaatatcaa accaatcatt    4440
attggatccg aagttcctat tctctagaaa gtataggaac ttcctcgagg actggatctt    4500
gaccaacttt ggtgccacct tcttgcagta cggtatcatt accccagatg tcagcagaaa    4560
gatttcctcc gagcacttcc cagccttgtg tgccaaggtt agaccaaacg ttgttggttt    4620
gactgatggt ttcaacttga ctgacatgat gaccaatgct gctattggta gatatgatgg    4680
taacgtctac gaacactact tcgaaactgt caaggctttg aacccaccag aaaacaccaa    4740
ggctccatac tccaaggctt tggaagacat gttgaaccgt ccagacgaga cg            4792
```

<210> SEQ ID NO 147
<211> LENGTH: 4792
<212> TYPE: DNA
<213> ORGANISM: Artificial sequence
<220> FEATURE:
<223> OTHER INFORMATION: Sequence of resulting second targeting
      construct for the deletion of a second allele of POX5 in Candida
      tropicalis

<400> SEQUENCE: 147

```
cgtctctttg gtatgactga gttggcccac ggttccaacg tccaaggtat tgaaaccacc     60 gccactttg acgaagacac tgacgagttt gtcatcaaca ccccacacat tggtgccacc    120
aagtggtgga tcggtggtgc tgcgcactcc gccacccact gctccgtcta cgccagattg    180
aaggtcaaag gaaaggacta cggtgtcaag acctttgttg tcccattgag agactccaac    240
cacgacttcg agccaggtgt gactgttggt gacattggtg ccaagatggg taaagacggt    300
atcgcggccg ctctagaact agtggatctg aagttcctat tctctagaaa gtataggaac    360
```

```
ttcctgcagg accacctttg attgtaaata gtaataatta ccaccctctat ctaattattt    420 atttaactta tttatttatt tattatacat atatacaaat ctaataaagt gaaaatctcc    480
cccttcacac ttcacatatg ttaggcgtca tcctgtgctc ccgagaacca gtaccagtac    540
atcgctgttt cgttcgagac ttgaggtcta gttttatacg tgaagaggtc aatgccgccg    600
agagtaaagc cacattttgc gtacaaattg caggcaggta cattgttcgt ttgtgtctct    660
aatcgtatgc caaggagctg tctgcttagt gcccacttt tcgcaaattc gatgagactg    720
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtagggctc    900 acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaattttc agttggcttg gtttcaattc aatgttcgtt   1140
tttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740 attttttaa tattaatatc gagataatgt ttctaagaaa gaaagaaaac caggagtgaa   1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atctttttt ctttttctc    1980 tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctatttat agtcttaact ttttaatgta tatttgtttt   2400
gtttttttac ataataatac tttataaaag ctaagctaaa ttcaagtaaa atttcaatct   2460
ctcaaataaa acatttttct ctttttctta aatttagttt tatatattta taaaatatac   2520
aaagattttt ttaaaaaagt aacaagttat atatgtaata acaaaagaa gaataacaag   2580 aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
```

| | | | | |
|---|---|---|---|---|
| ctcatccttc | aatgctatca | tttcctttga | tattggatca | tatgcatagt accgagaaac | 2820 |
| tagtgcgaag | tagtgatcag | gtattgctgt | tatctgatga | gtatacgttg tcctggccac | 2880 |
| ggcagaagca | cgcttatcgc | tccaatttcc | cacaacatta | gtcaactccg ttaggccctt | 2940 |
| cattgaaaga | aatgaggtca | tcaaatgtct | tccaatgtga | gattttgggc cattttttat | 3000 |
| agcaaagatt | gaataaggcg | cattttttctt | caaagcttta | ttgtacgatc tgactaagtt | 3060 |
| atctttaat | aattggtatt | cctgtttatt | gcttgaagaa | ttgccggtcc tatttactcg | 3120 |
| ttttaggact | ggttcagaat | tcctcaaaaa | ttcatccaaa | tatacaagtg gatcgatcct | 3180 |
| acccttgcg | ctaagaagt | atatgtgcct | actaacgctt | gtctttgtct ctgtcactaa | 3240 |
| acactggatt | attactccca | aatacttatt | ttggactaat | ttaaatgatt tcggatcaac | 3300 |
| gttcttaata | tcgctgaatc | ttccacaatt | gatgaaagta | gctaggaaga ggaattggta | 3360 |
| taaagttttt | gttttttgtaa | atctcgaagt | atactcaaac | gaatttagta tttttctcagt | 3420 |
| gatctcccag | atgctttcac | cctcacttag | aagtgcttta | agcatttttt tactgtggct | 3480 |
| atttcctta | tctgcttctt | ccgatgattc | gaactgtaat | tgcaaactac ttacaatatc | 3540 |
| agtgatatca | gattgatgtt | tttgtccata | gtaaggaata | attgtaaatt cccaagcagg | 3600 |
| aatcaattc | tttaatgagg | cttccaaaat | tgttgctttt | tgcgtcttgt atttaaactg | 3660 |
| gagtgattta | ttgacaatat | cgaaactcaa | cgaattgctt | atgatagtat tatagctcat | 3720 |
| gaatgtggct | ctcttgattg | ctgttccgtt | atgtgtaatc | atccaacata aataggttag | 3780 |
| ttcagcagca | cataatgcta | tttttctcacc | tgaaggtctt | tcaaacccttt ccacaaactg | 3840 |
| acgaacaagc | accttaggtg | gtgttttaca | taatatatca | aattgtggca tgtcgacgat | 3900 |
| tattagttaa | accactgcaa | aaagttgggg | aaaattttgc | ccatttttat accgtgtctt | 3960 |
| cgtctatcgc | ctccccccact | ccccaatctt | tgaattattc | cgaaatattc agcgaacggg | 4020 |
| gtgtacacaa | aaactaacat | tctcaactgc | ataatttgaa | aaatggcgtg ggacaagaaa | 4080 |
| aaaaaaaaat | tctcaaccat | agcaatcatg | gaatacggta | aatttgtgtt gttcggtgac | 4140 |
| tccatcaccc | agtttagttg | tacccagtat | ggctttcatc | cagcattaca gaatgtgtat | 4200 |
| atccgaaaat | tggatgttat | taaccgtggt | ttcagtggct | acaactcaga gcacgctaga | 4260 |
| caaattcttc | caaaaatttt | agagtcggaa | accaatatca | aattgatgac aatatttttt | 4320 |
| ggaactaacg | atgcatacga | ctacatcaat | gaaatccaga | cagtcgagtt agacagatat | 4380 |
| aaagataatt | taagtgtaat | ggtacagatg | gtactagaca | aaaatatcaa accaatcatt | 4440 |
| attggatccg | aagttcctat | tctctagaaa | gtataggaac | ttcctcgagt actccgactg | 4500 |
| ggttgtccaa | tgtacctggg | aaggtgacaa | caacatcttg | gccatgaacg ttgccaagcc | 4560 |
| aatggttaga | gacttgttga | aggagccaga | acaaagggga | ttggttctct ccagcgttgc | 4620 |
| cgacttggac | gacccagcca | agttggttaa | ggctttcgac | cacgcccttt ccggcttggc | 4680 |
| cagagacatt | ggtgctgttg | ctgaagacaa | gggtttcgac | attaccggtc caagtttggt | 4740 |
| tttggttttcc | aagttgaacg | ctcacagatt | cttgattgac | ggtttcgaga cg | 4792 |

<210> SEQ ID NO 148
<211> LENGTH: 30
<212> TYPE: DNA
<213> ORGANISM: Candida Tropicalis

<400> SEQUENCE: 148

| | |
|---|---|
| atgcctaccg aacttcaaaa agaaagagaa | 30 |

```
<210> SEQ ID NO 149
<211> LENGTH: 30
<212> TYPE: DNA
<213> ORGANISM: Artificial Sequence
<220> FEATURE:
<223> OTHER INFORMATION: Probe for analysis of Candida tropicalis
      constructs

<400> SEQUENCE: 149
ttaactggac aagatttcag cagcttcttc                                    30
```